(12) United States Patent
Kossen et al.

(10) Patent No.: US 8,304,413 B2
(45) Date of Patent: Nov. 6, 2012

(54) COMPOUNDS AND METHODS FOR TREATING INFLAMMATORY AND FIBROTIC DISORDERS

(75) Inventors: Karl Kossen, Brisbane, CA (US); Scott D. Seiwert, Pacifica, CA (US); Vladimir Serebryany, Burlingame, CA (US); Donald Ruhrmund, San Francisco, CA (US); Leonid Beigelman, San Mateo, CA (US); Luca Francesco Mario Raveglia, Milan (IT); Stefania Vallese, Cardano al Campo (IT); Ivana Bianchi, Fagnano Olona (IT); Tao Hu, Shanghai (CN)

(73) Assignee: Intermune, Inc., Brisbane, CA (US)

( * ) Notice: Subject to any disclaimer, the term of this patent is extended or adjusted under 35 U.S.C. 154(b) by 395 days.

(21) Appl. No.: 12/477,715

(22) Filed: Jun. 3, 2009

(65) Prior Publication Data

US 2009/0318455 A1 Dec. 24, 2009

Related U.S. Application Data

(60) Provisional application No. 61/058,436, filed on Jun. 3, 2008, provisional application No. 61/074,446, filed on Jun. 20, 2008.

(51) Int. Cl.
*A61K 31/50* (2006.01)
*A61K 31/497* (2006.01)
*A61K 31/437* (2006.01)
*A61K 31/44* (2006.01)

(52) U.S. Cl. ............ 514/247; 514/252.1; 514/300; 514/345; 544/239; 544/408; 546/113; 546/290

(58) Field of Classification Search .......... 546/216, 546/113, 290; 514/327, 247, 252.1, 300, 514/345; 544/239, 408
See application file for complete search history.

(56) References Cited

U.S. PATENT DOCUMENTS

| | | |
|---|---|---|
| 3,014,034 A | 12/1961 | Druey et al. |
| 3,622,340 A | 11/1971 | Lamon |
| 3,839,346 A | 10/1974 | Sheekrishna et al. |
| 3,974,281 A | 8/1976 | Gadekar |
| 4,042,699 A | 8/1977 | Gadekar |
| 4,052,509 A | 10/1977 | Gadekar |
| 4,256,640 A | 3/1981 | Makisumi et al. |
| 4,325,863 A | 4/1982 | Hinsken et al. |
| 4,397,854 A | 8/1983 | Sircar |
| 4,404,203 A | 9/1983 | Sircar |
| 4,473,696 A | 9/1984 | Hartmann et al. |
| 4,576,942 A | 3/1986 | Youssefyeh |
| 4,645,839 A | 2/1987 | Kruse et al. |
| 4,650,804 A | 3/1987 | Kitaura et al. |
| 4,698,349 A | 10/1987 | Kitaura et al. |
| 4,820,309 A | 4/1989 | Holliger |
| 4,898,654 A | 2/1990 | Toda et al. |
| 5,019,365 A | 5/1991 | Bedell |
| 5,077,142 A | 12/1991 | Sakon et al. |
| 5,080,710 A | 1/1992 | Rueb et al. |
| 5,167,941 A | 12/1992 | Bedell |
| 5,241,065 A | 8/1993 | Berger et al. |
| 5,310,562 A | 5/1994 | Margolin |
| 5,356,904 A | 10/1994 | Freidinger et al. |
| 5,401,738 A | 3/1995 | Mederski et al. |
| 5,457,099 A | 10/1995 | Shogaki et al. |
| 5,518,729 A | 5/1996 | Margolin |
| 5,543,521 A | 8/1996 | Chan et al. |
| 5,552,409 A | 9/1996 | Michelotti et al. |
| 5,716,632 A | 2/1998 | Margolin |
| 5,719,155 A | 2/1998 | Cho et al. |
| 5,731,106 A | 3/1998 | Tsutsumi et al. |
| 5,741,793 A | 4/1998 | Young et al. |
| 5,808,015 A | 9/1998 | Hamprecht |
| 5,817,700 A | 10/1998 | Dube et al. |
| 5,859,041 A | 1/1999 | Liverton et al. |
| 5,962,478 A | 10/1999 | Margolin |
| 6,090,822 A | 7/2000 | Margolin |
| 6,114,353 A | 9/2000 | Margolin |
| 6,174,901 B1 | 1/2001 | Mantlo et al. |
| 6,265,350 B1 | 7/2001 | Schnatterer et al. |
| 6,300,349 B1 | 10/2001 | Margolin |
| 6,307,047 B1 | 10/2001 | Black et al. |
| 6,509,354 B1 | 1/2003 | Toriyabe et al. |
| 6,521,656 B1 | 2/2003 | Kaneko et al. |
| 6,551,963 B1 | 4/2003 | Linker et al. |
| 6,586,447 B1 | 7/2003 | Lyssikatos et al. |

(Continued)

FOREIGN PATENT DOCUMENTS

AT      333774 B      12/1976

(Continued)

OTHER PUBLICATIONS

Katritzky et al., Journal of Heterocyclic Chemistry (1996), 33(6), 2031-2036.*

(Continued)

*Primary Examiner* — Niloofar Rahmani
(74) *Attorney, Agent, or Firm* — Knobbe Martens Olson & Bear LLP

(57) ABSTRACT

Disclosed are compounds and methods for treating inflammatory and fibrotic disorders, including methods of modulating a stress activated protein kinase (SAPK) system with an active compound, wherein the active compound exhibits low potency for inhibition of the p38 MAPK; and wherein the contacting is conducted at a SAPK-modulating concentration that is at a low percentage inhibitory concentration for inhibition of the p38 MAPK by the compound. Also disclosed are derivatives and analogs of pirfenidone, useful for modulating a stress activated protein kinase (SAPK) system.

Mederski et al., Tetrahedron (1999), 55(44), 12757-12770.*

Azuma et al., "A placebo control and double blind phase II clinical study of pirfenidone in patients with idiopathic pulmonary fibrosis in Japan", *Am J Respir Crit Care Med.*, 165:A729 (2002).

Badger, et al., "Pharmacological profile of SB 203580, a selective inhibitor of cytokine suppressive binding protein/p38 kinase, in animal models of arthritis, bone resorption, endotoxin shock and immune function", *J. Pharmacol. Exp. Ther.* 279:1453-61 (1996).

19 Claims, No Drawings

U.S. PATENT DOCUMENTS

| | | |
|---|---|---|
| 6,602,826 B1 | 8/2003 | Andree et al. |
| 7,067,540 B2 | 6/2006 | Devadas et al. |
| 7,728,013 B2 | 6/2010 | Blatt et al. |
| 7,939,549 B2 | 5/2011 | Nagato et al. |
| 2002/0077486 A1 | 6/2002 | Scarborough et al. |
| 2003/0065175 A1 | 4/2003 | Natsan et al. |
| 2003/0162130 A1 | 8/2003 | Murota |
| 2003/0194748 A1 | 10/2003 | Nagasaki |
| 2003/0199692 A1 | 10/2003 | Biediger et al. |
| 2003/0220368 A1 | 11/2003 | Ozaki et al. |
| 2004/0006082 A1 | 1/2004 | Harada et al. |
| 2004/0014986 A1 | 1/2004 | Hendel et al. |
| 2004/0023973 A1 | 2/2004 | Nagato et al. |
| 2004/0082619 A1 | 4/2004 | Tada et al. |
| 2004/0097560 A1 | 5/2004 | Warshakoon et al. |
| 2004/0102494 A1 | 5/2004 | Selvakumar et al. |
| 2004/0142950 A1 | 7/2004 | Bunker et al. |
| 2004/0157738 A1 | 8/2004 | Tsukamoto et al. |
| 2004/0180906 A1 | 9/2004 | Flynn et al. |
| 2004/0235886 A1 | 11/2004 | Charifson et al. |
| 2004/0259864 A1 | 12/2004 | Geneste et al. |
| 2004/0259865 A1 | 12/2004 | Harada et al. |
| 2005/0004149 A1 | 1/2005 | Harada et al. |
| 2005/0020594 A1 | 1/2005 | Hepperle et al. |
| 2005/0038247 A1 | 2/2005 | Charifson et al. |
| 2005/0054631 A1 | 3/2005 | Jiang et al. |
| 2005/0065144 A1 | 3/2005 | Feng et al. |
| 2005/0101590 A1 | 5/2005 | Yasui et al. |
| 2005/0130943 A1 | 6/2005 | Wallace et al. |
| 2005/0130976 A1 | 6/2005 | Wallace et al. |
| 2005/0153941 A1 | 7/2005 | Miyabayashi et al. |
| 2005/0153942 A1 | 7/2005 | Wallace et al. |
| 2005/0176775 A1 | 8/2005 | Devadas et al. |
| 2005/0250782 A1 | 11/2005 | Marlow et al. |
| 2005/0256123 A1 | 11/2005 | Marlow et al. |
| 2005/0256136 A1 | 11/2005 | Charifson et al. |
| 2005/0288286 A1 | 12/2005 | Flynn et al. |
| 2006/0025337 A1 | 2/2006 | Sinclair et al. |
| 2006/0025424 A1 | 2/2006 | Charifson et al. |
| 2006/0069260 A1 | 3/2006 | Zhang et al. |
| 2006/0084135 A1 | 4/2006 | Howitz et al. |
| 2006/0100193 A1 | 5/2006 | Zhu et al. |
| 2006/0111355 A1 | 5/2006 | Garrick et al. |
| 2006/0189616 A1 | 8/2006 | Pelletier et al. |
| 2006/0189617 A1 | 8/2006 | Pelletier et al. |
| 2006/0211577 A1 | 9/2006 | Hamprecht et al. |
| 2006/0247269 A1 | 11/2006 | Brookings et al. |
| 2006/0258861 A1 | 11/2006 | Anderskewitz et al. |
| 2006/0270612 A1 | 11/2006 | Blatt et al. |
| 2006/0287319 A1 | 12/2006 | Jiang et al. |
| 2007/0037808 A1 | 2/2007 | Flynn et al. |
| 2007/0037973 A1 | 2/2007 | Momiyama et al. |
| 2007/0049624 A1 | 3/2007 | Yi |
| 2007/0092488 A1 | 4/2007 | Strieter et al. |
| 2007/0112038 A1 | 5/2007 | Marlow et al. |
| 2007/0142640 A1 | 6/2007 | Arimoto et al. |
| 2007/0149513 A1 | 6/2007 | Chen et al. |
| 2007/0179165 A1 | 8/2007 | Gyorkos et al. |
| 2007/0185092 A1 | 8/2007 | Zhu et al. |
| 2007/0191336 A1 | 8/2007 | Flynn et al. |
| 2007/0219182 A1 | 9/2007 | Lubisch et al. |
| 2007/0259924 A1 | 11/2007 | Song et al. |
| 2007/0265308 A1 | 11/2007 | Nakai et al. |
| 2008/0020010 A1 | 1/2008 | Nair et al. |
| 2008/0081825 A1 | 4/2008 | Nakai et al. |
| 2008/0139557 A1 | 6/2008 | Blomgren et al. |
| 2008/0161361 A1 | 7/2008 | Wu et al. |
| 2008/0234332 A1 | 9/2008 | Cai et al. |
| 2008/0249090 A1 | 10/2008 | Hu et al. |
| 2008/0255083 A1 | 10/2008 | Stenkamp et al. |
| 2008/0269287 A1 | 10/2008 | Ohtake et al. |
| 2008/0280930 A1 | 11/2008 | Yao |
| 2008/0306053 A1 | 12/2008 | Tachdjian et al. |
| 2008/0306093 A1 | 12/2008 | Servant et al. |
| 2008/0312284 A1 | 12/2008 | Omae et al. |
| 2009/0030017 A1 | 1/2009 | Hanada et al. |
| 2009/0030036 A1 | 1/2009 | Dalton et al. |
| 2009/0088574 A1 | 4/2009 | Urawa et al. |
| 2009/0246198 A1 | 10/2009 | Dong et al. |
| 2010/0063104 A1 | 3/2010 | Nakai et al. |
| 2010/0120862 A1 | 5/2010 | Tafesse |
| 2010/0137317 A1 | 6/2010 | Ripka et al. |
| 2010/0190731 A1 | 7/2010 | Olgin et al. |
| 2010/0197651 A1 | 8/2010 | Taniguchi et al. |
| 2010/0222592 A1 | 9/2010 | Takabe et al. |
| 2010/0233710 A1 | 9/2010 | McDougall et al. |
| 2010/0240704 A1 | 9/2010 | Blatt et al. |
| 2010/0266717 A1 | 10/2010 | Asolkar et al. |
| 2010/0267767 A1 | 10/2010 | Narayanan et al. |
| 2010/0305326 A1 | 12/2010 | Sem |
| 2011/0034495 A1 | 2/2011 | Seiwert et al. |
| 2011/0067612 A1 | 3/2011 | Ito et al. |
| 2011/0224265 A1 | 9/2011 | Magana Castro et al. |
| 2012/0014917 A1 | 1/2012 | Kossen et al. |
| 2012/0015984 A1 | 1/2012 | Radhakrishnan et al. |
| 2012/0016133 A1 | 1/2012 | Pyles et al. |
| 2012/0046321 A1 | 2/2012 | Olgin et al. |
| 2012/0077850 A1 | 3/2012 | Bradford et al. |

FOREIGN PATENT DOCUMENTS

| | | |
|---|---|---|
| CA | 2603763 | 10/2006 |
| CH | 312530 A | 12/1955 |
| CH | 312531 A | 12/1955 |
| CH | 333366 | 11/1958 |
| CN | 1349982 | 5/2002 |
| CN | 1386737 | 12/2002 |
| CN | 1417209 | 5/2003 |
| CN | 1676518 A | 10/2005 |
| CN | 1817862 | 8/2006 |
| CN | 1927923 | 3/2007 |
| CN | 1962642 A | 5/2007 |
| CN | 101235030 | 8/2008 |
| DE | 1070639 | 4/1964 |
| DE | 1936231 | 10/1970 |
| DE | 2557342 A1 | 6/1977 |
| DE | 2707268 A1 | 8/1978 |
| DE | 149666 A1 | 7/1981 |
| DE | 4423934 A1 | 3/1995 |
| DE | 19754348 | 6/1998 |
| DE | 19754348 A1 | 6/1998 |
| DE | 19821263 A1 | 11/1998 |
| DE | 19726241 A1 | 12/1998 |
| DE | 19729061 | 1/1999 |
| DE | 19918725 A1 | 10/2000 |
| DE | 10024938 | 11/2001 |
| DE | 10345648 A1 | 4/2005 |
| EP | 0104860 A1 | 4/1984 |
| EP | 0241006 A2 | 10/1987 |
| EP | 0259048 A2 | 3/1988 |
| EP | 0311010 A2 | 4/1989 |
| EP | 0319957 A2 | 6/1989 |
| EP | 0381374 A1 | 8/1990 |
| EP | 0393936 A1 | 10/1990 |
| EP | 0409435 A1 | 1/1991 |
| EP | 0478195 A1 | 4/1992 |
| EP | 0531578 A1 | 3/1993 |
| EP | 0548680 A1 | 6/1993 |
| EP | 0577325 A1 | 1/1994 |
| EP | 0579059 A1 | 1/1994 |
| EP | 0602515 A1 | 6/1994 |
| EP | 0626377 A1 | 11/1994 |
| EP | 0648760 | 4/1995 |
| EP | 0733629 A1 | 9/1996 |
| EP | 0738716 A2 | 10/1996 |
| EP | 0760208 A2 | 3/1997 |
| EP | 0835865 A1 | 4/1998 |
| EP | 0856255 A2 | 8/1998 |
| EP | 1186318 A2 | 3/2002 |
| EP | 1213288 A1 | 6/2002 |
| EP | 1400243 A1 | 3/2004 |
| FR | 2046068 A5 | 3/1971 |
| FR | 2774986 A1 | 8/1999 |
| FR | 2797629 A1 | 2/2001 |
| GB | 788393 | 1/1958 |
| GB | 0889317 | 2/1962 |
| GB | 1458048 A | 12/1976 |
| GB | 1458049 A | 12/1976 |

| | | |
|---|---|---|
| JP | 42002264 | 2/1967 |
| JP | 51128438 A | 11/1976 |
| JP | 57077671 A | 5/1982 |
| JP | 63290821 A | 11/1988 |
| JP | 3043744 A | 2/1991 |
| JP | 4223457 A | 8/1992 |
| JP | 6256187 A | 9/1994 |
| JP | 7128793 A | 5/1995 |
| JP | 7233072 A | 9/1995 |
| JP | 7295165 A | 11/1995 |
| JP | 7295166 A | 11/1995 |
| JP | 8134371 A | 5/1996 |
| JP | 9244235 A | 9/1997 |
| JP | 9249567 A | 9/1997 |
| JP | 9319023 A | 12/1997 |
| JP | 11049755 A | 2/1999 |
| JP | 11180952 A | 7/1999 |
| JP | 2002371078 A | 12/2002 |
| JP | 2003012645 A | 1/2003 |
| JP | 2003238611 A | 8/2003 |
| JP | 2003261535 A | 9/2003 |
| JP | 2004269469 A | 9/2004 |
| JP | 2004315594 A | 11/2004 |
| JP | 2005013152 A | 1/2005 |
| JP | 2005145882 A | 6/2005 |
| JP | 2005255675 A | 9/2005 |
| JP | 2006142666 A | 6/2006 |
| JP | 2007063268 A | 3/2007 |
| JP | 2007145819 | 6/2007 |
| JP | 2008039883 | 2/2008 |
| JP | 2008076948 | 4/2008 |
| JP | 2008214225 A | 9/2008 |
| KR | 20080045538 A | 5/2008 |
| WO | WO 91/14674 | 10/1991 |
| WO | 9213451 * | 8/1992 |
| WO | WO 92/13451 | 8/1992 |
| WO | WO 92/20642 | 11/1992 |
| WO | WO 92/20816 | 11/1992 |
| WO | WO 93/21185 | 10/1993 |
| WO | WO 93/23404 | 11/1993 |
| WO | WO 94/17059 | 8/1994 |
| WO | WO 94/26249 | 11/1994 |
| WO | WO 95/16712 | 6/1995 |
| WO | WO 95/18128 | 7/1995 |
| WO | WO 96/18770 | 6/1996 |
| WO | WO 96/27374 | 9/1996 |
| WO | WO 96/33994 | 10/1996 |
| WO | WO 97/05109 | 2/1997 |
| WO | WO 97/05137 | 2/1997 |
| WO | WO 97/10712 | 3/1997 |
| WO | WO 97/29107 | 8/1997 |
| WO | WO 97/36863 | 10/1997 |
| WO | WO 97/41830 | 11/1997 |
| WO | WO 98/13361 | 4/1998 |
| WO | WO 98/29119 | 7/1998 |
| WO | WO 98/51772 | 11/1998 |
| WO | WO 98/52948 | 11/1998 |
| WO | WO 99/02501 | 1/1999 |
| WO | WO 99/05123 | 2/1999 |
| WO | WO 99/05125 | 2/1999 |
| WO | WO 99/05913 | 2/1999 |
| WO | WO 99/10331 | 3/1999 |
| WO | WO 99/10332 | 3/1999 |
| WO | WO 99/12903 | 3/1999 |
| WO | WO 99/21837 | 5/1999 |
| WO | WO 99/26944 | 6/1999 |
| WO | WO 99/28313 | 6/1999 |
| WO | WO 99/32448 | 7/1999 |
| WO | WO 99/38857 | 8/1999 |
| WO | WO 99/47140 | 9/1999 |
| WO | WO 99/50263 | 10/1999 |
| WO | WO 99/52878 | 10/1999 |
| WO | WO 99/55676 | 11/1999 |
| WO | WO 99/62900 | 12/1999 |
| WO | WO 00/16775 | 3/2000 |
| WO | WO 00/25789 | 5/2000 |
| WO | WO 00/44381 | 8/2000 |
| WO | WO 00/68188 | 11/2000 |
| WO | WO 01/12600 | 2/2001 |
| WO | WO 01/56992 | 8/2001 |
| WO | WO 01/57019 | 8/2001 |
| WO | WO 01/57021 | 8/2001 |
| WO | WO 01/57037 | 8/2001 |
| WO | WO 01/58448 | 8/2001 |
| WO | WO 01/62253 | 8/2001 |
| WO | WO 01/70746 | 9/2001 |
| WO | WO 01/72708 | 10/2001 |
| WO | 0196308 * | 12/2001 |
| WO | WO 01/96308 | 12/2001 |
| WO | WO 02/06244 | 1/2002 |
| WO | WO 02/22587 | 3/2002 |
| WO | WO 02/24650 | 3/2002 |
| WO | WO 02/40448 | 5/2002 |
| WO | WO 02/067675 | 9/2002 |
| WO | WO 02/085858 | 10/2002 |
| WO | WO 02/090334 | 11/2002 |
| WO | WO 02/098853 | 12/2002 |
| WO | WO 03/014087 | 2/2003 |
| WO | WO 03/033502 | 4/2003 |
| WO | WO 03/035650 | 5/2003 |
| WO | WO 03/045912 | 6/2003 |
| WO | WO 03/047347 | 6/2003 |
| WO | WO 03/047577 | 6/2003 |
| WO | WO 03/059871 | 7/2003 |
| WO | WO 03/059891 | 7/2003 |
| WO | WO 03/068230 | 8/2003 |
| WO | WO 03/082265 | 10/2003 |
| WO | WO 03/093273 | 11/2003 |
| WO | WO 03/097062 | 11/2003 |
| WO | WO 03/106452 | 12/2003 |
| WO | WO 2004/000355 | 12/2003 |
| WO | WO 2004/000846 | 12/2003 |
| WO | WO 2004/005286 | 1/2004 |
| WO | WO 2004/006906 | 1/2004 |
| WO | WO 2004/009560 | 1/2004 |
| WO | WO 2004/014859 | 2/2004 |
| WO | WO 2004/014892 | 2/2004 |
| WO | WO 2004/019863 | 3/2004 |
| WO | WO 2004/024078 | 3/2004 |
| WO | WO 2004/024152 | 3/2004 |
| WO | WO 2004/031145 | 4/2004 |
| WO | WO 2004/031188 | 4/2004 |
| WO | WO 2004/037159 | 5/2004 |
| WO | WO 2004/048314 | 6/2004 |
| WO | WO 2004/058256 | 7/2004 |
| WO | WO 2004/060306 | 7/2004 |
| WO | WO 2004/072033 | 8/2004 |
| WO | WO 2004/074282 | 9/2004 |
| WO | WO 2004/078174 | 9/2004 |
| WO | WO 2004/105684 | 12/2004 |
| WO | WO 2004/110245 | 12/2004 |
| WO | WO 2004/113347 | 12/2004 |
| WO | WO 2005/000818 | 1/2005 |
| WO | WO 2005/002672 | 1/2005 |
| WO | WO 2005/007632 | 1/2005 |
| WO | WO 2005/012288 | 2/2005 |
| WO | WO 2005/018557 | 3/2005 |
| WO | WO 2005/026123 | 3/2005 |
| WO | WO 2005/039598 | 5/2005 |
| WO | WO 2005/040758 | 5/2005 |
| WO | WO 2005/053707 | 6/2005 |
| WO | WO 2005/075438 | 8/2005 |
| WO | WO 2005/085200 | 9/2005 |
| WO | WO 2005/090294 | 9/2005 |
| WO | WO 2005/096784 | 10/2005 |
| WO | WO 2005/099688 | 10/2005 |
| WO | WO 2005/105743 | 11/2005 |
| WO | WO 2005/105790 | 11/2005 |
| WO | WO 2006/004107 | 1/2006 |
| WO | WO 2006/011024 | 2/2006 |
| WO | WO 2006/017443 | 2/2006 |
| WO | WO 2006/020145 | 2/2006 |
| WO | WO 2006/026305 | 3/2006 |
| WO | WO 2006/030032 | 3/2006 |
| WO | WO 2006/032631 | 3/2006 |
| WO | WO 2006/038734 | 4/2006 |
| WO | WO 2006/044405 | 4/2006 |
| WO | WO 2006/055918 | 5/2006 |

| | | |
|---|---|---|
| WO | WO 2006/056427 | 6/2006 |
| WO | WO 2006/060122 | 6/2006 |
| WO | WO 2006/066079 | 6/2006 |
| WO | WO 2006/076681 | 7/2006 |
| WO | WO 2006/079021 | 7/2006 |
| WO | WO 2006/107859 | 10/2006 |
| WO | WO 2006/107860 | 10/2006 |
| WO | WO2006/108354 | 10/2006 |
| WO | WO 2006/116713 | 11/2006 |
| WO | WO 2006/122154 | 11/2006 |
| WO | WO 2006/129076 | 12/2006 |
| WO | WO 2006/131186 | 12/2006 |
| WO | WO 2006/133147 | 12/2006 |
| WO | WO 2006/138418 | 12/2006 |
| WO | WO 2007/006591 | 1/2007 |
| WO | WO 2007/008548 | 1/2007 |
| WO | WO 2007/024021 | 3/2007 |
| WO | WO 2007/026950 | 3/2007 |
| WO | WO 2007/037543 | 4/2007 |
| WO | WO 2007/044796 | 4/2007 |
| WO | WO 2007/048065 | 4/2007 |
| WO | WO 2007/053685 | 5/2007 |
| WO | WO 2007/057329 | 5/2007 |
| WO | WO 2007/058392 | 5/2007 |
| WO | WO 2007/062167 | 5/2007 |
| WO | WO 2007/064797 | 6/2007 |
| WO | WO 2007/100990 | 9/2007 |
| WO | WO 2007/104034 | 9/2007 |
| WO | WO 2007/107545 | 9/2007 |
| WO | WO 2007/108968 | 9/2007 |
| WO | WO 2007/117482 | 10/2007 |
| WO | WO 2007/117559 | 10/2007 |
| WO | WO 2007/117778 | 10/2007 |
| WO | WO 2007/120842 | 10/2007 |
| WO | WO 2007/127474 | 11/2007 |
| WO | WO 2007/127475 | 11/2007 |
| WO | WO 2007/129040 | 11/2007 |
| WO | WO 2007/139150 | 12/2007 |
| WO | WO 2007/147297 | 12/2007 |
| WO | WO 2007/148093 | 12/2007 |
| WO | WO 2008/002490 | 1/2008 |
| WO | WO 2008/013838 | 1/2008 |
| WO | WO 2008/016239 | 2/2008 |
| WO | WO 2008/065428 | 6/2008 |
| WO | WO 2008/072784 | 6/2008 |
| WO | WO 2008/076562 | 6/2008 |
| WO | WO 2008/079277 | 7/2008 |
| WO | WO 2008/079787 | 7/2008 |
| WO | WO 2008/080056 | 7/2008 |
| WO | WO 2008/086188 | 7/2008 |
| WO | WO 2008/091555 | 7/2008 |
| WO | WO 2008/099000 | 8/2008 |
| WO | WO 2008/103277 | 8/2008 |
| WO | WO 2008/106202 | 9/2008 |
| WO | WO 2008/110793 | 9/2008 |
| WO | WO 2008/112715 | 9/2008 |
| WO | WO 2008/121407 | 10/2008 |
| WO | WO 2008/121877 | 10/2008 |
| WO | WO 2008/124323 | 10/2008 |
| WO | WO 2008/124575 | 10/2008 |
| WO | WO 2008/124582 | 10/2008 |
| WO | WO 2008/132155 | 11/2008 |
| WO | WO 2008/141119 | 11/2008 |
| WO | WO 2008/144720 | 11/2008 |
| WO | WO 2008/147169 | 12/2008 |
| WO | WO 2008/147170 | 12/2008 |
| WO | WO 2008/157786 | 12/2008 |
| WO | WO 2009/011410 | 1/2009 |
| WO | WO 2009/011411 | 1/2009 |
| WO | WO 2009/011412 | 1/2009 |
| WO | WO 2009/012275 | 1/2009 |
| WO | WO 2009/016118 | 2/2009 |
| WO | WO2009/026816 | 3/2009 |
| WO | WO 2009/029625 | 3/2009 |
| WO | WO 2009/035598 | 3/2009 |
| WO | WO2009/039773 | 4/2009 |
| WO | WO 2009/054543 | 4/2009 |
| WO | WO-2009/054544 | 4/2009 |
| WO | WO 2009/057827 | 5/2009 |
| WO | WO 2009/060835 | 5/2009 |
| WO | WO 2009/073620 | 6/2009 |
| WO | WO 2009/074810 | 6/2009 |
| WO | WO 2009/082038 | 7/2009 |
| WO | WO 2009/082039 | 7/2009 |
| WO | WO 2009/094427 | 7/2009 |
| WO | WO 2009/097309 | 8/2009 |
| WO | WO 2009/111785 | 9/2009 |
| WO | WO 2009/124119 | 10/2009 |
| WO | WO 2009/124553 | 10/2009 |
| WO | WO 2009/135299 | 11/2009 |
| WO | WO 2009/142732 | 11/2009 |
| WO | WO 2009/149188 | 12/2009 |
| WO | WO 2009/156484 | 12/2009 |
| WO | WO 2009/158393 | 12/2009 |
| WO | WO 2009/158473 | 12/2009 |
| WO | WO 2010/006191 | 1/2010 |
| WO | WO 2010/009183 | 1/2010 |
| WO | WO 2010/021693 | 2/2010 |
| WO | WO 2010/025087 | 3/2010 |
| WO | WO 2010/027567 | 3/2010 |
| WO | WO 2010/029299 | 3/2010 |
| WO | WO 2010/044885 | 4/2010 |
| WO | WO 2010/048716 | 5/2010 |
| WO | WO 2010/065755 | 6/2010 |
| WO | WO 2010/066028 | 6/2010 |
| WO | WO 2010/068253 | 6/2010 |
| WO | WO 2010/075561 | 7/2010 |
| WO | WO 2010/077680 | 7/2010 |
| WO | WO 2010/080795 | 7/2010 |
| WO | WO 2010/104818 | 9/2010 |
| WO | WO 2010/104830 | 9/2010 |
| WO | WO 2010/129467 | 11/2010 |
| WO | WO 2010/135470 | 11/2010 |
| WO | WO 2010/141538 | 12/2010 |
| WO | WO 2010/141539 | 12/2010 |
| WO | WO 2010/141540 | 12/2010 |
| WO | WO 2010/141545 | 12/2010 |

OTHER PUBLICATIONS

Boehm et al. "New inhibitors of p38 kinase", *Exp Opin Ther Pat.*, 10:25-37 (2000).

Dong et al., "MAP kinases in the immune response", *Annu Rev Immunol*., 20:55-72 (2002).

English, et al., "Pharmacological inhibitors of MAPK pathways", *Trends Pharmacol Sci*., 23:40-5 (2002).

Furukawa et al., "p38 MAPK mediates fibrogenic signal through Smad3 phosphorylation in rat myofibroblasts", *Hepatology*, 38: 879-89 (2003).

Gehl et al., "Effect of pirfenidone on the pulmonary fibrosis of Hermansky-Pudlak syndrome", *Mol Genet Metab*., 76:234-42 (2002).

Griswold et al., "Differentiation in vivo of classical non-steroidal antiinflammatory drugs from cytokine suppressive antiinflammatory drugs and other pharmacological classes using mouse tumour necrosis factor alpha production", *Drugs Exp. Clin. Res.* 19:243-8 1993).

Higuchi et al., *Pro-drugs as Novel Delivery Systems*, vol. 14 of the A.C.S. Symposium Series.

International Search Report for corresponding International Application No. PCT/US09/46136 dated Oct. 2, 2009.

Jiang et al., "Characterization of the structure and functon of a new mitogen-activated protein kinase (p38beta)", *J Biol Chem* 271:17920-6 (1996).

Joe et al., "Animal models of rheumatoid and related inflammation", *Curr. Rheumatol. Rep.* 1:139-48 (1999).

Korb et al., "Differential tissue expression and activation of p38 MAPK α, β, γ, and δ isoforms rheumatoid arthritis", *Arthritis and Rheumatism*, 54: 2745-56 (2006).

Kumar et al., "Novel homologues of CSBP/p38 MAP kinase: activation, substrate specificity and sensitivity to inhibition by pyridinyl imidazoles", *Biochem Biophys Res Comm*., 235:533-8 (1997).

Laufer et al., "An in-vitro screening assay for the detection of inhibitors of proinflammatory cytokine synthesis: a useful tool for the development of new antiarthritic and disease modifying drugs", Osteoarthritis Cartilage, 10:961-7 (2002).

Laufer et al., "From imidazoles to pyrimidines: new inhibitors of cytokine release", *J Med. Chem.*, 45: 2733-40 (2002).

Lee et al., "A protein kinase involved in the regulation of inflammatory cytokine biosynthesis", *Nature*, 372:739-46 (1994).

Lee et al., "Bicyclic imdazoles as a novel class of cytokine biosynthesis inhibitors", *Ann NY Acad Sci*., 696:149-70 (1993).

Lee et al., "Inhibition of monocyte IL-1 production by the anti-inflammatory compound, SK&F 86002", *Int J Immunopharmacol*., 10:835-43 (1988).

Lee et al., "Inhibition of p38 MAP kinase as a therapeutic strategy", *Immunopharmacol*., 47:185-201 (2000).

Lee et al., "p38 mitogen-activated protein kinase inhibitors—mechanisms and therapeutic potentials", *Pharmacol Ther*., 82:389-97 (1999).

Lee et al., "Pirfenidone: a novel pharmacological agent that inhibits leiomyoma cell proliferation and collagen production", *J Clin Endocrinol Metab*., 83:219-23 (1998).

Li. et al., "The primary structure of p38 gamma: a new member of p38 group of MAP kinases", *Biochem Biophys Res Comm*., 228:334-40 (1996).

Lowrey et al., "Transcreener: screening enzymes involved in covalent regulation", *Expert Opin Ther Targets*, 10:179-90 (2006).

Matsuoka et al., "A p38 MAPK inhibitor, FR-167653, ameliorates murine bleomycin-induced pulmonary fibrosis", *Am J Physiol Lung Cell Mol Physiol*., 283:L103-L112 (2002).

Nagai et al., "Open-label compassionate use one year-treatment with pirfenidone to patients with chronic pulmonary fibrosis.", *Intern Med*., 41:1118-23 (2002).

Ono et al., "The p38 signal transduction pathway: activation and function", *Cell. Signal.*, 12:1-13 (2000).

Raghu et al., "Treatment of idiopathic pulmonary fibrosis with a new antifibrotic agent, pirfenidone: results of a prospective, open-label Phase II study", *Am J Respir Crit Care Med* 159:1061-9 (1999).

Roche, ed., *Bioreversible Carriers in Drug Design*, American Pharmaceutical Association and Pergamon Press, 1987.

Salituro et al., "Inhibitors of p38 MAP kinase: therapeutic intervention in cytokine-mediated diseases", *Curr Med Chem*., 6:807-823 (1999).

Stambe et al., "The role of p38alpha mitogen-activated protein kinase activation in renal fibrosis", *J. Am Soc Nephrol.*, 15: 370-9 (2004).

Stein et al., "p38-2, a novel mitogen-activated protein kinase with distinct properties", *J Biol Chem*., 272:19509-17 (1997).

Trifilieff et al., "CGH2466, a combined adenosine receptor antagonist, p38 mitogen-activated protein kinase and phosphodiesterase type 4 inhibitor with potent in vitro and in vivo anti-inflammatory activities", *Br. J. Pharmacol.*, 144:1002-10 (2005).

Underwood et al., "Inhibition of p38 MAP kinase", *Prog Respir Res.*, 31:342-5 (2001)).

Underwood et al., "SB 239063, a p38 MAPK inhibitor, reduces neutrophilia, inflammatory cytokines, MMP-9, and fibrosis in lung", *Am J Physiol Lung Cell Mol Physiol*., 279:L895-L902 (2000).

Wang et al., "Requirement of mitogen-activated protein kinase kinase 3 (MKK3) for activation of p38alpha and p38delta MAPK isoforms by TGF-beta 1 in murine mesangial cells", *J. Biol. Chem.*, 277: 47257-62 (2002).

Wang et al., "Molecular cloning and characterization of a novel p38 mitogen-activated protein kinase", *J Biol Chem*., 272:23668-74 (1997).

Altman et al., Orthogonal Pd-and Cu-based catalyst systems for C- and N-arylation of oxindoles, J Am Chem Soc. (Jul. 2008) 130(29): 9613-9620.

Ammar et al., Novel Pirfenidone Analogues: Synthesis of Pyridin-2-ones for the Treatment of Pulmonary Fibrosis, Arch Pharm Chem Life Sci., (Apr. 2006) 339: 1-8.

Anonymous, Verfahren zur Hestellung von 6-Arylyridazinon-3 Verbindungen, (Mar. 1990), Research Disclosure No. 311123, The Industry Standard Disclosure Publication Service, Questel Ireland Ltd., pp. 1-5.

Border et al., Transforming growth factor beta in tissue fibrosis, N Engl J Med., (1994) 331(19): 1286-1292.

Brinkman et al., Engagement of Tumor Necrosis Factor (TNF) Receptor 1 Leads to ATF-2- and p38 Mitogen-activated Protein Kinase-dependent TNF-alpha Gene Expression, J Biol Chem., (Oct. 1999) 274(43): 20882-30886.

Cambpell et al., A Novel Mechanism for TNF-alpha Regulation by p38 MAPK: Involvement of NF-kB with Implications for Therapy in Rheumatoid Arthritis, J Immunol., 173(11): 6928-6937.

Elbashir et al., Duplexes of 21-nucleotide RNAs mediate RNA interference in cultured mammalian cells, Nature (2001) 411(6836): 494-498.

Fitzgerald et al., Structural basis for p38alpha MAP kinase quinazolinone and pyridol-pyrimidine inhibitor specificity, Nat Struct Biol (2003) 10(9): 764-769.

Fuchs et al., Stability of the ATF2 Transcription Factor is Regulated by Phosphorylation and Dephosphorylation, J Biol Chem., (Apr. 2000), 275(17): 12560-12564.

Greene et al, Protective Groups in Organic Synthesis. John Wiley & Sons, 3rd Edition, 1999, Table of Contents Only.

Hoogenband van den, et al., An efficient synthesis of 4-bromo-N-substituted oxindoles by an intramolecular copper-catalyzed amidation reation, Tetra Lttrs. (May 2007) 48(26): 4461-4465.

Kaminska et al., TGF beta signalling and its role in tumour pathogenesis, Acta Biochim Pol., (Jun. 2005) 52(2): 329-337.

Katritzky et al., J Hetero Chem., Synthesis and Some Transformations 4-Benzotriazolyl-3,4-dihydropyrid-2-ones (1996) 33(6): 2031-2036.

Kisteneva, Azomethine Dyes from Oxindole Derivatives. I, The Journal of General Chemistry of the U.S.S.R. (1956) 26(3): 1327-1332.

Kisteneva, Azomethine Dyes from Oxindole Derivatives. II, The Journal of General Chemistry of the U.S.S.R. (1956) 26(7): 2251-2255.

Lam et al., Copper-catalyzed general C-N and C-O bond cross-coupling with arylboronic acid, Tetrahedron Lett. (2001) 42: 3415-3418.

Laurent, Biochemical pathways leading to collagen deposition in pulmonary fibrosis, Ciba Found Symp. (1985) 114: 222-233.

Liverton et al., Design and Synthesis of Potent, Selective, and Orally Bioavailable Tetrasubstituted Imidazole Inhibitors of p38 Mitogen-Activated Protein Kinase, J Med Chem. (1999) 42(12): 2180-2190.

McIntyre et al., Pyridazine Based Inhibitors of p38 MAPK, Bioorg Med Chem Lttr., (2002) 12: 689-692.

Mederski et al., N-Aryl Heterocycles via Coupling Reactions with Arylboronic Acids, Tetrahedron (1999) 55(44): 12757-12770.

Muddu et al., Resolving fibrosis in the diseased liver: translating the scientific promise to the clinic, Int J Biochem Cell Biol., (2007) 39(4): 695-714 [Online Oct. 7, 2006].

Newton et al., New aspects of p38 mitogen activated protein kinase (MAPK) biology in lung inflammation, Drug Discovery Today: Disease Mechanisms, (2006) 3: 53-61.

Noble et al., Idiopathic pulmonary fibrosis: new insights into pathogenesis, Clin Chest Med. (2004) 25(4): 749-758.

Ozes et al., 697 Preclinical activity of pirfenidone (5-methyl-1phenyl-2(IH)-pyridone) in cell-based models of nonalcoholic steatohepatitis, Hepatology, (2003) 38: 495-.

Pargellis et al., Inhibition of p38 MAP kinase by utilizing a novel allosteric binding site, Nat Struct Biol. (2002) 9(4): 268-272.

Przheval'skii et al., Mono(m-substituted) Chloroacetyldiarylamines in the Stollé Reaction, Chem Heterocycl Compd. (1982) 18(7): 716-719.

Raingeaud et al., Pro-inflammatory Cytokines and Environmental Stress Cause p38 Mitogen-activated Protein Kinase Activation by Dual Phosphorylation on Tyrosine and Threonine, J Biol Chem., (1995) 270(13): 7420-7426.

Richards et al., Biochemical and cellular mechanisms of pulmonary fibrosis, Toxicol Pathol. (1991) 19: 526-539.

Sarges et al., A Novel Class of "GABAergic" Agents: 1-Aryl-3-(aminoalkylidene)oxindoles, (1989) 32(2): 437-444.

Stollé, Über N-substituierte Oxindole and Isatine, Journal für Praktische Chemie, (1930), 128: 1-43.

Sugahara et al., A facile copper-catalyzed Ullmann condensation: N-arylation of heterocyclic compounds containing an -NHCO-moiety, Chem Pharm Bull., (1997) 45(4): 719-721.

Ting et al., Substituted 1,3-Dihydro-2H-pyrrolo[2,3-b]pyridin-2-ones as Potential Antiinflammatory Agents, J Med Chem. (1990) 33(10): 2697-2706.

Vippagunta et al., Crystalline solids, Advanced Drug Delivery Reviews (2001) 48: 3-26.

IPRP and WO dated Dec. 6, 2010 for PCT/US2009/046136, filed Jun. 3, 2009.

European Patent Application No. 09759347.9 Search Report dated Feb. 6, 2012.

Lam et al., Copper-promoted C-N bond cross-coupling with phenylstannane, Tetrahedron Letters (2002) 43: 3091-3094.

Results from Chemical Abstract Services Search of May 9, 2012 in REGISTRY/CAPLUS 1907-date, WPINDEX DCR 1999-date, USPATFULL 1971-date, USPATOLD 1790-1975, and REAXYSFILE 1771-2009.

\* cited by examiner

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 1

Lys Arg Glu Leu Val Glu Pro Leu Thr Pro Ser Gly Glu Ala Pro Asn
1               5                   10                  15

Gln Ala Leu Leu Arg
            20

COMPOUNDS AND METHODS FOR TREATING INFLAMMATORY AND FIBROTIC DISORDERS

CROSS-REFERENCE TO RELATED APPLICATIONS

This application claims the priority benefit under 35 USC §119(e) of U.S. Provisional Application No. 61/058,436, filed Jun. 3, 2008 and U.S. Provisional Application No. 61/074,446, filed Jun. 20, 2008, each of which is incorporated by reference in its entirety.

BACKGROUND

1. Field of the Invention

This invention relates to compounds and methods useful in treating various inflammatory and fibrotic conditions, including those associated with enhanced activity of kinase p38.

2. Background of the Invention

A large number of chronic and acute conditions have been recognized to be associated with perturbation of the inflammatory response. A large number of cytokines participate in this response, including IL-1, IL-6, IL-8 and TNFα. It appears that the activity of these cytokines in the regulation of inflammation may be associated with the activation of an enzyme on the cell signaling pathway, a member of the MAP kinase family generally known as p38 and also known as SAPK, CSBP and RK.

Several inhibitors of p38, such as NPC 31169, SB239063, SB203580, FR-167653, and pirfenidone have been tested in vitro and/or in vivo and found to be effective for modulating inflammatory responses.

There continues to be a need for safe and effective drugs to treat various inflammatory conditions such as inflammatory pulmonary fibrosis.

SUMMARY

Disclosed herein are compounds of formula I

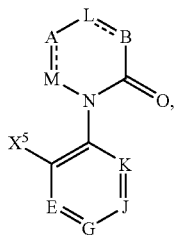

(I)

wherein M is N or $CR^1$; A is N or $CR^2$; L is N or $CR^3$; B is N or $CR^4$; E is N or $CX^4$; G is N or $CX^3$; J is N or $CX^2$; K is N or $CX^1$; a dashed line is a single or double bond, except when B is $CR^4$, then each dashed line is a double bond;

$R^1$ is selected from the group consisting of hydrogen, alkyl, cycloalkyl, alkenyl, cyano, sulfonamido, halo, aryl, alkenylenearyl, and heteroaryl;

$R^2$ is selected from the group consisting of hydrogen, alkyl, haloalkyl, halo, cyano, aryl, alkenyl, alkenylenearyl, heteroaryl, haloalkylcarbonyl, cycloalkyl, hydroxylalkyl, sulfonamido, and cycloheteroalkyl or $R^2$ and $R^1$ together form an optionally substituted 5-membered nitrogen-containing heterocyclic ring;

$R^3$ is selected from the group consisting of hydrogen, aryl, alkenylenearyl, heteroaryl, alkyl, alkenyl, haloalkyl, amino, and hydroxy;

$R^4$ is selected from the group consisting of hydrogen, alkyl, haloalkyl, cyano, alkoxy, aryl, alkenyl, alkenylenearyl, and heteroaryl; and $X^1$, $X^2$, $X^3$, $X^4$, and $X^5$ are independently selected from the group consisting of hydrogen, alkyl, alkenyl, halo, hydroxy, amino, aryl, cycloalkyl, thioalkyl, alkoxy, haloalkyl, haloalkoxy, alkoxyalkyl, cyano, aldehydo, alkylcarbonyl, amido, haloalkylcarbonyl, sulfonyl, and sulfonamide, or $X^2$ and $X^3$ together form a 5- or 6-membered ring comprising —$O(CH_2)_nO$—, wherein n is 1 or 2, with the proviso that when all of A, B, E, G, J, K, L, and M are not N, then (a) at least one of $X^1$, $X^2$, $X^3$, $X^4$, and $X^5$ is not selected from the group consisting of hydrogen, halo, alkoxy, and hydroxy or (b) at least one of $R^1$, $R^2$, $R^3$, or $R^4$ is not selected from the group consisting of hydrogen, alkyl, alkenyl, haloalkyl, hydroxyalkyl, alkoxy, phenyl, substituted phenyl, halo, hydroxy, and alkoxyalkyl, or a pharmaceutically acceptable salt, ester, or solvate thereof.

In some embodiments, the compounds of formula (I) have a structure of formula (II) or (III):

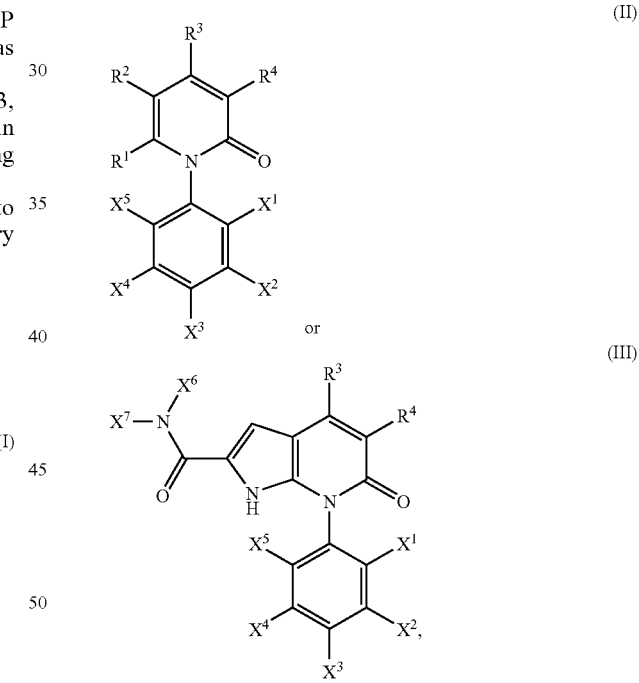

wherein $X^6$ and $X^7$ are independently selected from the group consisting of hydrogen, aryl, heteroaryl, cycloalkyl, heterocycloalkyl, alkylenylaryl, alkylenylheteroaryl, alkylenylheterocycloalkyl, alkylenylcycloalkyl, or $X^6$ and $X^7$ together form an optionally substituted 5 or 6 membered heterocyclic ring. In a specific class of embodiments, the compound of formula (I) is a compound selected from the group recited in Table 1, below.

A compound disclosed herein preferably exhibits an $IC_{50}$ in the range of about 0.1 μM to about 1000 μM, and preferably about 1 μM to about 800 μM, about 1 μM to about 500 μM, about 1 μM to about 300 μM, about 1 μM to about 200 μM, or about 1 μM to about 100 μM for inhibition of p38 MAPK.

Also disclosed herein is a composition including the compound of formula (I) and a pharmaceutically acceptable excipient.

In another aspect, disclosed herein are methods of modulating a stress activated protein kinase (SAPK) system by contacting a compound disclosed herein with a p38 mitogen-activated protein kinase (MAPK), wherein the compound exhibits an $IC_{50}$ in the range of about 0.1 µM to about 1000 µM for inhibition of the p38 MAPK; and wherein the contacting is conducted at a SAPK-modulating concentration that is less than an $IC_{30}$ for inhibition of the p38 MAPK by the compound. Contemplated p38 MAPKs include, but are not limited to, p38α, p38β, p38γ, and p38δ. In a preferred composition, the concentration of the compound disclosed herein is effective to alter TNFα release in whole blood by at least 15%.

In yet another aspect, disclosed herein are methods of modulating a SAPK system in a subject in need thereof, comprising administering to the subject a therapeutically effective amount of a compound as disclosed herein, wherein the compound exhibits an $IC_{50}$ in the range of about 0.1 µM to about 1000 µM for inhibition of p38 MAPK; and the therapeutically effective amount produces a blood or serum concentration of the compound that is less than an $IC_{30}$ for inhibition of p38 mitogen-activated protein kinase (MAPK). In some embodiments, the subject suffers from an inflammatory condition. The subject preferably is a mammal, more preferably human. The compound can be administered to the subject on a schedule selected from the group consisting of three times a day, twice a day, once a day, once every two days, three times a week, twice a week, and once a week.

For the compositions and methods described herein, preferred features, such as components, compositional ranges thereof, conditions, and steps, can be selected from the various examples provided herein.

DETAILED DESCRIPTION

It has now been discovered that a high therapeutic effect in treating various disorders associated with enhanced activity of kinase p38 can be achieved by using a relatively low-potency p38 kinase inhibitor compound.

Therefore, in one embodiment there is provided a method of modulating a stress-activated kinase (SAPK) system by contacting a compound as described herein with a p38 mitogen-activated protein kinase (MAPK). A preferred compound exhibits an $IC_{50}$ in the range of about 0.1 µM to about 1000 µM, and preferably about 1 µM to about 800 µM, about 1 µM to about 500 µM, about 1 µM to about 300 µM, about 1 µM to about 200 µM, or about 1 µM to about 100 µM for inhibition of p38 MAPK. The concentration at which the compound is contacted with p38 MAPK is preferably less than $IC_{30}$ for inhibition of the p38 by this compound.

Mitogen-activated protein kinases are evolutionarily conserved serine/threonine kinases involved in the regulation of many cellular events. Several MAPK groups have been identified in mammalian cells, including extracellular signal-regulated kinase (ERK), p38, and SAPK/JNK. It is believed that MAPKs are activated by their specific MAPK kinases (MAPKKs): ERK by MEK1 and MEK2, p38 by MKK3 and MKK6, and SAPK/JNK by SEK1 (also known as MKK4) and MKK7 (SEK2). These MAPKKs may also be activated by various MAPKK kinases (MAPKKKs) such as Raf, MLK, MEKK1, TAK1, and ASK1.

It is believed that the MAPK network involves at least twelve cloned highly conserved, proline-directed serine-threonine kinases which, when activated by cell stresses (e.g., oxidative stress, DNA damage, heat or osmotic shock, ultraviolet irradiation, ischemia-reperfusion), exogenous agents (e.g., anisomycin, Na arsenite, lipopolysaccharide, LPS) or pro-inflammatory cytokines, TNF-α and IL-1β, can phosphorylate and activate other kinases or nuclear proteins such as transcription factors in either the cytoplasm or the nucleus.

p38 MAPK

As used herein, "p38 MAPK" is a member (sub family) of the stress-activated protein kinase family, which includes at least 4 isoforms (α, β, γ, δ), several of which are considered important in processes critical to the inflammatory response and tissue remodeling (Lee et al. *Immunopharmacol.* 47:185-201 (2000)). Unless indicated otherwise, reference to "p38 MAPK," "a p38 MAPK," or "the p38 MAPK" contemplates any one, all, or a subset of the subfamily members. The predominant kinases in monocytes and macrophages, p38α and p38β, appear more widely expressed compared to p38γ (skeletal muscle) or p38δ (testes, pancreas, prostate, small intestine, and in salivary, pituitary and adrenal glands). A number of substrates of p38 MAP kinase have been identified including other kinases (MAPKAP K2/3, PRAK, MNK 1/2, MSK1/RLPK, RSK-B), transcription factors (ATF2/6, myocyte enhancer factor 2, nuclear transcription factor-β, CHOP/GADD153, Elk1 and SAP-1A1) and cytosolic proteins (stathmin), many of which are important physiologically.

Jiang et al. *J Biol Chem* 271:17920-17926 (1996) reported characterization of p38β as a 372-amino acid protein closely related to p38α. Both p38α and p38β are activated by proinflammatory cytokines and environmental stress, p38β is preferentially activated by MAP kinase kinase-6 (MKK6) and preferentially activated transcription factor 2. Kumar et al. *Biochem Biophys Res Comm* 235:533-538 (1997) and Stein et al. *J Biol Chem* 272:19509-19517 (1997) reported a second isoform of p38β, p38β2, containing 364 amino acids with 73% identity to p38α. It is believed that p38β is activated by proinflammatory cytokines and environmental stress, although the second reported p38β isoform, p38β2, appears to be preferentially expressed in the central nervous system (CNS), heart and skeletal muscle, compared to the more ubiquitous tissue expression of p38α. Furthermore, it is believed that activated transcription factor-2 (ATF-2) is a better substrate for p38β2 than for p38α.

The identification of p38γ was reported by Li. et al. *Biochem Biophys Res Comm* 228:334-340 (1996) and of p38δ by Wang et al. *J Biol Chem* 272:23668-23674 (1997) and by Kumar et al. *Biochem Biophys Res Comm* 235:533-538 (1997). These two p38 isoforms (γ and δ) represent a unique subset of the MAPK family based on their tissue expression patterns, substrate utilization, response to direct and indirect stimuli, and susceptibility to kinase inhibitors. It is believed that p38α and β are closely related, but diverge from γ and δ, which are more closely related to each other.

A characterization of p38 isoforms that are espressing in affected tissue from patients with Rheumatoid Arthritis suggests that p38α and γ are the most significantly expressed isoforms (Korb, Tohidats-Akrad, Cetin, Axmann, Smolen, and Schett, 2006, Arthritis and Rheumatism 54(9): 2745-56). The authors found that p38α and γ were the predominant isoforms in macrophages, p38β and γ were expressed in synovial fibroblasts, and p38δ was expressed in granulocytes. These data suggest that p38 isoforms in addition to p38α is more broad than suggested by the results of in initial studies.

Typically the p38 MAP kinase pathway is directly or indirectly activated by cell surface receptors, such as receptor tyrosine kinases, chemokines or G protein-coupled receptors, which have been activated by a specific ligand, e.g., cytokines, chemokines or lipopolysaccharide (LPS) binding to a cognate receptor. Subsequently, p38 MAP kinase is activated by phosphorylation on specific threonine and tyrosine residues. After activation, p38 MAP kinase can phosphorylate other intracellular proteins, including protein kinases, and can be translocated to the cell nucleus, where it phosphorylates and activates transcription factors leading to the expression of pro-inflammatory cytokines and other proteins that contribute to the inflammatory response, cell adhesion, and proteolytic degradation. For example, in cells of myeloid lineage, such as macrophages and monocytes, both IL-1β and TNFα are transcribed in response to p38 activation. Subsequent translation and secretion of these and other cytokines initiates a local or systemic inflammatory response in adjacent tissue and through infiltration of leukocytes. While this response is a normal part of physiological responses to cellular stress, acute or chronic cellular stress leads to the excess, unregulated, or excess and unregulated expression of pro-inflammatory cytokines. This, in turn, leads to tissue damage, often resulting in pain and debilitation.

In alveolar macrophages, inhibition of p38 kinases with p38 inhibitor, SB203580, reduces cytokine gene products. It is believed that inflammatory cytokines (TNF-α, IFN-γ, IL-4, IL-5) and chemokines (IL-8, RANTES, eotaxin) are capable of regulating or supporting chronic airway inflammation. The production and action of many of the potential mediators of airway inflammation appear to be dependent upon the stress-activated MAP kinase system (SAPK) or p38 kinase cascade (Underwood et al. *Prog Respir Res* 31:342-345 (2001)). Activation of the p38 kinase pathway by numerous environmental stimuli results in the elaboration of recognized inflammatory mediators whose production is considered to be translationally regulated. In addition, a variety of inflammatory mediators activate p38 MAPK which may then activate downstream targets of the MAPK system including other kinases or transcription factors, thus creating the potential for an amplified inflammatory process in the lung.

Downstream Substrates of p38 Group of MAP Kinases

Protein kinase substrates of p38α or p38β include MAP kinase-activated protein kinase 2 (MAPKAPK2 or M2), MAP kinase interaction protein kinase (MNK1), p38 regulated/activated kinase (PRAK), mitogen- and stress-activated kinase (MSK: RSK-B or RLPK).

Transcription factors activated by p38 include activating transcription factor (ATF)-1, 2 and 6, SRF accessory protein 1 (Sap 1), CHOP (growth arrest and DNA damage inducible gene 153, or GADD153), p53, C/EBPβ, myocyte enhance factor 2C (MEF2C), MEF2A, MITF1, DDIT3, ELK1, NFAT, and high mobility group-box protein (HBP1).

Other types of substrates for p38 include cPLA2, Na+/H+ exchanger isoform-1, tau, keratin 8, and stathmin.

Genes regulated by the p38 pathway include c-jun, c-fos, junB, IL-1, TNF, IL-6, IL-8, MCP-1, VCAM-1, iNOS, PPARγ, cyclooxygenase (COX)-2, collagenase-1 (MMP-1), Collagenase-3 (MMP-13), HIV-LTR, Fgl-2, brain natriuretic peptide (BNP), CD23, CCK, phosphoenolpyruvate carboxykinase-cytosolic, cyclin D1, and LDL receptor (Ono et al. *Cellular Signalling* 12:1-13 (2000)).

Biological Consequences of p38 Activation

P38 and inflammation: Acute and chronic inflammation are believed to be central to the pathogenesis of many diseases such as rheumatoid arthritis, asthma, chronic obstructive pulmonary disease (COPD) and acute respiratory distress syndrome (ARDS). The activation of the p38 pathway may play an central role in: (1) production of proinflammatory cytokines such as IL-1β, TNF-α and IL-6; (2) induction of enzymes such as COX-2, which controls connective tissue remodeling in pathological condition; (3) expression of an intracellular enzyme such as iNOS, which regulates oxidation; (4) induction of adherent proteins such as VCAM-1 and many other inflammatory related molecules. In addition to these, the p38 pathway may play a regulatory role in the proliferation and differentiation of cells of the immune system. p38 may participate in GM-CSF, CSF, EPO, and CD40-induced cell proliferation and/or differentiation.

The role of the p38 pathway in inflammatory-related diseases was studied in several animal models. Inhibition of p38 by SB203580 reduced mortality in a murine model of endotoxin-induced shock and inhibited the development of mouse collagen-induced arthritis and rat adjuvant arthritis. A recent study showed that SB220025, which is a more potent p38 inhibitor, caused a significant dose-dependent decrease in vascular density of the granuloma. These results indicate that p38 or the components of the p38 pathway can be a therapeutic target for inflammatory disease.

P38 and fibrosis: The uncontrolled and/or excessive deposition of extracellular matrix is a defining aspect of fibrotic diseases such as pulmonary fibrosis, liver cirrhosis, renal fibrosis, and focal segmental glomerulosclerosis. Fibrosis is also an important factor in the progression and pathology of disease states that are not primarily considered to be fibrotic diseases. Several studies have implicated the p38 signaling cascade in fibrosis. (Wang L, Ma R, Flavell R A, and Choi M E 2002 Journal of Biological Chemistry 277: 47257-62; Stambe C, Atkins R C, Tesch G H, Masaki T, Schreiner G F, Nikolic-Paterson D J 2004 J. Am Soc Nephrol 15: 370-9; Furukawa F, Matsuzaki K, et al 2003 Hepatology 38: 879-89).

p38 and apoptosis: It appears that concomitant activation of p38 and apoptosis is induced by a variety of agents such as NGF withdrawal and Fas ligation. Cysteine proteases (caspases) are central to the apoptotic pathway and are expressed as inactive zymogens. Caspase inhibitors may then block p38 activation through Fas cross-linking. However, overexpression of dominant active MKK6b can also induce caspase activity and cell death. The role of p38 in apoptosis is cell type- and stimulus-dependent. While p38 signaling has been shown to promote cell death in some cell lines, in different cell lines p38 has been shown to enhance survival, cell growth, and differentiation.

p38 in the cell cycle: Overexpression of p38α in yeast leads to significant slowing of proliferation, indicating involvement of p38α in cell growth. A slower proliferation of cultured mammalian cells was observed when the cells were treated with p38α/β inhibitor, SB203580.

p38 and cardiomyocyte hypertrophy: Activation and function of p38 in cardiomyocyte hypertrophy has been studied. During progression of hypertrophy, both p38α and p38β levels were increased and constitutively active MKK3 and MKK6-elicited hypertrophic responses enhanced by sarcomeric organization and elevated atrial natriuretic factor expression. Also, reduced signaling of p38 in the heart promotes myocyte differentiation via a mechanism involving calcineurin-NFAT signaling.

p38 and development: Despite the non-viability of p38 knockout mice, evidence exists regarding the differential role of p38 in development. p38 has been linked to placental angiogenesis but not cardiovascular development in several studies. Furthermore, p38 has also been linked to erythropoietin expression suggesting a role in erythropoiesis. PRAK has recently been implicated in cell development in murine implantation. PRAK mRNA, as well as p38 isoforms, were found to be expressed throughout blastocyst development p38 and cell differentiation: p38α and/or p38β were found to play an important role in cell differentiation for several different cell types. The differentiation of 3T3-L1 cells into adipocytes and the differentiation of PC12 cells into neurons both require p38α and/or β. The p38 pathway was found to be necessary and sufficient for SKT6 differentiation into hemoglobinized cells as well as C2C112 differentiation in myotubules.

p38 in senescence and tumor suppression: p38 has a role in tumorigenesis and senescence. There have been reports that activation of MKK6 and MKK3 led to a senescent phenotype dependent upon p38 MAPK activity. Also, p38 MAPK activity was shown responsible for senescence in response to telomere shortening, $H_2O_2$ exposure, and chronic RAS oncogene signaling. A common feature of tumor cells is a loss of senescence and p38 is linked to tumorigenesis in certain cells. It has been reported that p38 activation is reduced in tumors and that loss of components of the p38 pathway such as MKK3 and MKK6 resulted in increased proliferation and likelihood of tumorigenic conversion regardless of the cell line or the tumor induction agent used in these studies.

p38 MAP Kinase Inhibitors

A "p38 MAPK inhibitor" is a compound that inhibits the activity of p38. The inhibitory effects of a compound on the activity of p38 may be measured by various methods well-known to a skilled artisan. For example, the inhibitory effects may be measured by measuring the level of inhibition of lipopolysaccharide (LPS)-stimulated cytokine production (Lee et al. *Int J Immunopharmacol* 10:835-843 (1988); Lee et al. *Ann NY Acad Sci* 696:149-170 (1993); Lee et al. *Nature* 372:739-746 (1994); Lee et al. *Pharmacol Ther* 82:389-397 (1999)).

Efforts to develop p38 MAPK inhibitors have focused on increasing potency. SB203580 and other 2,4,5-triaryl imidazoles were found to be potent p38 kinase inhibitors with $IC_{50}$ values in nanomolar range. For example, for SB203580 the $IC_{50}$ was found to be 48 nM. The pyridinylimidazoles SKF 86002 (1) and SB203580 (2) shown below have been used as the template for the majority of p38 inhibitors. Recent publications (Lee et al. *Immunopharmacology* 47:185-201 (2000)) have disclosed the p38 inhibitors (3-6) shown below. Notable among these inhibitors is the relatively high potency and selectivity described for compound 4 (p38 $IC_{50}$=0.19 nM) and the inhibition of inflammation driven angiogenesis by SB 220025 (6).

Two p38 inhibitors reported to be in clinical development are HEP689 (7, anti-inflammatory for psoriasis and other skin disorders) and VX-745 (8, anti-inflammatory for rheumatoid arthritis).

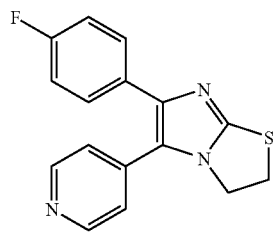

1 SKF 86002

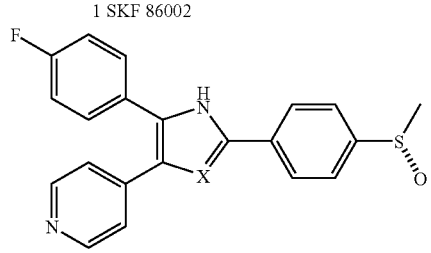

2 X = N; SB 203580
3 X = CH; L-167307

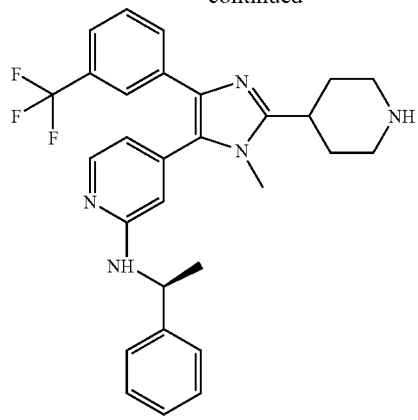

4

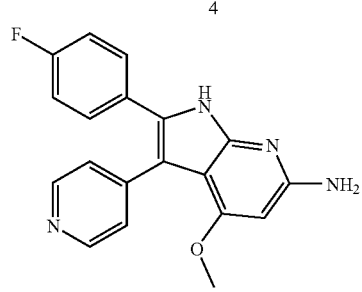

5 RWJ 68354

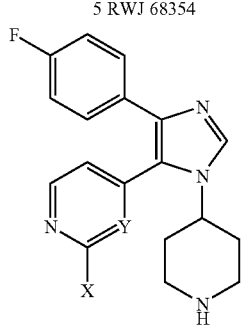

6 X = H, Y = CH; HEP 689 (SB 235699)
7 X = HN₂, Y = N; SB 220025

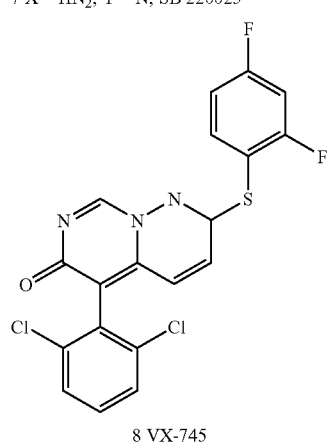

8 VX-745

Further discussion of new p38 inhibitors can be found in Boehm et al. *Exp Opin Ther Pat* 10:25-37 (2000); and Salituro et al. *Curr Med Chem* 6:807-823 (1999).

Preferred p38 inhibitors described herein are pirfenidone derivatives and analogs that exhibit relatively low potency of p38 inhibition while, surprisingly, still having a relatively high therapeutic effect (e.g., for modulating an SAPK system) as a result of such inhibition. Preferably, the p38 inhibitors of the embodiments exhibit $IC_{50}$ in the range of about 0.1 μM to about 1000 μM, or more preferably about 1 μM to about 800 μM, about 1 μM to about 500 μM, about 1 μM to about 300 μM, about 1 μM to about 200 μM, or about 1 μM to about 100 μM for inhibition of p38 MAPK.

Pirfenidone Derivatives and Analogs

Pirfenidone (5-methyl-1-phenyl-2-(1H)-pyridone) itself is a known compound and its pharmacological effects are disclosed, for example, in Japanese Patent Application KOKAI (Laid-Open) Nos. 87677/1974 and 1284338/1976. U.S. Pat. Nos. 3,839,346; 3,974,281; 4,042,699; and 4,052,509, each of which is hereby incorporated by reference in its entirety, describe methods of manufacture of 5-methyl-1-phenyl-2-(1H)-pyridone and its use as an anti-inflammatory agent.

Pirfenidone and derivatives and analogs thereof are useful compounds for modulating a stress activated protein kinase (SAPK) system.

The term "alkyl" used herein refers to a straight or branched chain hydrocarbon group of one to ten carbon atoms, including, but not limited to, methyl, ethyl, n-propyl, isopropyl, n-butyl, isobutyl, tert-butyl, n-hexyl, and the like. Alkyls of one to six carbon atoms are also contemplated. The term "alkyl" includes "bridged alkyl," i.e., a bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. Alkyl groups optionally can be substituted, for example, with hydroxy (OH), halo, aryl, heteroaryl, cycloalkyl, heterocycloalkyl, and amino. It is specifically contemplated that in the analogs described herein the alkyl group consists of 1-40 carbon atoms, preferably 1-25 carbon atoms, preferably 1-15 carbon atoms, preferably 1-12 carbon atoms, preferably 1-10 carbon atoms, preferably 1-8 carbon atoms, and preferably 1-6 carbon atoms.

As used herein, the term "cycloalkyl" refers to a cyclic hydrocarbon group, e.g., cyclopropyl, cyclobutyl, cyclohexyl, and cyclopentyl. "Heterocycloalkyl" is defined similarly as cycloalkyl, except the ring contains one to three heteroatoms independently selected from the group consisting of oxygen, nitrogen, and sulfur. Nonlimiting examples of heterocycloalkyl groups include piperdine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected from the group consisting of alkyl, alkyleneOH, C(O)NH₂, NH₂, oxo (═O), aryl, haloalkyl, halo, and OH. Heterocycloalkyl groups optionally can be further N-substituted with alkyl, hydroxyalkyl, alkylenearyl, or alkyleneheteroaryl.

The term "alkenyl" used herein refers to a straight or branched chain hydrocarbon group of two to ten carbon atoms containing at least one carbon double bond including, but not limited to, 1-propenyl, 2-propenyl, 2-methyl-1-propenyl, 1-butenyl, 2-butenyl, and the like.

The term "halo" used herein refers to fluoro, chloro, bromo, or iodo.

The term "alkylene" used herein refers to an alkyl group having a substituent. For example, the term "alkylene aryl" refers to an alkyl group substituted with an aryl group. The alkylene group is optionally substituted with one or more substituent previously listed as an optional alkyl substituent. For example, an alkylene group can be —CH₂CH₂—.

As used herein, the term "alkenylene" is defined identical as "alkylene," except the group contains at least one carbon-carbon double bond.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, haloalkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, haloalkoxy, amino, $CO_2H$, $CO_2$alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "haloalkyl" used herein refers to one or more halo groups appended to an alkyl group.

The term "nitroalkyl" used herein refers to one or more nitro groups appended to an alkyl group.

The term "thioalkyl" used herein refers to one or more thio groups appended to an alkyl group.

The term "hydroxyalkyl" used herein refers to one or more hydroxy groups appended to an alkyl group.

The term "alkoxy" used herein refers to straight or branched chain alkyl group covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "alkoxyalkyl" used herein refers to one or more alkoxy groups appended to an alkyl group.

The term "arylalkoxy" used herein refers to a group having an aryl appended to an alkoxy group. A non-limiting example of an arylalkoxy group is a benzyloxy (Ph-CH₂—O—).

The term "amino" as used herein refers to —NR₂, where R is independently hydrogen or alkyl. Non-limiting examples of amino groups include NH₂ and N(CH₃)₂.

The term "amido" as used herein refers to —NHC(O)alkyl or —NHC(O)H. A non-limiting example of an amido group is —NHC(O)CH₃.

The term "carboxy" or "carboxyl" used herein refers to —COOH or its deprotonated form —COO⁻.

The term "alkoxycarbonyl" refers to —(CO)—O-alkyl. Examples of alkoxycarbonyl groups include, but are not limited to, methoxycarbonyl group, ethoxycarbonyl group, propoxycarbonyl group, and the like.

The term "alkylcarbonyl" refers to —(CO)-alkyl. Examples of alkylcarbonyl groups include, but are not limited to, methylcarbonyl group, ethylcarbonyl group, propylcarbonyl group, and the like.

The term "sulfonamido" refers to —SO₂NR₂ where R is independently hydrogen or an alkyl group. Examples of a sulfonamido group include, but are not limited to, —SO₂N(CH₃)₂ and —SO₂NH₂.

The term "sulfonyl" refers to —SO$_2$alkyl. One example of a sulfonyl group is methylsulfonyl (e.g., —SO$_2$CH$_3$).

Carbohydrates are polyhydroxy aldehydes or ketones, or substances that yield such compounds upon hydrolysis. Carbohydrates comprise the elements carbon (C), hydrogen (H) and oxygen (O) with a ratio of hydrogen twice that of carbon and oxygen. In their basic form, carbohydrates are simple sugars or monosaccharides. These simple sugars can combine with each other to form more complex carbohydrates. The combination of two simple sugars is a disaccharide. Carbohydrates consisting of two to ten simple sugars are called oligosaccharides, and those with a larger number are called polysaccharides.

The term "uronide" refers to a monosaccharide having a carboxyl group on the carbon that is not part of the ring. The uronide name retains the root of the monosaccharide, but the -ose sugar suffix is changed to -uronide. For example, the structure of glucuronide corresponds to glucose.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, a substituted group is derived from the unsubstituted parent structure in which there has been an exchange of one or more hydrogen atoms for another atom or group. When substituted, the substituent group(s) is (are) one or more group(s) individually and independently selected from alkyl, cycloalkyl, aryl, fused aryl, heterocyclyl, heteroaryl, hydroxy, alkoxy, aryloxy, mercapto, alkylthio, arylthio, cyano, halo, carbonyl, thiocarbonyl, alkoxycarbonyl, nitro, silyl, trihalomethanesulfonyl, trifluoromethyl, and amino, including mono and di substituted amino groups, and the protected derivatives thereof. The protecting groups that can form the protective derivatives of the above substituents are known to those of skill in the art and can be found in references such as Greene and Wuts, *Protective Groups in Organic Synthesis;* 3$^{rd}$ Edition, John Wiley and Sons: New York, 2006. Wherever a substituent is described as "optionally substituted" that substituent can be substituted with the above-described substituents.

Asymmetric carbon atoms can be present. All such isomers, including diastereomers and enantiomers, as well as the mixtures thereof, are intended to be included in the scope of the disclosure herein. In certain cases, compounds can exist in tautomeric forms. All tautomeric forms are intended to be included in the scope of the disclosure herein. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated.

One family of such compounds is a compound of formula (I)

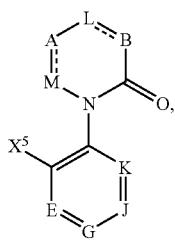

(I)

wherein M is N or CR$^1$; A is N or CR$^2$; L is N or CR$^3$; B is N or CR$^4$; E is N or CX$^4$; G is N or CX$^3$; J is N or CX$^2$; K is N or CX$^1$; a dashed line is a single or double bond, except when B is CR$^4$, then each dashed line is a double bond;

R$^1$ is selected from the group consisting of hydrogen, alkyl, cycloalkyl, alkenyl, cyano, sulfonamido, halo, aryl, alkenylenearyl, and heteroaryl;

R$^2$ is selected from the group consisting of hydrogen, alkyl, haloalkyl, halo, cyano, aryl, alkenyl, alkenylenearyl, heteroaryl, haloalkylcarbonyl, cycloalkyl, hydroxyalkyl, sulfonamido, and cycloheteroalkyl or R$^2$ and R$^1$ together form an optionally substituted 5-membered nitrogen-containing heterocyclic ring;

R$^3$ is selected from the group consisting of hydrogen, aryl, alkenylenearyl, heteroaryl, alkyl, alkenyl, haloalkyl, amino, and hydroxy;

R$^4$ is selected from the group consisting of hydrogen, alkyl, haloalkyl, cyano, alkoxy, aryl, alkenyl, alkenylenearyl, and heteroaryl; and X$^1$, X$^2$, X$^3$, X$^4$, and X$^5$ are independently selected from the group consisting of hydrogen, alkyl, alkenyl, halo, hydroxy, amino, aryl, cycloalkyl, thioalkyl, alkoxy, haloalkyl, haloalkoxy, alkoxyalkyl, cyano, aldehydo, alkylcarbonyl, amido, haloalkylcarbonyl, sulfonyl, and sulfonamide, or X$^2$ and X$^3$ together form a 5- or 6-membered ring comprising —O(CH$_2$)$_n$O—, wherein n is 1 or 2, with the proviso that when all of A, B, E, G, J, K, L, and M are not N, then either (a) at least one of X$^1$, X$^2$, X$^3$, X$^4$, and X$^5$ is not selected from the group consisting of hydrogen, halo, alkoxy, and hydroxy or (b) at least one of R$^1$, R$^2$, R$^3$, or R$^4$ is not selected from the group consisting of hydrogen, alkyl, alkenyl, haloalkyl, hydroxyalkyl, alkoxy, phenyl, substituted phenyl, halo, hydroxy, and alkoxyalkyl.

In some embodiments, only A is N. In various embodiments, only E and J are each N. In some embodiments, only B is N. In various embodiments, only G is N. In some embodiments, only K is N. In various embodiments, only E is N. In some embodiments, only J is N. In some embodiments, only L is N. In various embodiments, only M is N.

In some embodiments, R$^1$ is selected from the group consisting of hydrogen, 4-pyridyl, cyclopropanyl, 4-fluorophenyl, 2-furanyl, cyano, H$_2$NSO$_2$, (CH$_3$)$_2$NSO$_2$, 4-sulfonamido-phenyl, fluoro, 4-(3,5-dimethyl)-isoxazolyl, 4-pyrazolyl, 4-(1-methyl)-pyrazolyl, 5-pyrimidinyl, 1-piperazinyl, 1-morpholinyl, 1-pyrrolidinyl, 2-imidazolyl, and thiazolyl.

In some embodiments, the compound of formula (I) is a compound of formula (II):

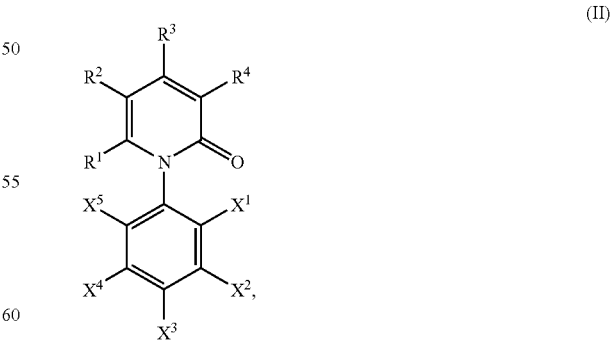

(II)

wherein at least one of R$^1$, R$^2$, R$^3$, or R$^4$ is not selected from the group consisting of hydrogen, alkyl, alkenyl, haloalkyl, hydroxyalkyl, alkoxy, phenyl, substituted phenyl, halo, hydroxy, and alkoxyalkyl.

In some embodiments, R$^1$ and R$^2$ together form an optionally substituted 5-membered nitrogen-containing heterocyclic ring. In a specific class of embodiments, the compound of formula (I) is a compound of formula (III) or formula (IV):

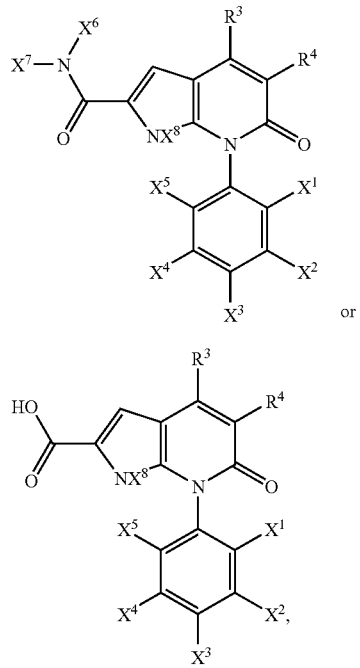

wherein $X^8$ is hydrogen or alkyl; $X^6$ and $X^7$ are independently selected from the group consisting of hydrogen, aryl, heteroaryl, cycloalkyl, heterocycloalkyl, alkylenylaryl, alkylenylheteroaryl, alkylenylheterocycloalkyl, alkylenylcycloalkyl, or $X^6$ and $X^7$ together form an optionally substituted 5 or 6 membered heterocyclic ring. In some embodiments, $X^7$ is hydrogen. In various embodiments, $X^8$ is methyl.

In some embodiments, at least one of $X^1$, $X^2$, $X^3$, $X^4$, or $X^5$ is alkyl, for example, haloalkyl. In various embodiments, at least one of $X^1$, $X^2$, $X^3$, $X^4$, or $X^5$ is alkenyl. In some embodiments, at least one of $X^1$, $X^2$, $X^3$, $X^4$, or $X^5$ is amino. In various embodiments, at least one of $X^1$, $X^2$, $X^3$, $X^4$, or $X^5$ is thioalkyl. In some embodiments, at least one of $X^1$, $X^2$, $X^3$, $X^4$, or $X^5$ is aryloxy. In various embodiments, at least one of $X^1$, $X^2$, $X^3$, $X^4$, or $X^5$ is arylalkoxy. In some embodiments, at least one of $X^1$, $X^2$, $X^3$, $X^4$, or $X^5$ is alkoxyalkyl. In various embodiments, at least one of $X^1$, $X^2$, $X^3$, $X^4$, or $X^5$ is alkylcarbonyl. In various embodiments, at least one of $X^1$, $X^2$, $X^3$, $X^4$, or $X^5$ is amido. In some embodiments, at least one of $X^1$, $X^2$, $X^3$, $X^4$, or $X^5$ is sulfonyl.

Specific preferred compounds of formula (I) are listed in the following Table 1.

TABLE 1

| Cmpd No. | Structure |
|---|---|
| 1 | |
| 2 | 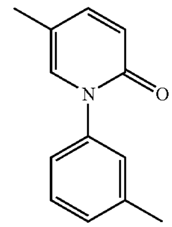 |
| 3 | 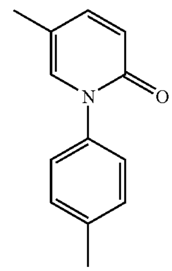 |
| 4 | 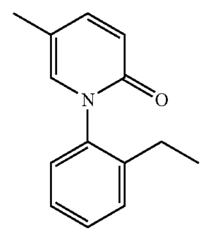 |
| 5 | 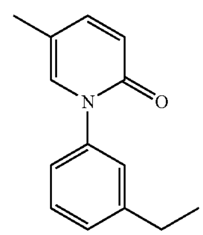 |
| 6 | 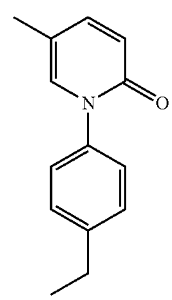 |
| 7 | 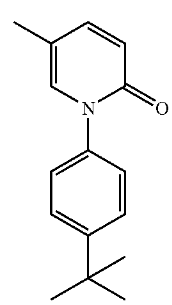 |

TABLE 1-continued
| Cmpd No. | Structure |
|---|---|
| 8 | 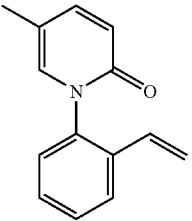 |
| 9 | 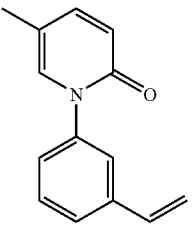 |
| 10 | 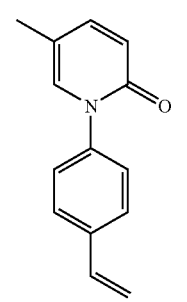 |
| 11 | 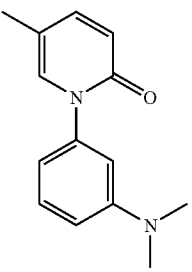 |
| 12 | 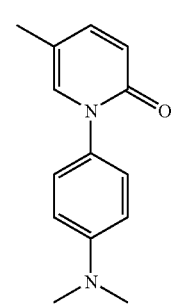 |
| 13 | 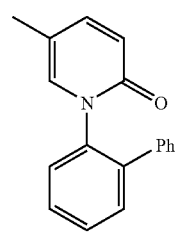 |
TABLE 1-continued
| Cmpd No. | Structure |
|---|---|
| 14 | 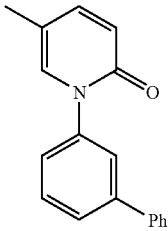 |
| 15 | 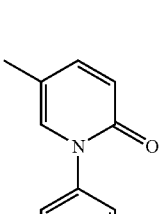 |
| 16 | 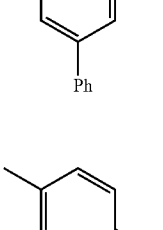 |
| 17 | 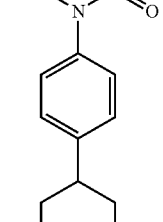 |
| 18 | 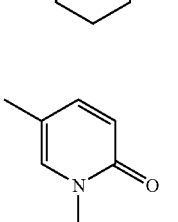 |

TABLE 1-continued
| Cmpd No. | Structure |
|---|---|
| 19 | 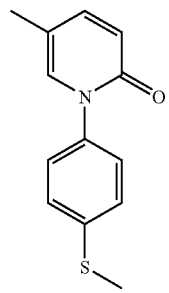 |
| 20 | 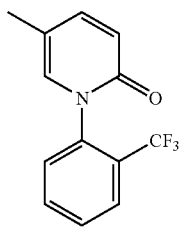 |
| 21 | 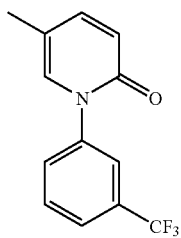 |
| 22 | 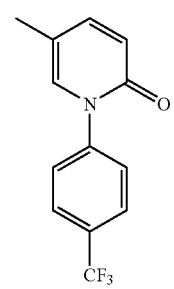 |
| 23 | 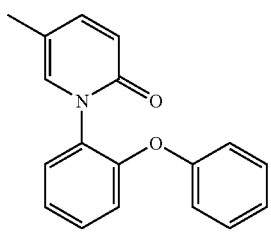 |
| 24 | 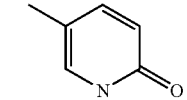 |
| 25 | 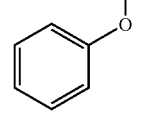 |
| 26 | 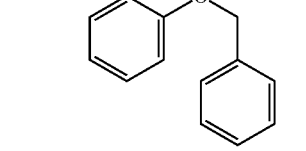 |
| 27 | 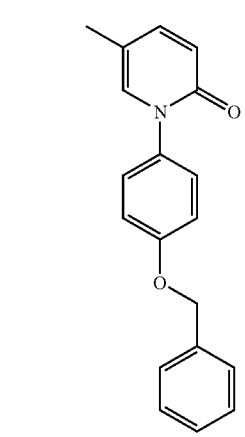 |
| 28 | 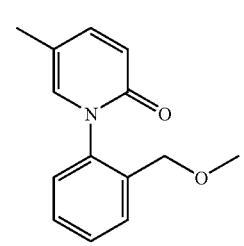 |

TABLE 1-continued
| Cmpd No. | Structure |
|---|---|
| 29 | 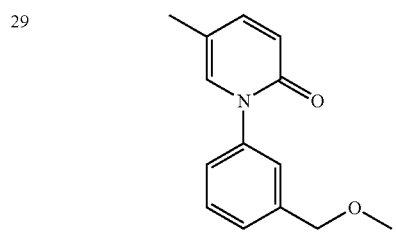 |
| 30 | 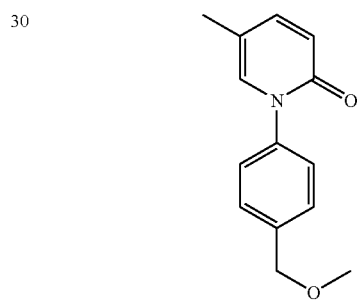 |
| 31 | 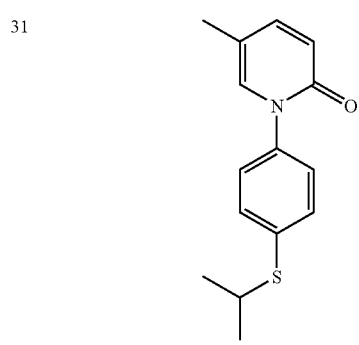 |
| 32 | 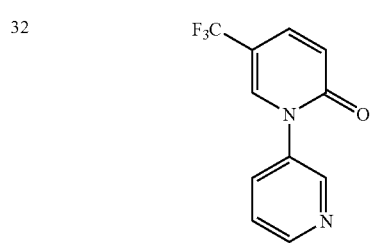 |
| 33 | 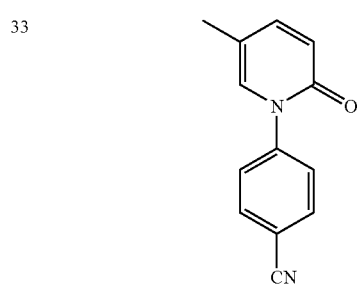 |
TABLE 1-continued
| Cmpd No. | Structure |
|---|---|
| 34 | 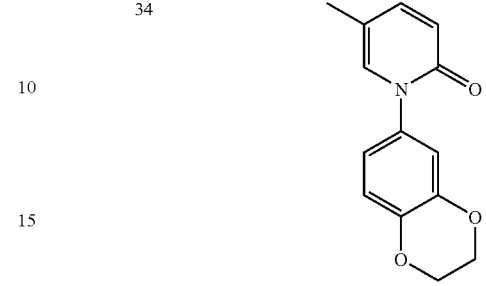 |
| 35 | 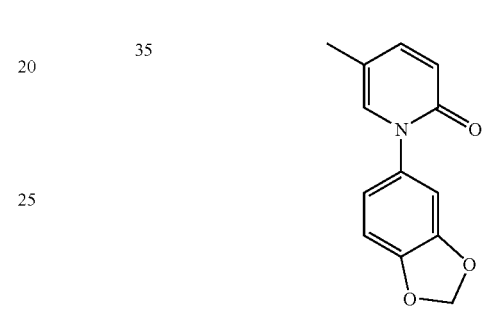 |
| 36 | 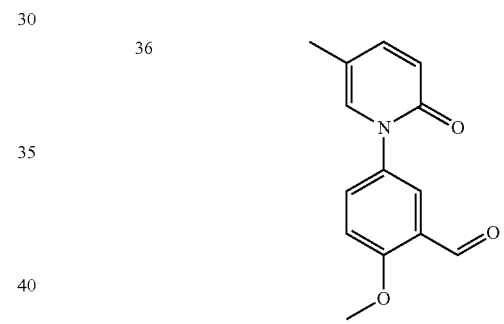 |
| 37 | 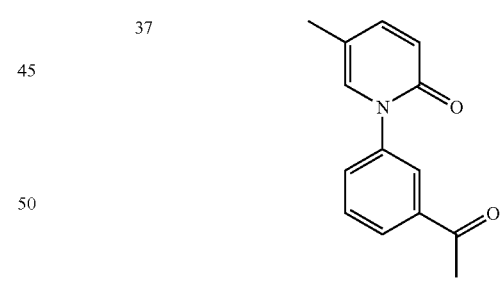 |
| 38 | 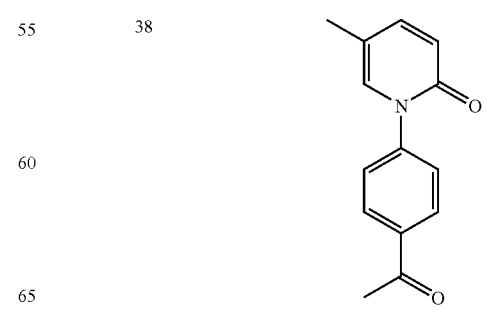 |

TABLE 1-continued

| Cmpd No. | Structure |
|---|---|
| 39 | 5-methyl-1-(3-acetamidophenyl)pyridin-2(1H)-one |
| 40 | 5-methyl-1-(pyrimidin-5-yl)pyridin-2(1H)-one |
| 41 | 5-(trifluoromethyl)-1-(3-(trifluoromethyl)phenyl)pyridin-2(1H)-one |
| 42 | 5-(trifluoromethyl)-1-(4-(trifluoromethyl)phenyl)pyridin-2(1H)-one |
| 43 | 5-(trifluoromethyl)-1-(4-(methylthio)phenyl)pyridin-2(1H)-one |
| 44 | 5-(trifluoromethyl)-1-(pyrimidin-3-yl)pyridin-2(1H)-one |
| 45 | 3-cyano-1-phenylpyridin-2(1H)-one |
| 46 | 5-cyano-1-phenylpyridin-2(1H)-one |
| 47 | 5-bromo-1-phenylpyrimidin-2(1H)-one |
| 48 | 4-amino-1-phenyl-1,3,5-triazin-2(1H)-one |
| 49 | 1-phenylpyrimidine-2,4(1H,3H)-dione |
| 50 | 5-methyl-1-phenylpyrimidine-2,4(1H,3H)-dione |

TABLE 1-continued

| Cmpd No. | Structure |
|---|---|
| 51 | 5-(trifluoromethyl)-1-(pyridin-4-yl)pyridin-2(1H)-one |
| 52 | 5-(trifluoromethyl)-1-(pyridin-2-yl)pyridin-2(1H)-one |
| 53 | 1-phenyl-3-(thiophen-2-yl)pyridin-2(1H)-one |
| 54 | 4-(benzyloxy)-1-phenylpyridin-2(1H)-one |
| 55 | 1-phenyl-4-styrylpyridin-2(1H)-one |
| 56 | 1-phenyl-4-(thiophen-2-yl)pyridin-2(1H)-one |
| 57 | 1-phenyl-5-styrylpyridin-2(1H)-one |
| 58 | 1-phenyl-5-(thiophen-2-yl)pyridin-2(1H)-one |
| 59 | 1-phenyl-6-styrylpyridin-2(1H)-one |
| 60 | 1-phenyl-6-(thiophen-2-yl)pyridin-2(1H)-one |

TABLE 1-continued

| Cmpd No. | Structure |
|---|---|
| 61 | 4-CF3, 1-(3-(methoxymethyl)phenyl)pyridin-2(1H)-one |
| 62 | 4-CF3, 1-(3-(dimethylamino)phenyl)pyridin-2(1H)-one |
| 63 | 4-CF3, 1-(4-(trifluoromethyl)phenyl)pyridin-2(1H)-one |
| 64 | 5-CHF2, 1-(3-(trifluoromethyl)phenyl)pyridin-2(1H)-one |
| 65 | 5-CHF2, 1-(4-(trifluoromethyl)phenyl)pyridin-2(1H)-one |
| 66 | 5-CHF2, 1-(4-ethylphenyl)pyridin-2(1H)-one |
| 67 | 5-CHF2, 1-(4-(methylthio)phenyl)pyridin-2(1H)-one |
| 68 | 5-CHF2, 1-(pyridin-4-yl)pyridin-2(1H)-one |
| 69 | 5-CHF2, 1-(pyridin-3-yl)pyridin-2(1H)-one |
| 70 | 5-CHF2, 1-(pyridin-2-yl)pyridin-2(1H)-one |

TABLE 1-continued
| Cmpd No. | Structure |
|---|---|
| 71 | 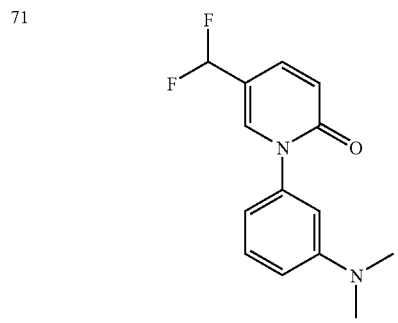 |
| 72 | 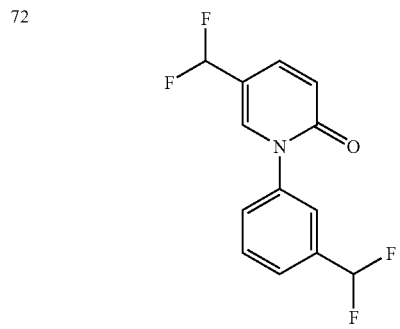 |
| 73 | 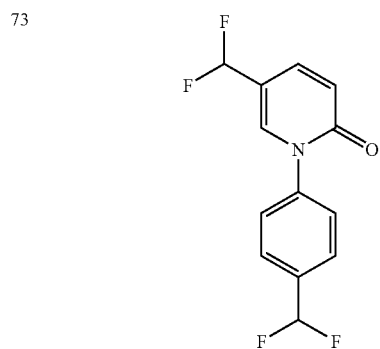 |
| 74 | 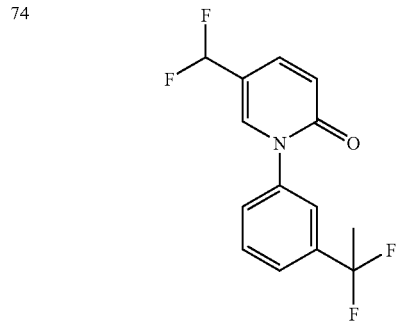 |
| 75 | 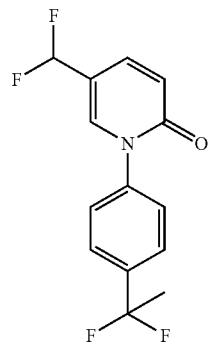 |
| 76 | 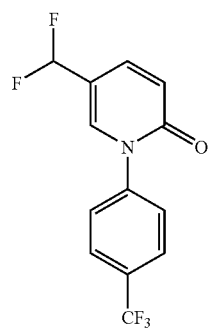 |
| 77 | 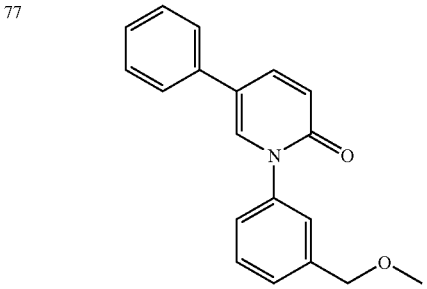 |
| 78 | 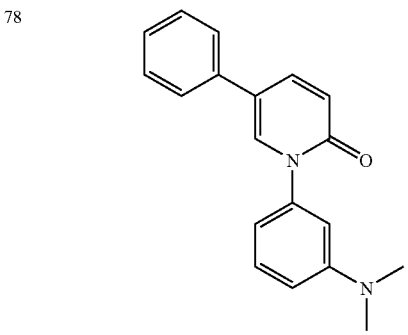 |

TABLE 1-continued
| Cmpd No. | Structure |
|---|---|
| 79 | 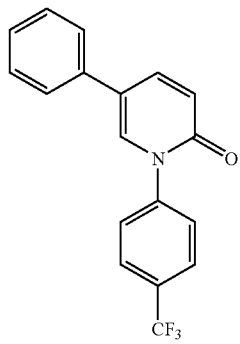 |
| 80 | 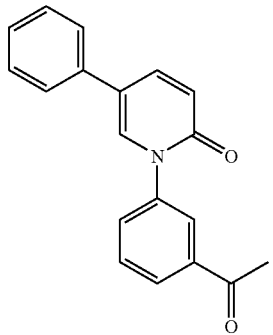 |
| 81 | 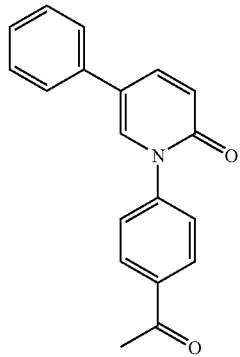 |
| 82 | 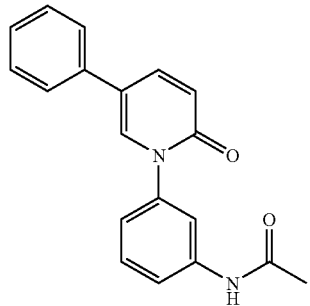 |
TABLE 1-continued
| Cmpd No. | Structure |
|---|---|
| 83 | 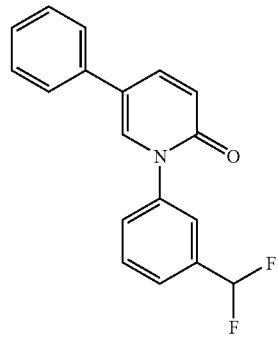 |
| 84 | 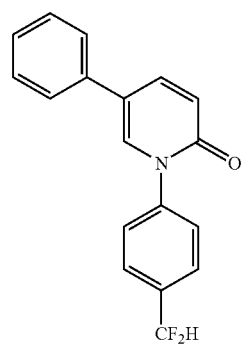 |
| 85 | 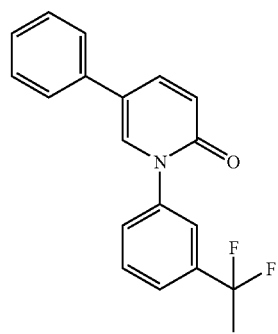 |
| 86 | 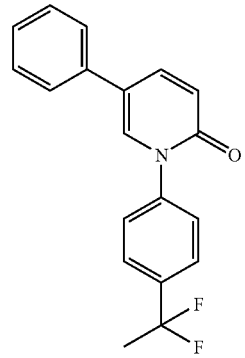 |

TABLE 1-continued
| Cmpd No. | Structure |
|---|---|
| 87 | 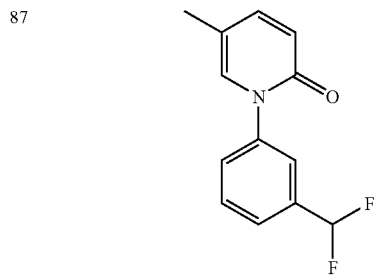 |
| 88 | 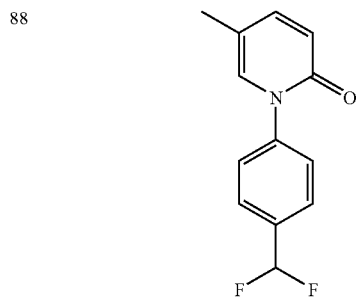 |
| 89 | 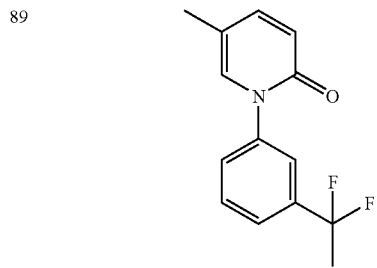 |
| 90 | 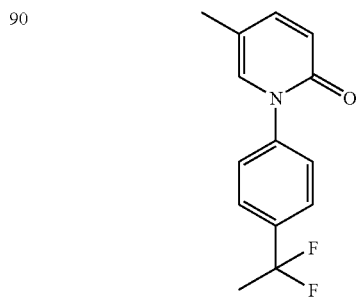 |
| 91 | 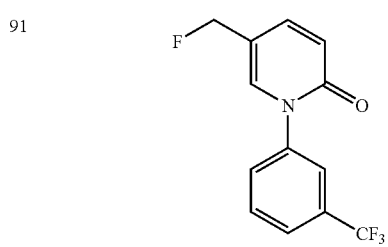 |
TABLE 1-continued
| Cmpd No. | Structure |
|---|---|
| 92 | 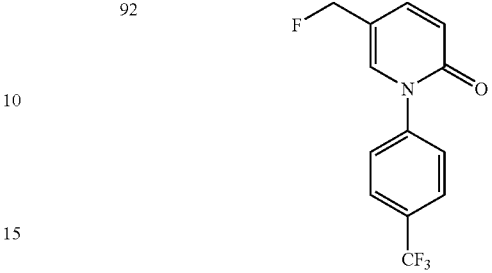 |
| 93 | 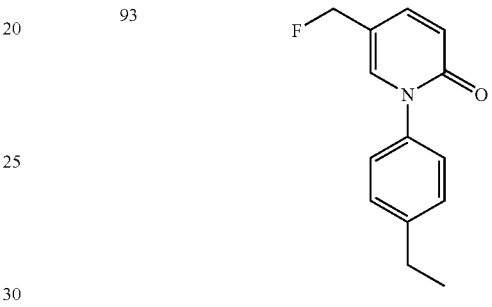 |
| 94 | 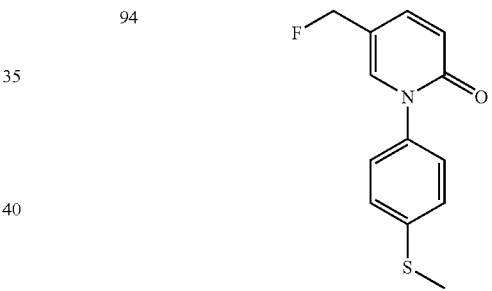 |
| 95 | 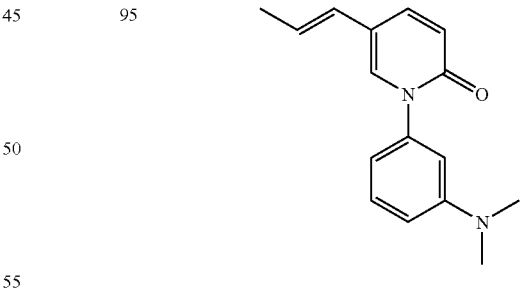 |
| 96 | 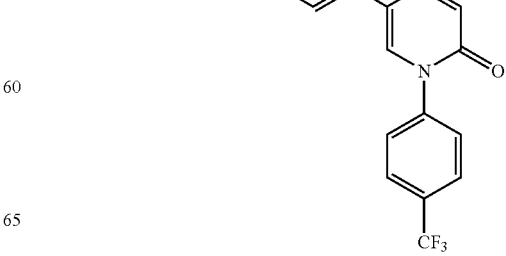 |

TABLE 1-continued

| Cmpd No. | Structure |
|---|---|
| 97 | 5-(prop-1-enyl)-1-(4-(difluoromethyl)phenyl)pyridin-2(1H)-one |
| 98 | 5-methyl-1-(3-(methylsulfonyl)phenyl)pyridin-2(1H)-one |
| 99 | 5-methyl-1-(4-(methylsulfonyl)phenyl)pyridin-2(1H)-one |
| 100 | 5-(difluoromethyl)-1-(4-(methylsulfonyl)phenyl)pyridin-2(1H)-one |
| 101 | 5-(2,2,2-trifluoroacetyl)-1-phenylpyridin-2(1H)-one |
| 102 | 5-(trifluoromethyl)-1-(4-formylphenyl)pyridin-2(1H)-one |
| 103 | 5-(trifluoromethyl)-1-(4-(2,2,2-trifluoro-1-hydroxyethyl)phenyl)pyridin-2(1H)-one |
| 104 | 5-(trifluoromethyl)-1-(4-(2,2,2-trifluoroacetyl)phenyl)pyridin-2(1H)-one |
| 105 | 5-(trifluoromethyl)-1-(4-(1,2,2,2-tetrafluoroethyl)phenyl)pyridin-2(1H)-one |
| 106 | 5-(trifluoromethyl)-1-(4-(1,1,2,2,2-pentafluoroethyl)... |

TABLE 1-continued
| Cmpd No. | Structure |
|---|---|
| 107 | 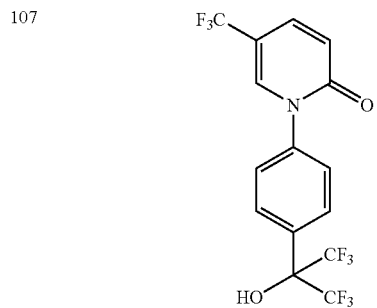 |
| 108 | 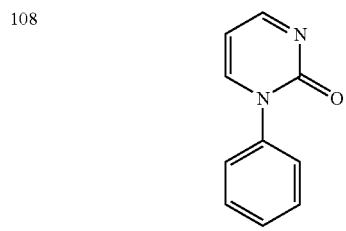 |
| 109 | 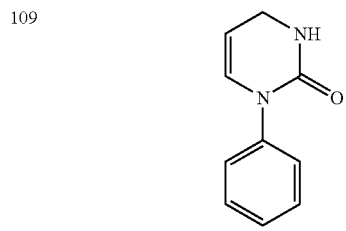 |
| 110 | 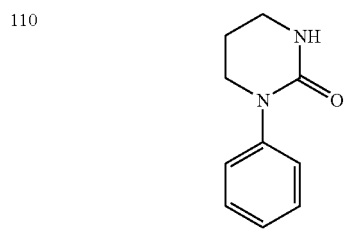 |
| 111 | 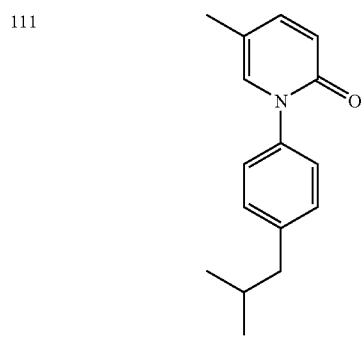 |
TABLE 1-continued
| Cmpd No. | Structure |
|---|---|
| 112 | 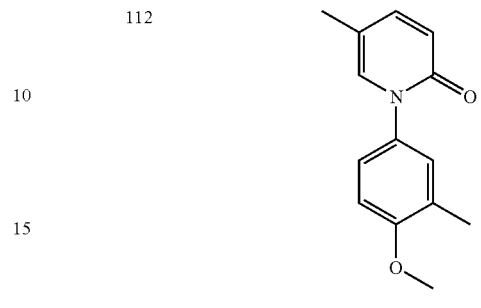 |
| 113 | 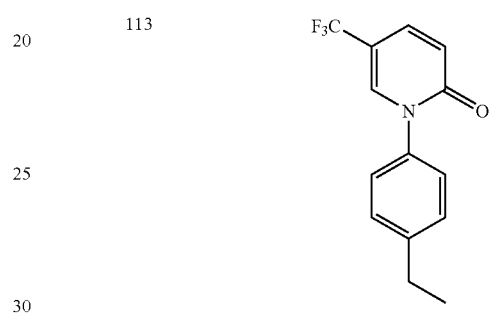 |
| 114 | 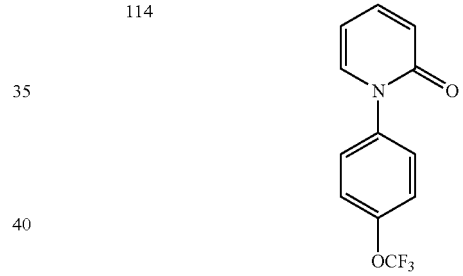 |
| 115 | 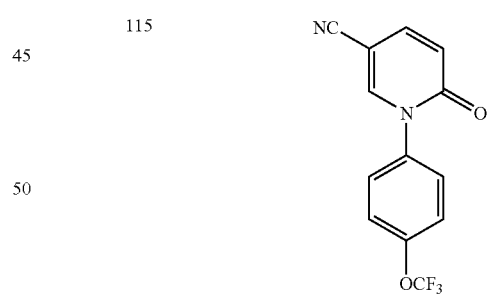 |
| 116 | 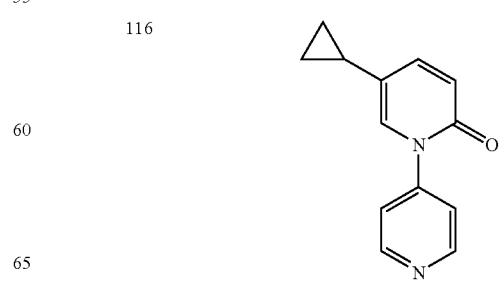 |

TABLE 1-continued
| Cmpd No. | Structure |
|---|---|
| 117 | 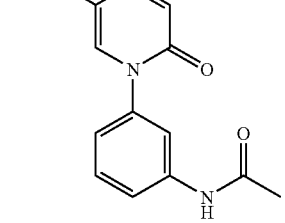 |
| 118 | 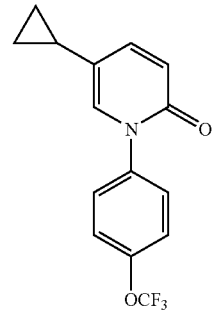 |
| 119 | 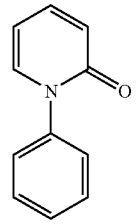 |
| 120 | 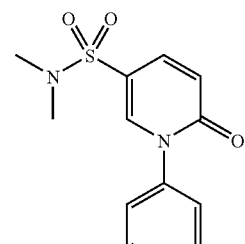 |
| 121 | 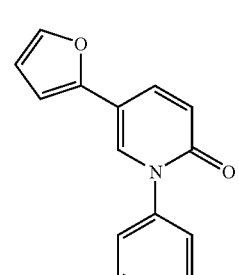 |
TABLE 1-continued
| Cmpd No. | Structure |
|---|---|
| 122 | 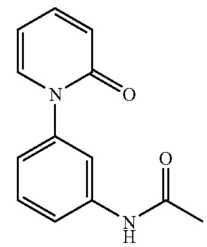 |
| 123 | 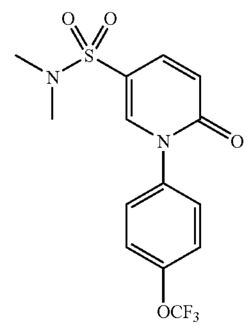 |
| 124 | 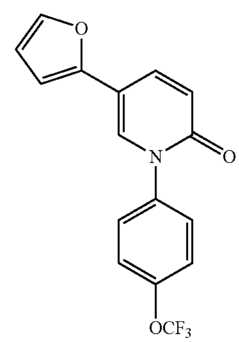 |
| 125 | 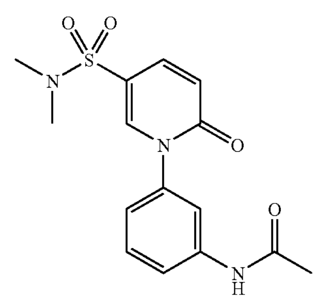 |
| 126 | 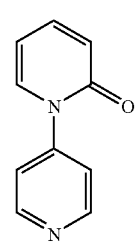 |

TABLE 1-continued

| Cmpd No. | Structure |
|---|---|
| 127 | 5-cyano-1-(3-acetamidophenyl)pyridin-2(1H)-one |
| 128 | 5-(furan-2-yl)-1-(3-acetamidophenyl)pyridin-2(1H)-one |
| 129 | 5-cyclopropyl-1-(4-sulfamoylphenyl)pyridin-2(1H)-one |
| 130 | 5-(4-sulfamoylphenyl)-1-phenylpyridin-2(1H)-one |
| 131 | 5-(4-sulfamoylphenyl)-1-(4-trifluoromethoxyphenyl)pyridin-2(1H)-one |
| 132 | 5-cyclopropyl-1-phenylpyridin-2(1H)-one |
| 133 | 5-(furan-2-yl)-1-(pyridin-4-yl)pyridin-2(1H)-one |
| 134 | 5-(4-fluorophenyl)-1-(4-sulfamoylphenyl)pyridin-2(1H)-one |
| 135 | 5-(4-fluorophenyl)-1-(3-acetamidophenyl)pyridin-2(1H)-one |
| 136 | 5-(4-fluorophenyl)-1-phenylpyridin-2(1H)-one |

TABLE 1-continued
| Cmpd No. | Structure |
|---|---|
| 137 | 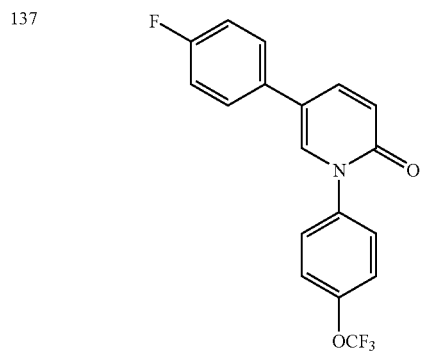 |
| 138 | 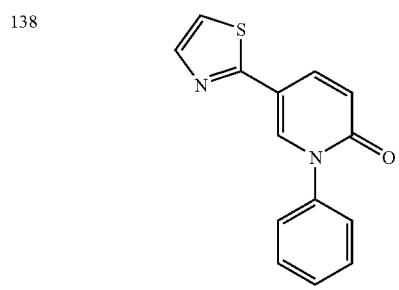 |
| 139 | 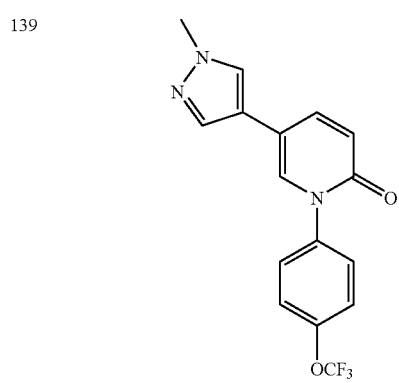 |
| 140 | 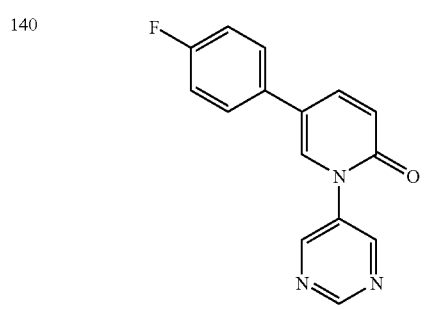 |
TABLE 1-continued
| Cmpd No. | Structure |
|---|---|
| 141 | 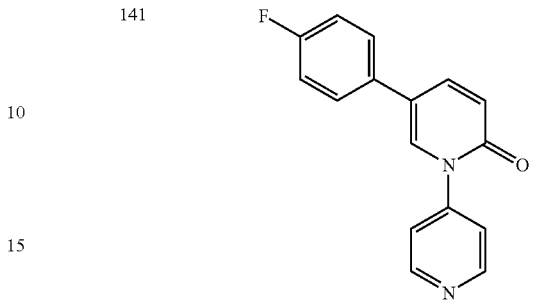 |
| 142 | 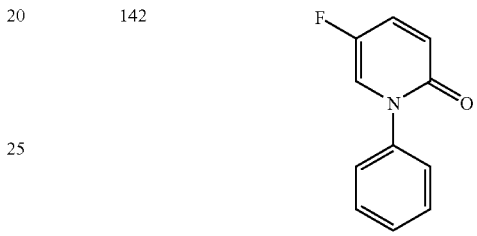 |
| 143 | 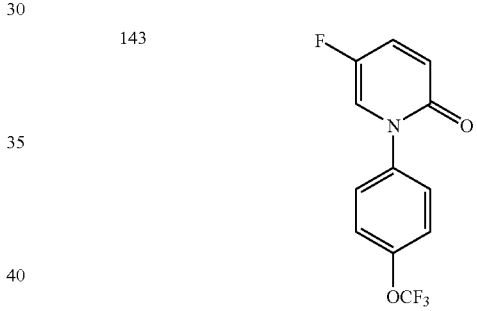 |
| 144 | 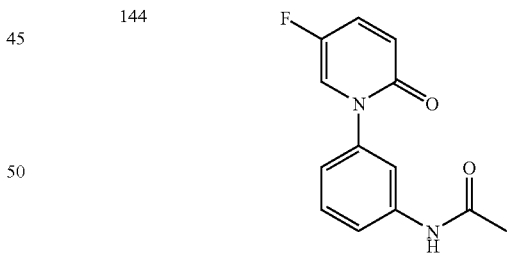 |
| 145 | 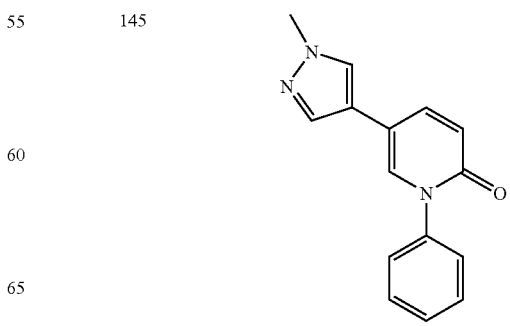 |

TABLE 1-continued

| Cmpd No. | Structure |
|---|---|
| 146 | 5-(furan-2-yl)-1-(pyrimidin-5-yl)pyridin-2(1H)-one |
| 147 | 1-(4-(trifluoromethoxy)phenyl)-5-(pyrimidin-5-yl)pyridin-2(1H)-one |
| 148 | N-(3-(2-oxo-5-(pyrimidin-5-yl)pyridin-1(2H)-yl)phenyl)acetamide |
| 149 | 1-phenyl-5-(pyrimidin-5-yl)pyridin-2(1H)-one |
| 150 | 4-(6-oxo-1-(pyrimidin-5-yl)-1,6-dihydropyridin-3-yl)benzenesulfonamide |
| 151 | N-(3-(2-oxo-5-(pyridin-4-yl)pyridin-1(2H)-yl)phenyl)acetamide |
| 152 | 1-phenyl-5-(pyridin-4-yl)pyridin-2(1H)-one |
| 153 | 5-(pyridin-4-yl)-1-(4-(trifluoromethoxy)phenyl)pyridin-2(1H)-one |
| 154 | 4-(2-oxopyridin-1(2H)-yl)benzenesulfonamide |
| 155 | N-(3-(5-(1-methyl-1H-pyrazol-4-yl)-2-oxopyridin-1(2H)-yl)phenyl)acetamide |

TABLE 1-continued
| Cmpd No. | Structure |
|---|---|
| 156 | 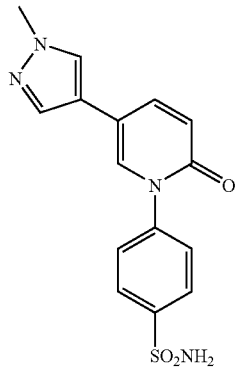 |
| 157 | 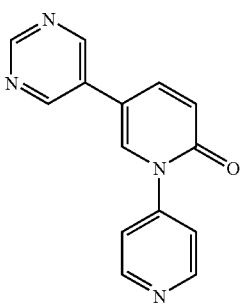 |
| 158 | 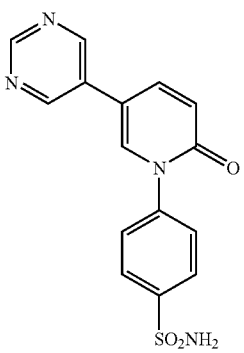 |
| 159 | 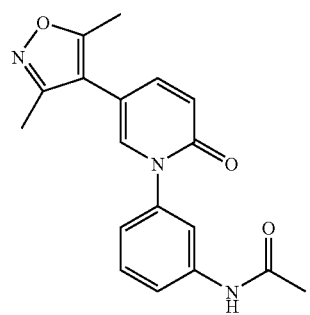 |
| 160 | 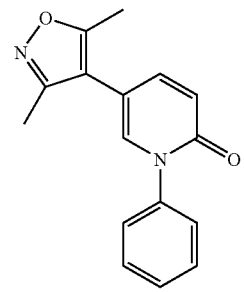 |
| 161 | 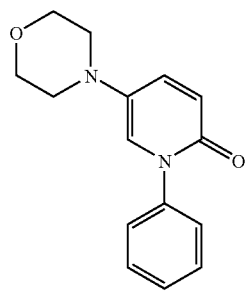 |
| 162 | 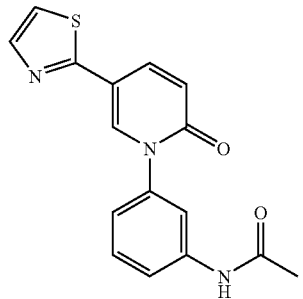 |
| 163 | 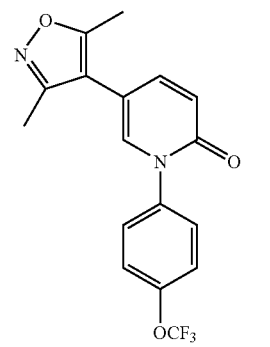 |
| 164 | 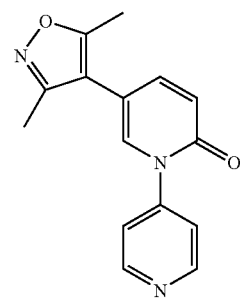 |

TABLE 1-continued
| Cmpd No. | Structure |
|---|---|
| 165 | 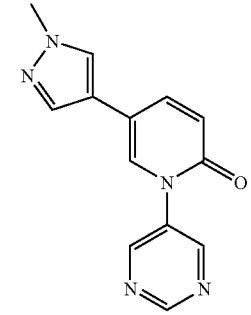 |
| 166 | 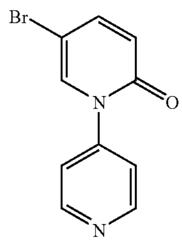 |
| 167 | 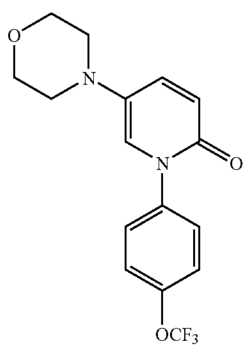 |
| 168 | 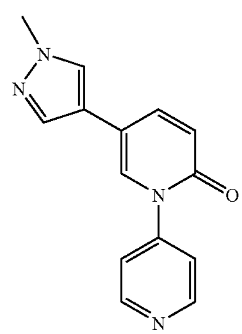 |
| 169 | 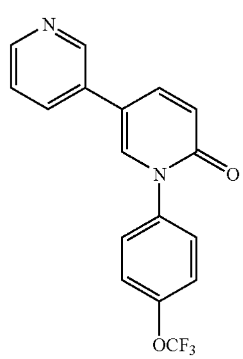 |
| 170 | 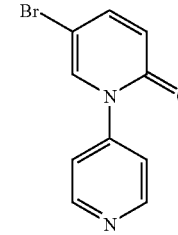 |
| 171 | |
| 172 | |
| 173 | |
| 174 | |

TABLE 1-continued

| Cmpd No. | Structure |
|---|---|
| 175 | (4-methylpiperazin-1-yl)carbonyl-pyrrolo[2,3-b]pyridin-6(7H)-one, N7-(4-isopropoxyphenyl) |
| 176 | 5-(pyridin-3-yl)-1-(pyridin-4-yl)pyridin-2(1H)-one |
| 177 | N-(3-methoxybenzyl)-6-oxo-7-(4-isopropoxyphenyl)-6,7-dihydro-1H-pyrrolo[2,3-b]pyridine-2-carboxamide |
| 178 | N-benzyl-6-oxo-7-(4-isopropoxyphenyl)-6,7-dihydro-1H-pyrrolo[2,3-b]pyridine-2-carboxamide |
| 179 | N-(thiazol-2-yl)-6-oxo-7-(4-isopropoxyphenyl)-6,7-dihydro-1H-pyrrolo[2,3-b]pyridine-2-carboxamide |
| 180 | (4-methylpiperazin-1-yl)carbonyl-6-oxo-7-(4-methoxyphenyl)-6,7-dihydro-1H-pyrrolo[2,3-b]pyridine |
| 181 | pyrrolidin-1-yl-carbonyl-6-oxo-7-(4-trifluoromethoxyphenyl)-6,7-dihydro-1H-pyrrolo[2,3-b]pyridine |
| 182 | morpholin-4-yl-carbonyl-6-oxo-7-(4-trifluoromethoxyphenyl)-6,7-dihydro-1H-pyrrolo[2,3-b]pyridine |

TABLE 1-continued

| Cmpd No. | Structure |
|---|---|
| 183 | 5-(1H-pyrazol-4-yl)-1-phenylpyridin-2(1H)-one |
| 184 | 5-sulfamoyl-1-(4-(trifluoromethoxy)phenyl)pyridin-2(1H)-one |
| 185 | 5-(2-fluorophenyl)-1-(3-acetamidophenyl)pyridin-2(1H)-one |
| 186 | 5-(2-fluorophenyl)-1-phenylpyridin-2(1H)-one |
| 187 | 5-(2-fluorophenyl)-1-(4-(trifluoromethoxy)phenyl)pyridin-2(1H)-one |
| 188 | 5-(1-phenyl-1H-imidazol-2-yl)-1-phenylpyridin-2(1H)-one |
| 189 | 5-(1H-pyrazol-4-yl)-1-(pyridin-4-yl)pyridin-2(1H)-one |
| 190 | 5-sulfamoyl-1-phenylpyridin-2(1H)-one |
| 191 | 5-(pyrimidin-5-yl)-1-(pyridin-3-yl)pyridin-2(1H)-one |
| 192 | 5-(pyridin-3-yl)-1-(4-sulfamoylphenyl)pyridin-2(1H)-one |

TABLE 1-continued

| Cmpd No. | Structure |
|---|---|
| 193 | 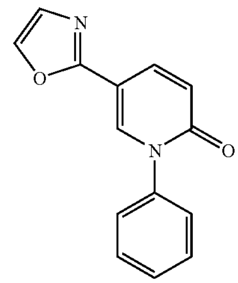 |
| 194 | 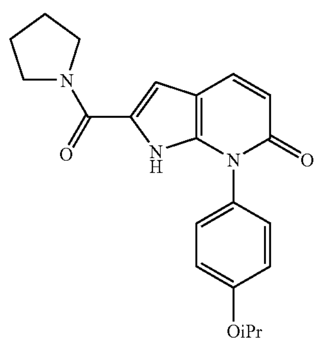 |
| 195 | 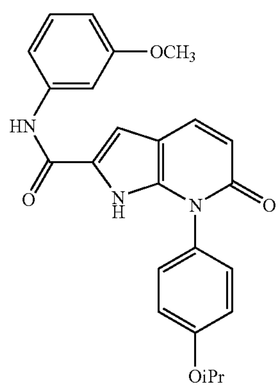 |
| 196 | 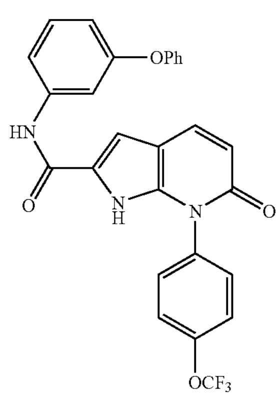 |
| 197 | |
| 198 | |
| 199 | |
| 200 | |

TABLE 1-continued

| Cmpd No. | Structure |
|---|---|
| 201 | 5-(2-fluorophenyl)-1-(pyrimidin-4-yl)pyridin-2(1H)-one |
| 202 | 5-cyclopropyl-1-(pyrimidin-5-yl)pyridin-2(1H)-one |
| 203 | 1-(4-(trifluoromethoxy)phenyl)-5-(thiazol-2-yl)pyridin-2(1H)-one |
| 204 | N-(3-chlorophenyl)-7-oxo-7-(4-(trifluoromethoxy)phenyl)-6,7-dihydro-1H-pyrrolo[2,3-b]pyridine-2-carboxamide |
| 205 | 7-oxo-7-(4-(trifluoromethoxy)phenyl)-N-((tetrahydrofuran-2-yl)methyl)-6,7-dihydro-1H-pyrrolo[2,3-b]pyridine-2-carboxamide |
| 206 | N-(4-isopropoxyphenyl)-7-oxo-7-(4-phenoxyphenyl)-6,7-dihydro-1H-pyrrolo[2,3-b]pyridine-2-carboxamide |
| 207 | ethyl 6-oxo-7-phenyl-6,7-dihydro-1H-pyrrolo[2,3-b]pyridine-2-carboxylate |
| 208 | ethyl 7-(4-hydroxyphenyl)-6-oxo-6,7-dihydro-1H-pyrrolo[2,3-b]pyridine-2-carboxylate |

TABLE 1-continued
| Cmpd No. | Structure |
|---|---|
| 209 | 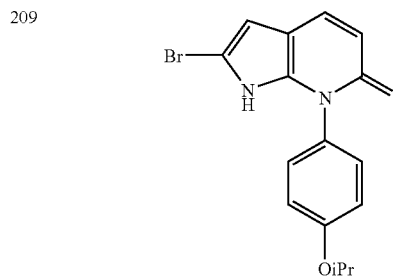 |
| 210 | 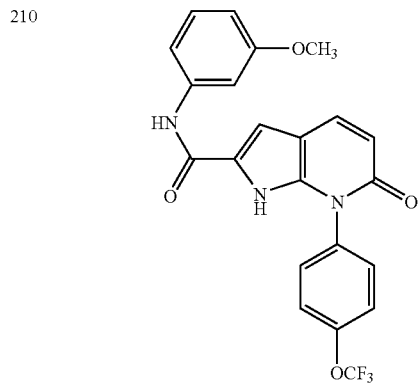 |
| 211 | 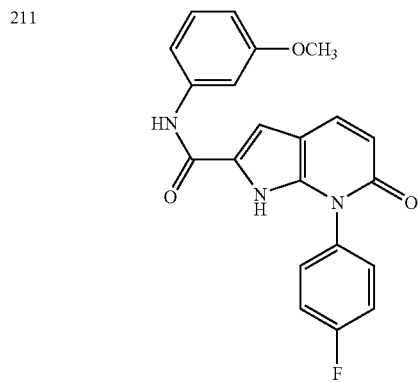 |
| 212 | 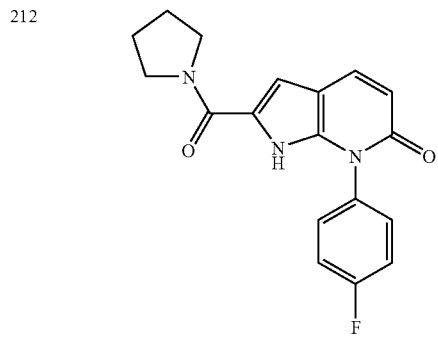 |
| 213 | 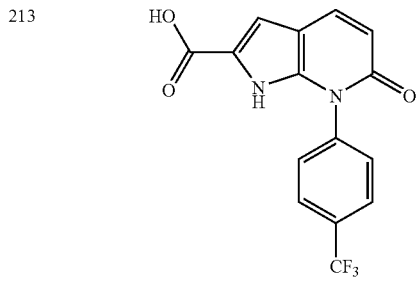 |
| 214 | 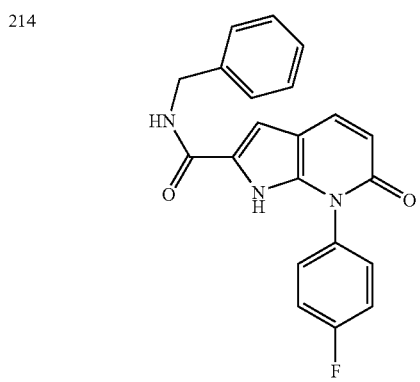 |
| 215 | 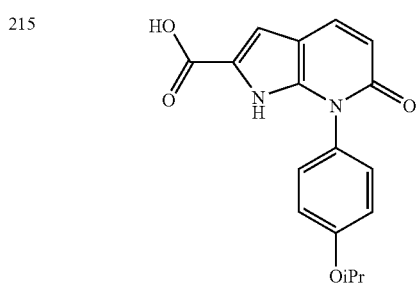 |
| 216 | 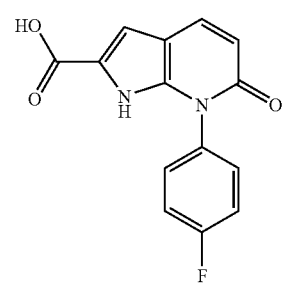 |

TABLE 1-continued
| Cmpd No. | Structure |
|---|---|
| 217 | 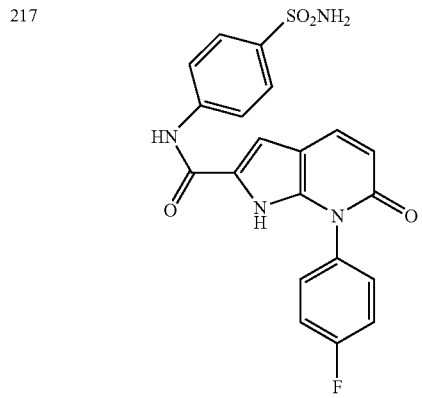 |
| 218 | 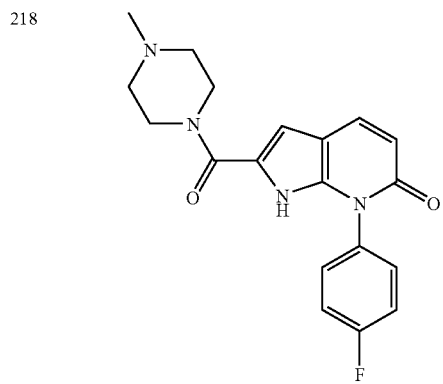 |
| 219 | 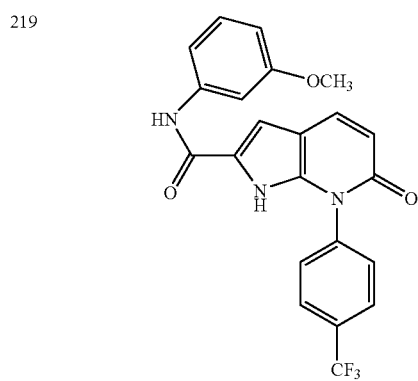 |
| 220 | 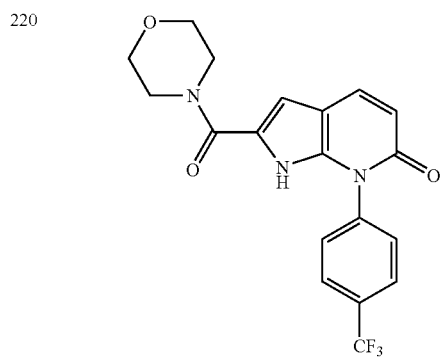 |
| 221 | 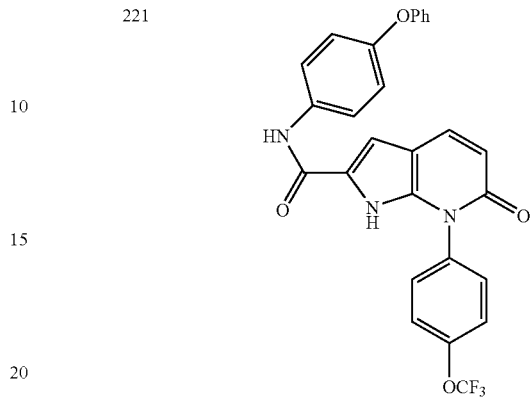 |
| 222 | 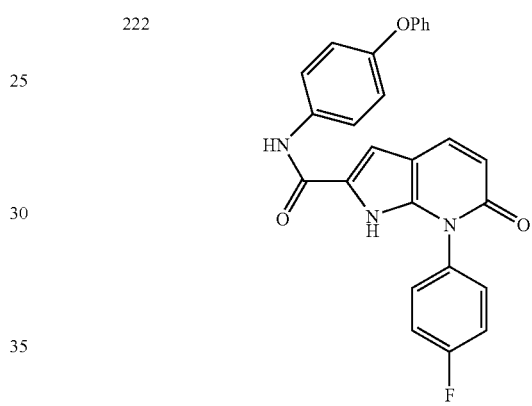 |
| 223 | 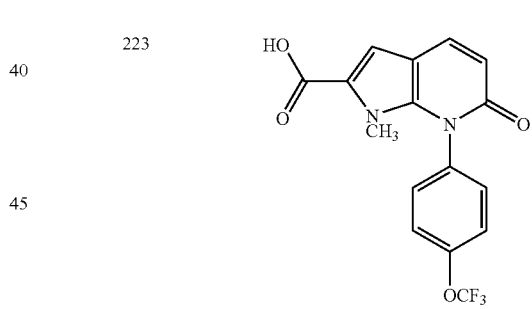 |
| 224 | 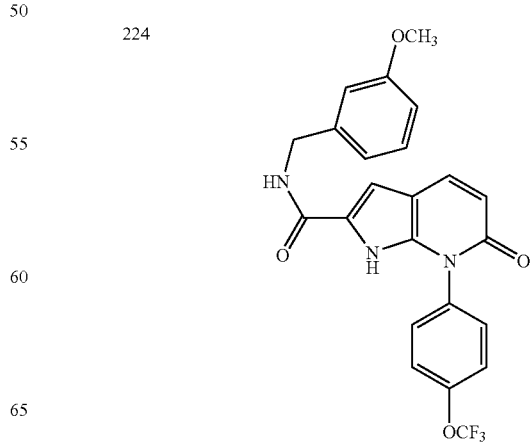 |

TABLE 1-continued

| Cmpd No. | Structure |
|---|---|
| 225 | 7-(4-chlorophenyl)-6-oxo-6,7-dihydro-1H-pyrrolo[2,3-b]pyridine-2-carboxylic acid |
| 226 | 7-(4-(trifluoromethyl)phenyl)-2-(pyrrolidine-1-carbonyl)-1H-pyrrolo[2,3-b]pyridin-6(7H)-one |
| 227 | 7-(4-fluorophenyl)-2-(morpholine-4-carbonyl)-1H-pyrrolo[2,3-b]pyridin-6(7H)-one |
| 228 | N-(3-chlorophenyl)-7-(4-fluorophenyl)-6-oxo-6,7-dihydro-1H-pyrrolo[2,3-b]pyridine-2-carboxamide |
| 229 | 2-(4-methylpiperazine-1-carbonyl)-7-(4-(trifluoromethyl)phenyl)-1H-pyrrolo[2,3-b]pyridin-6(7H)-one |
| 230 | N-isopropyl-N-methyl-6-oxo-7-(4-(trifluoromethyl)phenyl)-6,7-dihydro-1H-pyrrolo[2,3-b]pyridine-2-carboxamide |
| 231 | 7-(4-fluorophenyl)-N-isopropyl-N-methyl-6-oxo-6,7-dihydro-1H-pyrrolo[2,3-b]pyridine-2-carboxamide |
| 232 | N-((tetrahydrofuran-2-yl)methyl)-6-oxo-7-(4-(trifluoromethyl)phenyl)-6,7-dihydro-1H-pyrrolo[2,3-b]pyridine-2-carboxamide |

TABLE 1-continued
| Cmpd No. | Structure |
|---|---|
| 233 | 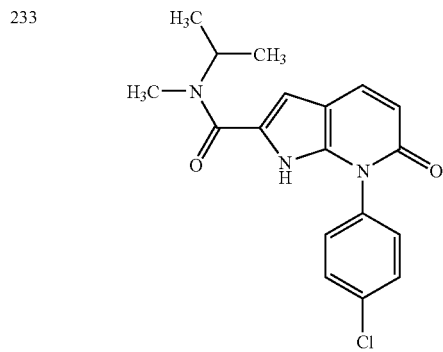 |
| 234 | 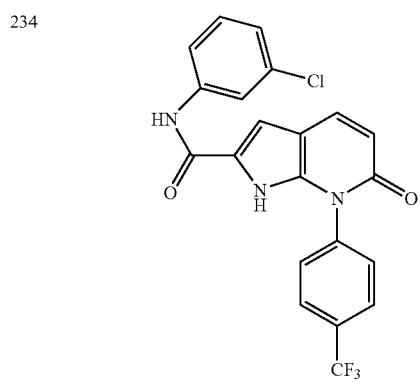 |
| 235 | 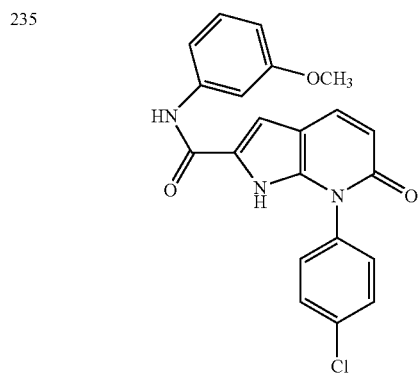 |
| 236 | 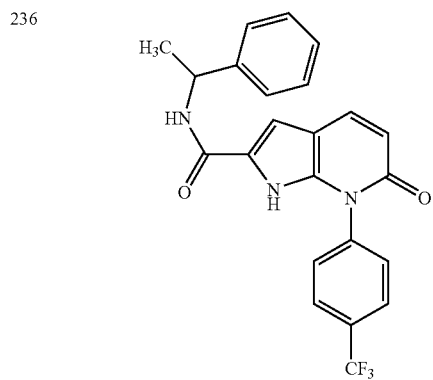 |
TABLE 1-continued
| Cmpd No. | Structure |
|---|---|
| 237 | 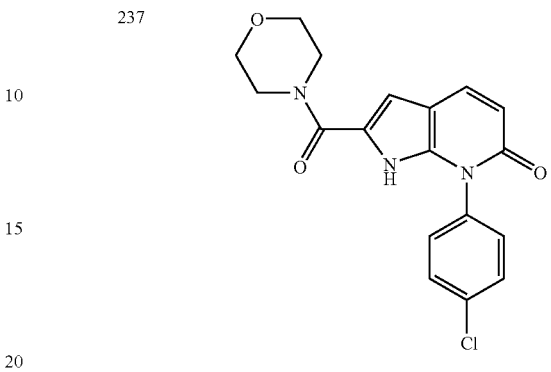 |
| 238 | 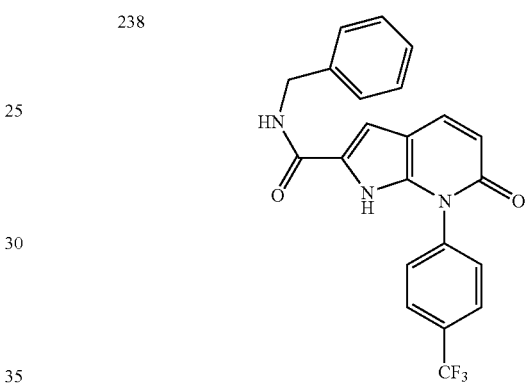 |
| 239 | 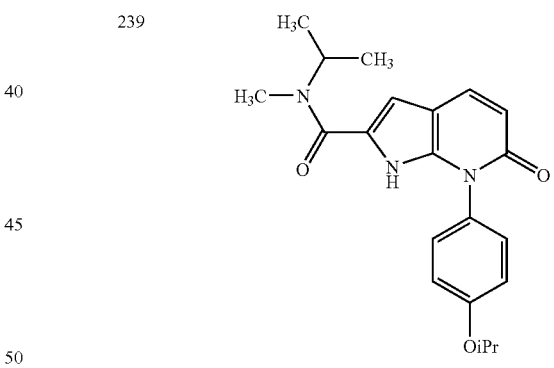 |
| 240 | 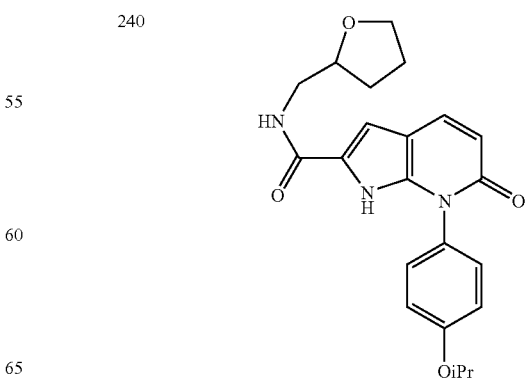 |

TABLE 1-continued
| Cmpd No. | Structure |
|---|---|
| 241 | 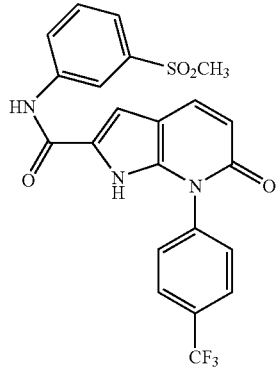 |
| 242 | 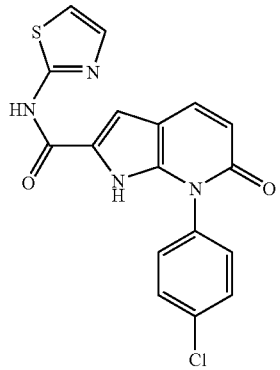 |
| 243 | 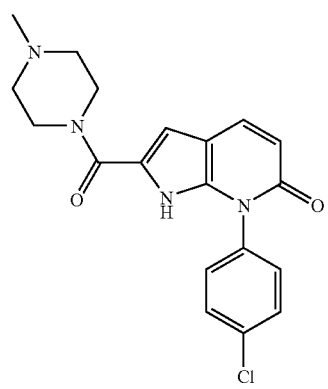 |
| 244 | 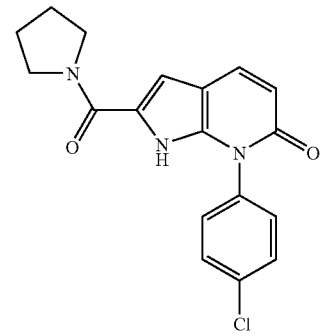 |
| 245 | 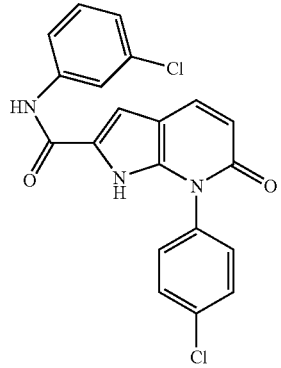 |
| 246 | 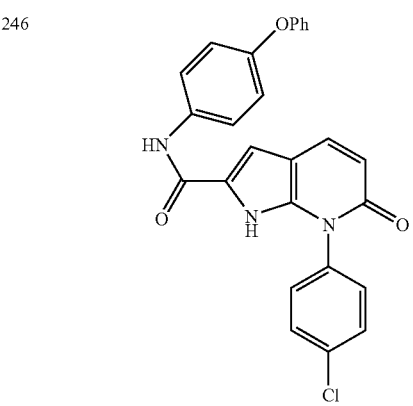 |
| 247 | 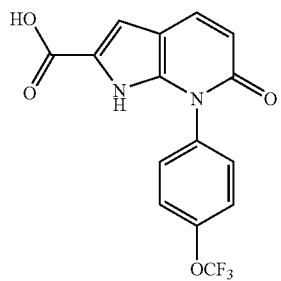 |
| 248 | 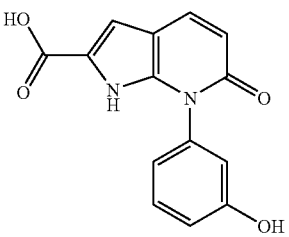 |

TABLE 1-continued
| Cmpd No. | Structure |
|---|---|
| 249 | 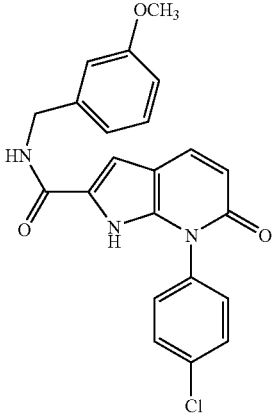 |
| 250 | 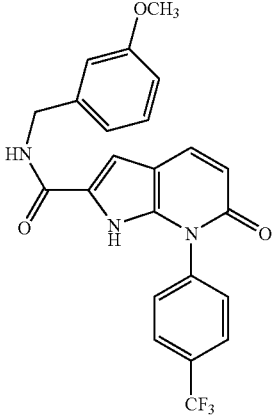 |
| 251 | 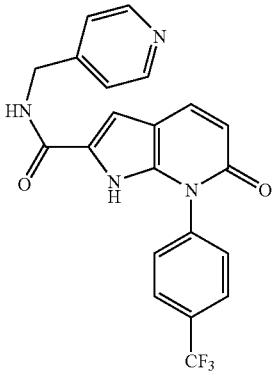 |→ |
TABLE 1-continued
| Cmpd No. | Structure |
|---|---|
| 252 | 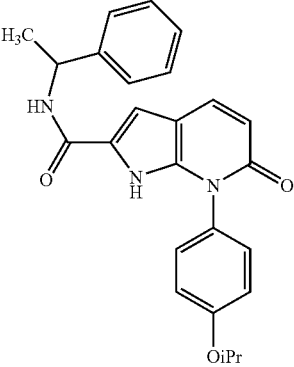 |
| 253 | 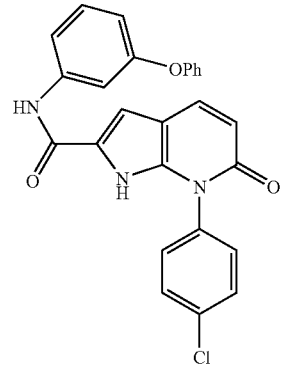 |
| 254 | 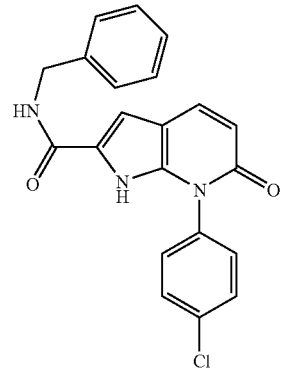 |
| 255 | 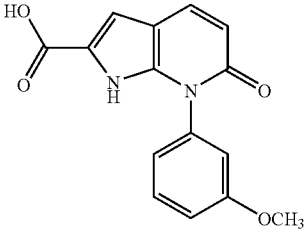 |

TABLE 1-continued

| Cmpd No. | Structure |
|---|---|
| 256 | N-methyl 7-(4-isopropoxyphenyl)-6-oxo-6,7-dihydro-1H-pyrrolo[2,3-b]pyridine-2-carboxamide |
| 257 | N-(thiazol-2-yl) 7-(4-trifluoromethylphenyl)-6-oxo-6,7-dihydro-1H-pyrrolo[2,3-b]pyridine-2-carboxamide |
| 258 | N-((tetrahydrofuran-2-yl)methyl) 7-(4-chlorophenyl)-6-oxo-6,7-dihydro-1H-pyrrolo[2,3-b]pyridine-2-carboxamide |
| 259 | 2-(piperazin-1-ylcarbonyl) 7-(4-chlorophenyl)-6-oxo-6,7-dihydro-1H-pyrrolo[2,3-b]pyridine |
| 260 | N-methyl 7-(4-chlorophenyl)-6-oxo-6,7-dihydro-1H-pyrrolo[2,3-b]pyridine-2-carboxamide |
| 261 | N-(2-(pyrrolidin-1-yl)ethyl) 7-(4-chlorophenyl)-6-oxo-6,7-dihydro-1H-pyrrolo[2,3-b]pyridine-2-carboxamide |
| 262 | N-((1H-benzimidazol-2-yl)methyl) 7-(4-chlorophenyl)-6-oxo-6,7-dihydro-1H-pyrrolo[2,3-b]pyridine-2-carboxamide |
| 263 | 7-(4-isopropoxyphenyl)-6-oxo-6,7-dihydro-1H-pyrrolo[2,3-b]pyridine-2-carboxamide |

TABLE 1-continued

| Cmpd No. | Structure |
|---|---|
| 264 | 7-azaindole-2-carboxamide, N,N-dimethyl, N7-(4-isopropoxyphenyl)-6-oxo |
| 265 | 7-azaindole-2-carboxamide, N-(4-phenoxyphenyl), N7-(4-trifluoromethylphenyl)-6-oxo |
| 266 | 7-azaindole-2-carboxamide, N-((1H-benzimidazol-2-yl)methyl), N7-(4-trifluoromethylphenyl)-6-oxo |
| 267 | 7-azaindole-2-carboxamide, N-(3-phenoxyphenyl), N7-(4-fluorophenyl)-6-oxo |
| 268 | 7-azaindole-2-carboxamide, N-methyl-N-phenyl, N7-(4-trifluoromethoxyphenyl)-6-oxo |
| 269 | 7-azaindole-2-carboxamide, N-methyl, N7-(4-fluorophenyl)-6-oxo |
| 270 | 7-azaindole-2-carboxamide, N-methyl, N7-(4-trifluoromethoxyphenyl)-6-oxo |
| 271 | 7-azaindole-2-carboxamide, N-((1H-benzimidazol-2-yl)methyl), N7-(4-trifluoromethoxyphenyl)-6-oxo |

TABLE 1-continued
| Cmpd No. | Structure |
|---|---|
| 272 | 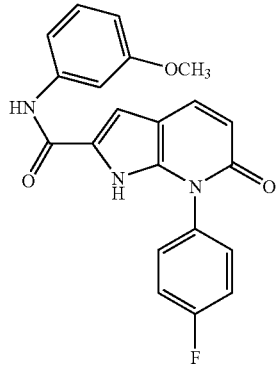 |
| 273 | 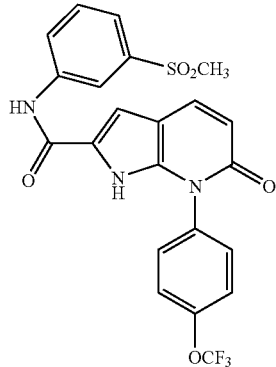 |
| 274 | 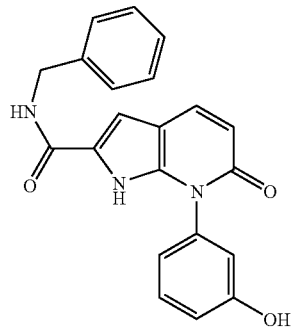 |
| 275 | 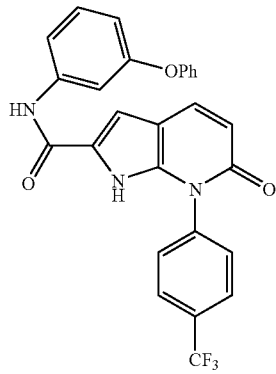 |
| 276 | 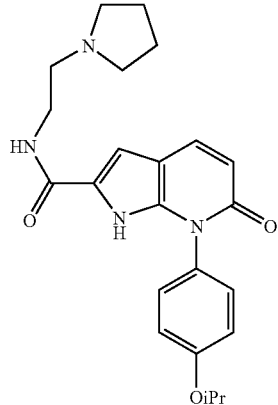 |
| 277 | 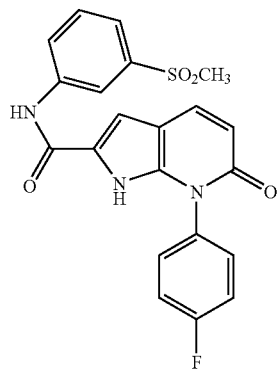 |
| 278 | 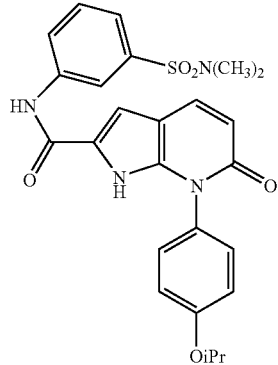 |
| 279 | 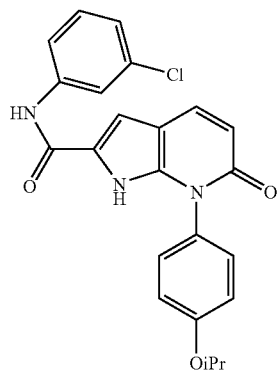 |

TABLE 1-continued
| Cmpd No. | Structure |
|---|---|
| 280 | 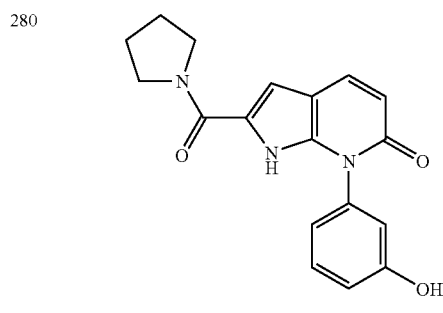 |
| 281 | 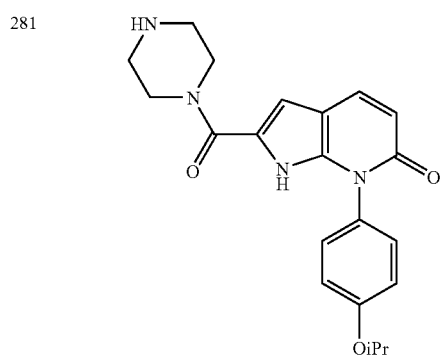 |
| 282 | 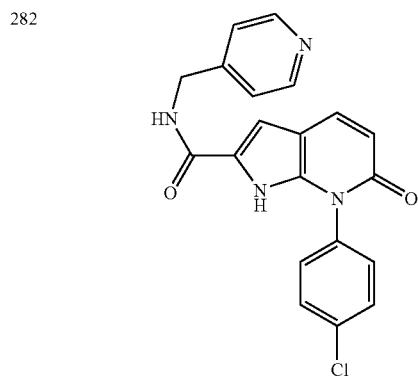 |
| 283 | 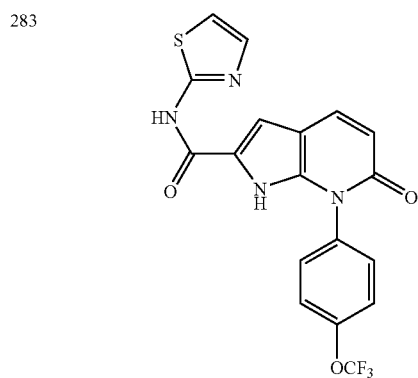 |
| 284 | 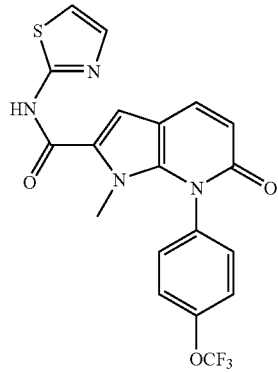 |
| 285 | 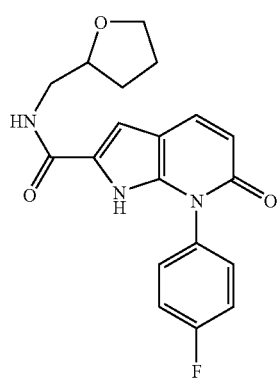 |
| 286 | 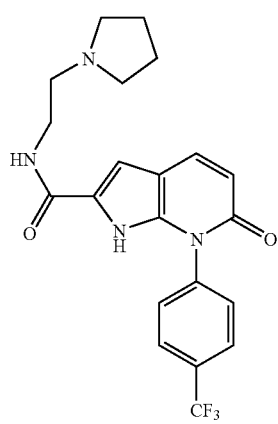 |
| 287 | 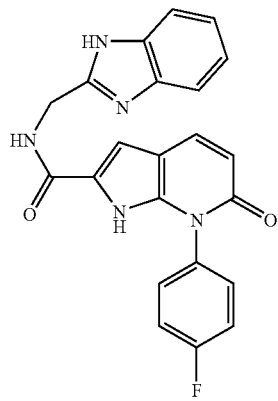 |

TABLE 1-continued

| Cmpd No. | Structure |
|---|---|
| 288 | 7-(4-isopropoxyphenyl)-N-(3-(methylsulfonyl)phenyl)-6-oxo-6,7-dihydro-1H-pyrrolo[2,3-b]pyridine-2-carboxamide |
| 289 | N-benzyl-7-(4-(trifluoromethoxy)phenyl)-6-oxo-6,7-dihydro-1H-pyrrolo[2,3-b]pyridine-2-carboxamide |
| 290 | 7-(4-chlorophenyl)-N-(3-(methylsulfonyl)phenyl)-6-oxo-6,7-dihydro-1H-pyrrolo[2,3-b]pyridine-2-carboxamide |
| 291 | N-(3-chlorophenyl)-7-(3-hydroxyphenyl)-6-oxo-6,7-dihydro-1H-pyrrolo[2,3-b]pyridine-2-carboxamide |
| 292 | N-((1H-benzimidazol-2-yl)methyl)-7-(4-isopropoxyphenyl)-6-oxo-6,7-dihydro-1H-pyrrolo[2,3-b]pyridine-2-carboxamide |
| 293 | N-methyl-7-(4-(trifluoromethyl)phenyl)-6-oxo-6,7-dihydro-1H-pyrrolo[2,3-b]pyridine-2-carboxamide |
| 294 | 7-(4-fluorophenyl)-6-oxo-N-(thiazol-2-yl)-6,7-dihydro-1H-pyrrolo[2,3-b]pyridine-2-carboxamide |
| 295 | 7-(4-chlorophenyl)-6-oxo-N-(3-sulfamoylphenyl)-6,7-dihydro-1H-pyrrolo[2,3-b]pyridine-2-carboxamide |

TABLE 1-continued

| Cmpd No. | Structure |
|---|---|
| 296 | *1H-pyrrolo[2,3-b]pyridin-6(7H)-one, N-(1-phenylethyl)-2-carboxamide, 7-(4-fluorophenyl)-* |
| 297 | *1H-pyrrolo[2,3-b]pyridin-6(7H)-one, N-(3-fluoro-4-methoxyphenyl)-2-carboxamide, 7-(4-isopropoxyphenyl)-* |
| 298 | *5-methyl-1-(2-hydroxyphenyl)pyridin-2(1H)-one* |
| 299 | *5-methyl-1-(6-hydroxypyridin-3-yl)pyridin-2(1H)-one* |
| 300 | *5-methyl-1-(3-fluorophenyl)pyridin-2(1H)-one* |
| 301 | *5-methyl-1-(2-chlorophenyl)pyridin-2(1H)-one* |
| 302 | *5-methyl-1-(3-chlorophenyl)pyridin-2(1H)-one* |
| 303 | *5-methyl-1-(2-methoxyphenyl)pyridin-2(1H)-one* |
| 304 | *5-methyl-1-(3-methoxyphenyl)pyridin-2(1H)-one* |
| 305 | *5-methyl-1-(4-methoxyphenyl)pyridin-2(1H)-one* |
| 306 | *5-methyl-1-(2-isopropoxyphenyl)pyridin-2(1H)-one* |

TABLE 1-continued
| Cmpd No. | Structure |
|---|---|
| 307 | 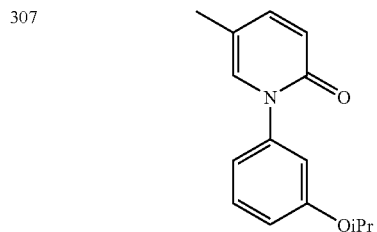 |
| 308 | 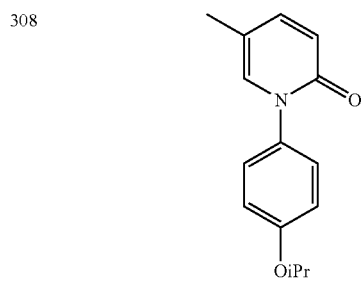 |
| 309 | 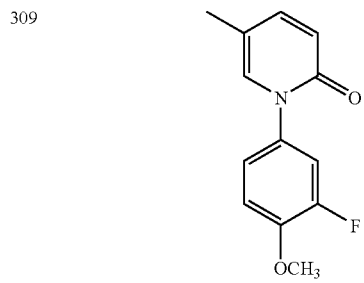 |
| 310 | 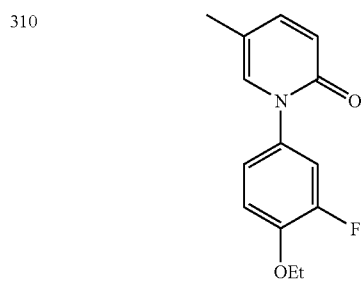 |
| 311 | 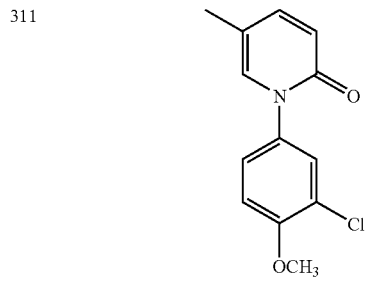 |
TABLE 1-continued
| Cmpd No. | Structure |
|---|---|
| 312 | 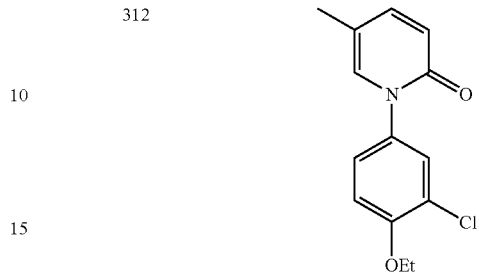 |
| 313 | 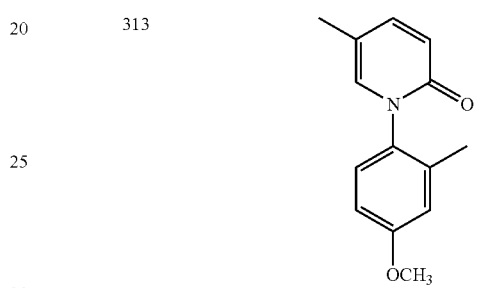 |
| 314 | 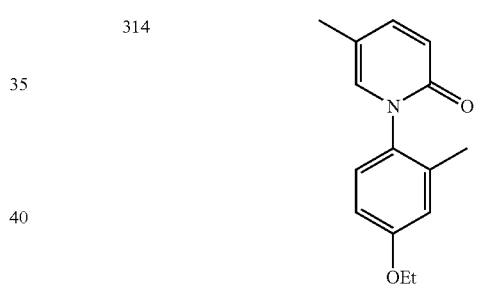 |
| 315 | 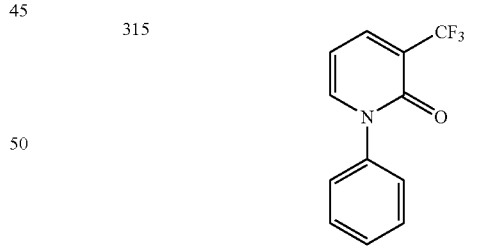 |
| 316 | 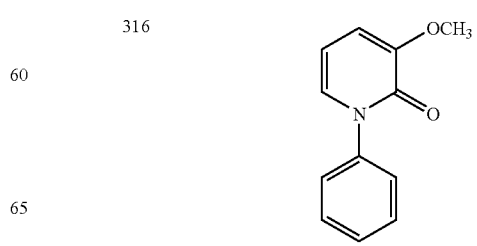 |

TABLE 1-continued

| Cmpd No. | Structure |
|---|---|
| 317 | 4-methyl-1-phenylpyridin-2(1H)-one |
| 318 | 4-hydroxy-1-phenylpyridin-2(1H)-one |
| 319 | 5-chloro-1-phenylpyridin-2(1H)-one |
| 320 | 4-(trifluoromethyl)-1-phenylpyridin-2(1H)-one |
| 321 | 6-chloro-1-phenylpyridin-2(1H)-one |
| 322 | 1-phenyl-3-(prop-1-en-1-yl)pyridin-2(1H)-one |
| 323 | 1-phenyl-3-styrylpyridin-2(1H)-one |
| 324 | 1,4-diphenylpyridin-2(1H)-one |
| 325 | 1-phenyl-4-(prop-1-en-1-yl)pyridin-2(1H)-one |
| 326 | 1-phenyl-5-(prop-1-en-1-yl)pyridin-2(1H)-one |
| 327 | 1,6-diphenylpyridin-2(1H)-one |
| 328 | 1-phenyl-6-(prop-1-en-1-yl)pyridin-2(1H)-one |

TABLE 1-continued
| Cmpd No. | Structure |
|---|---|
| 329 | 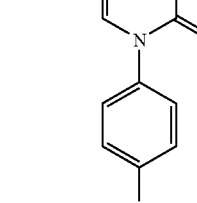 |
| 330 | 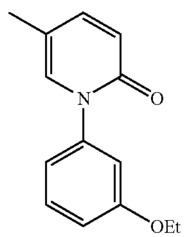 |
| 331 | 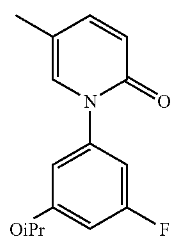 |
| 332 | 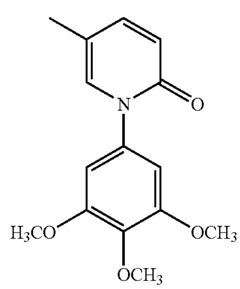 |
| 333 | 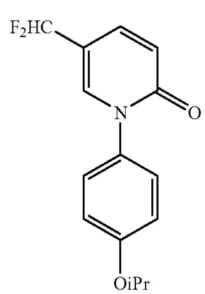 |
TABLE 1-continued
| Cmpd No. | Structure |
|---|---|
| 334 | 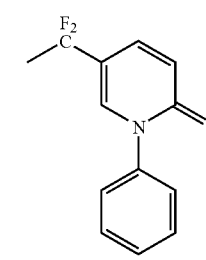 |
| 335 | |
| 336 | |
| 337 | |
| 338 | |

TABLE 1-continued
| Cmpd No. | Structure |
|---|---|
| 339 | 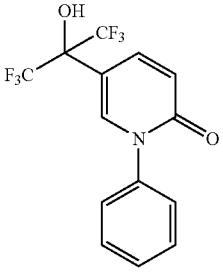 |
| 340 | 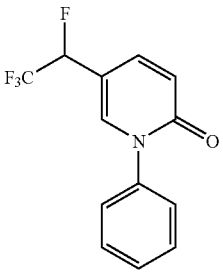 |
| 341 | 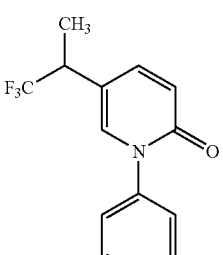 |
| 342 | 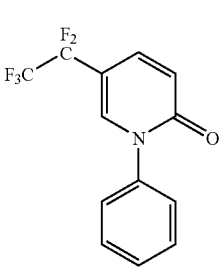 |
| 343 | 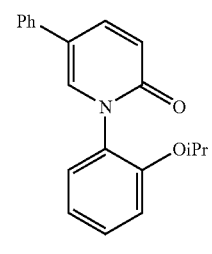 |
| 344 | 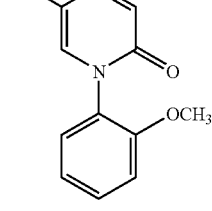 |
TABLE 1-continued
| Cmpd No. | Structure |
|---|---|
| 345 | 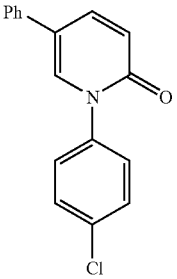 |
| 346 | 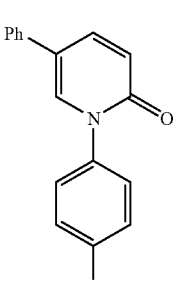 |
| 347 | 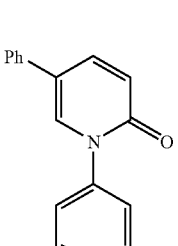 |
| 348 | 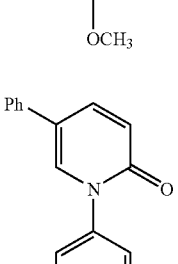 |
| 349 | 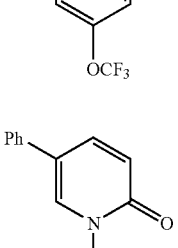 |

TABLE 1-continued
| Cmpd No. | Structure |
|---|---|
| 350 | 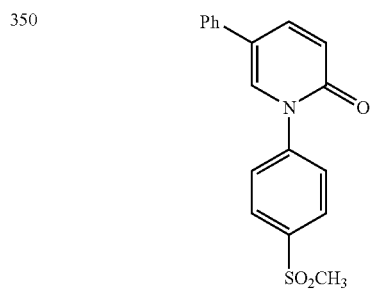 |
| 351 | 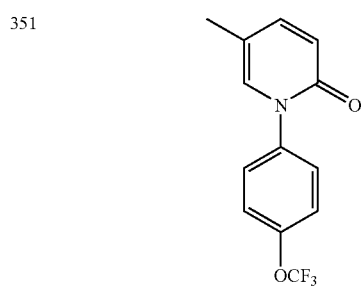 |
| 352 | 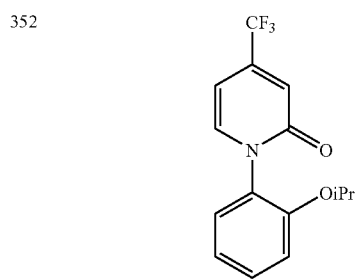 |
| 353 | 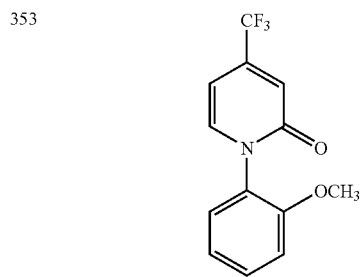 |
| 354 | 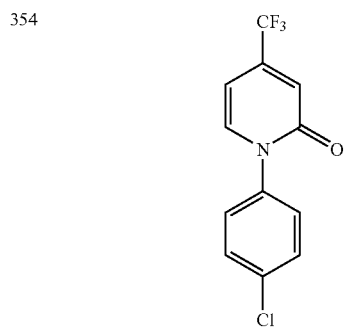 |
| 355 | 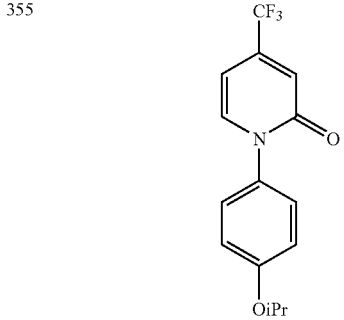 |
| 356 | 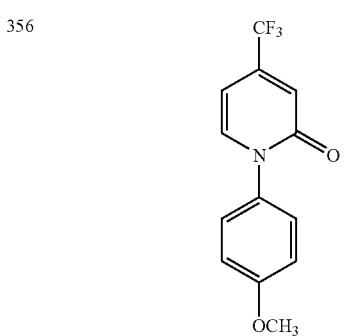 |
| 357 | 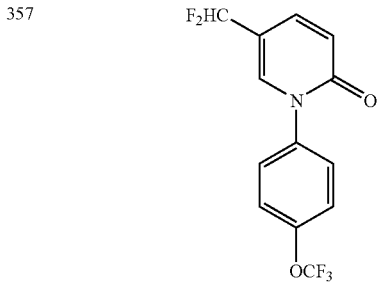 |
| 358 | 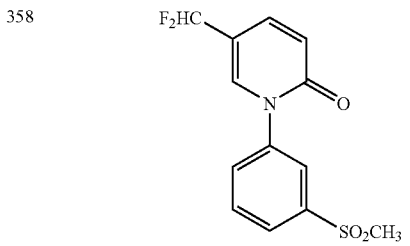 |
| 359 | 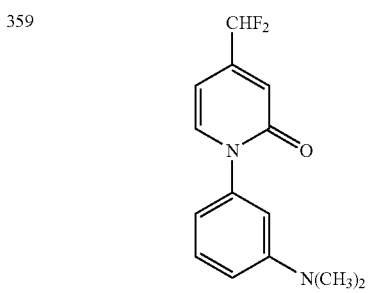 |

TABLE 1-continued
| Cmpd No. | Structure |
|---|---|
| 360 | 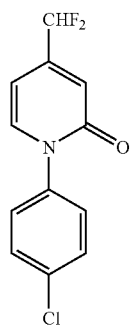 |
| 361 | 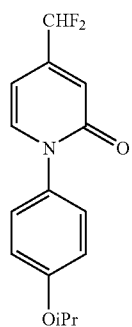 |
| 362 | 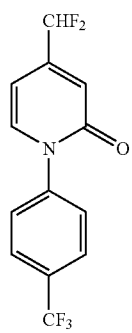 |
| 363 | 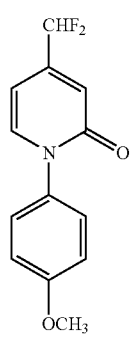 |
| 364 | 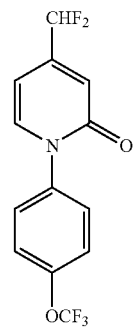 |
| 365 | 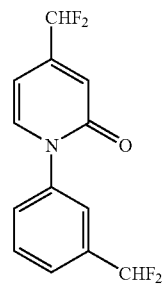 |
| 366 | 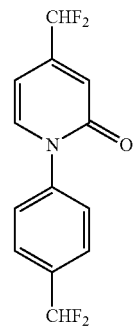 |
| 367 | 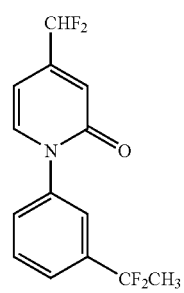 |
| 368 | 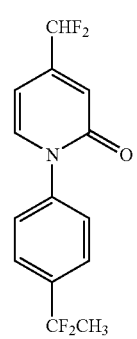 |

TABLE 1-continued
| Cmpd No. | Structure |
|---|---|
| 369 | 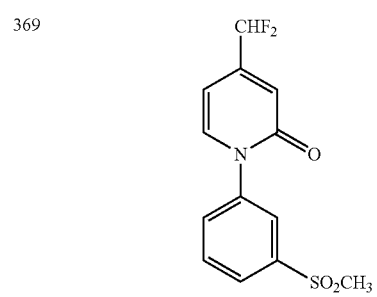 |
| 370 | 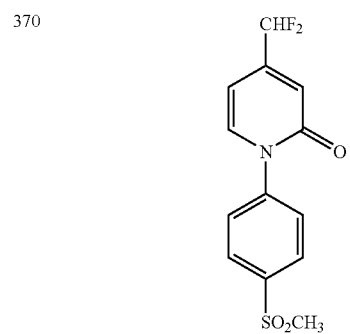 |
| 371 | 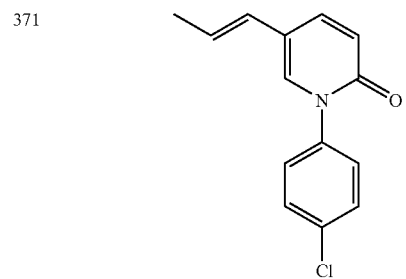 |
| 372 | 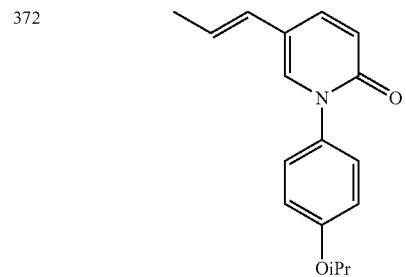 |
| 373 | 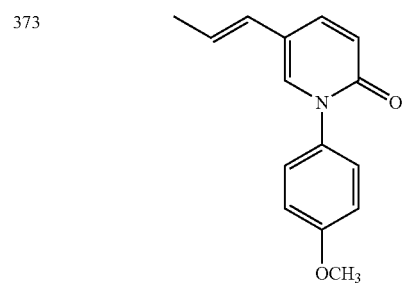 |
TABLE 1-continued
| Cmpd No. | Structure |
|---|---|
| 374 | 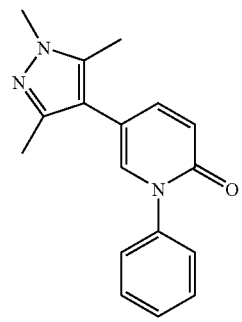 |
| 375 | Intentionally blank |
| 376 | 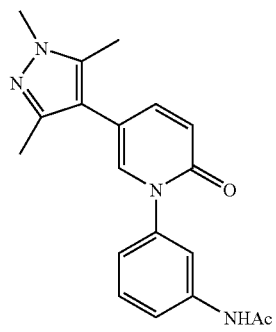 |
| 377 | 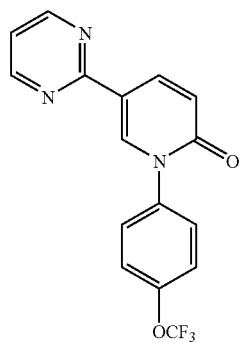 |
| 378 |  |

TABLE 1-continued

| Cmpd No. | Structure |
|---|---|
| 379 | 5-(1H-pyrazol-4-yl)-1-(3-acetamidophenyl)pyridin-2(1H)-one |
| 380 | 5-(4-methoxyphenyl)-1-(4-trifluoromethoxyphenyl)pyridin-2(1H)-one |
| 381 | 5-(pyrimidin-2-yl)-1-phenylpyridin-2(1H)-one |
| 382 | 5-(pyrimidin-2-yl)-1-(3-acetamidophenyl)pyridin-2(1H)-one |
| 383 | 5-(3-trifluoromethyl-1-methyl-1H-pyrazol-5-yl)-1-phenylpyridin-2(1H)-one |
| 384 | 5-(oxazol-2-yl)-1-(3-acetamidophenyl)pyridin-2(1H)-one |
| 385 | 5-(4-fluorophenyl)-1-(4-ethoxyphenyl)pyridin-2(1H)-one |
| 386 | 5-(1-methyl-1H-pyrazol-4-yl)-1-(4-ethoxy-2-methylphenyl)pyridin-2(1H)-one |
| 387 | 5-(1-methyl-1H-pyrazol-4-yl)-4-methyl-1-phenylpyridin-2(1H)-one |

TABLE 1-continued
| Cmpd No. | Structure |
|---|---|
| 388 | 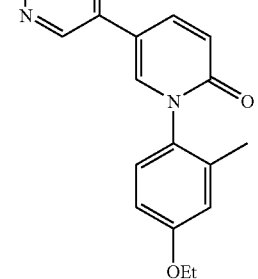 |
| 389 | 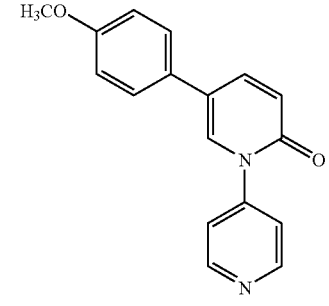 |
| 390 | 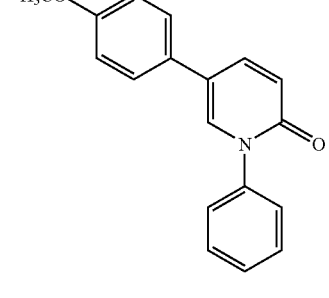 |
| 391 | 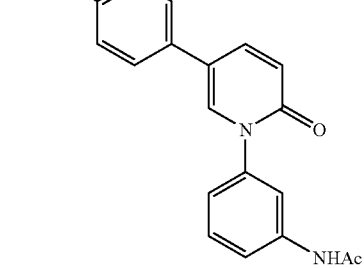 |
TABLE 1-continued
| Cmpd No. | Structure |
|---|---|
| 392 | 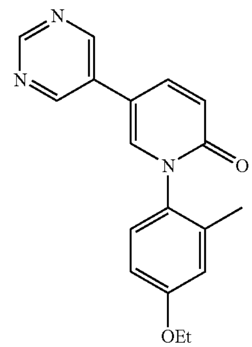 |
| 393 | 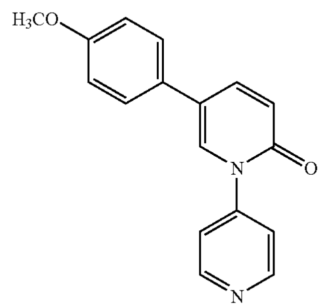 |
| 394 | 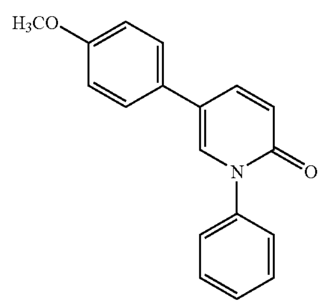 |
| 395 | 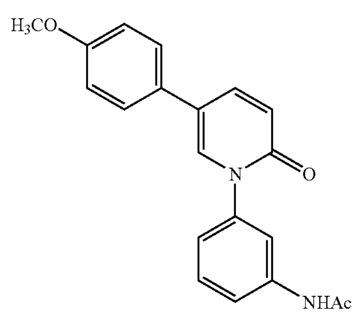 |

TABLE 1-continued
| Cmpd No. | Structure |
|---|---|
| 396 | 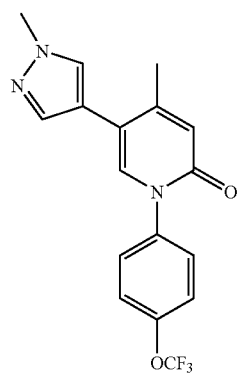 |
| 397 | 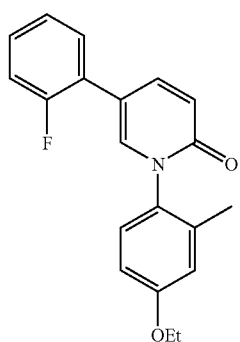 |
| 398 | 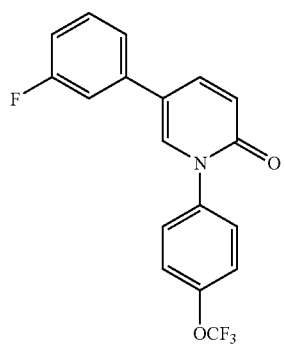 |
| 399 | 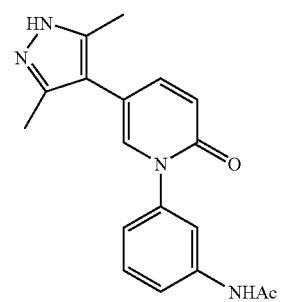 |Нн
TABLE 1-continued
| Cmpd No. | Structure |
|---|---|
| 400 | 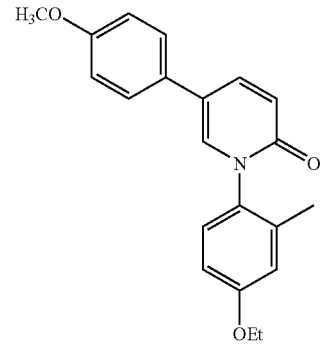 |
| 401 | 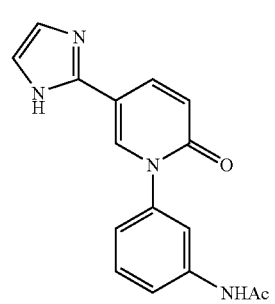 |
| 402 | 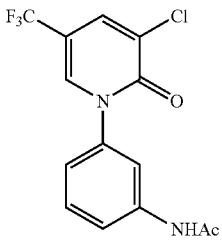 |
| 403 | 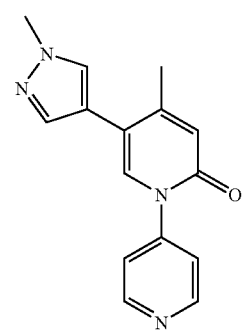 |
| 404 | 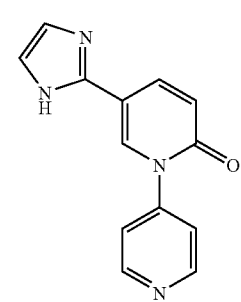 |

TABLE 1-continued

| Cmpd No. | Structure |
|---|---|
| 405 | 5-sulfamoyl-1-(2-methyl-4-ethoxyphenyl)pyridin-2(1H)-one |
| 406 | 3-chloro-5-(trifluoromethyl)-1-phenylpyridin-2(1H)-one |
| 407 | 5-(3-methoxyphenyl)-1-phenylpyridin-2(1H)-one |
| 408 | 5-(3-methoxyphenyl)-1-(4-trifluoromethoxyphenyl)pyridin-2(1H)-one |
| 409 | 5-(2-methoxyphenyl)-1-phenylpyridin-2(1H)-one |
| 410 | 5-(2-methoxyphenyl)-1-(4-trifluoromethoxyphenyl)pyridin-2(1H)-one |
| 411 | 5-(3,5-dimethyl-1H-pyrazol-4-yl)-1-phenylpyridin-2(1H)-one |
| 412 | 5-(2-methoxyphenyl)-1-(2-methyl-4-ethoxyphenyl)pyridin-2(1H)-one |
| 413 | 5-phenyl-1-phenylpyrazin-2(1H)-one |
| 414 | 5-(pyrimidin-2-yl)-1-(pyridin-4-yl)pyridin-2(1H)-one |

TABLE 1-continued

| Cmpd No. | Structure |
|---|---|
| 415 | 5-(3-methoxyphenyl)-1-(3-acetamidophenyl)pyridin-2(1H)-one |
| 416 | 5-(4-chlorophenyl)-1-phenylpyridin-2(1H)-one |
| 417 | 5-(4-chlorophenyl)-1-(3-acetamidophenyl)pyridin-2(1H)-one |
| 418 | 5-(3-methoxyphenyl)-1-(4-ethoxy-2-methylphenyl)pyridin-2(1H)-one |
| 419 | 5-(trifluoromethyl)-3-chloro-1-(4-trifluoromethoxyphenyl)pyridin-2(1H)-one |
| 420 | 5-(4-chlorophenyl)-1-(4-ethoxy-2-methylphenyl)pyridin-2(1H)-one |
| 421 | 5-(4-chlorophenyl)-1-(4-trifluoromethoxyphenyl)pyridin-2(1H)-one |
| 422 | 5-(4-fluorophenyl)-1-phenylpyrazin-2(1H)-one |
| 423 | 5-(3-methoxyphenyl)-1-(pyridin-4-yl)pyridin-2(1H)-one |

TABLE 1-continued
| Cmpd No. | Structure |
|---|---|
| 424 | 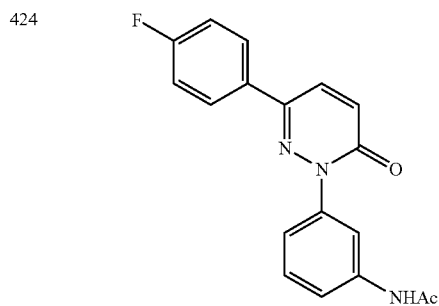 |
| 425 | 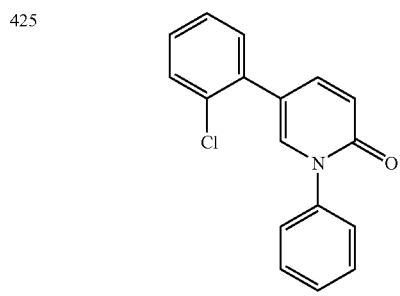 |
| 426 | 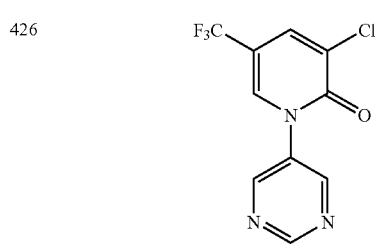 |
| 427 | 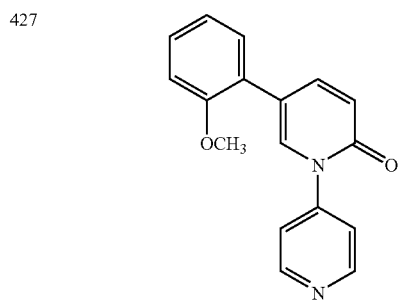 |
| 428 | 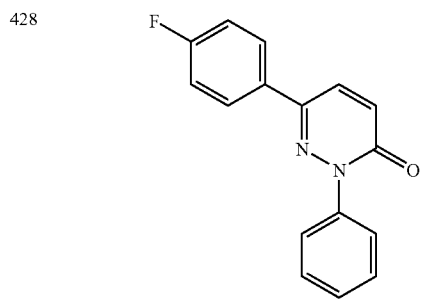 |
TABLE 1-continued
| Cmpd No. | Structure |
|---|---|
| 429 | 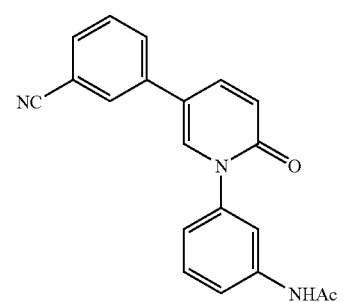 |
| 430 | 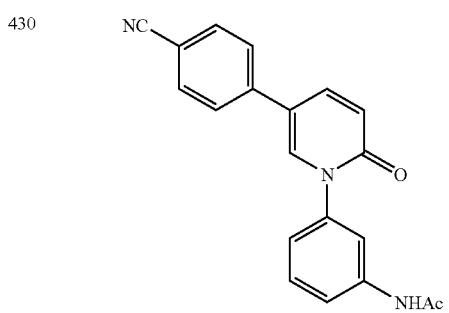 |
| 431 | 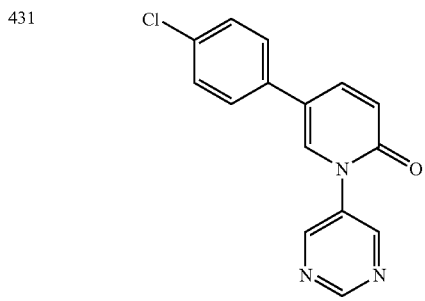 |
| 432 | 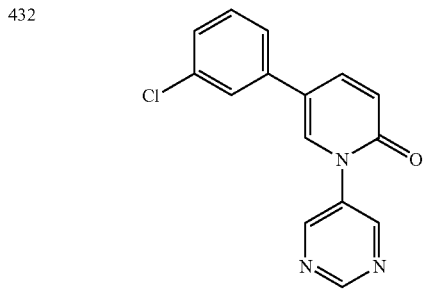 |
| 433 | 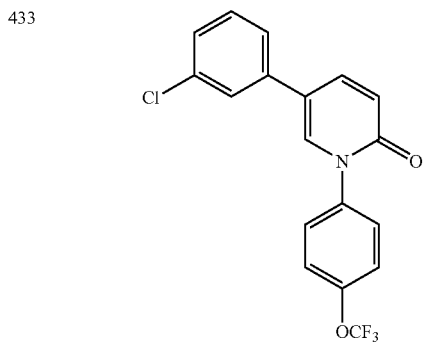 |

TABLE 1-continued
| Cmpd No. | Structure |
|---|---|
| 434 | 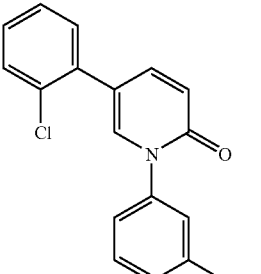 |
| 435 | 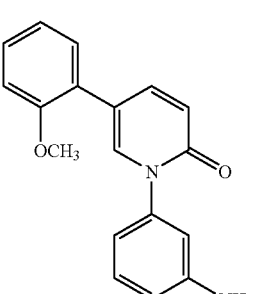 |
| 436 | 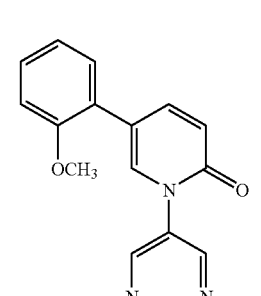 |
| 437 | 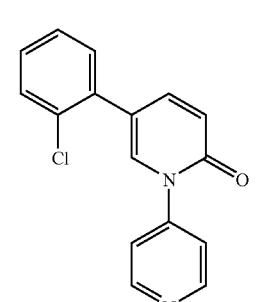 |
| 438 | 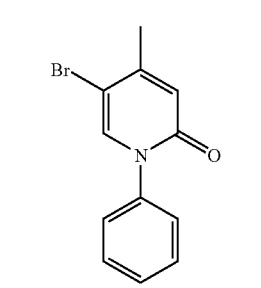 |
TABLE 1-continued
| Cmpd No. | Structure |
|---|---|
| 439 | 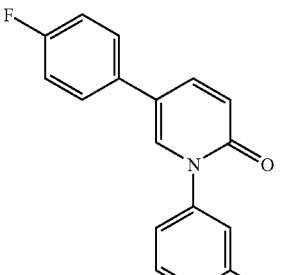 |
| 440 | 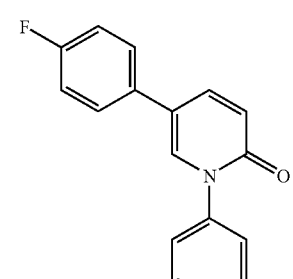 |
| 441 | 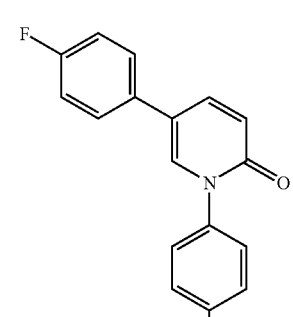 |
| 442 | 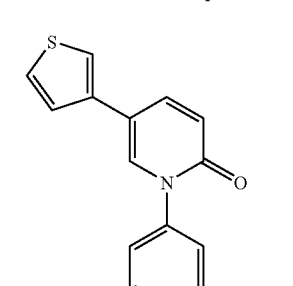 |
| 443 | 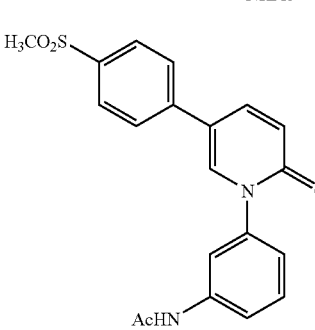 |

TABLE 1-continued

| Cmpd No. | Structure |
|---|---|
| 444 | 3-(methylsulfonyl)phenyl at 5-position; N-(3-acetamidophenyl) 2-pyridinone |
| 445 | 5-(4-fluorophenyl)-1-(4-chlorophenyl)pyridin-2(1H)-one |
| 446 | 5-(3-cyanophenyl)-1-phenylpyridin-2(1H)-one |
| 447 | 5-(4-fluorophenyl)-1-(4-methoxyphenyl)pyridin-2(1H)-one |
| 448 | 5-(4-fluorophenyl)-1-(2-methoxyphenyl)pyridin-2(1H)-one |
| 449 | 5-(4-fluorophenyl)-1-(3-chlorophenyl)pyridin-2(1H)-one |
| 450 | 5-(3-(methylsulfonyl)phenyl)-1-phenylpyridin-2(1H)-one |
| 451 | 5-(thiophen-3-yl)-1-phenylpyridin-2(1H)-one |
| 452 | 5-(2-acetamidophenyl)-1-phenylpyridin-2(1H)-one |

TABLE 1-continued
| Cmpd No. | Structure |
|---|---|
| 453 | 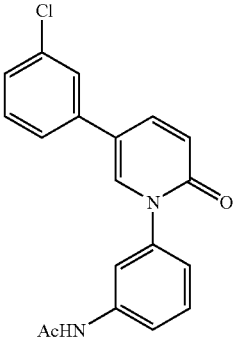 |
| 454 | 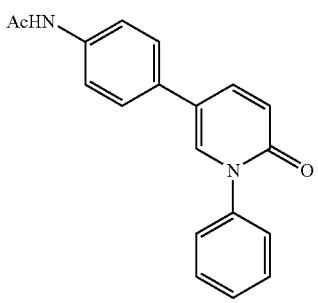 |
| 455 | 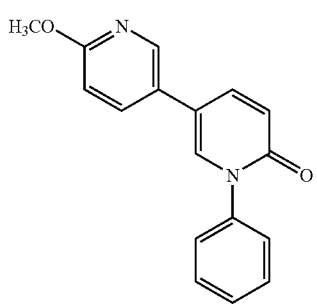 |
| 456 | 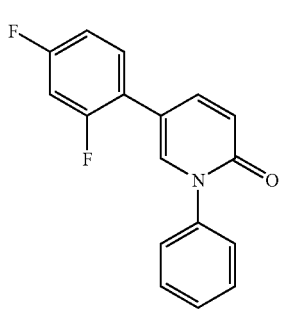 |
| 457 | 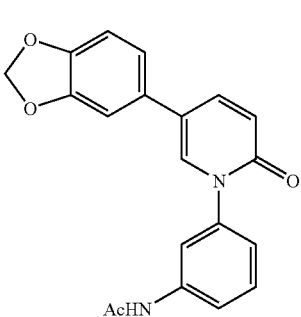 |
| 458 | 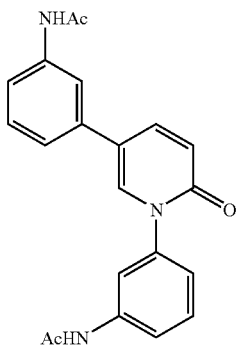 |
| 459 | 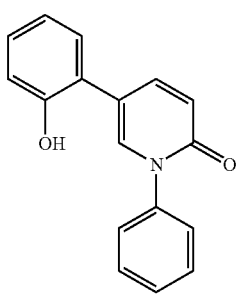 |
| 460 | 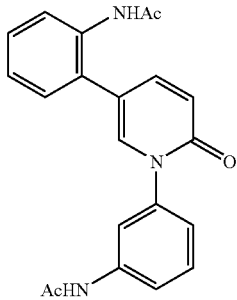 |
| 461 | 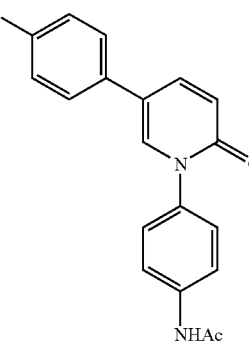 |
| 462 | 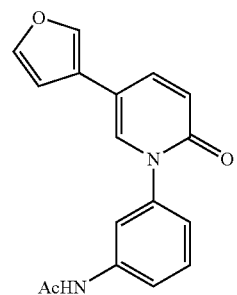 |

TABLE 1-continued

| Cmpd No. | Structure |
|---|---|
| 463 | [structure: 5-(4-methylsulfonylphenyl)-1-phenylpyridin-2(1H)-one] |
| 464 | [structure: 5-(1-methyl-1H-pyrazol-5-yl)-1-phenylpyridin-2(1H)-one] |
| 465 | [structure: 1-(3-acetamidophenyl)-5-(4-methylthiophen-2-yl)pyridin-2(1H)-one] |
| 466 | [structure: 1-(3-acetamidophenyl)-5-(3-hydroxyphenyl)pyridin-2(1H)-one] |
| 467 | [structure: 1-(3-acetamidophenyl)-5-(6-methoxypyridin-3-yl)pyridin-2(1H)-one] |
| 468 | [structure: 3-(1-(3-acetamidophenyl)-6-oxo-1,6-dihydropyridin-3-yl)benzamide] |
| 469 | [structure: 4-(1-(3-acetamidophenyl)-6-oxo-1,6-dihydropyridin-3-yl)benzamide] |
| 470 | [structure: 1-(3-acetamidophenyl)-5-(1-methyl-1H-indol-5-yl)pyridin-2(1H)-one] |
| 471 | [structure: 5-(1-methyl-1H-indol-5-yl)-1-phenylpyridin-2(1H)-one] |
| 472 | [structure: 7-(3-hydroxyphenyl)-N-methyl-6-oxo-6,7-dihydro-1H-pyrrolo[2,3-b]pyridine-2-carboxamide] |

TABLE 1-continued

| Cmpd No. | Structure |
|---|---|
| 473 | 5-(3-methylthiophen-2-yl)-1-(3-acetamidophenyl)pyridin-2(1H)-one |
| 474 | 5-(4-fluorophenyl)-1-(2-acetamidophenyl)pyridin-2(1H)-one |
| 475 | 5-(4-ethoxyphenyl)-1-(3-acetamidophenyl)pyridin-2(1H)-one |
| 476 | 5-(3-acetamidophenyl)-1-phenylpyridin-2(1H)-one |
| 477 | 5-(3-hydroxyphenyl)-1-phenylpyridin-2(1H)-one |
| 478 | 5-(3-methylthiophen-2-yl)-1-phenylpyridin-2(1H)-one |
| 479 | 5-(4-methylthiophen-2-yl)-1-phenylpyridin-2(1H)-one |
| 480 | 5-(4-hydroxyphenyl)-1-phenylpyridin-2(1H)-one |
| 481 | 5-(benzo[d][1,3]dioxol-5-yl)-1-phenylpyridin-2(1H)-one |
| 482 | 5-(3-(N,N-dimethylsulfamoyl)phenyl)-1-phenylpyridin-2(1H)-one |

TABLE 1-continued

| Cmpd No. | Structure |
|---|---|
| 483 | 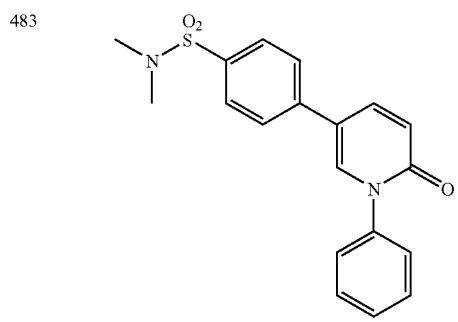 |
| 484 | 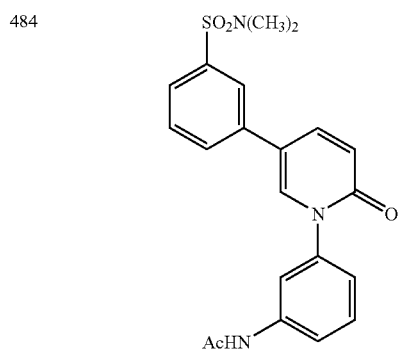 |
| 485 | 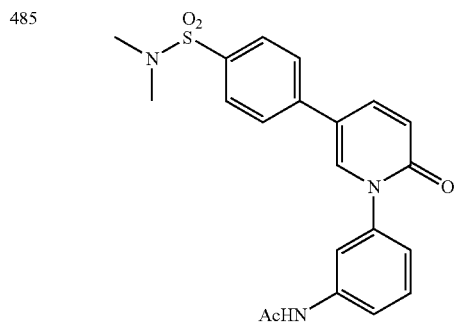 |
| 486 | 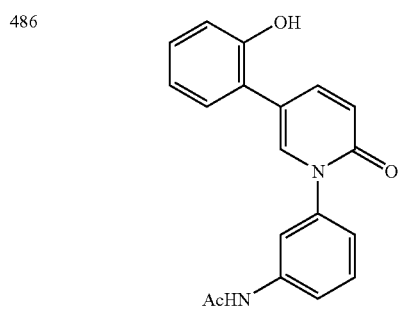 |

TABLE 1-continued

| Cmpd No. | Structure |
|---|---|
| 487 | 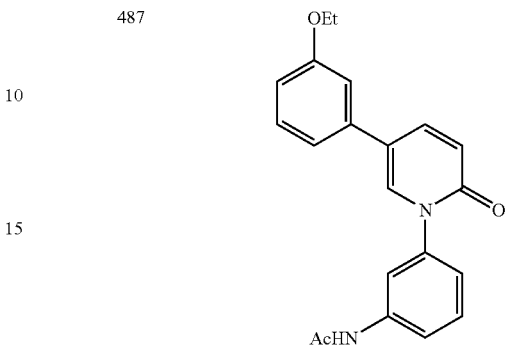 |

Synthetic Processes

The compounds of Formula (I) can be synthesized using known techniques. One means of synthesizing these compounds is via a Suzuki coupling, as shown in Scheme 1, and another is via an Ullmann condensation, as shown in Scheme 2. The starting reagents are chosen to provide the desired substitutions in the final product. These reagents can themselves be prepared using known techniques or can be purchased from commercial sources, such as Sigma-Aldrich (Milwaukee, Wis.).

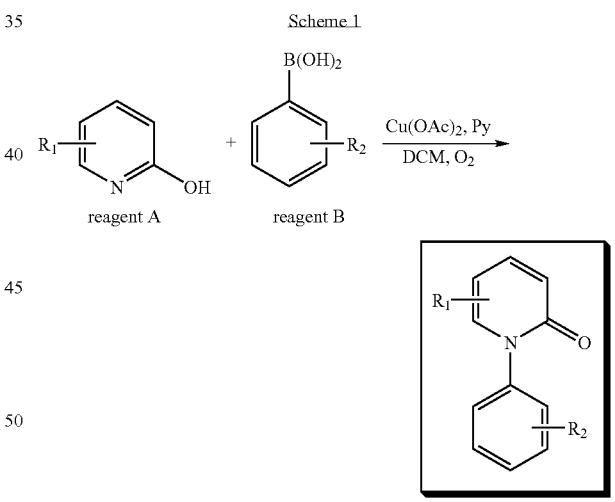

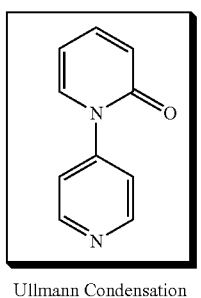

Ullmann Condensation

General procedure A (Coupling): A mixture of reagent A (0.5-1 mmol, 1 eq.), boronic acid B (2 eq.), copper(II) acetate (0.1-0.2 eq.), pyridine (2 eq.) and molecular sieves 4 Å in dichloromethane (5 mL/1 mmol reagent A) is stirred overnight at room temperature (e.g., 20-25° C.), opened to the air. The reaction is monitored by TLC, and when no starting material is detected, the reaction mixture is washed with saturated sodium bicarbonate and ethylenediaminetetraacetic acid (EDTA) and dried over sodium sulfate. Target products are isolated by prep-TLC (typically using ethyl acetate/petroleum ether as solvent).

General procedure B (Ulmann condensation): A mixture of reagent A (1 eq.), reagent B (1.2 eq.), copper iodide (CuI, 0.2 eq.) and potassium carbonate ($K_2CO_3$, 2 eq) in dimethylformamide (DMF) is refluxed overnight under nitrogen. The reaction is monitored by TLC, and when no starting material is detected, the reaction mixture is washed with saturated sodium bicarbonate, extracted with ethyl acetate (EA) and dried over sodium sulfate. Target products are isolated by prep-TLC.

In some embodiments, the intermediate aryl bromide for the Suzuki coupling is synthesized. A synthetic route is outlined in Scheme 3, below.

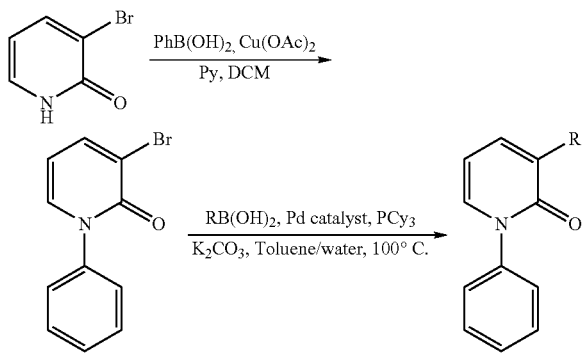

General procedure C (including synthesis of aryl bromide intermediate): For some compounds, two Suzuki couplings are used to synthesize the final compound. The first intermediate aryl bromide is prepared as described for General procedure A. Then, to a solution of Br-substituted-1-phenyl-1H-pyridin-2-one (1 eq), a second boronic acid (1.2 eq), potassium carbonate (3.5 eq) and tricyclohexylphosphine (0.1 eq) in toluene/water (2/1, v/v) under a nitrogen atmosphere is added palladium acetate (0.05 eq). The mixture is heated to 100° C. for 2-3 h, and then cooled to room temperature. Water is added, and the mixture is extracted with EA, the combined organics are washed with brine and water, dried over anhydrous sodium sulfate, and concentrated in vacuo. The residue is purified by prep-TLC to afford the desired compound.

The compound can also be synthesized using a scheme as depicted below, where a triflate intermediate is used in the Suzuki coupling.

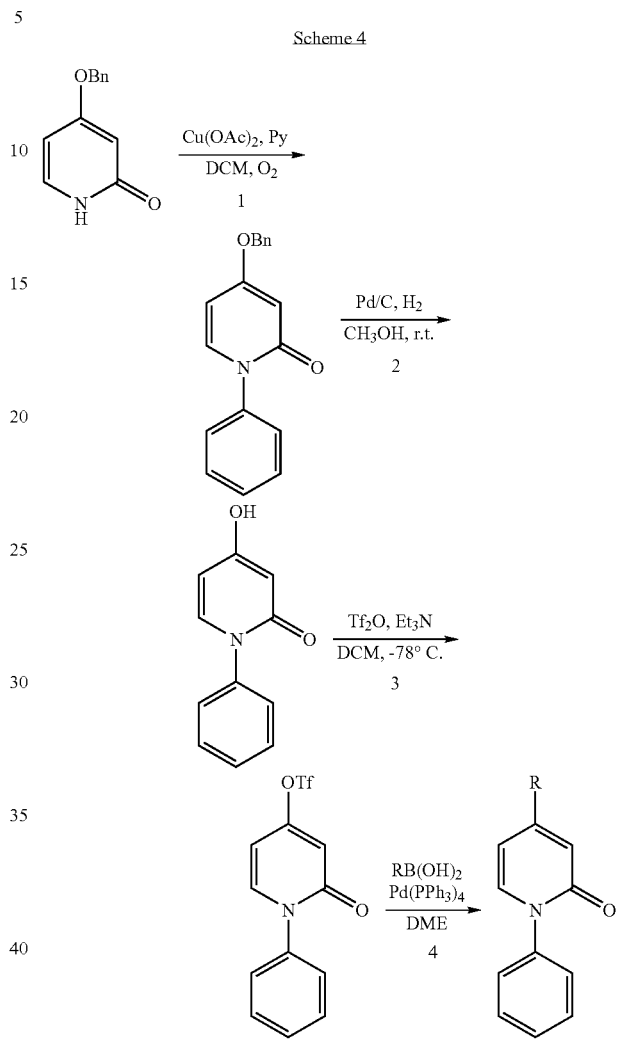

General procedure D: For step 1, the procedure is the same as for general procedure A. For step 2, a solution of the intermediate benzyl protected phenol (3.5 g, 10.8 mmol) in methanol (200 ml) is added to a Pd/C (300 mg) catalyst under $N_2$ atmosphere, and then stirred for 2 h under $H_2$ atmosphere (1 atm, 25° C.). The catalyst is filtered off through a celite pad, and the filtrate is concentrated in vacuo to give the free phenolic hydroxyl. For step 3, a solution of the resulting phenol intermediate (2.2 g, 11.8 mmol) in dichloromethane (DCM, 120 mL) is added to triethylamine (1.7 g, 16.8 mmol) at −78° C., followed by the addition of trifluoromethanesulfonic anhydride (4.76 g, 16.9 mmol). The resulting mixture is stirred at −78° C. for 15 min and quenched with ammonium chloride solution (10 mL). After warming to room temperature, water (30 mL) and DCM (50 mL) are added and separated. The target product is obtained by washing the crude mixture with methanol. For step 4, a solution of trifluoromethanesulfonic acid intermediate (0.79 mmol) and tetrakis(triphenylphosphine)palladium (0.011 g, 0.0095 mmol) in dimethoxyethane (DME, 1 mL) is stirred at room temperature for 15 min followed by the addition of the solution arylboronic acid (0.21 mmol) in DME (1 mL) and 2M sodium carbonate (1 mL). The resulting mixture is refluxed for 14 hr and cooled down to room temperature. Water and ethyl acetate are added. After separation, the aqueous layer is extracted with ethyl acetate. The combined ethyl acetate solution is dried over sodium sulfate and filtered. The filtrate is concentrated in vacuo to dryness. Target products are isolated by prep-TLC.

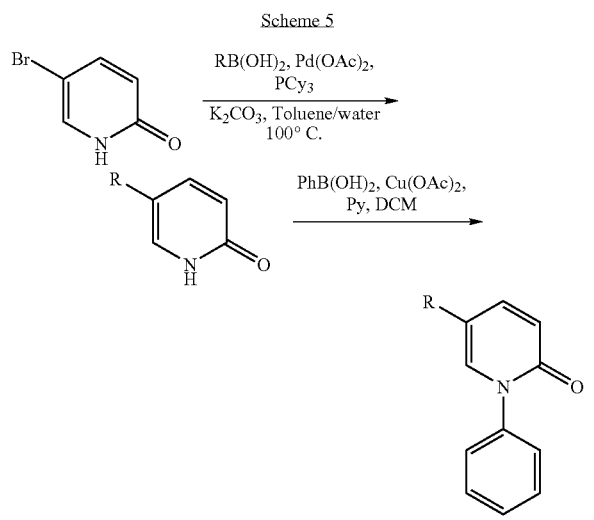

Scheme 5

General procedure E: (Alternative Suzuki coupling reaction conditions) To a solution of 5-bromo-2-hydroxypyridine (1 eq.), corresponding boronic acid (1.2 eq), potassium carbonate (3.5 eq) and tricyclohexylphosphine (0.1 eq) in toluene/water (2:1, v:v) under nitrogen atmosphere is added palladium acetate (0.05 eq). The mixture is heated to 100° C. for 2-3 h, and then cooled to room temperature, water is added and the mixture extracted with EA; the combined organics are washed with brine, dried over sodium sulfate, and concentrated in vacuo. Purification by prep-TLC affords the desired 5-substituted-2-hydroxypyridine. The second coupling, a Suzuki coupling, of the intermediate 5-substituted-2-hydroxypyridine with an aryl boronic acid is performed following General Procedure A, as described above.

In some embodiments, the compound of formula (I) has at least one fluorine atom as a substituent. Introduction of the fluorine can be accomplished, as outlined in Scheme 6.

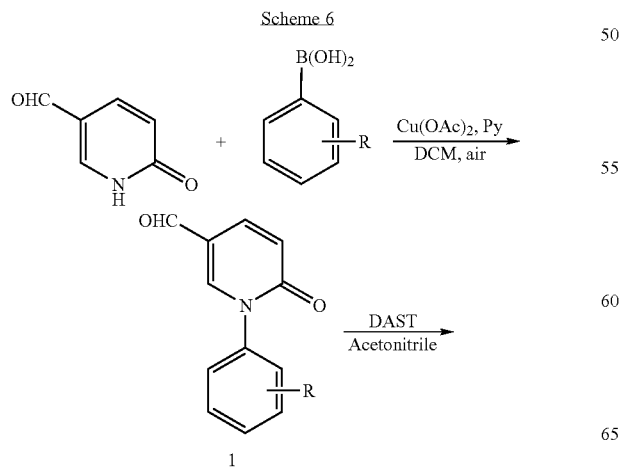

Scheme 6

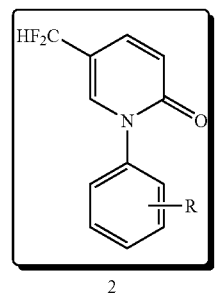

General procedure F (fluorination): 1 (1 eq) is dissolved in acetonitrile, diethyl amino sulfur trifluoride (DAST, 2.2 eq) is added, and fluorination is carried out at 80° C. in a capped plastic tube for 4 to 8 hours. After cooling to room temperature, the reaction mixture is diluted with DCM and poured into saturated bicarbonate solution. The organic phase is separated and dried over sodium sulfate. The product is isolated by prep-TLC.

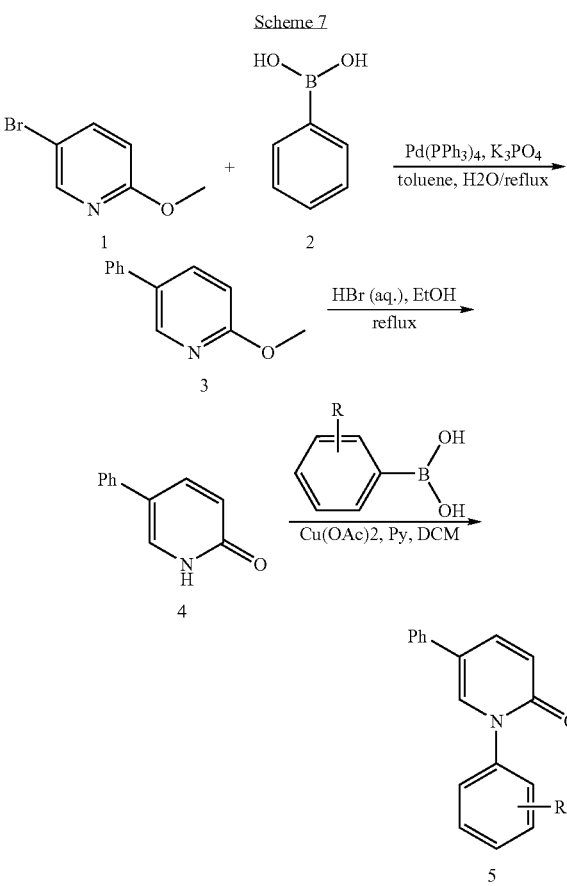

Scheme 7

General procedure G: This procedure exemplified in Scheme 7, above. To a solution of 1 (3.0 g, 16 mmol), 2 (2.5 g, 21 mmol), K₃PO₄ (12.5 g, 57 mmol) in toluene/water (60 mL/3 mL) under a nitrogen atmosphere is added Pd(PPh₃)₄ (2.0 g, 1.6 mmol). The mixture is heated to reflux for 3 h and then cooled to room temperature. Water is added and the mixture extracted with EA. The combined organics are washed with brine, dried over Na₂SO₄ and concentrated in vacuo. The product is isolated by column chromatography to afford 3. 3 (2.0 g, 11 mmol) in HBr (aq. 40%)/ethanol (20 mL/4 mL) is heated to reflux for 2 h, and monitored by TLC. When no starting material is detected, the mixture is cooled to room temperature, and neutralized by addition of NaHCO$_3$, extracted with EA, and then washed with brine, dried over Na$_2$SO$_4$ and concentrated in vacuo to afford 4. 5 is prepared using general procedure A.

Scheme 8

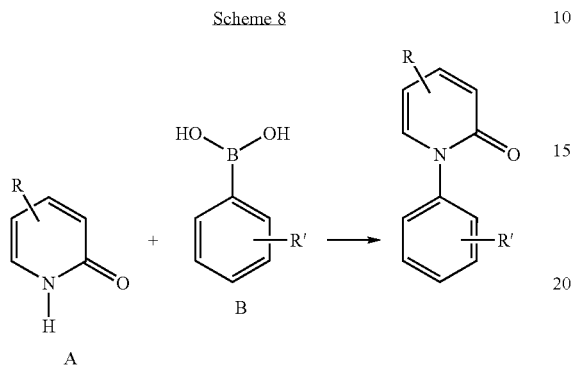

General procedure H: In some embodiments, the compounds of formula I are prepared using a Chan-Lam reaction, as depicted in Scheme 8, above. In one embodiment, the Chan-Lam synthetic procedure is as follows (Method H1A—where reagent A is a solid): to a solution of A (0.5 mmol) in 6 mL of DCM and 2 mL of DMF, copper (II) acetate (1.0 mmol, 2 eq), boronic acid B (1.2 eq), pyridine (2 eq) and finely ground, activated 4 Å molecular sieves (600 mg) are added. When the reagent A is a hydrobromide salt, TEA (2 mL) is added. The mixture is stirred at room temperature in the open air for 12 hours up to about 4 days. Additional boronic acid B can be added to the reaction mixture. Then, concentrated NH$_4$OH is added. The solvents are evaporated under vacuum, and the crude product absorbed on a silica pad and purified by chromatographic column. In some specific cases, the product is further purified on reverse-phase preparative HPLC.

Alternatively, Method H1B starts with reagent A as a solution in DMF. This procedure is as follows: to a solution of A (2.5 mL of DMF solution, 0.74 mmol) in 5 mL of DMF, copper (II) acetate (1.48 mmol, 2 eq), boronic acid B (1.2 eq), pyridine (2 eq) and finely ground, activated 4 Å molecular sieves (600 mg) are added. The mixture is stirred at room temperature in the open air for 12 hours up to about 4 days. Additional boronic acid B can be further added. Then, concentrated NH$_4$OH is added. The solvents are evaporated under vacuum, and the crude product is absorbed on silica pad and purified by chromatographic column. In some specific cases, the product is further purified on reverse-phase preparative HPLC.

In another procedure, the Chan-Lam reaction proceeds as follows (Method H2): to a 0.3 M solution of A in DMF, copper (II) acetate (2 eq), boronic acid B (1.2 eq) and pyridine (2 eq) are added. The mixture is heated 1 h at 100° C. under microwave irradiation, then concentrated NH$_4$OH is added. The reaction mixture then is diluted with EA and filtered through a celite pad. Solvents are evaporated, and the crude mixture absorbed on silica pad and purified by chromatographic column. In some specific cases, the product is further purified on reverse-phase preparative HPLC.

General Procedure I: Preparation of pyridones which are not commercially available can be achieved in the following manner, as outlined in Scheme 9.

Scheme 9

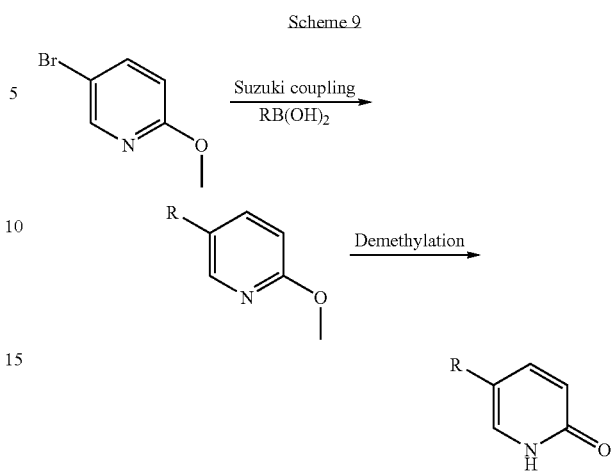

The 5-bromo-2-methoxy-pyridine (1 eq), the boronic acid (1.2 eq) and K$_2$CO$_3$ (3 eq) were dissolved in a 10:1 mixture of DME/H$_2$O (4 ml/mmol). The solution was degassed by bubbling N$_2$ for 15 min and then Pd(PPh$_3$)$_4$ (0.05 eq) was added. The reaction mixture was heated at 90° C. for 4-8 h and then cooled at room temperature, diluted with AcOEt and filtered on a celite plug. The filtrate was washed with brine. The separated organic phase was dried over Na$_2$SO$_4$ and concentrated under reduced pressure. The obtained residue was purified by column chromatography.

General Procedure J: Compounds of Formula III, as disclosed herein, are prepared as outlined in Scheme 10.

Scheme 10

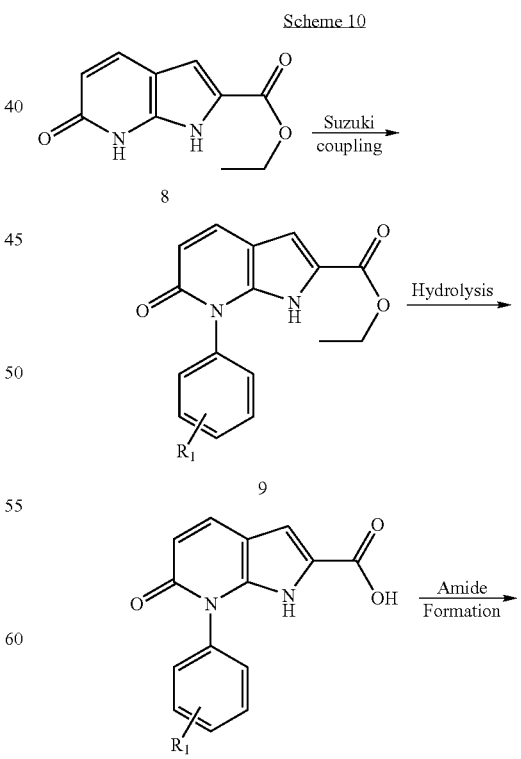

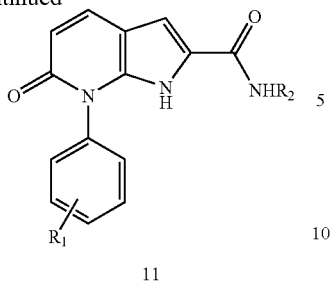

Suzuki Coupling: General procedure: A mixture of the appropriate ester 8 (1 eq), the phenylboronic acid (1.2 eq), copper(II) acetate (1.2 eq), pyridine (3 eq) and activated freshly crushed 4 Å molecular sieves in 1,2-dichloroethane (21 mL/mmol of ester) is stirred, in an open vessel, for 4 days at room temperature. The mixture is filtered through celite and the solution thus obtained is evaporated under vacuum. The residue is dissolved DCM, washed with an aqueous $NaHCO_3$ solution, water, dried over $Na_2SO_4$ and concentrated under vacuum. Purification by flash chromatography ($SiO_2$; DCM:MeOH mixture) affords the desired compound 9.

Hydrolysis: To a solution of the appropriate carboxylic ester 9 (1 eq) in a 1:1 mixture of $H_2O$ and THF (10 mL/mmol of ester), cooled to 0° C., a 6M aqueous solution of NaOH (10 eq) is added dropwise at 0° C. The reaction mixture is heated to 75° C. for 48 h. The remaining aqueous fraction, previously washed with $Et_2O$, is cooled at 0° C. and citric acid is added until the pH is 3-4. The precipitate thus formed is filtered and washed with plenty of water and $Et_2O$ to afford the pure desired compound 10.

Amide formation: General procedure A solution of the appropriate carboxylic acid 10 (150 mg, 0.44 mmol) in a 1:1 mixture of acetonitrile and EA (6 mL/mmol of acid), triethylamine (2 eq) is admixed. Pyrrolidine (1.2 eq) and TBTU (1.2 eq) are added. The reaction mixture is stirred at room temperature for 12 h. The solvents are removed under vacuum and the crude thus obtained is re-dissolved in DCM. The organic layer is washed with 10% aqueous solution of $NaHCO_3$, brine, dried over $Na_2SO_4$ and evaporated under vacuum. Purification by flash chromatography ($SiO_2$; DCM:MeOH mixture) affords the pure desired compound 11 of Formula III.

General Procedure K (synthesis of 8): Preparation began with synthesis of 8 via either route A or route B. Route A is detailed in the following Scheme 11.

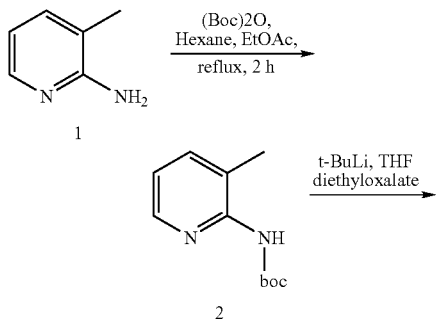

Scheme 11

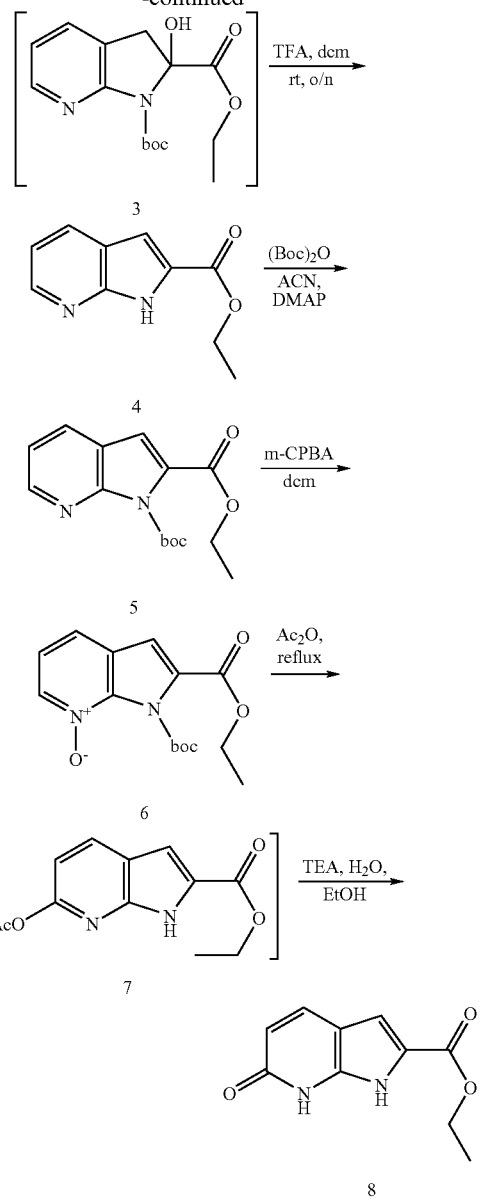

To a refluxing solution of di-tert-butyldicarbonate (211.7 g, 0.97 mol) in hexane (500 mL), a solution of 2-amino-3-methylpyridine (100 g, 0.9247 mol) in AcOEt (150 mL) was added over 30 min. The mixture was stirred at reflux temperature (65° C.) for an additional hour and then cooled to room temperature. The suspension was diluted with hexane (500 mL) and stirred for 1 h at room temperature. The product was isolated by filtration, washed with hexane and dried under vacuum to afford 130 g of 2 (tert-butyl 3-methylpyridin-2-ylcarbamate) that was used in the next step without further purification.

A solution of 2 (50 g, 0.24 mol) in THF was cooled at −45° C. and a 1.3 M solution of t-butyl lithium in pentane (500 mL, 0.65 mol) was added dropwise. After 1 h the reaction temperature was decreased to −80° C. and diethyloxalate (105.22 g, 0.72 mol) was added. The reaction mixture turned yellow and turbidity was observed. The mixture was kept at −50° C. for additional 2 h and then warmed at room temperature. The reaction was quenched by slowly adding 700 mL of water and extracted with EA, washed with brine and dried over $Na_2SO_4$ to obtain 100 g of 3 (1-tert-butyl 2-(ethoxycarbonyl)-2-hydroxy-2,3-dihydro-1H-pyrrolo[2,3-b]pyridine-1,2-dicarboxylate) as a crude orange oil.

Then, 3 (100 g) was dissolved in dry DCM (400 mL) and cooled at 0° C. TFA (300 mL) was added dropwise and the reaction mixture was stirred overnight. Volatile fractions were removed under vacuum and the residue TFA was neutralized with an aqueous solution of NaHCO$_3$. The pure 4 (ethyl 1H-pyrrolo[2,3-b]pyridine-2-carboxylate, 25 g, 54% yield over two steps) was obtained by filtration and washing with water.

Then, 4 (25 gm, 0.131 mol) was dissolved in acetonitrile (250 mL). 4-dimethylamino pyridine (27.29 g, 0.22 mol) and a 4 M solution of BOC anhydride (48.83 g, 0.22 mol) in acetonitrile were added to the reaction mixture. The reaction mixture was stirred for 1 h. EA was added to the reaction, the organic phase was separated and washed with water, brine, dried over Na$_2$SO$_4$ and evaporated under vacuum. Purification by flash chromatography (SiO$_2$; DCM:MeOH 99:1) 20 g (52% yield) of pure 5 (1-tert-butyl 2-(ethoxycarbonyl)-1H-pyrrolo[2,3-b]pyridine-1,2-dicarboxylate) as an off-white solid.

Next, to a solution of 5 (20 g, 0.064 mol) in DCM (200 mL) was added mCPBA (77 g, 0.44 mol), and the reaction was stirred at room temperature overnight. The mixture was purified by flash chromatography (SiO$_2$; DCM:MeOH 99:1) to afford 12 g (56% yield) of 6 (1-(tert-butoxycarbonyl)-2-(ethoxycarbonyl)-1H-pyrrolo[2,3-b]pyridine 7-oxide) as a colorless oil.

Then, 6 (12 g, 0.04 mol) was dissolved in acetic anhydride (120 mL) and refluxed overnight. The reaction mixture was concentrated under vacuum and the residue was evaporated by addition of toluene to afford crude 7 (ethyl 6-acetoxy-1H-pyrrolo[2,3-b]pyridine-2-carboxylate) that was dissolved in a 1:10:10 mixture of Et$_3$N:EtOH:H$_2$O and stirred overnight at room temperature. The reaction mixture was concentrated under vacuum and EA was added. The precipitate thus formed was filtered and washed with EA to afford 2.8 g (35% yield) of pure 8 (ethyl 6-oxo-6,7-dihydro-1H-pyrrolo[2,3-b]pyridine-2-carboxylate).

Alternatively, 8 can be prepared following Route B, where 6a is made directly from 4, as shown in Scheme 12.

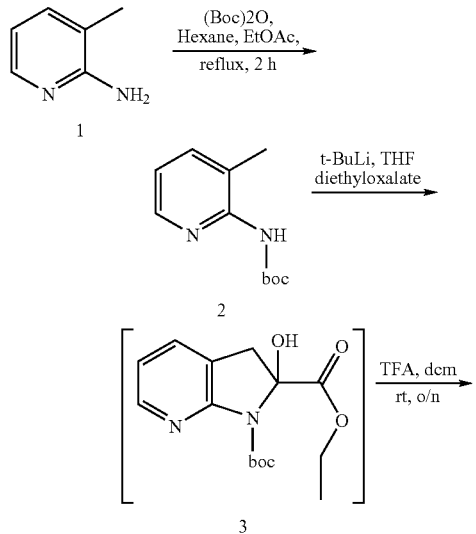

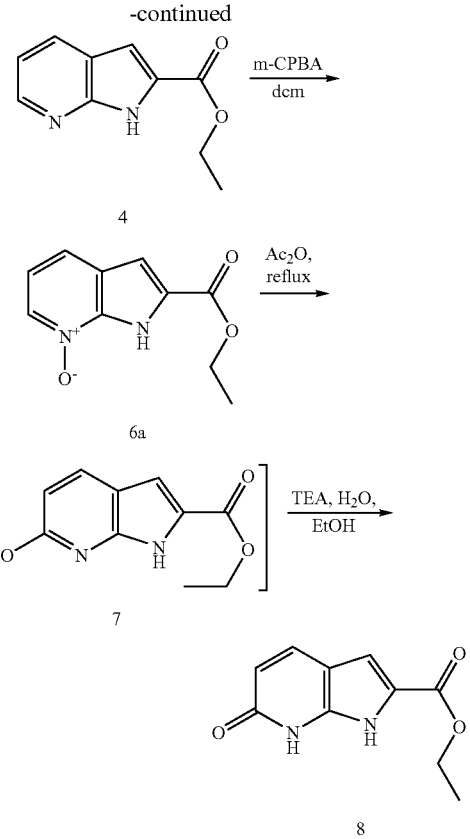

To a solution of 4 (25 g, 0.131 mol) in DCM (250 mL) mCPBA (90.5 g, 0.525 mol) was added, and the reaction was stirred, at room temperature, overnight. The mixture was purified by flash chromatography (SiO$_2$; DCM:MeOH 95:5) to afford 24 g (88% yield) of 6a (2-(ethoxycarbonyl)-1H-pyrrolo[2,3-b]pyridine 7-oxide) as a colorless oil.

Then, 6a (24 g, 0.08 mol) was dissolved in acetic anhydride (240 mL) and the reaction was refluxed overnight. The mixture was concentrated under vacuum and the residue was evaporated by addition of toluene to afford crude 7 that was dissolved in a 1:10:10 mixture of Et$_3$N:EtOH:H$_2$O and stirred overnight at room temperature. The reaction mixture was evaporated under vacuum and EA was added. The precipitate thus formed was filtered and washed with EA to afford 9.6 g (40% yield) of pure 8.

General Procedure L: Compounds as disclosed herein can be prepared using Buchwald-Hartwig coupling, using aryl bromides. Appropriate aryl bromides can be prepared via the following Scheme 13.

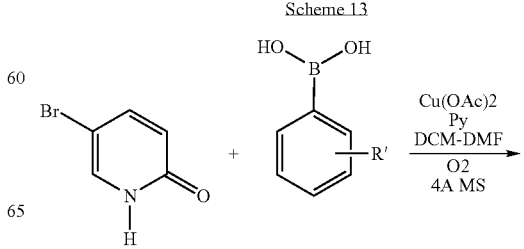

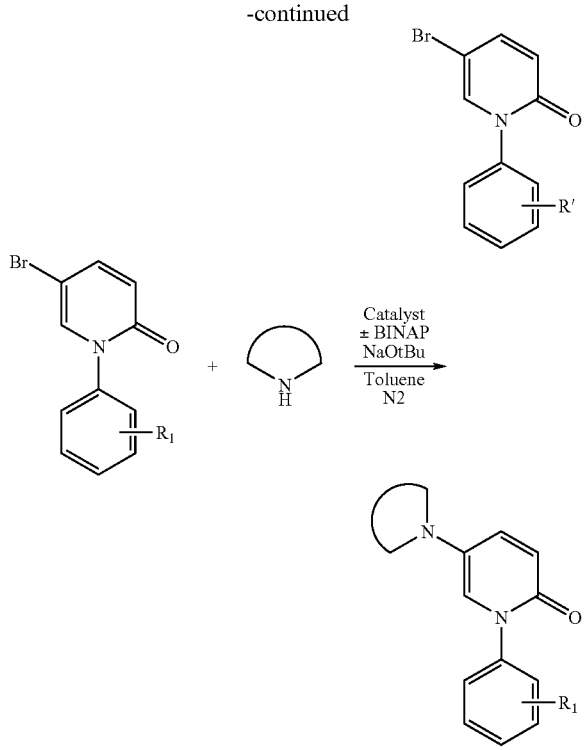

5-bromo-pyridin-2-one (1 eq.) is dissolved in DCM (5 mL/mmol of aryl halide) and N,N-dimethylformammide (0.7 mL/mmol of aryl halide). The appropriate boronic acid (1.2 eq.), copper(II) acetate (2.0 eq.), pyridine (2.0 eq.) and 4 Å molecular sieves are added to the solution and the reaction is stirred at room temperature in an open vessel for 3 days. The reaction is monitored by UPLC-MS. At the end of the reaction a concentrated solution of $NH_4OH$ is added. Solvents are removed at reduced pressure and the crude is purified by flash chromatography ($SiO_2$; Pet. Ether/EtOAc mixture). The bromopyridone intermediate is then used in the Buchwald-Hartwig coupling either via Method L1 or Method L2.

Method L1 is as follows: ±BINAP (0.2 eq.) is suspended in dry toluene (7.5 mL/mmol of aryl halide) and dissolved at 80° C. After dissolution, the mixture is cooled to room temperature and $Pd(OAc)_2$ (0.1 eq) is added. The mixture is stirred for 5 minutes, then the appropriate bromopyridone (1 eq.) is added, followed by the appropriate amine (5 eq.) and NaOtBu (1.4 eq.). The reaction is heated at 80° C. for 15 h. 3N HCl is added, at room temperature, to the mixture and the aqueous phase is separated and washed with EtOAc. The aqueous layer is then basified with $NH_4OH$ and back-extracted with EtOAc. The organic portions are collected, dried over $Na_2SO_4$ and concentrated under reduced pressure. The crude is purified by flash chromatography ($SiO_2$: Pet. Ether/EtOAc 3:1 up to pure EtOAc) then by reverse-phase preparative HPLC.

Method L2 is as follows: ±BINAP (0.2 eq.) is suspended in dry toluene (7.5 mL/mmol of aryl halide) and $Pd_2dba_3$ (0.1 eq) is added. The mixture is stirred for 15 minutes, then the appropriate bromopyridone (1 eq.) is added, followed by the appropriate amine (5 eq.) and NaOtBu (1.4 eq.). The reaction is heated at 80° C. for 15 h, and then cooled at room temperature. Solvents are evaporated and the crude product is purified by flash chromatography ($SiO_2$; Pet. Ether/EtOAc 3:1 up to pure EtOAc) then by reverse-phase preparative HPLC.

Other means of synthesizing the compounds of Formula I can be used. As pirfenidone derivatives and analogs, these compounds can also be synthesized by any conventional reactions known in the art based on the known synthetic schemes for pirfenidone, such as disclosed in U.S. Pat. Nos. 3,839,346; 3,974,281; 4,042,699; and 4,052,509.

Starting materials described herein are available commercially, are known, or can be prepared by methods known in the art. Additionally, starting materials not described herein are available commercially, are known, or can be prepared by methods known in the art. Starting materials can have the appropriate substituents to ultimately give desired products with the corresponding substituents. Alternatively, substituents can be added at any point of synthesis to ultimately give desired products with the corresponding substituents.

One skilled in the art will appreciate variations in the sequences and, further, will recognize variations in the appropriate reaction conditions from the analogous reactions shown or otherwise known which may be appropriately used in the processes described herein to make the compounds of Formula I.

In the processes described herein for the preparation of the compounds of Formula I, the use of protective groups is generally well recognized by one skilled in the art of organic chemistry, and accordingly the use of appropriate protecting groups may in some cases be implied by the processes of the schemes herein, although such groups may not be expressly illustrated. Introduction and removal of such suitable protecting groups are well known in the art of organic chemistry; see for example, T. W. Greene, *Protective Groups in Organic Synthesis*, Wiley (New York), 1999. The products of the reactions described herein may be isolated by conventional means such as extraction, distillation, chromatography, and the like.

The salts, e.g., pharmaceutically acceptable salts, of the compounds of Formula I may be prepared by reacting the appropriate base or acid with a stoichiometric equivalent of the compounds of Formula I. Similarly, pharmaceutically acceptable derivatives (e.g., esters), metabolites, hydrates, solvates and prodrugs of the compounds of Formula I may be prepared by methods generally known to those skilled in the art. Thus, another embodiment provides compounds that are prodrugs of an active compound. In general, a prodrug is a compound which is metabolized in vivo (e.g., by a metabolic transformation such as deamination, dealkylation, de-esterification, and the like) to provide an active compound. A "pharmaceutically acceptable prodrug" means a compound which is, within the scope of sound medical judgment, suitable for pharmaceutical use in a patient without undue toxicity, irritation, allergic response, and the like, and effective for the intended use, including a pharmaceutically acceptable ester as well as a zwitterionic form, where possible, of the compounds of Formula I. Examples of pharmaceutically-acceptable prodrug types are described in Higuchi and Stella, *Pro-drugs as Novel Delivery Systems*, Vol. 14 of the A.C.S. Symposium Series, and in Roche, ed., *Bioreversible Carriers in Drug Design*, American Pharmaceutical Association and Pergamon Press, 1987, both of which are incorporated herein by reference.

The compounds and compositions described herein may also include metabolites. As used herein, the term "metabolite" means a product of metabolism of a compound of the embodiments or a pharmaceutically acceptable salt, analog, or derivative thereof, that exhibits a similar activity in vitro or in vivo to a compound of Formula I. The compounds and compositions described herein may also include hydrates and solvates. As used herein, the term "solvate" refers to a complex formed by a solute (herein, a compound of Formula I)

and a solvent. Such solvents for the purpose of the embodiments preferably should not negatively interfere with the biological activity of the solute. Solvents may be, by way of example, water, ethanol, or acetic acid. In view of the foregoing, reference herein to a particular compound or genus of compounds will be understood to include the various forms described above, including pharmaceutically acceptable salts, esters, prodrugs, metabolites and solvates thereof.

Methods of Inhibiting p38 MAP Kinase

In an embodiment, methods are provided for modulating a SAPK system, in vitro or in vivo. The methods include contacting a SAPK-modulating concentration of a compound with a p38 MAPK (e.g., by contacting the compound with a cell or tissue containing the p38 MAPK), wherein the compound has a relatively low potency for inhibition of the p38 MAPK, corresponding to a relatively high inhibitory concentration for inhibition of the p38 MAPK by the compound.

The inhibitory concentration (IC) is a concentration that results in a reduction in the activity of p38 MAPK by a specified percentage (e.g., 50%, 40%, 30%, 20%, 10%) on a dose-response curve. For example, $IC_{50}$, $IC_{40}$, $IC_{30}$, $IC_{20}$ and $IC_{10}$ are determined as concentrations that result in reductions in the activity of p38 MAPK by 50%, 40%, 30%, 20% and 10%, respectively on a dose-response curve. The $IC_{50}$ of the SAPK system-modulating compound is preferably in the range of about 0.1 µM to about 1000 µM, and more preferably about 1 µM to about 800 µM, about 1 µM to about 500 µM, about 1 µM to about 300 µM, about 1 µM to about 200 µM, or about 1 µM to about 100 µM for inhibition of p38 MAPK. Thus, for example, modulation of the SAPK system may involve contacting a compound (e.g., a compound of Formula I) with a p38 MAPK at a concentration that is less than an $IC_{40}$, preferably less than $IC_{30}$, more preferably less than $IC_{20}$, even preferably less than $IC_{10}$ for inhibition of the p38 MAPK by the compound as determined on a concentration-response curve.

"Contacting a cell" refers to a condition in which a compound or other composition of matter is in direct contact with a cell or tissue, or is close enough to induce a desired biological effect in a cell or tissue. For example, contacting a cell or tissue containing p38 MAPK with a compound may be conducted in any manner that permits an interaction between p38 MAPK and the compound, resulting in the desired biological effect in a cell. Contacting a cell or tissue may be accomplished, for example, by intermixing or administering a compound (such as a compound of Formula I; and/or a salt, ester, prodrug and/or intermediate thereof, and/or a pharmaceutical composition comprising one or more of the foregoing).

Alternatively, contacting a cell or tissue may be accomplished by introducing a compound in a manner such that the compound will be targeted, directly or indirectly, to a cell or tissue containing p38 MAPK. Contacting a cell or tissue may be accomplished under conditions such that a compound binds to the p38 MAPK. Such conditions may include proximity of the compound and p38-containing cell or tissue, pH, temperature, or any condition that affects the binding of a compound to p38 MAPK.

In one class of embodiments, the cell is contacted with the compound in vitro; in other embodiments, the cell is contacted with the compound in vivo.

When the cell is contacted in vivo, the effective concentration (EC) is a concentration that results in a reduction in the activity of a p38 MAPK by a specified percentage (e.g., 50%, 40%, 30%, 20%, 10%) as measured by a specific physiological response which depends on the reduction of the activity of the p38 MAPK. Such physiological response may be, for example, reduction in blood or other bodily fluid concentration of TNFα. For example, $EC_{50}$, $EC_{40}$, $EC_{30}$, $EC_{20}$ and $EC_{10}$ are determined as concentrations that result in reductions in the activity of a p38 MAPK as measured by reduction in TNFα concentration by 50%, 40%, 30%, 20% and 10%, respectively on a dose-response curve. The $EC_{50}$ of the SAPK system-modulating compound is preferably in the range of about 100 µM to about 1000 µM, more preferably about 200 µM to about 800 µM for inhibition of the p38 MAPK. Thus, for example, modulation of the SAPK system may involve contacting a compound (e.g., a compound of Formula I) with a p38 MAPK at a concentration that is less than an $EC_{40}$, preferably less than $EC_{30}$, more preferably less than $EC_{20}$, even preferably less than $EC_{10}$ for inhibition of the p38 MAPK by the compound as determined on a dose-response curve in vivo.

The compound can be provided in the form of a pharmaceutical composition, together with a pharmaceutically acceptable carrier.

Screening a Library of Compounds for Low-Potency p38 Inhibitors

In another aspect, a method is provided for identifying a pharmaceutically active compound, e.g., for determining whether a compound is potentially useful as a therapeutic agent, e.g., for the prevention or treatment of an inflammatory condition (such as a p38- or cytokine-associated condition). The method includes assaying a plurality of compounds for inhibition of a p38 MAPK and selecting a compound which exhibits a relatively low potency for inhibiting p38 MAPK. Preferably, an $IC_{50}$ of such a low-potency p38 inhibitor compound is in the range of about 0.1 µM to about 1000 µM, and more preferably about 1 µM to about 800 µM, about 1 µM to about 500 µM, about 1 µM to about 300 µM, about 1 µM to about 200 µM, or about 1 µM to about 100 µM for inhibition of p38 MAPK. The plurality of compounds to be assayed is preferably selected from a library of potential compounds. The assaying of the plurality of compounds from the library may be conducted in various ways. For example, in some embodiments, the methods further comprise contacting a p38 MAPK with the plurality of compounds, and determining whether the compounds inhibit the activity of cytokines. The p38 MAPK is preferably selected from the group consisting of p38α, p38β, p38γ, and p38δ. In preferred embodiments, the contacting step takes place in vitro. In preferred embodiments, the contacting step comprises contacting a cell comprising p38 MAPK with the compound.

In yet another embodiment, methods are provided for inhibiting the activity of a p38 MAPK in a cell, in vitro or in vivo. In general, such methods include contacting a cell containing a p38 MAPK with an effective p38-inhibiting amount of a compound (e.g., a compound of Formula I), under conditions such that p38 activity in the cell is inhibited. Examples of such methods are provided in the EXAMPLES section below. The compound preferably exhibits an $IC_{50}$ in the range of about 0.1 µM to about 1000 µM, and more preferably about 1 µM to about 800 µM, about 1 µM to about 500 µM, about 1 µM to about 300 µM, about 1 µM to about 200 µM, or about 1 µM to about 100 µM for inhibition of p38 MAPK. The contacting of the p38 MAPK with the compound is preferably conducted at a SAPK system-modulating concentration that is less than $IC_{30}$, preferably less than $IC_{20}$, more preferably less than $IC_{10}$ for inhibition of the p38 MAPK by the compound.

In vivo methods include for example, introducing into a group of animals orally or by injection a compound of interest (e.g., a compound of Formula I) in various concentrations. Following the introduction of the compound, lipopolysaccharide is administered intravenously. Serum TNFα levels are measured and compared to that from control animals. The preferred compounds inhibit the release of TNFα, thus reducing TNFα levels in the blood samples of the tested animals. The compound preferably exhibits an $EC_{50}$ in the range of about 100 µM to about 1000 µM, preferably about 200 µM to about 800 µM for inhibition of the release of TNFα. In some cases, the compound exhibits an $EC_{50}$ in the range of about 10 to about 100 µM.

The method of identifying a pharmaceutically active compound may further include determining a mammalian toxicity of the selected compound. Such methods are generally known to those skilled in the art. The method of identifying a pharmaceutically active compound may also include administering the selected compound to a test subject, either in conjunction with the determination of mammalian toxicity or for other reasons. In an embodiment, the test subject test subject has or is at risk for having an inflammatory condition. Preferably the test subject is a mammal, and can be a human.

Methods of Treatment and/or Prevention

Another embodiment provides methods for treating or preventing disease states, e.g., inflammatory condition(s) and/or fibrotic conditions. The methods include identifying a subject at risk for or having an inflammatory condition and/or fibrotic condition and administering a compound to the subject in an effective amount to treat or prevent the inflammatory and/or fibrotic condition. In preferred embodiments, the compound exhibits an $IC_{50}$ in the range of about 0.1 µM to about 1000 µM, and more preferably about 1 µM to about 800 µM, about 1 µM to about 500 µM, about 1 µM to about 300 µM, about 1 µM to about 200 µM, or about 1 µM to about 100 µM for inhibition of p38 MAPK. In preferred embodiments, the effective amount produces a blood or serum or another bodily fluid concentration that is less than an $IC_{30}$ or, preferably, an $IC_{20}$ or, more preferably, an $IC_{10}$ for inhibition of a p38 MAPK by the compound. In preferred embodiments, the compound exhibits an $EC_{50}$ in the range of about 100 µM to about 1000 µM, preferably about 200 µM to about 800 µM for inhibition of TNFα secretion. In other preferred embodiments, the effective amount produces a blood or serum or another bodily fluid concentration that is less than an $EC_{30}$ or, preferably, an $EC_{20}$ or, more preferably, an $EC_{15}$ or, more preferably, an $EC_{10}$ for inhibition of LPS-stimulated TNFα release in a bodily fluid by the compound. The effective amount is preferably about 70% or less, more preferably less than about 50%, of an amount that causes an undesirable side effect in the subject, such as, but not limited to, drowsiness, gastrointestinal upset, and photosensitivity rash. The compound used for the treatment or prevention is preferably a compound of Formula I.

Methods for identifying a subject at risk for or having an inflammatory condition are known to those skilled in the art. Examples of inflammatory conditions that may be treated or prevented by the methods described herein include p38 associated conditions, e.g., conditions associated with altered cytokine activity, conditions associated with modulation of a SAPK system, autoimmune diseases, and diseases associated with acute and chronic inflammation. The cytokine (or cytokines) is (are) preferably selected from the group consisting of, but not limited to, IL-1β, IL-6, IL-8, and TNFα. In an embodiment, the compound used to treat or prevent the inflammatory condition is a compound that inhibits a kinase in the SAPK signaling pathway. Examples of preferred compounds include a compound of Formula I.

The term "p38-associated condition" means a disease or other deleterious condition in which the p38 MAP kinase signaling pathway is implicated, whether directly or indirectly. Examples of p38-associated conditions include conditions caused by IL-1β, TNFα, IL-6 or IL-8 dysregulation or overexpression resulting from sustained, prolonged, enhanced or elevated levels of p38 activity. Such conditions include, without limitation, inflammatory diseases, autoimmune diseases, fibrotic diseases, destructive bone disorders, proliferative disorders, infectious diseases, neurodegenerative diseases, allergies, reperfusion ischemia in stroke, heart attacks, angiogenic disorders, organ hypoxia, vascular hyperplasia, cardiac hypertrophy, thrombin-induced platelet aggregation, and conditions associated with the prostaglandin or cyclooxygenase pathways, e.g., conditions involving prostaglandin endoperoxide synthase. A p38-associated condition can include any condition associated with or mediated by an isoform of p38.

A "fibrotic condition," "fibroproliferative condition," "fibrotic disease," "fibroproliferative disease," "fibrotic disorder," and "fibroproliferative disorder" are used interchangeably to refer to a condition, disease or disorder that is characterized by dysregulated proliferation or activity of fibroblasts and/or pathologic or excessive accumulation of collagenous tissue. Typically, any such disease, disorder or condition is amenable to treatment by administration of a compound having anti-fibrotic activity. Fibrotic disorders include, but are not limited to, pulmonary fibrosis, including idiopathic pulmonary fibrosis (IPF) and pulmonary fibrosis from a known etiology, liver fibrosis, and renal fibrosis. Other exemplary fibrotic conditions include musculoskeletal fibrosis, cardiac fibrosis, post-surgical adhesions, scleroderma, glaucoma, and skin lesions such as keloids.

The term "modulating SAPK system" means increasing or decreasing activity of the stress-activated protein kinase system activity, e.g., by inhibiting p38 activity, whether in vitro or in vivo. In certain embodiments, the SAPK system is modulated when p38 activity in a cell is inhibited by about 50%, preferably by about 40%, more preferably by about 30%, even more preferably by about 20%, or yet even more preferably by about 10% compared to the p38 activity of an untreated control cell.

A condition associated with altered cytokine activity, as used herein, refers to a condition in which cytokine activity is altered compared to a non-diseased state. This includes, but is not limited to, conditions caused by IL-1β, TNFα, IL-6 or IL-8 overproduction or dysregulation resulting in sustained, prolonged, enhanced or elevated levels of cytokine activity, which may be associated with p38 activity. Such conditions include, without limitation, inflammatory diseases, autoimmune diseases, fibrotic diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with the cyclooxygenase and lipoxygenase signaling pathways, such as prostaglandin endoperoxide synthase. A cytokine-associated condition can include any condition associated with or mediated by IL-1 (particularly IL-1β), TNFα, IL-6 or IL-8, or any other cytokine which can be regulated by p38. In preferred embodiments, the cytokine associated condition is a condition associated with TNFα.

The methods described herein may also be used to treat autoimmune diseases and diseases associated with acute and chronic inflammation. These diseases include, but are not limited to: chronic obstructive pulmonary disease (COPD), idiopathic pulmonary fibrosis (IPF), rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute renal disease, chronic renal disease; renal fibrosis, irritable bowel syndrome; pyresis; restenosis; cerebral malaria; stroke injury, ischemic injury; neural trauma; Alzheimer's disease; Huntington's disease; Parkinson's disease; acute pain, chronic pain; allergies, including allergic rhinitis and allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, and non-small cell lung cancer; graft-versus-host reaction; and auto-immune diseases, such as Multiple Sclerosis, lupus and fibromyalgia; AIDS and other viral diseases such as Herpes Zoster, Herpes Simplex I or II, influenza virus, Severe Acute Respiratory Syndrome (SARS) and cytomegalovirus; and diabetes mellitus. In addition, the methods of the embodiments can be used to treat proliferative disorders (including both benign and malignant hyperplasias), including acute myelogenous leukemia, chronic myelogenous leukemia, Kaposi's sarcoma, metastatic melanoma, multiple myeloma, breast cancer, including metastatic breast carcinoma; colorectal. carcinoma; malignant melanoma; gastric cancer; non-small cell lung cancer (NSCLC); bone metastases, and the like; pain disorders including neuromuscular pain, headache, cancer pain, dental pain, and arthritis pain; angiogenic disorders including solid tumor angiogenesis, ocular neovascularization, and infantile hemangioma; conditions associated with the cyclooxygenase and lipoxygenase signaling pathways, including conditions associated with prostaglandin endoperoxide synthase-2 (including edema, fever, analgesia, and pain); organ hypoxia; thrombin-induced platelet aggregation. In addition, the methods described herein may be useful for the treatment of protozoal diseases in animals, including mammals.

A subject may include one or more cells or tissues, or organisms. A preferred subject is a mammal. A mammal can include any mammal. As non-limiting examples, preferred mammals include cattle, pigs, sheep, goats, horses, camels, buffalo, cats, dogs, rats, mice, and humans. A highly preferred subject mammal is a human. The compound(s) can be administered to the subject via any drug delivery route. Specific exemplary administration routes include oral, ocular, rectal, buccal, topical, nasal, ophthalmic, subcutaneous, intramuscular, intravenous (bolus and infusion), intracerebral, transdermal, and pulmonary.

The terms "therapeutically effective amount" and "prophylactically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, the assays disclosed in the following examples. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician. Preferably, the effective amount of the compound of the embodiments produces a blood or serum or another bodily fluid concentration that is less than an $IC_{30}$, $IC_{20}$ or $IC_{10}$ for inhibition of p38 MAP kinase. Preferably, the effective amount of the compound of the embodiments produces a blood or serum or another bodily fluid concentration that is effective to alter TNFα secretion from whole blood by 10%, 15%, 20%, 30%, 40% or 50%.

For any compound, the therapeutically or prophylactically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans.

Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. However, pharmaceutical compositions that exhibit narrow therapeutic indices are also within the scope of the invention. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the maximum plasma concentrations (Cmax) can range from about 0.1 µM to about 200 µM. Cmax can be about 0.5 µM to about 175 µM, about 65 µM to about 115 µM, or about 75 µM to about 105 µM, or about 85 µM to about 95 µM, or about 85 µM to about 90 µM depending upon the route of administration. In some embodiments, Cmax can be about 1 µM to about 50 µM, about 1 µM to about 25 µM, about 1 µM to about 20 µM, about 1 µM to about 15 µM, about 1 µM to about 10 µM, about 1 µM to about 5 µM. Specific Cmax values can be about 1 µM, about 2 µM, about 3 µM, about 4 µM, about 5 µM, about 6 µM, about 7 µM, about 8 µM, about 9 µM, about 10 µM, about 11 µM, about 12 µM, about 13 µM, about 14 µM, about 15 µM, about 16 µM, about 17 µM, about 18 µM, about 19 µM, about 20 µM, about 21 µM, about 22 µM, about 23 µM, about 24 µM, or about 25 µM. In general the dose will be in the range of about 100 mg/day to about 10 g/day, or about 200 mg to about 5 g/day, or about 400 mg to about 3 g/day, or about 500 mg to about 2 g/day, in single, divided, or continuous doses for a patient weighing between about 40 to about 100 kg (which dose may be adjusted for patients above or below this weight range, particularly children under 40 kg). Generally the dose will be in the range of about 1 mg/kg to about 100 mg/kg of body weight per day.

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

It will be appreciated that treatment as described herein includes preventing a disease, ameliorating symptoms, slowing disease progression, reversing damage, or curing a disease.

In one aspect, treating an inflammatory condition results in an increase in average survival time of a population of treated subjects in comparison to a population of untreated subjects. Preferably, the average survival time is increased by more than about 30 days; more preferably, by more than about 60 days; more preferably, by more than about 90 days; and even more preferably by more than about 120 days. An increase in survival time of a population may be measured by any reproducible means. In a preferred aspect, an increase in average survival time of a population may be measured, for example, by calculating for a population the average length of survival following initiation of treatment with an active compound. In an another preferred aspect, an increase in average survival time of a population may also be measured, for example, by calculating for a population the average length of survival following completion of a first round of treatment with an active compound.

In another aspect, treating an inflammatory condition results in a decrease in the mortality rate of a population of treated subjects in comparison to a population of subjects receiving carrier alone. In another aspect, treating an inflammatory condition results in a decrease in the mortality rate of a population of treated subjects in comparison to an untreated population. In a further aspect, treating an inflammatory condition results a decrease in the mortality rate of a population of treated subjects in comparison to a population receiving monotherapy with a drug that is not a compound of the embodiments, or a pharmaceutically acceptable salt, metabolite, analog or derivative thereof. Preferably, the mortality rate is decreased by more than about 2%; more preferably, by more than about 5%; more preferably, by more than about 10%; and most preferably, by more than about 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease related deaths per unit time following completion of a first round of treatment with an active compound.

In another aspect, treating an inflammatory condition results in a decrease in growth rate of a tumor. Preferably, after treatment, tumor growth rate is reduced by at least about 5% relative to/number prior to treatment; more preferably, tumor growth rate is reduced by at least about 10%; more preferably, reduced by at least about 20%; more preferably, reduced by at least about 30%; more preferably, reduced by at least about 40%; more preferably, reduced by at least about 50%; even more preferably, reduced by at least 60%; and most preferably, reduced by at least about 75%. Tumor growth rate may be measured by any reproducible means of measurement. In a preferred aspect, tumor growth rate is measured according to a change in tumor diameter per unit time.

In another aspect, treating an inflammatory condition results in a reduction in the rate of cellular proliferation. Preferably, after treatment, the rate of cellular proliferation is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating an inflammatory condition results in a reduction in the proportion of proliferating cells. Preferably, after treatment, the proportion of proliferating cells is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating an inflammatory condition results in a decrease in size of an area or zone of cellular proliferation. Preferably, after treatment, size of an area or zone of cellular proliferation is reduced by at least 5% relative to its size prior to treatment; more preferably, reduced by at least about 10%; more preferably, reduced by at least about 20%; more preferably, reduced by at least about 30%; more preferably, reduced by at least about 40%; more preferably, reduced by at least about 50%; even more preferably, reduced by at least about 60%; and most preferably, reduced by at least about 75%. Size of an area or zone of cellular proliferation may be measured by any reproducible means of measurement. In a preferred aspect, size of an area or zone of cellular proliferation may be measured as a diameter or width of an area or zone of cellular proliferation.

The methods described herein may include identifying a subject in need of treatment. In a preferred embodiment, the methods include identifying a mammal in need of treatment. In a highly preferred embodiment, the methods include identifying a human in need of treatment. Identifying a subject in need of treatment may be accomplished by any means that indicates a subject who may benefit from treatment. For example, identifying a subject in need of treatment may occur by clinical diagnosis, laboratory testing, or any other means known to one of skill in the art, including any combination of means for identification.

As described elsewhere herein, the compounds described herein may be formulated in pharmaceutical compositions, if desired, and can be administered by any route that permits treatment of the disease or condition. A preferred route of administration is oral administration. Administration may take the form of single dose administration, or the compound of the embodiments can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

The methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Diagnostic tests are contemplated as part of the methods described herein. For example, a tissue biopsy sample may be taken from a subject suffering from an inflammatory condition, e.g., a p38-associated or cytokine-associated condition. The biopsy sample can be tested to determine the level of p38 activity (or cytokine levels) present in the sample; the sample can then be contacted with a selected compound of the invention, and the p38 activity (or cytokine levels) measured to determine whether the compound has a desired effect (e.g., inhibition of p38 or cytokine activity with an $IC_{50}$ in the range of about about 0.1 µM to about 1000 µM, and preferably about 1 µM to about 800 µM, about 1 µM to about 500 µM, about 1 µM to about 300 µM, about 1 µM to about 200 µM, or about 1 µM to about 100 µM for inhibition of p38 MAPK). Such a test may be used to determine whether treatment with such a compound is likely to be effective in that subject. Alternatively, the sample may be contacted with a labeled compound (e.g., a fluorescently-labeled compound, or a radioactivity-labeled compound) and the sample then examined and the fluorescent or radioactive signal detected to determine the distribution of p38 in the tissue sample. Repeated biopsy samples taken during a course of treatment may also be used to study the efficacy of the treatment. Other diagnostic tests using the compounds described herein will be apparent to one of ordinary skill in the art in light of the teachings of this specification.

Thus, for example, an embodiment provides methods for determining the presence, location, or quantity, or any combination thereof of p38 protein in a cell or tissue sample. The methods include: a) contacting the cell or tissue sample with a compound of the invention under conditions such that the compound can bind to a p38 MAPK; and b) determining the presence, location, or quantity, or any combination thereof of the compound in the cell or tissue sample, thereby determining the presence, location, or quantity, or any combination thereof of the p38 MAPK in the cell or tissue sample. Determining the presence, location, or quantity, or any combination thereof of the compound in the cell or tissue sample may be conducted by any means that reveals the presence, location, or quantity, or any combination thereof of the compound in the cell or tissue. For example, as described previously, radioactive or fluorescent labeling methods may be used. Additional methods of determining the presence, location, or quantity, or any combination thereof of the compound will be apparent to a skilled artisan.

Another embodiment provides methods for determining: (1) whether a compound will be a useful therapeutic agent for treatment of a subject suffering from an inflammatory condition, or (2) the severity of disease or (3) the course of disease during treatment with a disease-modifying agent. The methods include: a) obtaining a cell or tissue sample from the subject before, during and after termination of treatment with a compound as described herein or another disease-modifying agent; b) contacting the sample with the compound; and c) determining the amount of the compound that binds to the sample, wherein binding to p38 MAPK by the compound is related to the amount of p38 MAPK in the sample.

Specific Examples of Diseases Contemplated to be Treated by the Compounds and Methods Described Herein

COPD

Chronic obstructive pulmonary disease (COPD) is characterized by a chronic inflammatory process in the lung that includes (1) increased number of inflammatory cells (neutrophils, macrophages and $SD8^+$ T cells) in the airways and parenchyma, (2) increased inflammatory cytokine and chemokine expression, and (3) increased number of proteases (elastases, cathepsins, and matrix metalloproteinases, MMPs). The production and action of many of potential mediators of airway inflammation are believed to be dependent on the stress-induced MAPK or p38 kinase cascade. Several reports support the association pf p38 kinase activation with as plethora of pulmonary events: LPS- and TNF-α-induced intercellular adhesion molecule-1 expression on pulmonary microvascular endothelial cells, MMP-9 activation, hypoxia-induced stimulation of pulmonary arterial cells, hyperosmolarity-induced IL-8 expression in bronchial epithelial cells, and enhanced eosinophil trafficking and survival.

Trifilieff et al. *Brit J Pharmacol* 144:1002-10 (2005) reported that CGH2466, a combined adenosine receptor antagonist, p38 MAPK and phosphodiesterase type 4 inhibitor showed potent in vitro and in vivo anti-inflammatory activities in diseases such as asthma and COPD. Underwood et al. *Am J Physiol Lung Cell Mol Physiol* 279:L895-L902 (2000) demonstrated that the potent and selective p38 MAPK inhibitor, SB239063, reduced proinflammatory cytokine production, including IL-1β, TNF-α, IL-6, and IL-8, which have been linked to airway fibrosis because of their ability to regulate fibroblast proliferation and matrix production that leads to diminished neutrophil trafficking and activation in the lung. Earlier, the same compound was found capable of altering responses associated with chronic fibrosis induced by bleomycin. This inhibitory activity was selective for the α and β isoforms of the p38. The compounds and methods described herein are useful in the treatment of COPD.

Pulmonary Fibrosis

Pulmonary fibrosis also called idiopathic pulmonary fibrosis (IPF), interstitial diffuse pulmonary fibrosis, inflammatory pulmonary fibrosis, or fibrosing alveolitis, is an inflammatory lung disorder and a heterogeneous group of conditions characterized by abnormal formation of fibrous tissue between alveoli caused by alveolitis comprising an inflammatory cellular infiltration into the alveolar septae with resulting fibrosis. The effects of IPF are chronic, progressive, and often fatal. p38 MAPK activation has been demonstrated in the lung of patients with pulmonary fibrosis. A number of investigations about pulmonary fibrosis have indicated that sustained and augmented expression of some cytokines in the lung are relevant to recruitment of inflammatory cells and accumulation of extracellular matrix components followed by remodeling of the lung architecture. In particular, proinflammatory cytokines such as TNF-α and interleukin IL-1β were demonstrated to play major roles in the formation of pneumonitis and pulmonary fibrosis. In addition, profibrotic cytokines such as TGF-α and CTGF also play critical roles in the pathogenesis of pulmonary fibrosis. Matsuoka et al. *Am J Physiol Lung Cell Mol Physiol* 283:L103-L112 (2002) have demonstrated that a p38 inhibitor, FR-167653, ameliorates murine bleomycin-induced pulmonary fibrosis. Furthermore, pirfenidone, a compound with combined anti-inflammatory, antioxidant and antifibrotic effects was found effective in experimental models of pulmonary fibrosis as well as in clinical studies (see Raghu et al. *Am J Respir Crit Care Med* 159:1061-1069 (1999); Nagai et al. *Intern Med* 41:1118-1123 (2002); Gahl et al. *Mol Genet Metab* 76:234-242 (2002); Azuma et al. *Am J Respir Crit Care Med* 165:A729 (2002)). The compounds and methods described herein are useful in the treatment of pulmonary fibrosis, such as IPF.

Renal Fibrosis

Irrespective of the nature of the initial insult, renal fibrosis is considered to be the common final pathway by which kidney disease progresses to end-stage renal failure. Stambe et al. *J Am Soc Nephrol* 15:370-379 (2004) tested an inhibitor of the active (phosphorylated) form of p38, NPC 31169, developed by Scios Inc. (San Francisco, Calif.) in a rat model of renal fibrosis, and reported a significant reduction in renal fibrosis assessed by interstitial volume, collagen IV deposition, and connective tissue growth mRNA levels. The compounds and methods described herein are useful in the treatment of renal fibrosis.

Leiomyoma

Uterine leiomyomas or fibroids are the most common pelvic tumors in women with no known long-term effective drug therapies available. Leiomyomas are characterized by increased cell proliferation and tissue fibrosis. Pirfenidone was tested on cell proliferation and collagen expression in cultured myometrial and leiomyoma smooth muscle cells, and was found to be an effective inhibitor of myometrial and leiomyoma cell proliferation (Lee et al. *J Clin Endocrinol Metab* 83:219-223 (1998)). The compounds and methods described herein are useful in the treatment of leiomyomas.

Endomyocardial Fibrosis

Endomyocardial fibrosis (EMF) is a disorder characterized by the development of restrictive cardiomyopathy. EMF is sometimes considered part of a spectrum of a single disease process that includes Löffler endocarditis (nontropical eosinophilic endomyocardial fibrosis or fibroplastic parietal endocarditis with eosinophilia). In EMF, the underlying process produces patchy fibrosis of the endocardial surface of the heart, leading to reduced compliance and, ultimately, restrictive physiology as the endomyocardial surface becomes more generally involved. Endocardial fibrosis principally involves the inflow tracts of the right and left ventricles and may affect the atrioventricular valves, leading to tricuspid and mitral regurgitation. MAPK activation was shown to contribute to arrhythmogenic atrial structural remodeling in EMF. The compounds and methods described herein are useful in the treatment and/or prevention of endomyocardial fibrosis.

Other Inflammatory Diseases

Many autoimmune diseases and diseases associated with chronic inflammation, as well as acute responses, have been linked to activation of p38 MAP kinase and overexpression or dysregulation of inflammatory cytokines. These diseases include, but are not limited to: rheumatoid arthritis; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synoviitis; muscle degeneration, bursitis; tendonitis; tenosynovitis; herniated, ruptures, or prolapsed intervertebral disk syndrome; osteopetrosis; thrombosis; cancer; restenosis; silicosis; pulmonary sarcosis; bone resorption diseases, such as osteoporosis; graft-versus-host reaction; and auto-immune diseases, such as Multiple Sclerosis, lupus and fibromyalgia; AIDS and other viral diseases such as Herpes Zoster, Herpes Simplex I or II, influenza virus and cytomegalovirus; and diabetes mellitus.

Many studies have shown that reducing the activity of p38 MAP kinase, its upstream activators or its downstream effectors, either through genetic or chemical means, blunts the inflammatory response and prevents or minimizes tissue damage (see, e.g., English, et al. *Trends Pharmacol Sci* 23:40-45 (2002); and Dong et al. *Annu Rev Immunol* 20:55-72 (2002)). Thus, inhibitors of p38 activity, which also inhibit excess or unregulated cytokine production and may inhibit more than a single pro-inflammatory cytokine, may be useful as anti-inflammatory agents and therapeutics. Furthermore, the large number of diseases associated with p38 MAP kinase-associated inflammatory responses indicates that there is a need for effective methods for treating these conditions.

Cardiovascular disease. Inflammation and leukocyte activation/infiltration play a major role in the initiation and progression of cardiovascular diseases including atherosclerosis and heart failure. Acute p38 mitogen-activated protein kinase (MAPK) pathway inhibition attenuates tissue damage and leukocyte accumulation in myocardial ischemia/reperfusion injury. The compounds and methods described herein are useful for treating cardiovascular disease.

Multiple sclerosis. Inflammation in the central nervous system occurs in diseases such as multiple sclerosis and leads to axon dysfunction and destruction. Both in vitro and in vivo observations have shown an important role for nitric oxide (NO) in mediating inflammatory axonopathy. p38 MAP kinase is activated by NO exposure and inhibition of p38 signalling was shown to lead to neuronal and axonal survival effects. OCM and IGF-1 reduced p38 activation in NO-exposed cortical neurons and improved axon survival in cultures exposed to NO, a process dependent on mitogen-activated protein kinase/extracellular signal-related kinase signalling. The compounds and methods described herein are useful for treating multiple sclerosis.

Primary graft nonfunction. Nonspecific inflammation is associated with primary graft nonfunction (PNF). Inflammatory islet damage is mediated at least partially by pro-inflammatory cytokines, such as interleukin-1β (IL-1β) and tumor necrosis factor-α (TNF-α) produced by resident islet macrophages. The p38 pathway is known to be involved in cytokine production in the cells of the monocyte-macrophage lineage. Inhibition of the p38 pathway by a chemical p38 inhibitor, SB203580, suppresses IL-1β and TNF-α production in human islets exposed to lipopolysaccharide (LPS) and/or inflammatory cytokines. Although IL-1β is predominantly produced by resident macrophages, ductal cells and islet vascular endothelial cells were found to be another cellular source of IL-1β in isolated human islets. SB203580 also inhibited the expression of inducible nitric oxide synthase (iNOS) and cyclooxygenase-2 (COX-2) in the treated islets. Furthermore, human islets treated with SB203580 for 1 h prior to transplantation showed significantly improved graft function. The compounds and methods described herein are useful for improving graft survival in clinical islet transplantation.

Acute renal injury. Cisplatin is an important chemotherapeutic agent but can cause acute renal injury. Part of this acute renal injury is mediated through tumor necrosis factor-α (TNF-α). Cisplatin activates p38 MAPK and induces apoptosis in cancer cells. p38 MAPK activation leads to increased production of TNF-α in ischemic injury and in macrophages. In vitro, cisplatin caused a dose dependent activation of p38 MAPK in proximal tubule cells. Inhibition of p38 MAPK activation led to inhibition of TNF-α production. In vivo, mice treated with a single dose of cisplatin developed severe renal dysfunction, which was accompanied by an increase in kidney p38 MAPK activity and an increase in infiltrating leukocytes. However, animals treated with the p38 MAPK inhibitor SKF86002 along with cisplatin showed less renal dysfunction, less severe histologic damage and fewer leukocytes compared with cisplatin+vehicle treated animals. The compounds and methods described herein are useful for preventing acute renal injury.

Periodontitis. The proinflammatory mediator bradykinin (BK) stimulates interleukin-8 (IL-8) production in human gingival fibroblasts in vitro and plays an important role in the pathogenesis of various inflammatory diseases including periodontitis. The specific p38 mitogen-activated protein kinase (MAPK) inhibitor SB 203580 reduced IL-8 production stimulated by the combination of BK and IL-1β as well as the IL-1β-stimulated IL-8 production. The compounds and methods described herein are useful for treating or preventing periodontitis.

Pharmaceutical Compositions

While it is possible for the compounds described herein to be administered alone, it may be preferable to formulate the compounds as pharmaceutical compositions. As such, in yet another aspect, pharmaceutical compositions useful in the methods of the invention are provided. More particularly, the pharmaceutical compositions described herein may be useful, inter alia, for treating or preventing inflammatory conditions, e.g., conditions associated with p38 activity or cytokine activity or any combination thereof. A pharmaceutical composition is any composition that may be administered in vitro or in vivo or both to a subject in order to treat or ameliorate a condition. In a preferred embodiment, a pharmaceutical composition may be administered in vivo. A subject may include one or more cells or tissues, or organisms. A preferred subject is a mammal. A mammal includes any mammal, such as by way of non-limiting example, cattle, pigs, sheep, goats, horses, camels, buffalo, cats, dogs, rats, mice, and humans. A highly preferred subject mammal is a human.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition may also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein may be formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds described herein may be formulated for oral administration in a lipid-based formulation suitable for low solubility compounds. Lipid-based formulations can generally enhance the oral bioavailability of such compounds.

As such, a preferred pharmaceutical composition comprises a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of $\alpha$-, $\beta$-, and $\gamma$-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the invention in the composition.

A pharmaceutical composition contains a total amount of the active ingredient(s) sufficient to achieve an intended therapeutic effect. More specifically, in some embodiments, the pharmaceutical composition contains a therapeutically effective amount (e.g., an amount of an SAPK-modulating compound that is effective in the prevention or treatment of the symptoms of an inflammatory disease or condition, wherein the compound exhibits an $IC_{50}$ in the range of about 0.1 µM to about 1000 µM, and preferably about 1 µM to about 800 µM, about 1 µM to about 500 µM, about 1 µM to about 300 µM, about 1 µM to about 200 µM, or about 1 µM to about 100 µM for inhibition of p38 MAPK). The total amounts of the compound that may be combined with the carrier materials to produce a unitary dosing form will vary depending upon the host treated and the particular mode of administration. Preferably, the compositions are formulated so that a dose of between 0.01 to 100 mg/kg body weight/day of an SAPK-modulating compound is administered to a patient receiving the compositions.

EXAMPLES

Synthesis of Compounds of Formula (I)

The following examples show the synthesis of specific compounds of Formula I, as depicted in Table 1, above.

Synthesis of Compound 1: Following general procedure A, compound 1 was prepared in 50% yield as an oil. MS-ESI: m/z=200.3 [M+1]$^+$ Synthesis of Compound 2: Following general procedure A, compound 2 was prepared in 73% yield as an oil. MS-ESI: m/z=200.3 [M+1]$^+$ Synthesis of Compound 3: Following general procedure A, compound 3 was prepared in 78% yield as an oil. MS-ESI: m/z=200.3 [M+1]$^+$ Synthesis of Compound 4: Following general procedure A, compound 4 was prepared in 46% yield as an oil. MS-ESI: m/z=214.3 [M+1]$^+$ Synthesis of Compound 5: Following general procedure A, compound 5 was prepared in 52% yield as a yellowish oil. MS-ESI: m/z=214.3 [M+1]$^+$ Synthesis of Compound 6: Following general procedure A, compound 6 was prepared in 86% yield as a solid. MS-ESI: m/z=214.3 [M+1]$^+$ Synthesis of Compound 7: Following general procedure A, compound 7 was prepared in 50% yield as a white solid. MS-ESI: m/z=242.2 [M+1]$^+$ Synthesis of Compound 8: Following general procedure A, compound 8 was prepared in 52% yield as an oil. MS-ESI: m/z=212.2 [M+1]$^+$ Synthesis of Compound 9: Following general procedure A, compound 9 was prepared in 79% yield as an oil. MS-ESI: m/z=212.3 [M+1]$^+$ Synthesis of Compound 10: Following general procedure A, compound 10 was prepared in 48% yield as a white solid. MS-ESI: m/z=212.3 [M+1]$^+$ Synthesis of Compound 11: Following general procedure A, compound 11 was prepared in 73% yield as an oil. MS-ESI: m/z=229.2 [M+1]$^+$ Synthesis of Compound 12: Following general procedure A, compound 12 was prepared in 81% yield as a white solid. MS-ESI: m/z=229.2 [M+1]$^+$ Synthesis of Compound 13: Following general procedure A, compound 13 was prepared in 5.5% yield as a white solid. MS-ESI: m/z=262.3 [M+1]$^+$ Synthesis of Compound 14: Following general procedure A, compound 14 was prepared in 35% yield as a white solid. MS-ESI: m/z=262.3 [M+1]$^+$ Synthesis of Compound 15: Following general procedure A, compound 15 was prepared in 49% yield as a white solid. MS-ESI: m/z=262.3 [M+1]$^+$ Synthesis of Compound 16: Following general procedure A, compound 16 was prepared in 75% yield as a solid. MS-ESI: m/z=268.3 [M+1]$^+$ Synthesis of Compound 17: Following general procedure A, compound 17 was prepared in 40% yield as a yellowish solid. MS-ESI: m/z=232.2 [M+1]$^+$ Synthesis of Compound 18: Following general procedure A, compound 18 was prepared in 79% yield as an oil. MS-ESI: m/z=232.2 [M+1]$^+$ Synthesis of Compound 19: Following general procedure A, compound 19 was prepared in 85% yield as a white solid. MS-ESI: m/z=232.2 [M+1]$^+$ Synthesis of Compound 20: Following general procedure A, compound 20 was prepared in 8% yield as an oil. MS-ESI: m/z=254.1 [M+1]$^+$ Synthesis of Compound 21: Following general procedure A, compound 21 was prepared in 62% yield as a white solid. MS-ESI: m/z=254.2 [M+1]$^+$ Synthesis of Compound 22: Following general procedure A, compound 22 was prepared in 57% yield as a white solid. MS-ESI: m/z=254.3 [M+1]$^+$ Synthesis of Compound 23: Following general procedure A, compound 23 was prepared in 30% yield as a white solid. MS-ESI: m/z=278.3 [M+1]$^+$ Synthesis of Compound 24: Following general procedure A, compound 24 was prepared in 93% yield as a white solid. MS-ESI: m/z=278.3 [M+1]$^+$ Synthesis of Compound 25: Following general procedure A, compound 25 was prepared in 17% yield as a yellowish solid. MS-ESI: m/z=292.2 [M+1]$^+$ Synthesis of Compound 26: Following general procedure A, compound 26 was prepared in 50% yield as an oil. MS-ESI: m/z=292.2 [M+1]$^+$ Synthesis of Compound 27: Following general procedure A, compound 27 was prepared in 73.5% yield as a white solid. MS-ESI: m/z=292.2 [M+1]$^+$ Synthesis of Compound 28: Following general procedure A, compound 28 was prepared in 4.5% yield as a white solid. MS-ESI: m/z=230.1 [M+1]$^+$ Synthesis of Compound 29: Following general procedure A, compound 29 was prepared in 25% yield as an oil. MS-ESI: m/z=230.1 [M+1]$^+$ Synthesis of Compound 30: Following general procedure A, compound 30 was prepared in 25% yield as an oil. MS-ESI: m/z=230.2 [M+1]$^+$ Synthesis of Compound 31: Following general procedure A, compound 31 was prepared in 52% yield as a white solid. MS-ESI: m/z=260.1 [M+1]$^+$ Synthesis of Compound 32: Following general procedure A, compound 32 was prepared in 23.8% yield as a solid, using triethylamine as a base, instead of pyridine. MS-ESI: m/z=241.2 [M+1]$^+$ Synthesis of Compound 33: Following general procedure A, compound 33 was prepared in 81% yield as a white solid. MS-ESI: m/z=211.2 [M+1]$^+$ Synthesis of Compound 34: Following general procedure A, compound 34 was prepared in 80% yield as a reddish solid, after crystallization. MS-ESI: m/z=244.4 [M+1]$^+$ Synthesis of Compound 35: Following general procedure A, compound 35 was prepared in 82% yield as a yellowish solid. MS-ESI: m/z=230.4 [M+1]$^+$ Synthesis of Compound 36: Following general procedure A, compound 36 was prepared in 71% yield as a solid. MS-ESI: m/z=244.2[M+1]$^+$ Synthesis of Compound 37: Following general procedure A, compound 37 was prepared in 72% yield as a white solid. MS-ESI: m/z=228.0 [M+1]$^+$ Synthesis of Compound 38: Following general procedure A, compound 38 was prepared in 75% yield as a white solid. MS-ESI: m/z=227.9 [M+1]$^+$ Synthesis of Compound 39: Following general procedure A, compound 39 was prepared in 38% yield as a white solid. MS-ESI: m/z=242.9 [M+1]$^+$ Synthesis of Compound 40: Following general procedure A, compound 40 was prepared in 81% yield as a white solid. MS-ESI: m/z=188.0 [M+1]$^+$ Synthesis of Compound 41: Following general procedure A, compound 41 was prepared in 85% yield as a white solid. MS-ESI: m/z=308.2 [M+1]$^+$ Synthesis of Compound 42: Following general procedure A, compound 42 was prepared in 91% yield as a white solid. MS-ESI: m/z=308.2 [M+1]$^+$ Synthesis of Compound 43: Following general procedure A, compound 43 was prepared in 70% yield as a solid. MS-ESI: m/z=286.1 [M+1]$^+$ Synthesis of Compound 44: Following general procedure A, compound 44 was prepared in 23.8% yield as a white solid. MS-ESI: m/z=241.2 [M+1]$^+$ Synthesis of Compound 45: Following general procedure A, compound 45 was prepared in 80% yield as a solid. MS-ESI: m/z=197.3 [M+1]$^+$ Synthesis of Compound 46:

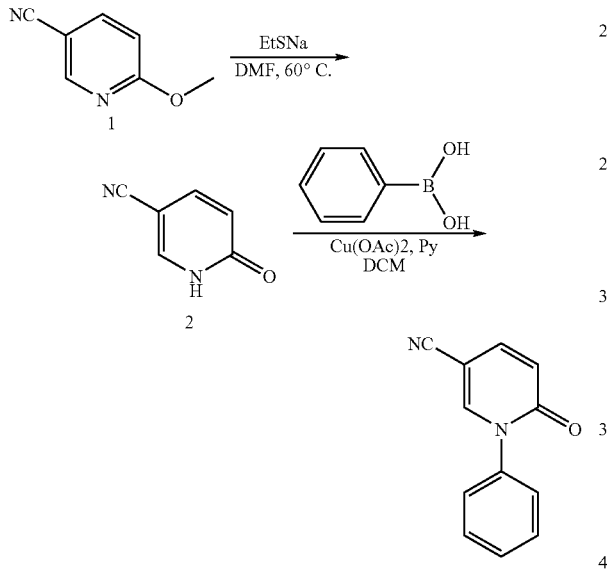

A solution of 1 (134 mg, 1 mmol), EtSNa (168 mg, 2 mmol) in DMF (5 ml) was heated to 60° C. for 4 h. To the reaction mixture was added HCl (aq.) until pH was about 6. The mixture was evaporated in vacuo to give 2. (110 mg, 92%). Pyridine (140 mg, 1.8 mmol) was slowly added to a mixture of 2 (110 mg, 0.9 mmol), phenylboronic acid (220 mg, 1.8 mmol) and Cu(OAc)$_2$ (18 mg) in DCM (5 mL). After the suspension was stirred overnight at room temperature, it was monitored by TLC. When no starting material was detected, the mixture was washed with saturated NaHCO$_3$. The organic layer was dried over sodium sulfate, evaporated in vacuo to afford the crude product, which was purified by preparative TLC to give compound 46 (50 mg, 25% yield) as a white solid. MS-ESI: m/z=197.3 [M+1]$^+$ Synthesis of Compound 47: Following general procedure A, compound 47 was prepared in 65% yield as a white solid. MS-ESI: m/z=251.2 [M+1]$^+$, 253.2 [M+3]$^+$ Synthesis of Compound 48: Following general procedure A, compound 48 was prepared in 23% yield as a solid. MS-ESI: m/z=189.2 [M+1]$^+$ Synthesis of Compound 49: Following general procedure A, compound 49 was prepared in 1% yield as a solid. MS-ESI: m/z=189.2 [M+1]$^+$ Synthesis of Compound 50: Following general procedure A, compound 50 was prepared in 2% yield as a white solid. MS-ESI: m/z=203.2 [M+1]$^+$ Synthesis of Compound 51: Following general procedure B, compound 51 was prepared in 34% yield as a white solid. MS-ESI: m/z=241.2 [M+1]$^+$ Synthesis of Compound 52: Following general procedure B, compound 52 was prepared in 22% yield as a white solid. MS-ESI: m/z=241.2 [M+1]$^+$ Synthesis of Compound 53: A mixture of 3-Bromo-1H-pyridin-2-one (150 mg, 0.6 mmol)), thienyl boromic acid (160 mg, 1.25 mmol)), Pd(PPh$_3$)$_2$Cl$_2$ (30 mg, 0.07 mmol) and Na$_2$CO$_3$ (200 mg, 1.88 mmol) in toluene (20 mL) and water (5 mL) was heated at 60° C. overnight under nitrogen atmosphere. Then, water (20 mL) was added and the aqueous layer was extracted with CH$_2$Cl$_2$ (30 mL×2). The organics were washed by water and brine, dried over Na$_2$SO$_4$, and concentrated in vacuo. The residue was purified by prep-TLC to give compound 52 (85 mg, 56% yields) as a yellowish solid. MS-ESI: m/z=254.3 [M+1]$^+$ Synthesis of Compound 54: Following general procedure A, compound 54 was prepared in 78% yield as a white solid. MS-ESI: m/z=278.1 [M+1]$^+$ Synthesis of Compound 55: Following general procedure D, compound 55 was prepared in 65% yield as a solid. MS-ESI: m/z=274.3 [M+1]$^+$ Synthesis of Compound 56: Following general procedure D, compound 56 was prepared in 60% yield as a solid. MS-ESI: m/z=254.3 [M+1]$^+$ Synthesis of Compound 57:

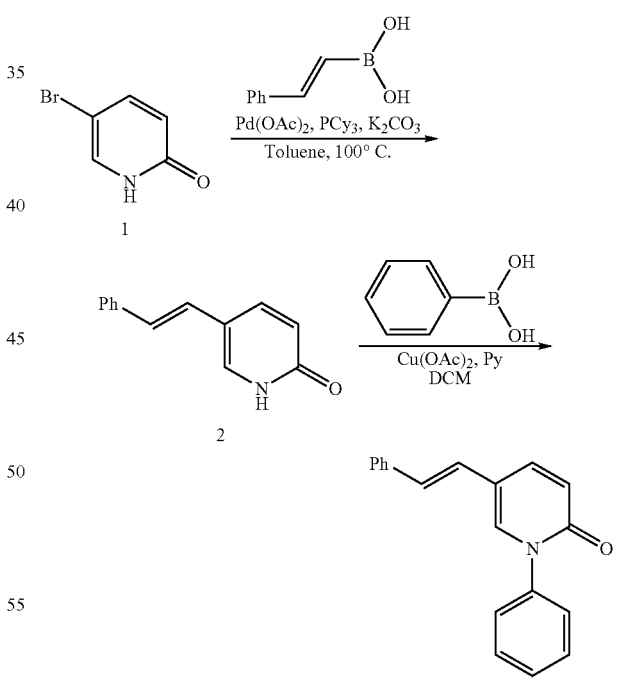

Following general procedure E, compound 57 was synthesized (yield of first step 51%; yield of second step 17%). MS-ESI: m/z=274.3 [M+1]$^+$ Synthesis of Compound 58: Following general procedure E, compound 58 was prepared in 61% yield as a solid. MS-ESI: m/z=254.3 [M+1]$^+$ Synthesis of Compound 59:

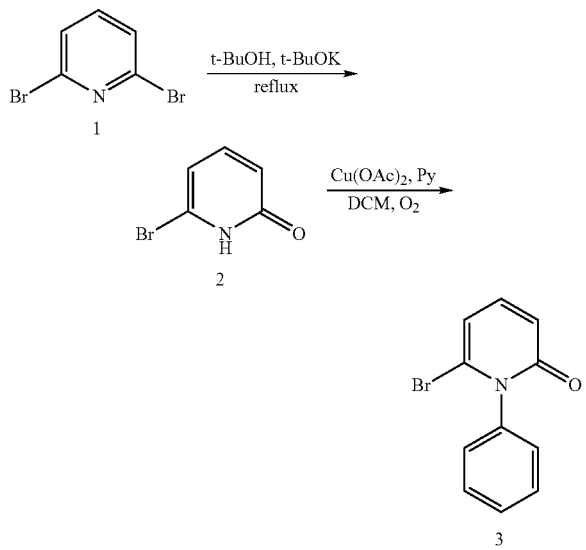

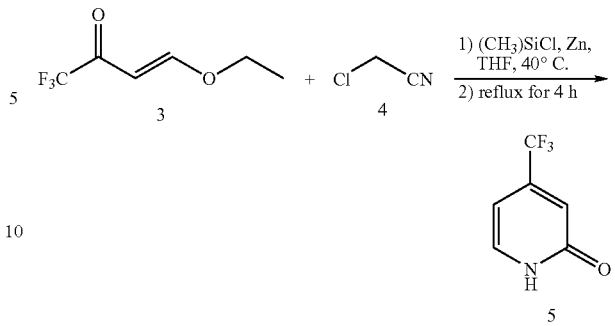

A mixture of 2, 6-dibromopyridine (1) (4 g, 17 mmol), potassium t-butoxide (20 g, 0.27 mol), and redistilled t-butyl alcohol (100 mL) was refluxed overnight. After cooling, the solvent was removed in vacuo, ice/water was carefully added, and the aqueous layer was extracted with chloroform (100 mL×2), which removed the unreacted staring material. The aqueous layer was acidified with 3 N HCl, extracted with chloroform (100 mL×2), washed with brine, dried over anhydrous $Na_2SO_4$ and concentrated affording pure 6-bromo-2-pyridone (2.5 g, 85% yields) as a white solid. The preparation of 3 followed the general procedure A, in a 73% yield. 3 was then subjected to the conditions of general procedure A to prepare compound 59 in 35% yield as a yellowish oil. MS-ESI: m/z=274.3 [M+1]$^+$ Synthesis of Compound 60: Compound 60 is synthesized in a similar fashion as compound 59, in 7.9% yield as a yellowish oil. MS-ESI: m/z=254.2 [M+1]$^+$ Synthesis of Compound 61:

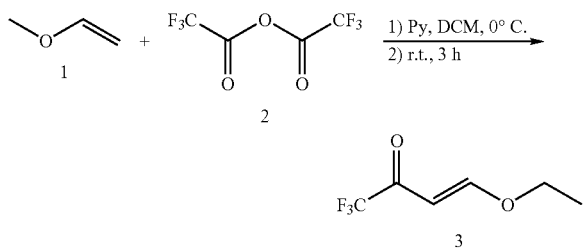

To a solution of ethyl vinyl ether (1, 40 mL) in 100 ml of dichloromethane, pyridine (36 mL) was added. Then a solution of trifluoroacetic anhydride (87.6 g) in 50 mL of dichloromethane was added at 0° C. After stirring at room temperature for 30 min, the solution was poured into 40 mL of $H_2O$. The layers were separated and the aqueous layer was extracted again with 40 mL of dichloromethane. The organic layers were combined, washed with $H_2O$ and dried over $MgSO_4$. Removal of solvent the gave crude 3, which was used directly in the next step.

Trimethylchlorosilane (26.5 mL, 150 mmol) was added to the solution of zinc powder (10 g, 150 mmol) in anhydrous THF (150 ml) under $N_2$. After stirring for 0.5 h, a solution of chloroacetonitrile (6.35 mL, 100 mmol) and trifluoroacetylvinyl ether (8.4 g, 50 mmol) in anhydrous THF (75 mL) was added dropwise slowly to keep the temperature at 40° C. The mixture was refluxed for 2 h. After cooling to room temperature, concentrated HCl (25 mL) was added. The mixture was refluxed for 1 h, then cooled to room temperature. The reaction mixture was then poured into ice water. The product was extracted with EA, and washed with brine. The organic layer was dried over anhydrous $Na_2SO_4$, filtered and evaporated to dryness to give the residue. The residue was purified by column chromatography to afford 8.3 g of 5.

Following general procedure A, compound 61 was prepared in 52% yield as a white solid. MS-ESI: m/z=284.0 [M+1]$^+$ Synthesis of Compound 62: Following general procedure outlined for compound 61, compound 62 was prepared in 80% yield as a solid. MS-ESI: m/z=283.0 [M+1]$^+$ Synthesis of Compound 63: Following general procedure outlined for compound 61, compound 63 was prepared in 78% yield as a white solid. MS-ESI: m/z=307.9 [M+1]$^+$ Synthesis of Compound 64: Following general procedure F, compound 64 was prepared in 79% for the first step and 65% for the second step, to produce an oil. MS-ESI: m/z=290.1 [M+1]$^+$ Synthesis of Compound 65: Following general procedure F, compound 65 was prepared in 64% for the first step and 60% for the second step, to produce a yellowish solid. MS-ESI: m/z=290.2 [M+1]$^+$ Synthesis of Compound 66: Following general procedure F, compound 66 was prepared in 80% for the first step and 56% for the second step. MS-ESI: m/z=250.2 [M+1]$^+$ Synthesis of Compound 67: Following general procedure F, compound 67 was prepared in 85% for the first step. The second step was performed at 0° C., using DCM as the solvent, giving compound 67 in 76% yield for the second step. MS-ESI: m/z=268.2 [M+1]$^+$ Synthesis of Compound 68: Following general procedure F, compound 68 was prepared in 10% for the first step and 15% for the second step to give a white solid. MS-ESI: m/z=222.7 [M+1]$^+$ Synthesis of Compound 69: Following general procedure F, compound 69 was prepared in 79% for the first step and 59% for the second step. MS-ESI: m/z=222.7 [M+1]$^+$ Synthesis of Compound 70: Following general procedure F, compound 70 was prepared in 75% for the first step and 63% for the second step. MS-ESI: m/z=223.2 [M+1]$^+$ Synthesis of Compound 71: Following general procedure F, compound 71 was prepared in 85% for the first step. The second step was carried out at room temperature in a capped plastic tube for 6 hours to give an oil in a 50% yield for the second step. MS-ESI: m/z=265.2 [M+1]$^+$ Synthesis of Compound 72:

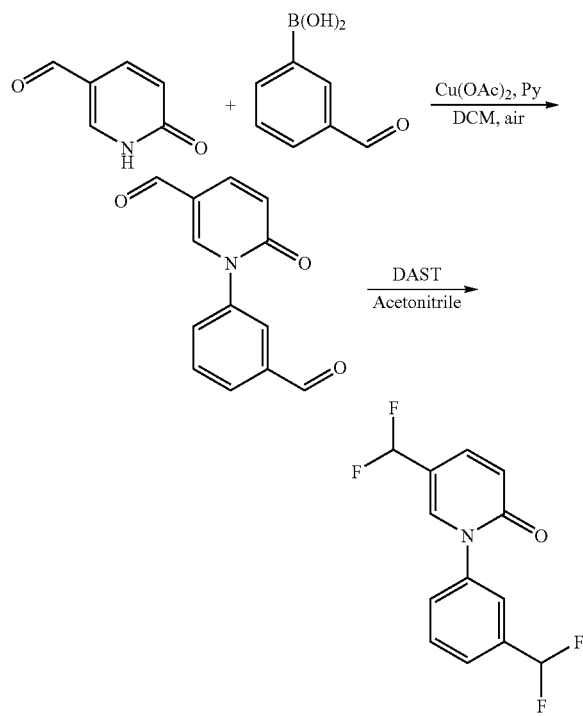

Following general procedure F, compound 72 was prepared in 89% for the first step and 53% for the second step, where in the second step, 4 eq of DAST was used. MS-ESI: m/z=272.0 [M+1]$^+$ Synthesis of Compound 73: Following general procedure F, compound 73 was prepared in 89% for the first step and 58% for the second step to give an oil, where in the second step, 4 eq of DAST was used. MS-ESI: m/z=272.0 [M+1]$^+$ Synthesis of Compound 74: Following general procedure F, compound 74 was prepared in 85% for the first step and 56% for the second step to give an oil, where in the second step, 6 eq of DAST was used. MS-ESI: m/z=286.0 [M+1]$^+$ Synthesis of Compound 75: Following general procedure F, compound 75 was prepared in 71.4% for the first step and 39% for the second step to give a white solid, where in the second step, 6 eq of DAST was used. MS-ESI: m/z=286.0 [M+1]$^+$ Synthesis of Compound 76: Following general procedure F, compound 76 was prepared in 89% for the first step and 57% for the second step to give a white solid. MS-ESI: m/z=290.0 [M+1]$^+$ Synthesis of Compound 77: Following general procedure G, compound 77 was prepared in 20% yield as a white solid. MS-ESI: m/z=291.9 [M+1]$^+$ Synthesis of Compound 78: Following general procedure G, compound 78 was prepared in 38% yield as a white solid. MS-ESI: m/z=291.0 [M+1]$^+$ Synthesis of Compound 79: Following general procedure G, compound 79 was prepared in 78% yield as a white solid. MS-ESI: m/z=315.9 [M+1]$^+$ Synthesis of Compound 80: Following general procedure G, compound 80 was prepared in 83% yield as a solid. MS-ESI: m/z=290.0 [M+1]$^+$ Synthesis of Compound 81: Following general procedure G, compound 81 was prepared in 85% yield as a solid. MS-ESI: m/z=290.0 [M+1]$^+$ Synthesis of Compound 82: Following general procedure G, compound 82 was prepared in 70% yield as a white solid. MS-ESI: m/z=304.9 [M+1]$^+$ Synthesis of Compound 83: Following general procedures G then F, compound 83 was prepared in 90% for first step and 25% yield for second step (fluorination) as a yellowish oil. MS-ESI: m/z=298 [M+1]$^+$ Synthesis of Compound 84: Following general procedures G then F, compound 84 was prepared in 83% for first step and 54% yield for second step (fluorination). MS-ESI: m/z=298.4 [M+1]$^+$ Synthesis of Compound 85: Following general procedures G then F, compound 85 was prepared in 86% for first step and 49% yield for second step (fluorination). MS-ESI: m/z=312.0 [M+1]$^+$ Synthesis of Compound 86: Following general procedures G then F, compound 86 was prepared in 82% for first step and 56% yield for second step (fluorination). MS-ESI: m/z=312.0 [M+1]$^+$ Synthesis of Compound 87: Following general procedures A then F, compound 87 was synthesized in 86% yield then 20% yield for the second step (fluorination). MS-ESI: m/z=236 [M+1]$^+$ Synthesis of Compound 88: Following general procedures A then F, compound 88 was synthesized in 65% yield then 25% yield for the second step (fluorination). MS-ESI: m/z=236 [M+1]$^+$ Synthesis of Compound 89: Following general procedures A then F, compound 89 was synthesized in 72% yield then 26% yield for the second step (fluorination). MS-ESI: m/z=250.0 [M+1]$^+$ Synthesis of Compound 90: Following general procedures A then F, compound 90 was synthesized in 75% yield then 27% yield for the second step (fluorination). MS-ESI: m/z=250.0 [M+1]$^+$ Synthesis of Compound 91:

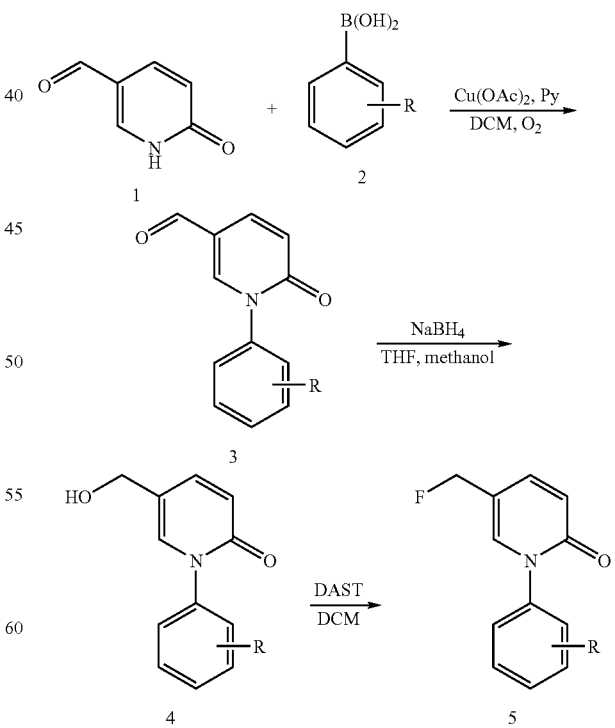

3, above, was prepared using general procedure A. 4 was prepared in the following manner. To a solution of 3 (1 eq) in tetrahydrofuran-methanol (10:1) was added sodium borohydride (5 eq) at 0° C. The mixture was stirred at room temperature for 30 min. Water was added and then mixture was extracted with EA. The organics were washed with brine, dried over $Na_2SO_4$ and concentrated in vacuo. 4 was isolated by prep-TLC. 5 was prepared according to general procedure F. Compound 91 was prepared under these reaction conditions to provide 86% yield of first step, 70% yield of second step, and 30% yield of third step. MS-ESI: m/z=272.2 [M+1]$^+$ Synthesis of Compound 92: Similar to synthesis of compound 91, compound 92 was prepared to provide 82% yield of first step, 85% yield of second step, and 15% yield of third step. MS-ESI: m/z=272.3 [M+1]$^+$ Synthesis of Compound 93: Similar to synthesis of compound 91, compound 93 was prepared to provide 80% yield of first step, 79.5% yield of second step, and 50% yield of third step. MS-ESI: m/z=232.3 [M+1]$^+$ Synthesis of Compound 94: Similar to synthesis of compound 91, compound 94 was prepared to provide 82.9% yield of first step, 51% yield of second step, and 32% yield of third step. MS-ESI: m/z=250.2 [M+1]$^+$ Synthesis of Compound 95:

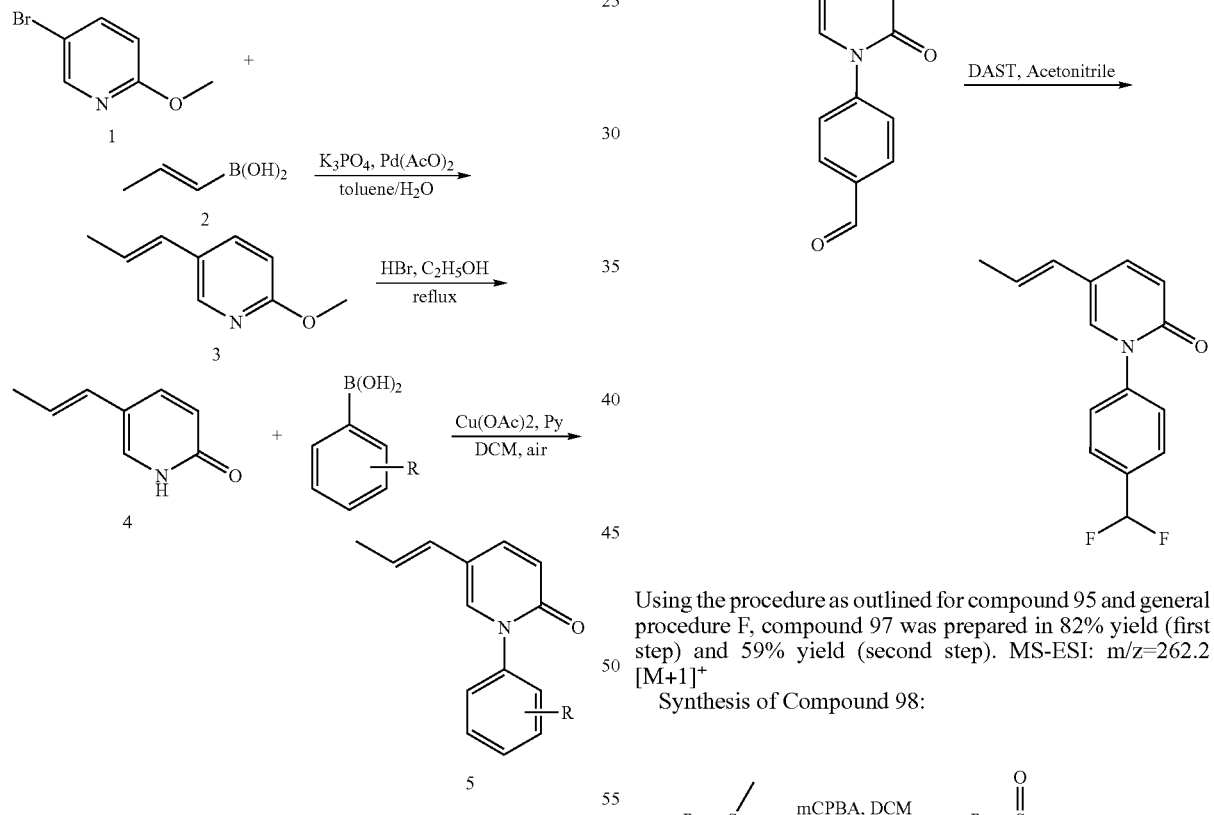

To a solution of 5-bromo-2-methoxy-pyridine (2.4 g, 8.94 mmol), (E)-prop-1-enylboronic acid (1 g, 11.6 mmol), $K_3PO_4$ (6.6 g, 31.3 mmol) and tricyclohexylphosphine (250 mg, 0.894 mmol) in toluene (40 mL) and water (2 mL) under a nitrogen atmosphere was added palladium acetate (100 mg, 0.447 mmol). The mixture was heated to 100° C. for 3 h and then cooled to room temperature. Water (100 mL) was added and the mixture extracted with EA (2×150 mL), the combined organics were washed with brine (100 mL), dried over $Na_2SO_4$ and concentrated in vacuo. The product was purified by column chromatography to give 1.3 g of compound 3 (68.4%, yield). Compound 3 (1.3 g, 8.72 mmol) was added to a stirred solution of hydrobromic acid (9.7 mL) in absolute ethanol (234 mL) under nitrogen and the mixture was heated under reflux for 5 hours. The cooled solution was evaporated in vacuo, and the residue partitioned between 10% sodium carbonate solution and DCM. The organic phase was dried with $Na_2SO_4$ and evaporated in vacuo to give 1.04 g of compound 4 as a white solid. (89% yield). Compound 5 was prepared using general procedure A. Compound 95 was prepared to give 85% yield of an oil. MS-ESI: m/z=255.3 [M+1]$^+$ Synthesis of Compound 96: Similar to synthesis of compound 95, compound 96 was prepared to provide 89% yield as a white solid. MS-ESI: m/z=280.2 [M+1]$^+$ Synthesis of Compound 97:

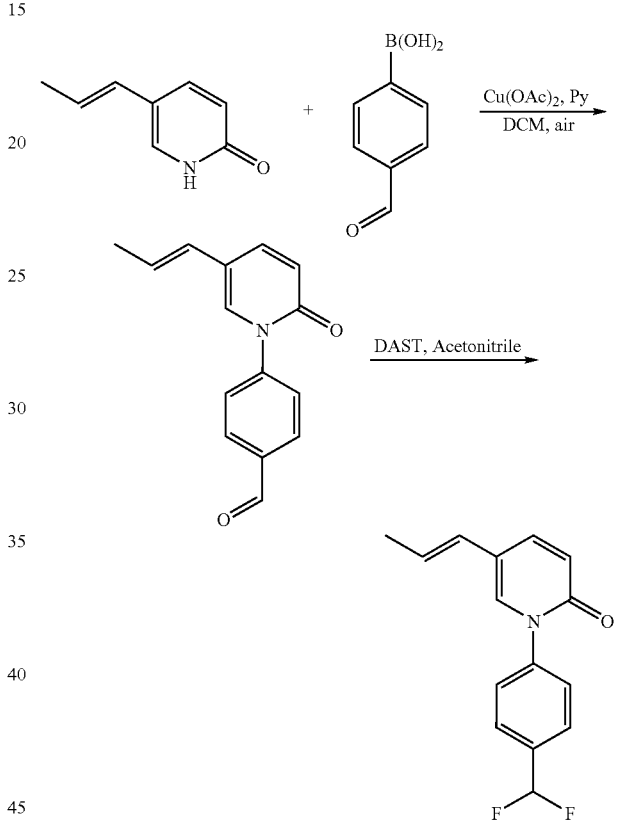

Using the procedure as outlined for compound 95 and general procedure F, compound 97 was prepared in 82% yield (first step) and 59% yield (second step). MS-ESI: m/z=262.2 [M+1]$^+$ Synthesis of Compound 98:

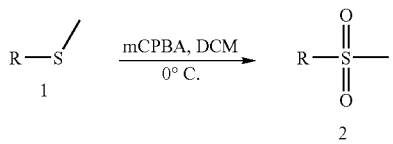

Meta-chloroperbenzoic acid (mCPBA, 5 eq.) was added to the solution of 1 in DCM at −78° C. The reaction was stirred at 0° C. for 20 minutes, then filtered. The reaction filtrate was purified by prep-TLC to give 2. Following this general procedure, compound 18 was subjected to these conditions to provide compound 98 in 22% yield as a white solid. MS-ESI: m/z=263.9 [M+1]$^+$ Synthesis of Compound 99: Similar to the synthesis of compound 98, compound 99 was prepared from compound 19 to provide compound 99 in 40% yield as a yellowish solid. MS-ESI: m/z=264 [M+1]+

Synthesis of Compound 100: Similar to the synthesis of compound 98, compound 100 was prepared from compound 67 to provide compound 100 in 80% yield as a white solid. MS-ESI: m/z=300.2 [M+1]+

Synthesis of Compound 101:

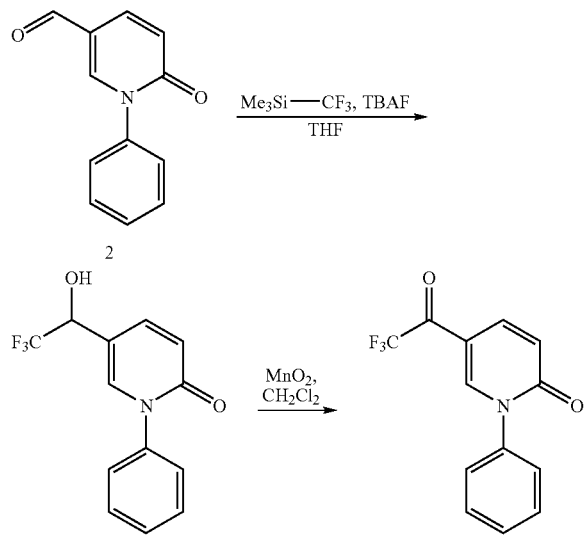

2 is prepared using general procedure A in 84% yield. A mixture of 2 (1 g, 5 mmol) and trimethyl-trifluoromethyl-silane (3.5 mL, 2M in THF, 7 mmol) in THF (20 mL) was cooled to 0° C. in an ice bath and treated with tetrabutylammonium fluoride (0.25 mL, 1 M in THF, 0.25 mmol) under nitrogen atmosphere at 0° C. for 30 min. The mixture was warmed to room temperature and stirred 24 h. Then, 1 M HCl (50 mL) was added, and the mixture was stirred overnight. The aqueous layer was extracted with EA (50 mL×2) and the organic layer was concentrated. The desired product was separated by column chromatography to give pure intermediate (0.94 g, 70% yield) as yellow solid. MS-ESI: m/z=270.2 [M+1]+ The intermediate (50 mg, 0.19 mmol) and manganese dioxide (165 mg, 1.9 mmol) were stirred overnight at room temperature in DCM (5 mL). The progress of the reaction was detected by TLC. Upon completion, the crude mixture was filtered through a pad of celite and the filtrate was concentrated. Compound 101 was isolated by washing the crude with petroleum ether to give pure product (36 mg, 70% yields) as a white solid. MS-ESI: m/z=268.2 [M+1]+

Synthesis of Compound 102: Following general procedure A, compound 102 was prepared in 80% yield as a white solid. MS-ESI: m/z=268.2 [M+1]+

Synthesis of Compound 103: Compound 103 was prepared from compound 102. A mixture of compound 102 (2 g, 10 mmol) and trimethyl-trifluoromethyl-silane (7 ml, 2M in THF, 15 mmol) in THF (40 mL) was cooled to 0° C. in an ice bath and then treated with tetrabutylammonium fluoride (0.5 ml, 1 M in THF, 0.5 mmol) under nitrogen atmosphere at 0° C. for 30 min. The mixture was warmed to room temperature and stirred 24 h. Then, 1 M HCl (50 mL) was added and the mixture was stirred overnight. The aqueous layer was extracted with EA (70 mL×2) and the organic layer was concentrated. The desired product was separated by column chromatography to give pure compound 103 (1.5 g, 45% yields) as a white solid.
MS-ESI: m/z=338.3 [M+1]+

Synthesis of Compound 104: Compound 104 was prepared from compound 103. Potassium bromate (16.6 g, 0.1 mol) was added over 0.5 h to a vigorously stirred mixture of 2-iodobenzoic acid (20 g, 0.08 mmol) and 180 mL 0.73 M H2SO4 (0.13 mol) in a 55° C. bath. The mixture was stirred for 4 h at 68° C., and the Br2 formed was removed by reduced pressure in the reaction process. The reaction was cooled to room temperature with an ice bath. Filtration and washing of the solid with ice water and iced ethanol gave the desired compound IBX (16 g, 70% yield). Compound 103 (1 g, 3 mmol) was dissolved in EA (50 mL), and IBX (4 g, 15 mmol) was added. The resulting suspension was immersed in an oil bath set to 80° C. and stirred vigorously open to the atmosphere overnight. The reaction was cooled to room temperature and filtered. The filter cake was washed with EA, and the combined filtrates were concentrated. The desired compound was obtained (0.98 g, 98% yields) as a white solid. MS-ESI: m/z=336 [M+1]+

Synthesis of Compound 105: Compound 105 was prepared from compound 104. Compound 104 (80 mg, 0.24 mmol) in dry DCM (1.5 mL) was added at the temperature of −78° C. under N2 atmosphere to a solution of DAST (50 mg, 0.31 mmol) in DCM (0.5 mL). The mixture was stirred at −78° C. for 2 h, and then warmed to room temperature overnight. The reaction mixture was diluted with DCM (20 mL), and poured into saturated NaHCO3 (30 mL). The organic phase was separated and dried over Na2SO4 and concentrated in vacuo. Compound 105 was isolated by thin-layer chromatography (42 mg, 50% yields) as a white solid. MS-ESI: m/z=340.2 [M+1]+

Synthesis of Compound 106: Compound 106 was prepared from compound 104. Compound 104 (100 mg, 0.3 mmol) was dissolved in acetonitrile (1.2 mL), and DAST (100 mg, 0.6 mmol) was added. Fluorination was carried out at 80° C. in a pressure vessel for 4 h. After cooling to room temperature, the reaction mixture was diluted with DCM (20 mL), and poured into the saturated sodium bicarbonate solution (30 mL). The organic phase was separated and dried over sodium sulfate. Compound 106 was isolated by prep-TLC (20 mg, 20% yields) as a yellowish solid. MS-ESI: m/z=357.7 [M+1]+

Synthesis of Compound 107: Compound 107 was prepared from compound 104. A mixture of Compound 104 (80 mg, 0.24 mmol) and trimethyl-trifluoromethyl-silane (0.07 mL pure, 0.49 mmol) in THF (2.5 mL) cooled to 0° C. in an ice bath is treated with tetrabutylammonium fluoride (0.5 mL, 0.024 M in THF, 0.012 mmol) under nitrogen atmosphere at 0° C. for 30 min. The mixture was raised to room temperature and stirred 24 h. Then, 1 M HCl (20 mL) was added and the mixture was stirred overnight. The aqueous layer was extracted with EA (30 mL×2) and the organic layers were concentrated. The desired product was separated out by washing the crude with EA to give Compound 107 (50 mg, 52% yield) as a yellowish solid. MS-ESI: m/z=406.2 [M+1]+

Synthesis of Compound 108: A slurry of pyrimidin-2(1H)-one (1 g, 10.4 mmol), triphenylbismuth (6.88 g, 15.6 mmol), anhydrous Cu(OAc)2 (2.84 g,15.6 mmol) and NEt3 (2.5 mL) in anhydrous DCM (16 mL) was stirred at room temperature under a nitrogen atmosphere. After a period of two days, the solution became gelatinous and changed from deep blue to light green. The reaction mixture was diluted with DCM then filtered. The filtrate was washed with NaHCO3, EDTA and NaCl (aq) and then dried with Na2SO4. Compound 108 was isolated by flash column chromatography (358 mg, 20% yield). MS-ESI: m/z=173.2 [M+1]+

Synthesis of Compounds 109 & 110: Compound 109 was prepared from compound 108. Sodium borohydride (200 mg 5.26 mmol) was added slowly to a solution of Compound 108 (90 mg, 0.526 mmol) in acetic acid (32 mL) and the mixture was stirred for 30 min at room temperature. The reaction mixture was neutralized cautiously with aqueous sodium hydroxide, on an ice-water bath, and then extracted with dichloromethane and dried over anhydrous magnesium sulfate. Compound 109 (78 mg, 39%, MS-ESI: m/z=173.2 [M+1]+) and Compound 110 (59 mg, 29%, MS-ESI: m/z=177.2 [M+1]+) were obtained by prep-TLC.

Synthesis of Compound 111: Following general procedure A, compound 112 was prepared in 45% yield as a white solid. MS-ESI: m/z=242.2 [M+1]+

Synthesis of Compound 112: Following general procedure A, compound 113 was prepared in 72% yield as an oil. MS-ESI: m/z=230.2 [M+1]+

Synthesis of Compound 113: Following general procedure A, compound 114 was prepared in 75% yield as a solid. MS-ESI: m/z=268.2 [M+1]+

Synthesis of Compound 114: Following General procedure H2, compound 114 was synthesized in 20% yield. '1H NMR (300 MHz, DMSO-d$_6$) ppm 7.68 (dd, 1H), 7.45-7.61 (m, 5H), 6.50 (dd, 1H), 6.33 (td, 1H)

Synthesis of Compound 115: A for compound 115 was prepared in the following manner. A solution of 5-cyano-2-methoxy pyridine (1 eq), sodium ethylsulfide (EtSNa) (2 eq) in DMF (5 ml/eq) was heated to 60° C. for 4 h. To the reaction mixture was added HCl-Et$_2$O until the mixture reached a pH of about 6, under nitrogen flush, in order to remove volatiles (Et2O and EtSH). The mixture was centrifuged and filtered, which removed the sodium chloride. The DMF solution was used as prepared in General procedure H2 to provide compound 115 in 21% yield. $^1$H NMR (300 MHz, DMSO-d6) ppm 8.63 (d, 1H), 7.77 (dd, 1H), 7.64 (m, 2H), 7.55 (m, 2H), 6.61 (d, 1H)

Synthesis of Compound 116: For compound 116, A was prepared according to general procedure I, as follows.

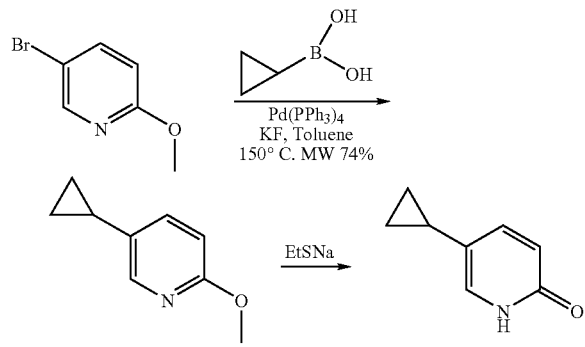

The 5-bromo-2-methoxy-pyridine (750 mg, 4 mmol), cyclopropyl boronic acid (1.08 g, 12.5 mmol) KF (760 mg, 13 mmol) and Pd(PPh$_3$)$_4$ were dissolved in toluene (12 ml) and the reaction mixture was heated at 150° C. by microwave for 1.5 h. The crude was purified by column chromatography to give the intermediate (1.33 g 74% yield) as colorless oil. To a magnetically stirred solution of 5-cyclopropyl-2-methoxy-pyridine (1.33 g, 8.9 mmol), in 30 mL of DMF, EtSNa (1.502 g, 17.8 mmol) was added. The mixture was heated at 90° C. for 24 h. The reaction was cooled at room temperature and HCl/Et$_2$O was added until pH 6. EtSH formed. The remaining HCl/Et$_2$O and EtSH was evaporated by bubbling N$_2$ at 40° C. The solution of A (concentration 40 mg/ml) was use as such for the next step. Following general procedure H1A, compound 116 was prepared in 25% yield. $^1$H NMR (300 MHz, DMSO-d6) ppm 8.65-8.77 (m, 2H), 7.51-7.57 (m, 2H), 7.48 (d, 1H), 7.30 (dd, 1H), 6.46 (d, 1H), 1.69-1.85 (m, 1H), 0.76-0.87 (m, 2H), 0.57-0.66 (m, 2H)

Synthesis of Compound 117: Compound A for compound 117 was prepared as stated for compound 116. The prepared compound A was used in General procedure H1A to provide compound 117 in 25% yield. $^1$H NMR (300 MHz, DMSO-d$_6$) ppm 10.10 (s, 1H), 7.65 (t, 1H), 7.51-7.61 (m, 1H), 7.36-7.45 (m, 2H), 7.25 (dd, 1H), 7.04 (ddd, 1H), 6.41 (d, 1H), 2.06 (s, 3H), 1.67-1.84 (m, 1H), 0.73-0.87 (m, 2H), 0.52-0.63 (m, 2H)

Synthesis of Compound 118: Compound A for compound 118 was prepared as stated for compound 116. The prepared compound A was used in General procedure H1A to provide compound 118 in 18% yield. $^1$H NMR (300 MHz, DMSO-d$_6$) ppm 7.56 (m, 2H), 7.49 (m, 2H), 7.46 (d, 1H), 7.28 (dd, 1H), 6.44 (d, 1H), 1.67-1.84 (m, 1H), 0.73-0.89 (m, 2H), 0.54-0.65 (m, 2H)

Synthesis of Compound 119: Following General procedure H2, compound 119 was synthesized in 45% yield. '1H NMR (300 MHz, DMSO-d$_6$) ppm 7.63 (ddd, 1H), 7.31-7.58 (m, 6H), 6.40-6.55 (m, 1H), 6.31 (td, 1H)

Synthesis of Compound 120: Following General procedure H2, compound 120 was synthesized in 30% yield. '1H NMR (300 MHz, DMSO-d$_6$) ppm 8.03 (dd, 1H), 7.73 (dd, 1 H), 7.45-7.60 (m, 5H), 6.63 (dd, 1H), 2.71 (s, 6H)

Synthesis of Compound 121: Following General procedure I, A was prepared as follows.

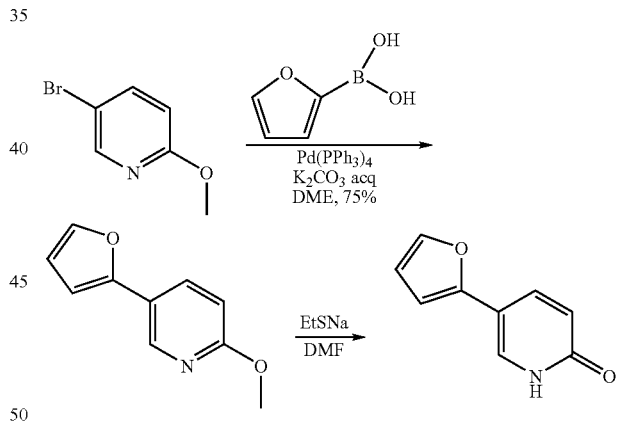

The 5-Furan-2-yl-1H-pyridin-2-one product was obtained by reaction of 2.66 g (14 mmol) of 5-bromo-2-methoxy-pyridine. After purification (SiO$_2$; Pet. Ether/AcOEt 9:1) 1.83 g (75% yield) of pure product were obtained as white solid. The obtained product was de-methylated using EtSNa. The obtained A in a DMF solution (10 mmol/30 ml) was used for the Chan Lam reaction, following General Procedure H2 to provide compound 121 in 19% yield. $^1$H NMR (300 MHz, DMSO-d6) ppm 7.85-7.94 (m, 2H), 7.66 (dd, 1H), 7.42-7.59 (m, 5H), 6.80 (dd, 1H), 6.60 (dd, 1H), 6.55 (dd, 1H)

Synthesis of Compound 122: Following General procedure H1A, compound 122 was synthesized in 53% yield. $^1$H NMR (300 MHz, DMSO-d$_6$) ppm 10.13 (s, 1H), 7.69 (t, 1H), 7.61 (ddd, 1H), 7.54-7.59 (m, 1H), 7.47-7.54 (m, 1H), 7.42 (t, 1H), 7.04 (ddd, 1H), 6.39-6.53 (m, 1H), 6.31 (td, 1H), 2.06 (s, 3H)

Synthesis of Compound 123: Following General procedure H1A, compound 123 was synthesized in 37% yield. $^1$H NMR (300 MHz, DMSO-d$_6$) ppm 8.13 (d, 1H), 7.73 (dd, 1H), 7.66 (m, 2H), 7.55 (m, 2H), 6.64 (d, 1H), 2.71 (s, 6H)

Synthesis of Compound 124: For compound 124, A was prepared as described for compound 121. The obtained A in a DMF solution (10 mmol/30 ml) was used for the Chan Lam reaction, following General Procedure H2 to provide compound 124 in 13% yield. $^1$H NMR (300 MHz, DMSO-d6) ppm 7.98 (d, 1H), 7.90 (dd, 1H), 7.66-7.68 (m, 1H), 7.66 (m, 2H), 7.54 (m, 2H), 6.81 (dd, 1H), 6.62 (dd, 1H), 6.56 (dd, 1H)

Synthesis of Compound 125: Following General procedure H2, compound 125 was synthesized in 20% yield. $^1$H NMR (300 MHz, DMSO-d$_6$) ppm 10.16 (s, 1H), 8.02 (d, 1H), 7.75 (t, 1H), 7.72 (dd, 1H), 7.57-7.66 (m, 1H), 7.46 (t, 1H), 7.15 (ddd, 1H), 6.63 (d, 1H), 2.71 (s, 6H), 2.07 (s, 3H)

Synthesis of Compound 126: Following General procedure H2, compound 126 was synthesized in 13% yield. $^1$H NMR (300 MHz, DMSO-d$_6$) ppm 8.73 (dd, 2H), 7.70 (ddd, 1 H), 7.49-7.60 (m, 3H), 6.52 (ddd, 1H), 6.37 (td, 1H)

Synthesis of Compound 127: Compound A for compound 127 was prepared as stated for compound 115. The prepared compound A was used in General procedure H2 to provide compound 127 in 33% yield. $^1$H NMR (300 MHz, DMSO-d$_6$) ppm 10.15 (s, 1H), 8.58 (d, 1H), 7.75 (dd, 1H), 7.72 (t, 1H), 7.60 (ddd, 1H), 7.45 (t, 1H), 7.10 (ddd, 1H), 6.59 (dd, 1H), 2.07 (s, 3H)

Synthesis of Compound 128: For compound 128, A was prepared as described for compound 121. The obtained demethylated A in a DMF solution (10 mmol/30 ml) was used for the Chan Lam reaction, following General Procedure H2 to provide compound 128 in 20% yield. 1H NMR (300 MHz, DMSO-d6) ppm 10.14 (s, 1H), 7.83-7.96 (m, 2H), 7.70-7.77 (m, 1H), 7.66 (dd, 1H), 7.60 (ddd, 1H), 7.45 (t, 1H), 7.13 (ddd, 1H), 6.80 (dd, 1H), 6.57-6.64 (m, 1H), 6.55 (dd, 1H), 2.07 (s, 3H)

Synthesis of Compound 129: Compound A for compound 129 was prepared as stated for compound 116. The prepared compound A was used in General procedure H1A to provide compound 129 in 23% yield. $^1$H NMR (300 MHz, DMSO-d$_6$) ppm 7.92 (m, 2H), 7.62 (m, 2H), 7.41-7.53 (m, 3H), 7.29 (dd, 1H), 6.45 (d, 1H), 1.68-1.84 (m, 1H), 0.74-0.88 (m, 2H), 0.52-0.67 (m, 2H)

Synthesis of Compound 130: Following General procedure I, A was prepared as follows.

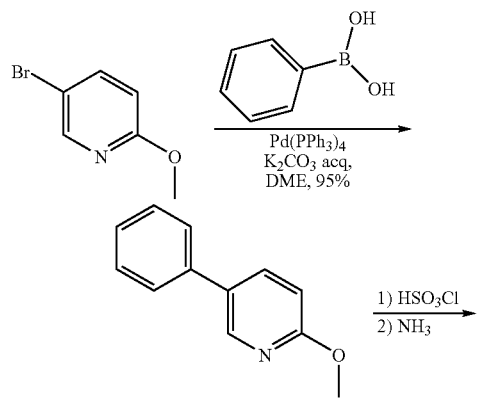

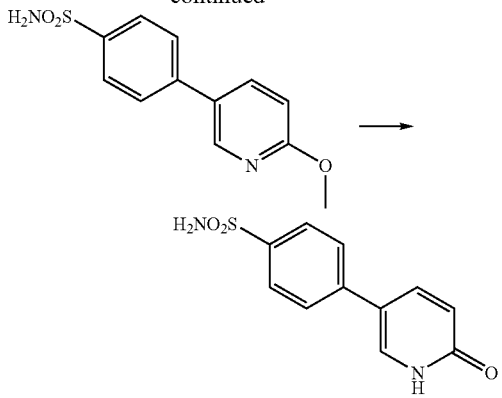

Following standard Suzuki coupling, the 2-Methoxy-5-phenyl-pyridine was obtained by reaction of 1.9 g (10 mmol) of 5-bromo-2-methoxy-pyridine. After purification (SiO$_2$; Pet. Ether/EA 9:1) 1.8 g (97% yield) of pure product were obtained as white solid. The 2-Methoxy-5-phenyl-pyridine (1 g, 5.4 mmol) was added to HSO$_3$Cl (2 ml) at 0° C. The dark solution was stirred at room temperature for 4 h and then poured onto ice. Concentrated ammonia was added, while maintaining the temperature<10° C. The intermediate was extracted with EA (1.2 g, 84% yield) and used for the next step without further purification. To a magnetically stirred solution of the intermediate (4-(6-Methoxy-pyridin-3-yl)-benzenesulfonamide, 1.2 g, 4.5 mmol), in 3 mL of EtOH, 15 mL of HBr were added. The mixture was heated at 80° C. for 20 h. The reaction was cooled at room temperature and poured into KHCO$_3$ saturated solution. EA was added and the mixture was transferred into a separator funnel. The aqueous layer was separated and extracted with additional portion of EA. The combined organics were washed once with water. The organic layer was dried with sodium sulfate, filtered and evaporated under vacuum, affording 300 mg of A. The aqueous layer was acidified and the solvent was evaporated under vacuum. Purification by flash column chromatography (EA) afforded 750 mg of A (89% of yield). A was used for the Chan Lam reaction, following General Procedure H1A to provide compound 130 in 77% yield. $^1$H NMR (300 MHz, DMSO-d6) ppm 8.12 (d, 1H), 8.00 (dd, 1H), 7.83 (m, 4H), 7.42-7.64 (m, 5H), 7.34 (s, 2H), 6.64 (d, 1H)

Synthesis of Compound 131: Compound A for compound 131 was prepared as stated for compound 130. The prepared compound A was used in General procedure H1A to provide compound 131 in 61% yield. $^1$H NMR (300 MHz, DMSO-d$_6$) ppm 8.18 (d, 1H), 8.02 (dd, 1H), 7.84 (m, 4H), 7.69 (m, 2H), 7.55 (m, 2H), 7.34 (s, 2H), 6.65 (d, 1H)

Synthesis of Compound 132: Compound A for compound 132 was prepared as stated for compound 116. The prepared compound A was used in General procedure H1A to provide compound 132 in 25% yield. $^1$H NMR (300 MHz, DMSO-d$_6$) ppm 7.42-7.57 (m, 3 H), 7.36-7.42 (m, 2H), 7.33 (dd, 1H), 7.13-7.24 (m, 1H), 6.80 (d, 1H), 1.66-1.81 (m, 1 H), 0.86-0.97 (m, 2H), 0.52-0.64 (m, 2H)

Synthesis of Compound 133: For compound 133, A was prepared as described for compound 121. The obtained A in a DMF solution (10 mmol/30 ml) was used for the Chan Lam reaction, following General Procedure H2 to provide compound 133 in 17% yield. $^1$H NMR (300 MHz, DMSO-d6) ppm 8.87-8.96 (m, 2H), 7.79-7.85 (m, 2H), 7.69-7.77 (m, 2H), 7.44 (dd, 1H), 6.76-6.84 (m, 1H), 6.47-6.57 (m, 2H)

Synthesis of Compound 134: Following General procedure I, A was prepared as follows.

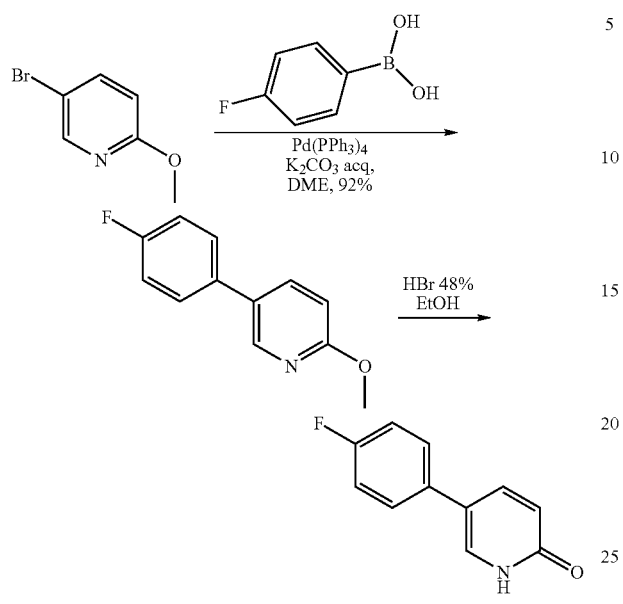

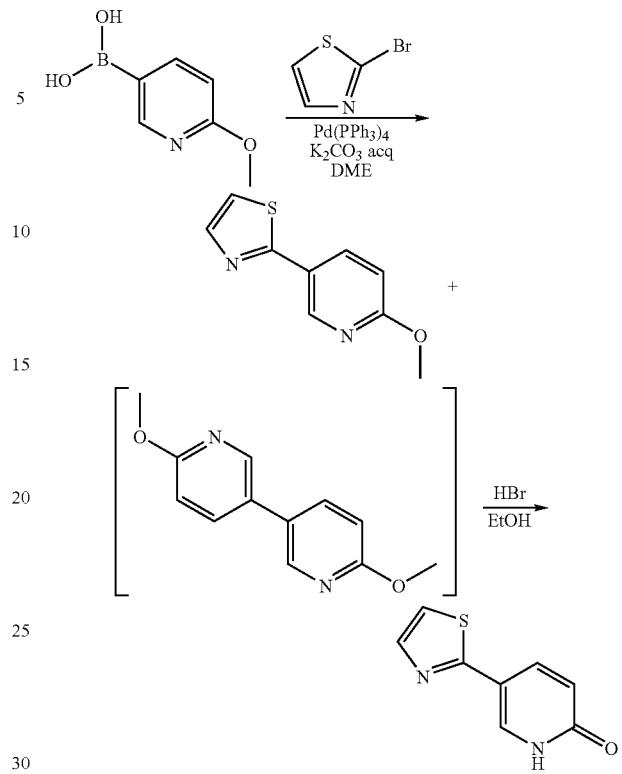

Following standard Suzuki coupling, an intermediate was obtained by reaction of 2.82 g (15 mmol) of 5-bromo-2-methoxy-pyridine. After purification (SiO$_2$; Pet. Ether/EA 9:1) 2.8 g (92% yield) of pure intermediate were obtained as white solid. The intermediate (900 mg) was dissolved in HBr 48% (10 ml) and EtOH (3 ml) and the solution was heated at reflux for 3 h. After evaporation of volatiles the desired A pyridone was obtained as white solid (780 mg, 93% yield). A was used in the Chan Lam reaction, following General Procedure H1A to provide compound 134 in 33% yield. $^1$H NMR (300 MHz, DMSO-d6) ppm 8.02 (d, 1H), 7.87-7.99 (m, 3H), 7.73 (m, 2H), 7.69 (m, 2H), 7.50 (s, 2H), 7.25 (m, 2H), 6.62 (d, 1H)

Synthesis of Compound 135: For compound 135, A was prepared as described for compound 134. A was used in the Chan Lam reaction, following General Procedure H1A to provide compound 135 in 59% yield. $^1$H NMR (300 MHz, DMSO-d6) ppm 10.13 (s, 1H), 7.86-7.96 (m, 2H), 7.74 (t, 1H), 7.55-7.71 (m, 3H), 7.44 (t, 1H), 7.23 (m, 2H), 7.14 (ddd, 1H), 6.55-6.64 (m, 1H), 2.06 (s, 3H)

Synthesis of Compound 136: For compound 136, A was prepared as described for compound 134. A was used in the Chan Lam reaction, following General Procedure H1A to provide compound 136 in 53% yield. $^1$H NMR (300 MHz, DMSO-d6) ppm 7.94 (d, 1H), 7.91 (dd, 1H), 7.68 (m, 2H), 7.40-7.59 (m, 5H), 7.23 (m, 2H), 6.60 (dd, 1H)

Synthesis of Compound 137: For compound 137, A was prepared as described for compound 134. A was used in the Chan Lam reaction, following General Procedure H1A to provide compound 137 in 53% yield. $^1$H NMR (300 MHz, DMSO-d6) ppm 8.01 (d, 1H), 7.93 (dd, 1H), 7.63-7.74 (m, 4H), 7.53 (m, 2H), 7.24 (m, 2H), 6.61 (dd, 1H)

Synthesis of Compound 138: For compound 138, A was prepared as follows:

1.53 g (10 mmol) of 2-methoxy-pyridine-5-boronic acid and 2.46 g (15 mmol) of 2-Bromo-thiazole and K$_2$CO$_3$ (3 eq) were dissolved in a 10:1 mixture of DME/H$_2$O (4 ml/mmol). The solution was degassed by bubbling N$_2$ for 15 min and then Pd(PPh$_3$)$_4$ (0.05 eq) was added. The reaction mixture was heated at 90° C. for 8 h an then cooled at room temperature, diluted with EA and filtered on a celite plug. The filtrate was washed with brine. The separated organic phase was dried over Na$_2$SO$_4$ and concentrated under reduced pressure. After purification (SiO$_2$; Pet. Ether/EA 9:1) 1.8 g (92% yield) of a 1:1 mixture of intermediate and the dimeric 2-methoxy-pyridine were obtained and used for the next step. The mixture (1.1 g) was dissolved in HBr 48% (10 ml) and EtOH (3 ml) and the solution was heated at reflux for 3 h. After evaporation of volatiles, the crude was purified by column chromatography (SiO$_2$; Pet. Ether/EA 9:1) leading to the desired pyridone A (350 mg). Following general procued H1A, compound 138 was prepared in 35% yield. $^1$H NMR (300 MHz, DMSO-d6) ppm 8.23 (d, 1H), 8.07 (dd, 1H), 7.84 (d, 1H), 7.70 (d, 1H), 7.41-7.63 (m, 5H), 6.64 (d, 1 H)

Synthesis of Compound 139: Following general procedure I, A was prepared as follows.

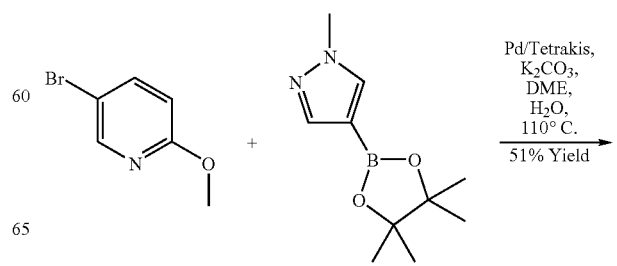

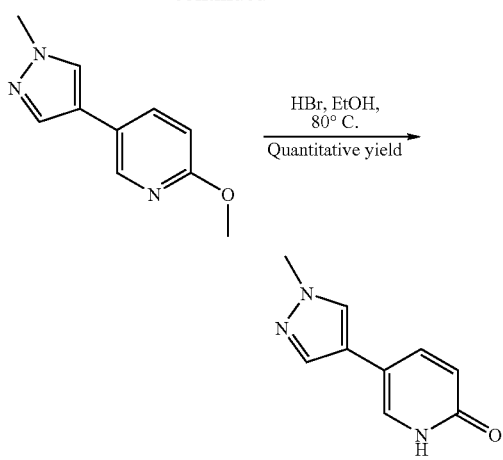

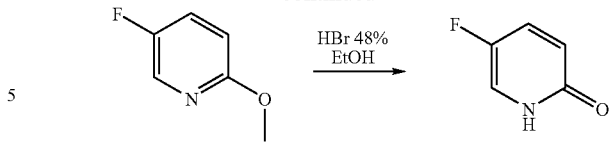

Following standard procedure for Suzuki coupling, the intermediate was obtained by reaction of 3 g (16 mmol) of 5-bromo-2-methoxy-pyridine. After purification (SiO$_2$; Hexane/EA 30/1 to EA) 2.2 g (51% yield) of the intermediate were obtained as white solid. To a magnetically stirred solution of 2-Methoxy-5-(1-methyl-1H-pyrazol-4-yl)-pyridine (1.2 g, 6.3 mmol), in 3 mL of EtOH, 15 mL of HBr were added. The mixture was heated at 80° C. for 20 h. The reaction was cooled at room temperature. The solvent was evaporated under vacuum. Purification by flash column chromatography (EA) afforded 1.1 g of A (quantitative yield). Following general procedure H1A, compound 139 was prepared in 63% yield. $^1$H NMR (300 MHz, DMSO-d6) ppm 8.04 (d, 1H), 7.94 (dd, 1H), 7.79 (d, 1H), 7.79 (dd, 1H), 7.62 (m, 2 H), 7.54 (m, 2H), 6.56 (d, 1H), 3.82 (s, 3H)

Synthesis of Compound 140: For compound 140, A was prepared as described for compound 134. A was used in the Chan Lam reaction, following General Procedure H1A to provide compound 140 in 30% yield. $^1$H NMR (300 MHz, DMSO-d6) ppm 9.26 (s, 1H), 9.08 (s, 2H), 8.18 (d, 1H), 7.99 (dd, 1H), 7.70 (m, 2H), 7.27 (m, 2H), 6.66 (d, 1H)

Synthesis of Compound 141: For compound 141, A was prepared as described for compound 134. A was used in the Chan Lam reaction, following General Procedure H1A to provide compound 141 in 45% yield. $^1$H NMR (300 MHz, DMSO-d6) ppm 8.68-8.81 (m, 2H), 8.02 (dd, 1H), 7.94 (dd, 1H), 7.70 (m, 2H), 7.62-7.66 (m, 2H), 7.26 (m, 2H), 6.64 (dd, 1H)

Synthesis of Compound 142: Compound A for compound 142 was prepared according to the following scheme.

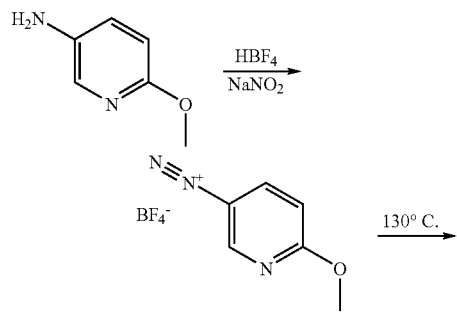

6-Methoxy-pyridin-3-ylamine (2.5 g 2 mmol) was dissolved in 48% HBF$_4$ (10 ml) and cooled at 0° C. NaNO$_2$ (2.4 g, 3.4 mmol) was added portionwise maintaining the temperature<5° C. The dark solution was stirred at low temperature for 1 h. The solid was collected by filtration and washed with water and then dried under vacuum. The desired diazonium salt was obtained (3.18 g, 72%) as white crystalline solid. The diazonium salt (2 g, 8.9 mmol) and celite (4 g) were finely mixed in a mortar, transferred to a reaction vessel, then gradually heated to 150° C., whereupon a rapid evolution of fumes occurred. The resulting solid was washed several times with abundant diethyl ether. The organic solution was washed with Et$_2$O/HCl then evaporated to provide the desired intermediate as its hydrochloric salt (1.2 g) as pale yellow viscous oil. The obtained fluoromethoxy pyridine (1.2 g) was dissolved in HBr 48% (10 ml) and EtOH (3 ml) and the solution was heated at reflux for 6 h. After evaporation of volatiles the desired pyridone A was obtained as amorphous solid in quantitative yield, and used in General procedure H1A to provide compound 142 in 28% yield. $^1$H NMR (300 MHz, DMSO-d6) ppm 7.85-7.97 (m, 1H), 7.59-7.73 (m, 1H), 7.34-7.57 (m, 5H), 6.45-6.57 (m, 1H)

Synthesis of Compound 143: Using A as prepared as described for compound 142, following General procedure H1A, compound 143 was prepared in 13% yield. $^1$H NMR (300 MHz, DMSO-d6) ppm 10.13 (br. s., 1H), 7.89 (ddd, 1H), 7.69-7.72 (m, 1H), 7.67 (ddd, 1 H), 7.57 (ddd, 1H), 7.35-7.48 (m, 1H), 6.97-7.16 (m, 1H), 6.51 (ddd, 1H), 2.06 (s, 3H)

Synthesis of Compound 144: Using A as prepared as described for compound 142, following General procedure HIA, compound 144 was prepared in 26% yield. $^1$H NMR (300 MHz, DMSO-d6) ppm 10.13 (br. s., 1H), 7.89 (ddd, 1H), 7.69-7.72 (m, 1H), 7.67 (ddd, 1 H), 7.57 (ddd, 1H), 7.35-7.48 (m, 1H), 6.97-7.16 (m, 1H), 6.51 (ddd, 1H), 2.06 (s, 3H)

Synthesis of Compound 145: For compound 145, A was prepared as described for compound 139. A was used in the Chan Lam reaction, following General Procedure H1A to provide compound 145 in 42% yield. $^1$H NMR (300 MHz, DMSO-d6) ppm 8.04 (s, 1H), 7.88 (dd, 1H), 7.71-7.83 (m, 2H), 7.36-7.61 (m, 5H), 6.54 (dd, 1H), 3.82 (s, 3H)

Synthesis of Compound 146: For compound 146, A was prepared as described for compound 121. The obtained demethylated A in a DMF solution (10 mmol/30 ml) was used for the Chan Lam reaction, following General Procedure H2 to provide compound 146 in 7% yield. $^1$H NMR (300 MHz, DMSO-d6) ppm 9.26 (s, 1H), 9.04 (s, 2H), 8.15 (d, 1H), 7.95 (dd, 1H), 7.70 (dd, 1H), 6.81 (dd, 1H), 6.67 (dd, 1H), 6.58 (dd, 1H)

Synthesis of Compound 147: Following general procedure I, A was prepared as follows.

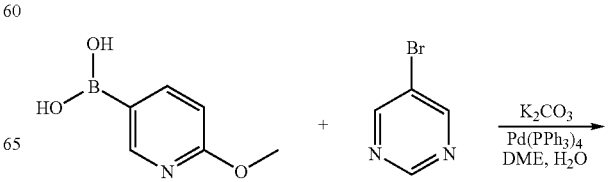

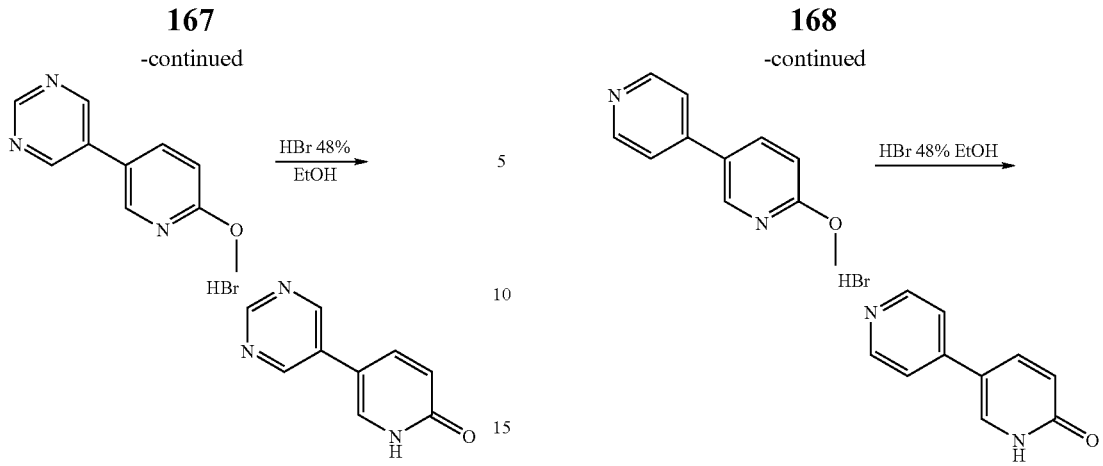

The 2-methoxy-pyridine-5-boronic acid (1.9 g, 12 mmol), the 5-bromo-pyrimidine (1.2 eq) and K2CO3 (3 eq) were dissolved in a 10:1 mixture of DME/H$_2$O (4 ml/mmol). The solution was degassed by bubbling N$_2$ for 15 min and then Pd(PPh$_3$)$_4$ (0.05 eq) was added. The reaction mixture was heated at 90° C. for 8 h an then cooled at room temperature, diluted with EA and filtered on a celite plug. The filtrate was washed with brine. The separated organic phase was dried over Na$_2$SO$_4$ and concentrated under reduced pressure. The obtained residue was purified by column chromatography. (SiO$_2$; Hexane/EA 30/1 to EA) 1.29 g (56% yield) of intermediate were obtained as white solid. A solution of 5-(6-Methoxy-pyridin-3-yl)-pyrimidine (1.29 g, 6.9 mmol) in EtOH (4 ml) and HBr 48% (10 ml) was stirred at 90° C. for 7 h. The solvent was evaporated and the crude A (as hydrobromide salt) was utilized in the next step without any purification. Following general procedure H1A, compound 147 was prepared in 22% yield. 1H NMR (300 MHz, DMSO-d6) ppm 9.12 (s, 2H), 9.11 (s, 1H), 8.32 (d, 1H), 8.06 (dd, 1H), 7.69 (m, 2H), 7.56 (m, 2H), 6.68 (d, 1H)

Synthesis of Compound 148: For compound 148, A was prepared as stated for compound 147. Following general procedure H1A, compound 148 was prepared in 37% yield. $^1$H NMR (300 MHz, DMSO-d6) ppm 10.15 (br. s., 1H), 9.10 (s, 3H), 8.25 (d, 1H), 8.04 (dd, 1H), 7.76 (s, 1H), 7.61 (d, 1H), 7.46 (dd, 1H), 7.15 (ddd, 1H), 6.65 (d, 1H), 2.06 (s, 3H)

Synthesis of Compound 149: For compound 149, A was prepared as stated for compound 147. Following general procedure HIA, compound 149 was prepared in 16% yield. $^1$H NMR (300 MHz, DMSO-d6) ppm 9.12 (br. s., 3H), 8.26 (d, 1H), 8.04 (dd, 1H), 7.32-7.66 (m, 5H), 6.66 (d, 1H)

Synthesis of Compound 150: For compound 150, A was prepared as stated for compound 130. The prepared A was used in General procedure H1A to provide compound 150 in 36.5% yield. $^1$H NMR (300 MHz, DMSO-d$_6$) ppm 9.27 (s, 1H), 9.09 (s, 2H), 8.33 (dd, 1H), 8.07 (dd, 1H), 7.86 (s, 4H), 7.36 (s, 2H), 6.70 (dd, 1H)

Synthesis of Compound 151: Following general procedure I, A was prepared in the following manner.

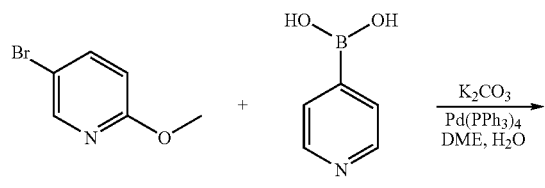

Following standard procedure for Suzuki coupling, the intermediate product was obtained by reaction of 2.5 g (13.3 mmol) of 5-bromo-2-methoxy-pyridine. After purification (SiO$_2$; Hexane/EA 30/1 to EA) 2.1 g (87% yield) of the intermediate product were obtained as white solid. A solution of 6-Methoxy-[3,4']bipyridinyl (2.1 g, 11.3 mmol) in EtOH (6 ml) and HBr 48% (12 ml) was stirred at 90° C. for 6 h. The solvent was evaporated and crude A (as hydrobromide salt) was utilized in the next step without any purification. Following general procedure H1A, compound 151 was prepared in 12% yield. $^1$H NMR (300 MHz, DMSO-d6) ppm 10.15 (s, 1H), 8.57 (br. s., 2H), 8.25 (d, 1H), 8.06 (dd, 1H), 7.75 (dd, 1 H), 7.66-7.73 (m, 2H), 7.62 (ddd, 1H), 7.46 (dd, 1H), 7.15 (ddd, 1H), 6.64 (d, 1H), 2.07 (s, 3H)

Synthesis of Compound 152: For compound 152, A was prepared as described for compound 151. A was used in the Chan Lam reaction, following General Procedure H1A to provide compound 152 in 29% yield. $^1$H NMR (300 MHz, DMSO-d6) ppm 8.45-8.64 (m, 2 H), 8.18 (dd, 1H), 8.00 (dd, 1H), 7.61-7.76 (m, 2H), 7.37-7.61 (m, 5H), 6.63 (dd, 1H)

Synthesis of Compound 153: For compound 153, A was prepared as described for compound 151. A was used in the Chan Lam reaction, following General Procedure H1A to provide compound 153 in 36% yield. $^1$H NMR (300 MHz, DMSO-d6) ppm 8.45-8.70 (m, 2 H), 8.32 (d, 1H), 8.07 (dd, 1H), 7.63-7.77 (m, 4H), 7.55 (d, 2H), 6.66 (d, 1H)

Synthesis of Compound 154: Compound 154 was synthesized in the following manner. To a solution of 2-pyridone (200 mg, 2.1 mmol) and 4-bromophenyl sulfonamide (994 mg, 4.2 mmol) in 0.9 mL NMP, K$_2$CO$_3$ (292 mg, 2.1 mmol) and copper (I) iodide (120 mg, 30%) were added, and the mixture heated at 160° C. for 30 seconds under MW irradiation. The crude mixture was then dissolved in EA and the product precipitated out as a solid. The solid was purified by prep-HPLC to give 31.4 mg of compound 154 as a white solid (3% yield). $^1$H NMR (300 MHz, DMSO-d$_6$) ppm 7.93 (m, 2H), 7.69 (ddd, 1H), 7.63 (m, 2H), 7.53 (ddd, 1H), 7.47 (s, 2H), 6.50 (dt, 1H), 6.35 (td, 1H)

Synthesis of Compound 155: For compound 155, A was prepared as described for compound 139. A was used in the Chan Lam reaction, following General Procedure H1A to provide compound 155 in 14% yield. $^1$H NMR (300 MHz, DMSO-d6) ppm 10.13 (s, 1H), 8.03 (s, 1H), 7.86 (dd, 1H), 7.78 (d, 1H), 7.78 (dd, 1H), 7.70 (t, 1H), 7.52-7.65 (m, 1H), 7.44 (t, 1H), 7.09 (ddd, 1H), 6.54 (dd, 1H), 3.82 (s, 3H), 2.06 (s, 3H)

Synthesis of Compound 156: For compound 156, A was prepared as described for compound 139. A was used in the Chan Lam reaction, following General Procedure H1A to provide compound 156 in 20% yield. $^1$H NMR (300 MHz, DMSO-d6) ppm 8.04 (s, 1H), 7.90-8.00 (m, 3H), 7.79 (d, 1H), 7.81 (dd, 1H), 7.68 (m, 2H), 7.49 (br. s., 2H), 6.57 (dd, 1H), 3.83 (s, 3H)

169

Synthesis of Compound 157: For compound 157, A was prepared in the following manner.

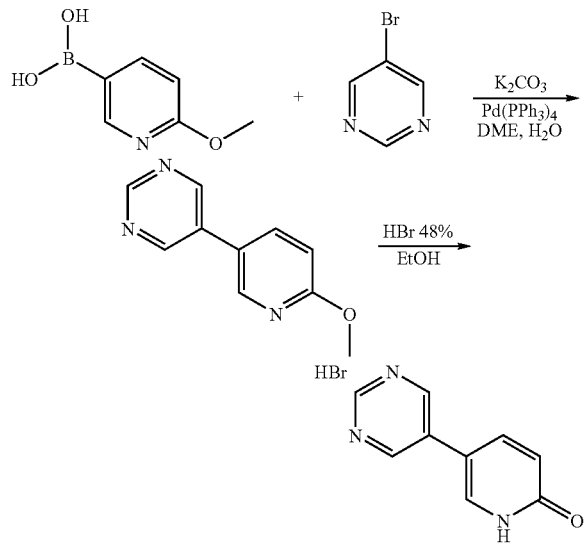

The 2-methoxy-pyridine-5-boronic acid (1.9 g, 12 mmol), the 5-bromo-pyrimidine (1.2 eq) and K$_2$CO$_3$ (3 eq) were dissolved in a 10:1 mixture of DME/H$_2$O (4 mL/mmol). The solution was degassed by bubbling nitrogen for 15 min and then Pd(PPh$_3$)$_4$ (0.05 eq) was added. The reaction mixture was heated at 90° C. for 8 h and then cooled at room temperature, diluted with EtOAc and filtered on a celite plug. The filtrate was washed with brine. The separated organic phase was dried over Na$_2$SO4 and concentrated under reduced pressure. The obtained residue was purified by column chromatography. (SiO$_2$; Hexanes/EtOAc 30/1 to EtOAc) 1.29 g (56% yield) of pure product were obtained as white solid. A solution of 5-(6-Methoxy-pyridin-3-yl)-pyrimidine (1.29 g, 6.9 mmol) in EtOH (4 ml) and HBr 48% (10 ml) was stirred at 90° C. for 7 h. The solvent was evaporated and the crude compound (as hydrobromide salt) was utilized in the next step without any purification. A was used in the Chan Lam reaction, following General Procedure H1A to provide compound 157 in 11% yield. $^1$H NMR (300 MHz, DMSO-d6) ppm 9.10-9.17 (m, 3H), 8.73-8.81 (m, 2H), 8.31 (dd, 1H), 8.07 (dd, 1H), 7.63-7.70 (m, 2H), 6.70 (dd, 1H)

Synthesis of Compound 158: For compound 158, A was prepared as stated for compound 147. Following general procedure HIA, compound 158 was prepared in 37% yield. $^1$H NMR (300 MHz, DMSO-d6) ppm 9.02-9.21 (m, 3H), 8.32 (d, 1H), 8.07 (dd, 1 H), 7.97 (m, 2H), 7.75 (m, 2H), 7.51 (s, 2H), 6.69 (d, 1H)

Synthesis of Compound 159: Following general procedure I, A was prepared as follows.

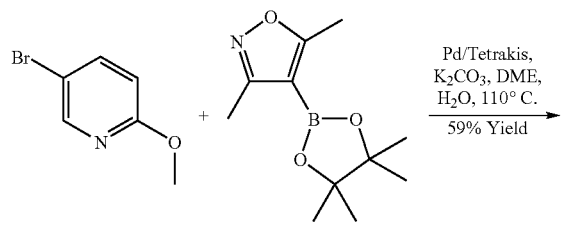

170

-continued

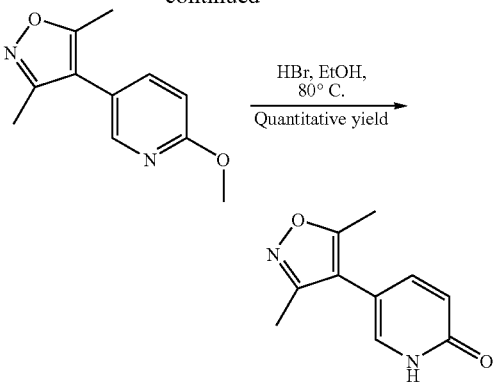

Following standard procedure for Suzuki coupling, the intermediate was obtained by reaction of 2.82 g (15 mmol) of 5-bromo-2-methoxy-pyridine. After purification (SiO$_2$; Hexane/EA 8/2) 1.8 g (59% yield) of pure intermediate were obtained as white solid. To a magnetically stirred solution of 2-Methoxy-5-(1-methyl-1H-pyrazol-4-yl)-pyridine (1 g, 4.9 mmol), in 3 mL of EtOH, 10 mL of HBr were added. The mixture was heated at 90° C. for 4 h. The reaction was cooled at room temperature. The solvent was evaporated under vacuum, afforded 1.34 g of A (quantitative yield). Following general procedure H1A, compound 159 was prepared in 11% yield. $^1$H NMR (300 MHz, DMSO-d6) ppm 10.13 (s, 1H), 7.74 (dd, 1 H), 7.69 (dd, 1H), 7.52-7.62 (m, 2H), 7.44 (dd, 1H), 7.11 (ddd, 1H), 6.58 (dd, 1H), 2.39 (s, 3H), 2.22 (s, 3H), 2.06 (s, 3H)

Synthesis of Compound 160: For compound 160, A was prepared as stated for compound 159. Following general procedure H1A, compound 160 was prepared in 23% yield. $^1$H NMR (300 MHz, DMSO-d6) ppm 7.71 (dd, 1H), 7.42-7.61 (m, 6H), 6.58 (dd, 1 H), 2.39 (s, 3H), 2.22 (s, 3H)

Synthesis of Compound 161: Compound A for compound 161 was preared as stated for compound 138. The prepared compound A was used in General procedure H1A to provide compound 161. $^1$H NMR (300 MHz, DMSO-d6) ppm 7.58 (dd, 1H), 7.38-7.54 (m, 5H), 6.90 (d, 1H), 6.47 (d, 1H), 3.61-3.77 (m, 4H), 2.79-2.97 (m, 4H)

Synthesis of Compound 162: Compound A for compound 162 was prepared as stated for compound 138. The prepared compound A was used in General procedure H1A to provide compound 162 in 65% yield. $^1$H NMR (300 MHz, DMSO-d$_6$) ppm 10.16 (s, 1H), 8.22 (dd, 1H), 8.06 (dd, 1H), 7.84 (d, 1H), 7.75 (t, 1H), 7.70 (d, 1H), 7.57-7.67 (m, 1H), 7.46 (t, 1H), 7.16 (ddd, 1H), 6.64 (dd, 1H), 2.07 (s, 3H)

Synthesis of Compound 163: For compound 163, A was prepared as stated for compound 159. Following general procedure H1A, compound 163 was prepared in 33% yield. $^1$H NMR (300 MHz, DMSO-d6) ppm 7.77 (dd, 1H), 7.45-7.71 (m, 5H), 6.60 (dd, 1 H), 2.39 (s, 3H), 2.23 (s, 3H)

Synthesis of Compound 164: For compound 164, A was prepared as stated for compound 159. Following general procedure H1A, compound 164 was prepared in 25% yield. $^1$H NMR (300 MHz, DMSO-d6) ppm 8.71-8.78 (m, 2H), 7.78 (dd, 1H), 7.54-7.66 (m, 3H), 6.62 (dd, 1H), 2.40 (s, 3H), 2.23 (s, 3H)

Synthesis of Compound 165: For compound 165, A was prepared as described for compound 139. A was used in the Chan Lam reaction, following General Procedure H1A to provide compound 165 in 4.6% yield. $^1$H NMR (300 MHz, DMSO-d6) ppm 9.25 (s, 1H), 9.04 (s, 2H), 8.08 (dd, 1H), 8.04 (d, 1H), 7.85 (dd, 1H), 7.79 (d, 1H), 6.62 (dd, 1H), 3.84 (s, 3H)

Synthesis of Compound 166: Following General procedure H1A, compound 166 was synthesized. '1H NMR (300 MHz, DMSO-d6) ppm 8.65-8.79 (m, 2H), 8.03 (dd, 1H), 7.65 (dd, 1H), 7.50-7.60 (m, 2H), 6.51 (dd, 1H)

Synthesis of Compound 167: Following General Procedure L1, compound 167 was prepared in 13% yield. $^1$H NMR (300 MHz, DMSO-d6) ppm 7.55-7.66 (m, 3H), 7.35-7.54 (m, 2H), 6.95 (d, 1H), 6.48 (d, 1H), 3.50-3.81 (m, 4H), 2.80-2.96 (m, 4H)

Synthesis of Compound 168: For compound 168, A was prepared as described for compound 139. A was used in the Chan Lam reaction, following General Procedure H1A to provide compound 168 in 7.4% yield. $^1$H NMR (300 MHz, CDCl$_3$) ppm 8.80 (m, 2H), 7.60 (d, 1H), 7.55 (dd, 1H), 7.49 (s, 1H), 7.46 (m, 2H), 7.41 (dd, 1H), 6.73 (dd, 1H), 3.95 (s, 3 H)

Synthesis of Compound 169: Following general procedure I, A was prepared as follows.

99:1) 2.1 g (55% yield) of 9 were obtained. Next, 10 was obtained starting from 2.1 g (6.2 mmol) of 9. After filtration 1.8 g (93.3% yield) of 10 were obtained. Then, from 10 amide formation with morpholine was performed to provide compound 170 in 46.2% yield. $^1$H NMR (300 MHz, DMSO-d6) ppm 11.32 (s, 1H), 7.80 (d, 1H), 7.42-7.58 (m, 4H), 6.86 (s, 1H), 6.20 (d, 1 H), 3.39-3.73 (m, 4H), 1.74-1.99 (m, 4H)

Synthesis of Compound 171: For compound 171, A was prepared as stated for compound 159. Following general procedure H1A, compound 171 was prepared in 5% yield.

$^1$H NMR (300 MHz, DMSO-d6) ppm 9.25 (s, 1H), 9.03 (s, 2H), 7.90 (dd, J=2.6, 0.6 Hz, 1 H), 7.65 (dd, J=9.5, 2.5 Hz, 1H), 6.66 (dd, J=9.4, 0.6 Hz, 1H), 2.41 (s, 3H), 2.24 (s, 3H)

Synthesis of Compound 172: For compound 172, A was prepared as stated for compound 169. Following general procedure H1A, compound 172 was prepared in 21% yield. $^1$H NMR (300 MHz, DMSO-d6) ppm 8.88 (br. s., 1H), 8.51 (br. s., 1H), 8.10 (dd, 1 H), 8.05 (dt, 1H), 7.95-8.02 (m, 1H), 7.39-7.58 (m, 6H), 6.63 (d, 1H)

Synthesis of Compound 173: Compound 173 was synthesized in the following manner.

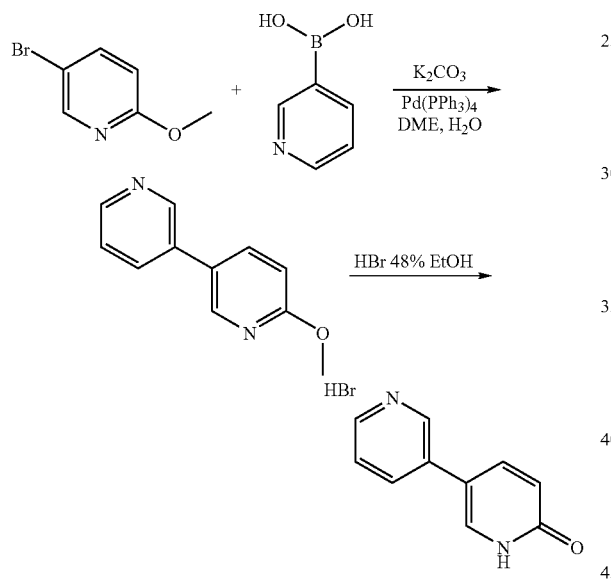

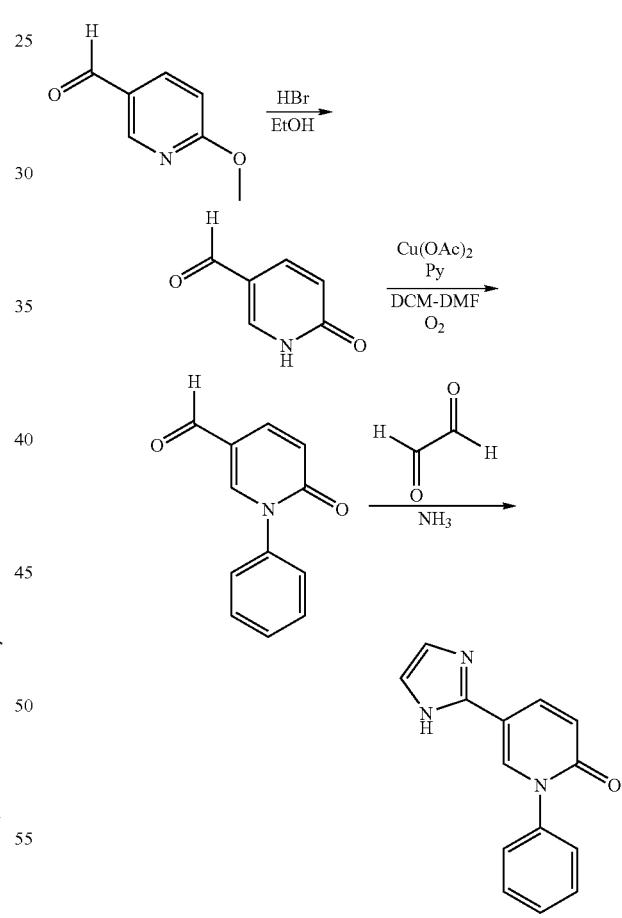

Following standard procedure for Suzuki coupling, the intermediate was obtained by reaction of 2 g (10.64 mmol) of 5-bromo-2-methoxy-pyridine. After purification (SiO$_2$; hexane/EA 20/1 to EA) 2.1 g (87% yield) of pure intermediate were obtained as white solid. A solution of 6-methoxy-3,3'-bipyridine (1.7 g, 11.3 mmol) in EtOH (6 ml) and HBr 48% (12 ml) was stirred at 80° C. for 20 h. The solvent was evaporated and crude A (as hydrobromide salt) was utilized in the next step without any purification (quantitative yield). Following general procedure H1A, with the addition of triethylamine, compound 169 was prepared in 14% yield. $^1$H NMR (300 MHz, DMSO-d6) ppm 8.89 (br. s., 1H), 8.51 (d, 1H), 8.18 (dd, 1H), 8.07 (ddd, 1H), 8.01 (dd, 1H), 7.64-7.74 (m, 2H), 7.49-7.60 (m, 2H), 7.44 (dd, 1H), 6.65 (dd, 1H)

Synthesis of Compound 170: Compound 170 is prepared as outlined in General Procedures K and J. Initialy, 8 is prepared according to procedure K, then 9 was prepared according to General Procedure J by reaction of 2.3 g ethyl 6-oxo-6,7-dihydro-1H-pyrrolo[2,3-b]pyridine-2-carboxylate (11.1 mmol), with 2.5 g of 4-isopropoxyphenylboronic acid (13.9 mmol). After purification (SiO$_2$; DCM:MeOH 6-methoxynicotinaldehyde (1.0 g, 7.2 mmol) was dissolved in HBr 48% (10 mL) and EtOH (3 mL) and the solution was heated at reflux for 2 h. After evaporation of volatiles, 1.6 g of the desired pyridone intermediate was obtained. The intermediate was used in the next step without further purification. To a solution of 6-oxo-1,6-dihydropyridine-3-carbaldehyde (640 mg, 5.2 mmol) in DCM (6 mL) and DMF (2 mL), Cu(OAc)$_2$ (1.8 g, 10.4 mmol), phenyl boronic acid (1.2 g, 10.4 mmol), pyridine (0.8 g, 10.4 mmol) and finely grounded, activated 4 Å molecular sieves (1 g) were added. The mixture was stirred at room temperature for 24 h. A concentrated solution of NH$_4$OH was added. The solvents were evaporated under vacuum, and the resulting crude was purified by chromatographic column (SiO$_2$; Pet. Ether/EtOAc 10/1 to 0/1). 300 mg (48% yield) of the second intermediate were obtained as a white solid. To a solution of the second intermediate (6-oxo-1-phenyl-1,6-dihydropyridine-3-carbaldehyde, 300 mg, 2.5 mmol) in of MeOH (20 mL), glyoxal (0.89 g, 10.4 mmol) was added at 0° C. Gaseous NH$_3$ was bubbled into the mixture at 0° C. for 1 h. The reaction was warmed at room temperature and stirred for 24 h. The solvent was evaporated under vacuum and the resulting crude was purified by flash chromatography (SiO$_2$, Pet. Ether/EtOAc 10/1 to 0/1) and by reverse-phase preparative HPLC. 80 mg (14% yield) of compound 173 were obtained. $^1$H NMR (300 MHz, DMSO-d6) ppm 14.16 (br. S., 1H), 8.49 (d, 1H), 8.03 (dd, 1H), 7.66 (s, 2H, 7.44-7.63 (m, 5H), 6.75 (d, 1H)

Synthesis of Compound 174: For compound 174, the iodopyridone intermediate was prepared as described for compound 189, below. The iodopyridone intermediate was then used in a Stille coupling.

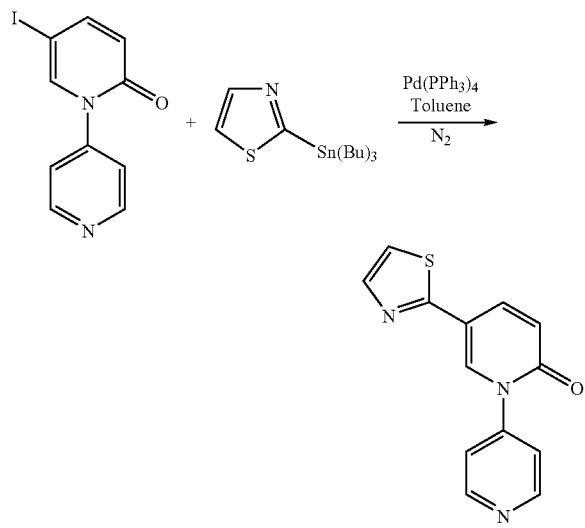

5-iodo-1-(pyridin-4-yl)pyridin-2(1H)-one (0.120 g, 0.4 mmol) was dissolved in dry and degassed toluene (10 mL), previously degassed. Pd(PPh$_3$)$_4$ (0.023 g, 0.02 mmol) was then added and the mixture was stirred for 10 minutes. 2-(tributylstannyl)thiazole (0.15 g, 0.4 mmol) was added and the reaction was heated at 90° C. for 4 h under nitrogen atmosphere. A large excess of a KF/H$_2$O solution was added and the mixture was stirred for 1 h. The aqueous phase was extracted with EtOAc. The solvent was removed under reduced pressure and the crude was purified by flash chromatography (SiO$_2$; EtOAc/MeOH 95:5) and then through titration in CH$_3$CN. 38.7 mg (38% yield) of compound 174 were obtained as a white solid. $^1$H NMR (300 MHz, DMSO-d6) ppm 8.65-8.86 (m, 2H), 8.31 (dd, 1H), 8.10 (dd, 1H), 7.86 (d, 1H), 7.72 (d, 1H), 7.58-7.68 (m, 2H), 6.60-6.74 (m, 1 H)

Synthesis of Compound 175: For compound 175, 10 was prepared as described for compound 170, then 10 was mixed with N-methylpiperdine under the amide formation conditions of General Procedure J to provide compound 175 in 28% yield. $^1$H NMR (300 MHz, DMSO-d6) ppm 11.18 (s, 1H), 7.74 (d, 1H), 7.22 (m, 2H), 7.05 (m, 2H), 6.64 (s, 1 H), 6.17 (d, 1H), 4.69 (spt, 1H), 3.42-3.80 (m, 4H), 2.25-2.36 (m, 4H), 2.19 (s, 3H), 1.34 (d, 6H)

Synthesis of Compound 176: For compound 176, A was prepared as stated for compound 169. Following general procedure H1A, compound 176 was prepared in 7.6% yield. $^1$H NMR (300 MHz, DMSO-d6) ppm 8.89 (dd, 1H), 8.76 (dd, 2H), 8.52 (dd, 1H), 8.16 (dd, 1H), 8.07 (ddd, 1H), 8.01 (dd, 1H), 7.62-7.69 (m, 2H), 7.44 (ddd, 1H), 6.67 (dd, 1H)

Synthesis of Compound 177: For compound 177, 10 was prepared as described for compound 170, then 10 was mixed with 3-methoxybenzylamine under the amide formation conditions of General Procedure J to provide compound 177 in 46.5% yield. $^1$H NMR (300 MHz, DMSO-d6) ppm Synthesis of Compound 178: For compound 178, 10 was prepared as described for compound 170, then 10 was mixed with benzylamine under the amide formation conditions of General Procedure J to provide compound 178 in 33.8% yield. $^1$H NMR (300 MHz, DMSO-d6) ppm 10.94 (s, 1H), 8.65 (t, 1H), 7.78 (d, 1H), 7.15-7.39 (m, 7H), 6.96-7.12 (m, 3H), 6.18 (d, 1H), 4.68 (quin, 1H), 4.42 (d, 2H), 1.33 (d, 6H)

Synthesis of Compound 179: For compound 179, 10 was prepared as described for compound 170, then 10 was mixed with 2-aminothiazole under the amide formation conditions of General Procedure J to provide compound 179 in 37% yield. $^1$H NMR (300 MHz, DMSO-d6) ppm 12.23 (br. s., 1H), 11.38 (br. s., 1H), 7.83 (d, 1H), 7.49 (d, 1H), 7.40 (s, 1H), 7.29 (m, 2H), 7.19 (d, 1H), 7.10 (m, 2H), 6.25 (d, 1H), 4.71 (spt, 1H), 1.36 (d, 6H)

Synthesis of Compound 180: For compound 180, 10 was prepared as described for compound 170, then 10 was mixed with N-methylpiperdine under the amide formation conditions of General Procedure J to provide compound 180 in 33.8% yield. $^1$H NMR (300 MHz, DMSO-d6) ppm 11.48 (s, 1H), 7.78 (d, 1H), 7.46-7.58 (m, 4H), 6.67 (s, 1H), 6.20 (d, 1H), 3.57-3.72 (m, 4H), 2.23-2.35 (m, 4H), 2.18 (s, 3H)

Synthesis of Compound 181: For compound 181, 10 was prepared as described for compound 170, then 10 was mixed with pyrole under the amide formation conditions of General Procedure J to provide compound 181 in 46.2% yield. $^1$H NMR (300 MHz, DMSO-d6) ppm 11.32 (s, 1H), 7.80 (d, 1H), 7.42-7.58 (m, 4H), 6.86 (s, 1H), 6.20 (d, 1H), 3.48-3.73 (m, 4H), 1.74-1.99 (m, 4H)

Synthesis of Compound 182: For compound 182, 10 was prepared as described for compound 170, then 10 was mixed with morphiline under the amide formation conditions of General Procedure J to provide compound 182 in 47% yield. $^1$H NMR (300 MHz, DMSO-d6) ppm 11.50 (br. s., 1H), 7.78 (d, 1H), 7.44-7.59 (m, 4H), 6.71 (s, 1H), 6.20 (d, 1H), 3.48-3.75 (m, 8H)

Synthesis of Compound 183: For compound 183, the general procedure outlined for compound 189 was used.

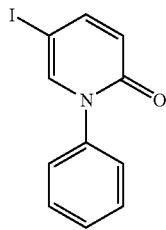

The iodopyridone intermediate above was obtained by reaction of 600 mg (2.7 mmol) of 5-iodo-2-pyridone with phenylboronic acid. After purification (SiO$_2$; Hexane/Acetate/MeOH 1/1/0 to 0/10/1). 600 mg (75% yield) of pure intermediate were obtained as a pale yellow solid. The Suzuki coupling, as outlined for compound 189, below, provided compound 183 in 38% yield. $^1$H NMR (300 MHz, DMSO-d6) ppm 7.98 (s, 2H), 7.91 (dd, 1H), 7.83 (dd, 1 H), 7.36-7.62 (m, 5H), 6.54 (dd, 1H)

Synthesis of Compound 184: For compound 184, intermediate sulfonamide was prepared as follows.

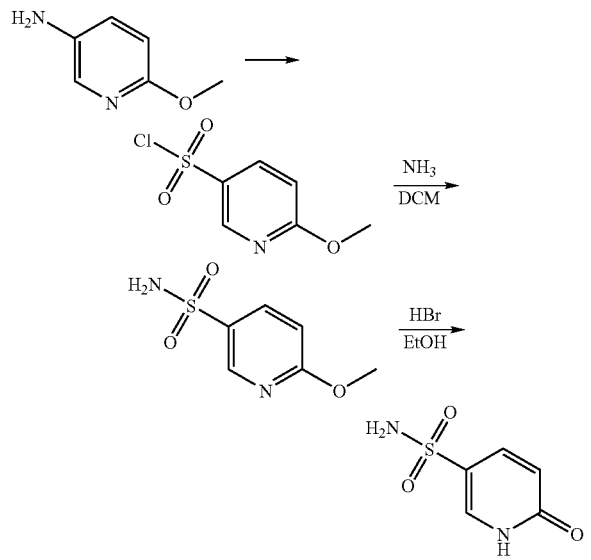

A mixture of 2-methoxy-5-aminopyridine (10 g, 0.08 mol) in AcOH (125 mL), and concentrated HCl (150 mL) was cooled at 0° C. in an ice/water bath. A solution of NaNO$_2$ (4.0 g, 0.058 mol) in water (15 mL) was added dropwise at 0° C. The resulting mixture was stirred for 45 minutes at 0° C. In a separate round bottom flask, 150 mL of concentrated HCl was added dropwise to a sodium bisulphite solution. The gaseous SO$_2$ thus formed was purged for 2-3 h into a third round bottom flask containing AcOH cooled at −20° C. CuCl$_2$ (18 g) was added, and the reaction was stirred for 20 minutes at −20° C. The mixture was added dropwise to the 2-methoxy-5-aminopyridine/AcOH/concentrated HCl mixture maintained at 0° C. The reaction was allowed to warm up to room temperature and stirred overnight. The mixture was quenched with water and the solid thus formed was filtered, re-dissolved in DCM and filtered through celite. The clear solution was dried over Na$_2$SO$_4$ and concentrated under vacuum to afford 10.2 g (61% yield) of pure 6-methoxy-pyridine-3-sulfonyl chloride. 6-Methoxy-pyridine-3-sulfonyl chloride (5.0 g, 0.025 mol) was dissolved in DCM and cooled at 0° C. Gaseous NH$_3$ was bubbled in the solution for 10 min. The resulting pale brown suspension was filtered and the solid was triturated with water. The resulting white solid was filtered and dried under vacuum to afford 3.2 g (70.6% yield) of pure 6-Methoxy-pyridine-3-sulfonamide. 6-Methoxy-pyridine-3-sulfonamide (0.752 g, 4.0 mmol) was dissolved in EtOH (6 mL). An excess of 48% HBr aqueous solution (12 mL) was added and the reaction was heated at 90° C. for 20 h. The solvent was removed under reduced pressure and the residual hydrobromic acid was further dried under reduced pressure, at 40° C., to provide the intermediate sulfonamide in quantitative yield. The sulfonamide was used in General Procedure H1A to provide compound 184 in 10% yield. $^1$H NMR (300 MHz, DMSO-d6) ppm 8.05 (dd, 1H), 7.79 (dd, 1H), 7.62 (m, 2H), 7.55 (m, 2H), 7.36 (s, 2H), 6.67 (dd, 1H)

Synthesis of Compound 185: For compound 185, A was prepared in the following manner.

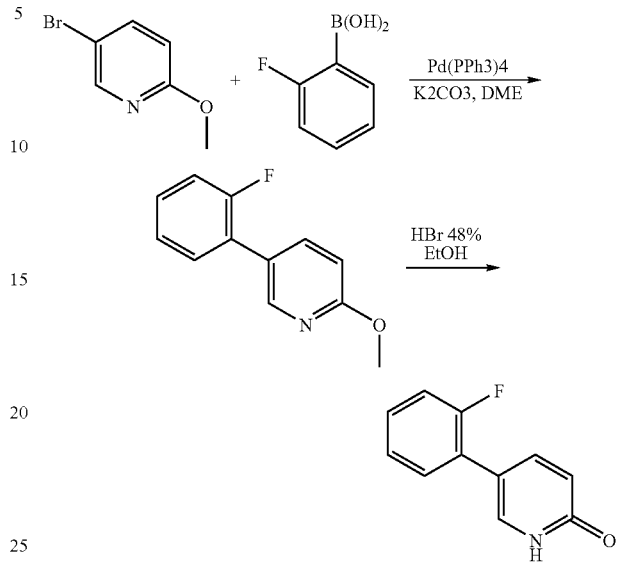

Following the general procedure I, 5-(2-fluorophenyl)-2-methoxypyridine was obtained by reaction of 3 g (16 mmol) of 5-bromo-2-methoxy-pyridine. After purification (SiO$_2$; Pet. Ether/EtOAc 1/1 to 0/1), 750 mg (31% yield) of pure product was obtained as a white solid. 5-(2-fluorophenyl)-2-methoxypyridine (750 mg) was dissolved in HBr 48% (10 mL) and EtOH (3 mL) and the solution was heated at reflux for 3 h. After evaporation of volatiles, 700 mg (quantitative yield) of the desired pyridone were obtained as a white solid. Following general procedure H1A, compound 185 was prepared in 58% yield. $^1$H NMR (300 MHz, DMSO-d6) ppm 10.13 (s, 1H), 7.69-7.90 (m, 3H), 7.51-7.65 (m, 2H), 7.20-7.50 (m, 4 H), 7.14 (dd, 1H), 6.60 (d, 1H), 2.06 (s, 3H)

Synthesis of Compound 186: For compound 186, A was prepared as described for compound 185. Following general procedure H1A, compound 186 was prepared in 43% yield. $^1$H NMR (300 MHz, DMSO-d6) ppm 7.82-7.88 (m, 1H), 7.78 (ddd, 1H), 7.35-7.62 (m, 7H), 7.22-7.36 (m, 2H), 6.61 (dd, 1H)

Synthesis of Compound 187: For compound 187, A was prepared as described for compound 185. Following general procedure H1A, compound 187 was prepared in 58% yield. $^1$H NMR (300 MHz, DMSO-d6) ppm 7.90 (d, 1H), 7.79 (ddd, 1H), 7.67 (m, 2H), 7.47-7.63 (m, 3H), 7.19-7.46 (m, 3H), 6.62 (dd, 1H)

Synthesis of Compound 188: The synthesis of compound 188 was achieved in the following manner.

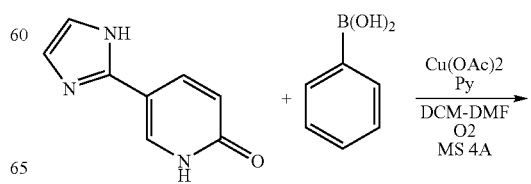

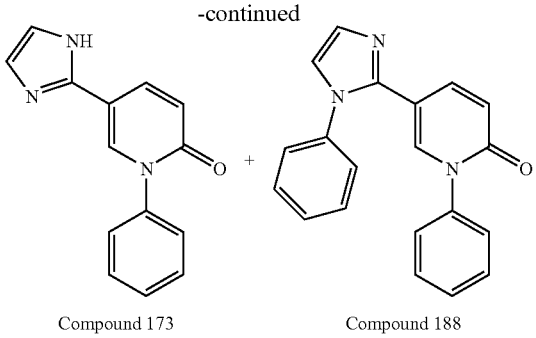

Compound 173   Compound 188

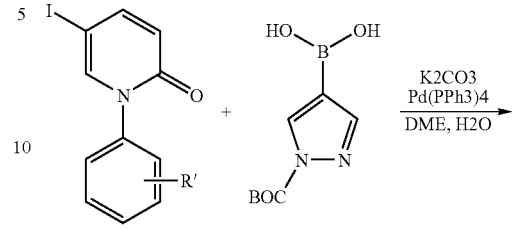

were obtained as a pale yellow solid. MS-ESI+: m/z=299 [MH+]

5-(1H-imidazol-2-yl)pyridin-2(1H)-one (0.097 g, 0.6 mmol) was dissolved in DCM (3 mL) and N,N-dimethylformammide (3 mL). Phenylboronic acid (0.087 g, 0.72 mmol), copper(II) acetate (0.21 g, 1.2 mmol), pyridine (0.095 g, 1.2 mmol) and 4 Å molecular sieves were added and the reaction was stirred at room temperature in an open vessel for nine days. The reaction was monitored by UPLC-MS. At the end of the reaction, a concentrated solution of NH$_4$OH was added. Solvents were removed at reduced pressure, and the crude was purified by flash chromatography (SiO$_2$; EtOAc/MeOH 1:0 to 95:5). Two main products were recovered: 24 mg of compound 173 (10% yield) and 7 mg of compound 188 (2% yield). $^1$H NMR (300 MHz, DMSO-d6) ppm 7.81-7.94 (m, 1H), 7.75 (d, 1H), 7.71 (br. s., 1H), 7.40-7.66 (m, 8H), 7.33 (dd, 1H), 7.22-7.30 (m, 2H), 6.50 (d, 1H)

Synthesis of Compound 189: For compound 189, an iodopyridone is the intermediate of the Suzuki reaction.

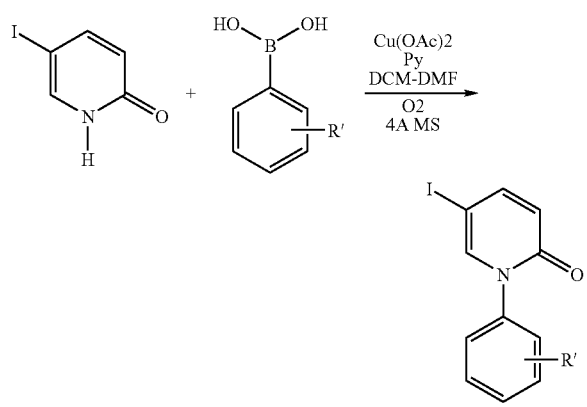

To a solution of 5-iodo-pyridin-2-one (1 eq) in DCM (5 mL/mmol of aryl halide) and DMF (0.7 mL/mmol of aryl halide), Cu(OAc)$_2$ (2 eq), the appropriate boronic acid (1.2 eq), pyridine (2 eq) and finely grounded, activated 4 Å molecular sieves were added. The mixture was stirred at room temperature in an open vessel for a variable time (from 12 hours to 7 days). Fresh Boronic acid was further added in sluggish reactions. A concentrated solution of NH$_4$OH was added. The solvents were evaporated under vacuum and the resulting crude was absorbed on silica pad and purified by flash chromatographic column (SiO$_2$; Pet. Ether/EtOAc mixture).

800 mg (4.2 mmol) of 5-iodo-2-pyridone with 4-pyridineboronic acid. After purification (SiO$_2$; Pet. Ether/EtOAc/MeOH 1/1/0 to 0/10/1). 387 mg (31% yield) of pure product

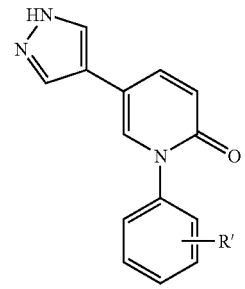

For the Suzuki coupling, the iodopyridone (1 eq), the appropriate boronic acid (1.2 eq) and K$_2$CO$_3$ (3 eq) were dissolved in a 10:1 mixture of DME/H$_2$O (4 mL/mmol). The solution was degassed by bubbling N$_2$ for 15 min and then Pd(PPh$_3$)$_4$ (0.05 eq) was added. The reaction mixture was heated at 90° C. for 18 h, after which time, BOC protecting group was completely cleaved. Mixture was cooled at room temperature, diluted with EtOAc and filtered on a celite plug. The filtrate was washed with brine. The separated organic phase was dried over Na$_2$SO$_4$ and concentrated under reduced pressure. The obtained residue was purified by column chromatography (SiO$_2$; Pet. Ether/EtOAc mixture).

Compound 189 was obtained in 42% yield. $^1$H NMR (300 MHz, DMSO-d6) ppm 8.71-8.92 (m, 2H), 8.00 (s, 2H), 7.98 (dd, 1H), 7.88 (dd, 1H), 7.66-7.78 (m, 2H), 6.60 (dd, 1H), 5.74 (br. s., 1H)

Synthesis of Compound 190: For compound 190, the intermediate sulfonamide was prepared as described for compound 184. The intermediate sulfonamide was used in General Procedure H1A to provide compound 190 in 9% yield. $^1$H NMR (300 MHz, DMSO-d6) ppm 7.99 (d, 1H), 7.78 (dd, 1H), 7.41-7.64 (m, 5H), 7.36 (s, 2H), 6.66 (d, 1H)

Synthesis of Compound 191: For compound 191, A was prepared as stated for compound 147. Following general procedure H1A, compound 191 was prepared. $^1$H NMR (300 MHz, DMSO-d6) ppm 9.13 (s, 1H), 9.12 (s, 1H), 8.76 (d, 1H), 8.67 (dd, 1H), 8.35 (dd, 1H), 8.08 (dd, 1H), 8.02 (ddd, 1H), 7.61 (ddd, 1H), 6.70 (dd, 1H)

Synthesis of Compound 192: For compound 192, A was prepared as stated for compound 169. Following general procedure H1A, compound 192 was prepared in 15% yield. $^1$H NMR (300 MHz, DMSO-d6) ppm 8.89 (d, 1H), 8.52 (dd, 1H), 8.17 (d, 1H), 8.06 (ddd, 1H), 8.01 (dd, 1H), 7.96 (m, 2H), 7.74 (m, 2H), 7.49 (s, 2H), 7.43 (ddd, 1H), 6.66 (d, 1H)

Synthesis of Compound 193: For compound 193, the iodopyridone intermediate was prepared as described for compound 189 and 183, above. The iodopyridone was then used in a Stille coupling.

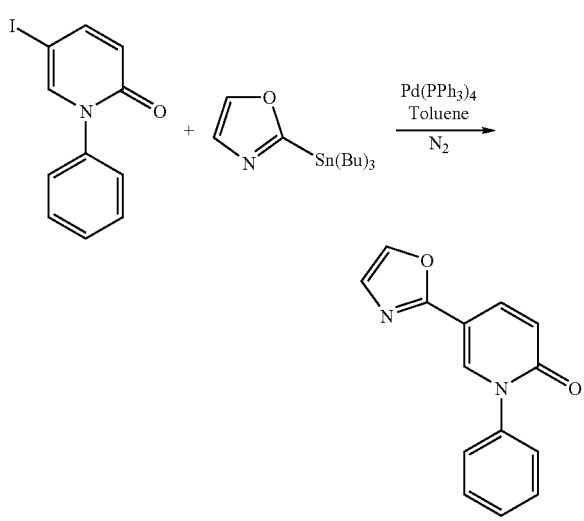

5-iodo-1-phenylpyridin-2(1H)-one (0.088 g, 0.3 mmol) was dissolved in dry and degassed toluene (7.5 mL/mmol). The catalyst was then added (0.017 g, 0.015 mmol) and the mixture was stirred for 10 minutes. 2-(tributylstannyl)oxazole (0.107 g, 0.3 mmol) was added and the reaction was heated at 90° C. for 18 h under nitrogen atmosphere. Conc. NH$_4$OH was added. The solvent was removed at reduced pressure and the crude was purified by flash chromatography (SiO$_2$; Pet. Ether/EtOAc 1:1) and then through titration in di-isopropylether. The residual product present in the mother liquor was recovered after purification with preparative. 36 mg (30% yield) of compound 193 were obtained as a pale yellow solid. $^1$H NMR (300 MHz, DMSO-d6) ppm 8.19 (dd, 1H), 8.14 (d, 1H), 8.02 (dd, 1H), 7.43-7.61 (m, 5H), 7.32 (d, 1H), 6.66 (dd, 1H)

Synthesis of Compound 194: For compound 194, 10 was prepared as described for compound 170, then 10 was mixed with pyrole under the amide formation conditions of General Procedure J to provide compound 194 in 29% yield. $^1$H NMR (300 MHz, DMSO-d6) ppm 10.72 (br. s., 1H), 7.76 (d, 1H), 7.22 (m, 2H), 7.05 (m, 2H), 6.85 (s, 1 H), 6.19 (d, 1 H), 4.69 (quin, 1H), 3.39-3.72 (m, 4H), 1.78-1.95 (m, 4H), 1.34 (d, 6H)

Synthesis of Compound 195: For compound 195, 10 was prepared as described for compound 170, then 10 was mixed with 3-methoxyaniline under the amide formation conditions of General Procedure J to provide compound 195 in 75% yield. $^1$H NMR (300 MHz, DMSO-d6) ppm 11.26 (br. s., 1H), 9.86 (s, 1H), 7.83 (d, 1H), 7.37-7.41 (m, 1H), 7.14-7.32 (m, 5H), 7.08 (m, 2H), 6.63 (ddd, 1H), 6.22 (d, 1H), 4.70 (quin, 1H), 3.73 (s, 3 H), 1.35 (d, 6H)

Synthesis of Compound 196: For compound 196, 10 was prepared as described for compound 170, then 10 was mixed with 3-phenoxyaniline under the amide formation conditions of General Procedure J to provide compound 196 in 20% yield. $^1$H NMR (300 MHz, DMSO-d6) ppm 11.64 (s, 1H), 9.94 (s, 1H), 7.86 (d, 1H), 7.28-7.57 (m, 10 H), 7.15 (dddd, 1H), 7.04 (m, 2H), 6.72 (ddd, 1H), 6.24 (d, 1H)

Synthesis of Compound 197: For compound 197, 10 was prepared as described for compound 170, then 10 was mixed with 3-aminobenzenesulfonamide under the amide formation conditions of General Procedure J to provide compound 197 in 21.4% yield. $^1$H NMR (300 MHz, DMSO-d6) ppm 11.31 (s, 1H), 10.16 (s, 1H), 8.12-8.18 (m, 1H), 7.89-8.01 (m, 1H), 7.84 (d, 1H), 7.43-7.57 (m, 2H), 7.30-7.35 (m, 3H), 7.27 (m, 2H), 7.09 (m, 2H), 6.23 (d, 1H), 4.71 (quin, 1H), 1.35 (d, 6H)

Synthesis of Compound 198: For compound 198, 10 was prepared as described for compound 170, then 10 was mixed with 3-methylaminopyridine under the amide formation conditions of General Procedure J to provide compound 198 in 28.4% yield. $^1$H NMR (300 MHz, DMSO-d6) ppm 11.02 (s, 1H), 8.62-8.92 (m, 1H), 8.35-8.58 (m, 2H), 7.79 (d, 1 H), 7.17-7.34 (m, 4H), 6.98-7.14 (m, 3H), 6.19 (d, 1H), 4.68 (quin, 1H), 4.43 (d, 2H), 1.33 (d, 6H)

Synthesis of Compound 199: For compound 199, 10 was prepared as described for compound 170, then 10 was mixed with 3-phenoxyaniline under the amide formation conditions of General Procedure J to provide compound 199 in 47% yield. $^1$H NMR (300 MHz, DMSO-d6) ppm 11.28 (s, 1H), 9.92 (s, 1H), 7.81 (d, 1H), 7.35-7.49 (m, 4H), 7.31 (dd, 1H), 7.20-7.27 (m, 3H), 7.10-7.19 (m, 1H), 6.98-7.10 (m, 4H), 6.72 (ddd, 1), 6.21 (d, 1H), 4.69 (quin, 1H), 1.34 (d, 6H)

Synthesis of Compound 200: Following General Procedure L2, compound 200 was prepared in 10% yield. $^1$H NMR (300 MHz, DMSO-d6) ppm 7.45-7.55 (m, 2H), 7.34-7.45 (m, 4H), 6.57 (d, 1H), 6.45 (dd, 1H), 2.99-3.12 (m, 4H), 1.78-1.97 (m, 4H)

Synthesis of Compound 201: For compound 201, A was prepared as described for compound 185. Following general procedure H1A, compound 201 was prepared in 13% yield. $^1$H NMR (300 MHz, DMSO-d6) ppm 9.25 (s, 1H), 9.07 (s, 2H), 8.06 (d, 1H), 7.79-7.88 (m, 1H), 7.55-7.65 (m, 1H), 7.20-7.47 (m, 3H), 6.66 (dd, 1H)

Synthesis of Compound 202: Compound A for compound 202 was prepared as stated for compound 116. The prepared compound A was used in General procedure H1A to provide compound 202 in 8% yield. $^1$H NMR (300 MHz, DMSO-d$_6$) 9.27 (s, 1H), 8.91 (s, 2 H), 7.29-7.35 (m, 1H), 7.11 (dt, 1H), 6.71 (d, 1H), 1.63-1.83 (m, 1H), 0.86-1.02 (m, 2 H), 0.51-0.69 (m, 2H)

Synthesis of Compound 203: For compound 203, the iodopyridone intermediate was obtained as described for compound 189.

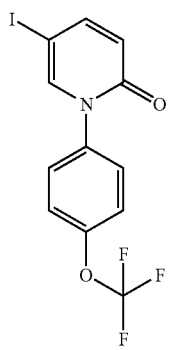

The product was obtained by reaction of 500 mg (2.25 mmol) of 5-iodo-2-pyridone with 4-trifluoromethoxy-phenyl-boronic acid. After flash chromatography (SiO2; Pet. Ether/EtOAc 2:1) 300 mg (35% yield) of the intermediate were obtained as a white solid. MS-ESI$^+$: m/z=380.9 [MH$^+$] The iodopyridone was then used in a Stille coupling.

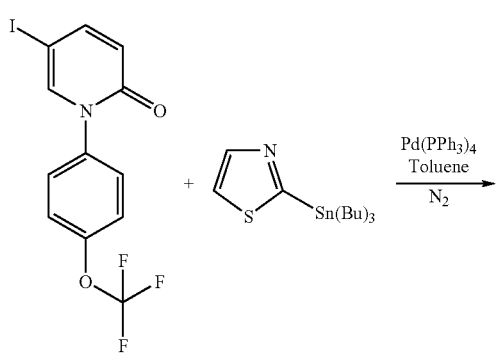

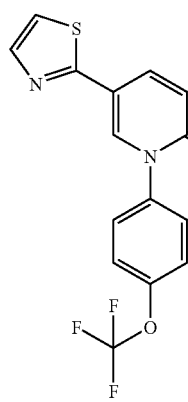

5-iodo-1-(4-(trifluoromethoxy)phenyl)pyridin-2(1H)-one (0.19 g, 0.5 mmol) was dissolved in dry and degassed toluene (10 mL). Pd(PPh₃)₄ (0.029 g, 0.025 mmol) was then added and the mixture was stirred for 10 minutes. 2-(tributylstannyl) thiazole (0.187 g, 0.5 mmol) was added and the reaction was heated at 90° C. for 4 h under nitrogen atmosphere. A large excess of a KF/H₂O solution was added and the mixture was stirred for 1 h. The aqueous phase was extracted with EtOAc. The solvent was removed under reduced pressure and the crude was purified by flash chromatography (SiO₂; Pet. Ether/EtOAc 7:3 to Hex/EtOAc 1:1) and then through titration in a Pet. Ether/EtOAc mixture. 62.5 mg (37% yield) of compound 203 were obtained as a white solid. ¹H NMR (300 MHz, DMSO-d6) ppm 8.30 (dd, 1H), 8.09 (dd, 1H), 7.85 (d, 1H), 7.60-7.75 (m, 3H), 7.55 (m, 2H), 6.66 (dd, 1H)

Synthesis of Compound 204: For compound 204, 10 was prepared as described for compound 170, then 10 was mixed with 3-chloroaniline under the amide formation conditions of General Procedure J to provide compound 204 in 32.3% yield. ¹H NMR (300 MHz, DMSO-d6) ppm 11.69 (s, 1H), 10.04 (s, 1H), 7.82-7.97 (m, 2H), 7.63 (ddd, 1 H), 7.46-7.59 (m, 4H), 7.27-7.41 (m, 2H), 7.10 (ddd, 1H), 6.26 (d, 1H)

Synthesis of Compound 205: For compound 205, 10 was prepared as described for compound 170, then 10 was mixed with 2-methylaminotetrahydrofuran under the amide formation conditions of General Procedure J to provide compound 205 in 16.5% yield. ¹H NMR (300 MHz, DMSO-d6) ppm 11.15-11.41 (m, 1H), 8.11-8.29 (m, 1H), 7.81 (d, 1 H), 7.47-7.63 (m, 4H), 7.04 (d, 1H), 6.20 (d, 1H), 3.83-3.97 (m, 1H), 3.68-3.81 (m, 1 H), 3.53-3.67 (m, 1H), 3.18-3.37 (m, 2H), 1.69-1.98 (m, 3H), 1.43-1.60 (m, 1H)

Synthesis of Compound 206: For compound 206, 10 was prepared as described for compound 170, then 10 was mixed with 4-phenoxyaniline under the amide formation conditions of General Procedure J to provide compound 206 in 34.7% yield. ¹H NMR (300 MHz, DMSO-d6) ppm 11.25 (s, 1H), 9.91 (s, 1H), 7.83 (d, 1H), 7.60-7.75 (m, 2H), 7.31-7.44 (m, 2H), 7.19-7.31 (m, 3H), 7.04-7.16 (m, 3H), 6.90-7.04 (m, 4H), 6.22 (d, 1H), 4.64-4.76 (m, 1H), 1.35 (d, 6H)

Synthesis of Compound 207: For compound 207, general procedures K and J were used to obtain compound 207 in 70% yield. ¹H NMR (300 MHz, CDCl₃): ppm 1.34 (t, J=7.1 Hz, 3H); 4.30 (q, J=7.1 Hz, 2H); 6.47 (d, J=9.3 Hz, 1H); 7.03 (d, J=2.4 Hz, 1H); 7.26-7.43 (m, 2H); 7.57-7.69 (m, 4H); 8.27 (s, 1H); MS-ESI: m/z=283.1 [M+1]+

Synthesis of Compound 208: For compound 208, general procedures K and J were used to obtain compound 208 in 41% yield. ¹H NMR (300 MHz, CDCl₃): ppm 1.34 (t, J=7.2 Hz, 3H); 4.30 (q, J=7.1 Hz, 2H); 6.54 (d, J=9.3 Hz, 1H); 6.79 (d, J=8.7 Hz, 2H); 7.01-7.11 (m, 3H); 7.76 (d, J=9.0 Hz, 1H); 7.89-8.57 (br., 1H); 8.425 (s, 1H); MS-ESI: m/z=299.0 [M+1]⁺

Synthesis of Compound 209: For compound 209, the following synthesis was used.

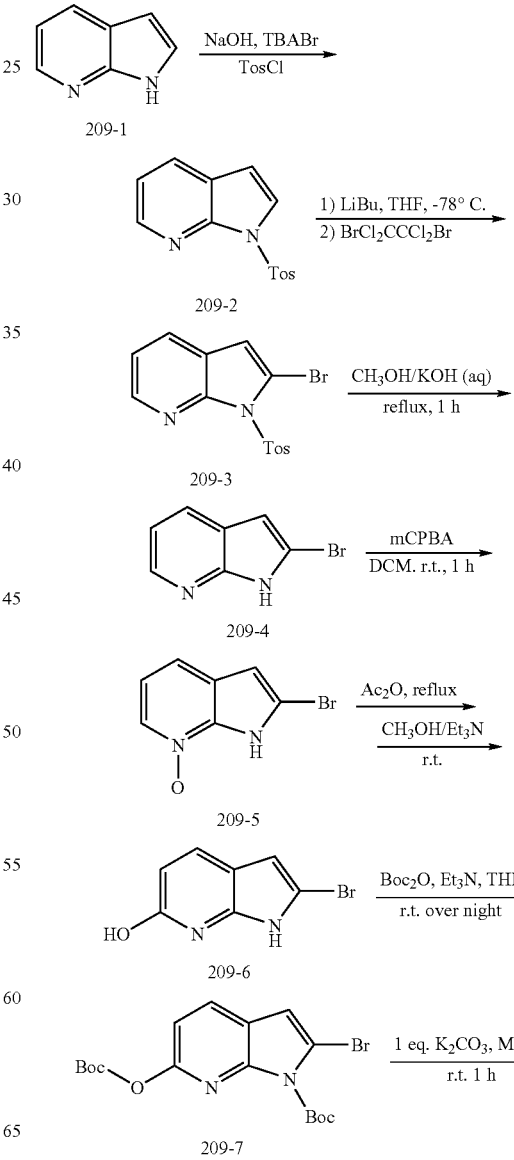

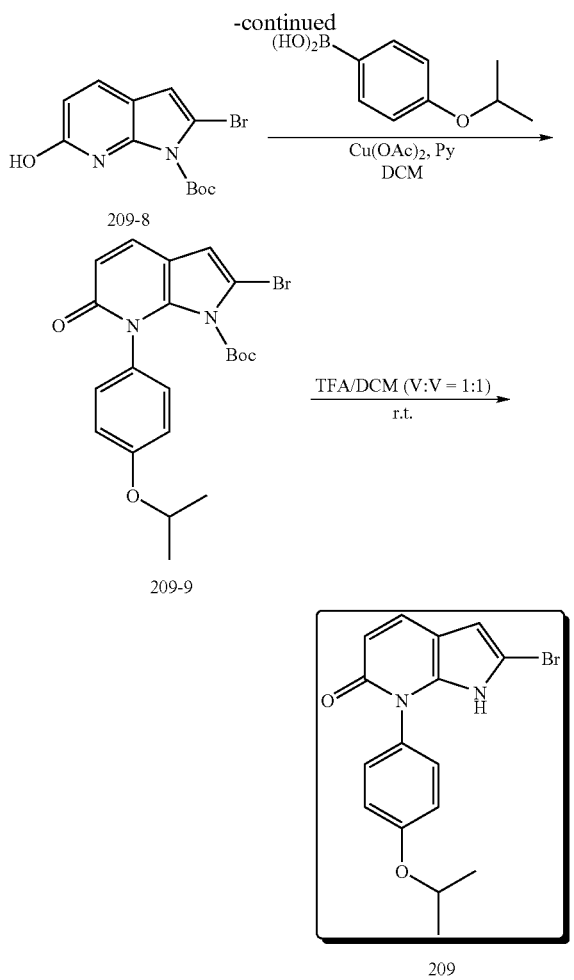

To a mixture of 209-1 (45.0 g, 381.4 mmol), para-toluenesulfonyl chloride (80.1 g, 421.6 mmol) and a catalytic amount of tetrabutyl ammonium bromide (TBABr) in toluene (540 ml) was added aq. NaOH (288.0 g in 900 ml water, 7.2 mol). The biphasic solution was stirred at ambient temperature for 4 h, and then extracted twice with toluene. The organic phase was dried over anhydrous $Na_2SO_4$ and concentrated. The crude product was triturated in ethyl acetate/petroleum ether (V:V=1:20) and filtrated to afford the compound 209-2 (90 g, 87% yield). MS-ESI: m/z=273.1 $[M+1]^+$ A solution of 209-2 (50.0 g, 183.8 mmol) in dry THF cooled to −78° C. and n-BuLi (81 ml, 2.5 M in hexane) was added over 20 minutes. The resulted solution was maintained at −78° C. for 1 h, and then a solution of $BrCl_2CCCl_2Br$ (71.0 g, 220.5 mmol) in dry THF was added. The mixture was stirred −78° C. for 30 min and allowed to warm slowly to room temperature. The solvent was removed under vacuum and the residue was partitioned between EtOAc and water. The organic layer was dried over anhydrous $Na_2SO_4$ and concentrated. The crude product was purified by column chromatography (5% ethyl acetate in petroleum ether to 20% ethyl acetate in petroleum ether as the eluent) to afford 209-3 (37 g, 58% yield). MS-ESI: m/z=351.0 $[M+1]^+$ A mixture of 209-3 (30 g, 0.085 mol), methanol (850 mL) and aqueous potassium hydroxide (5 mol/L, 100 mL) was heated under reflux overnight. The majority of the solvent was removed under vacuum, and the residue was partitioned between EtOAc and water. The organic layer was dried over anhydrous $Na_2SO_4$ and concentrated to give 209-4 (24 g, 80% yield) which was used without further purification. 1H NMR (400 MHz, DMSO): 6.550 (s, 1H); 7.039 (dd, J=5.2 Hz, J=3.2 Hz, 1H); 7.857 (dd, J=1.6 Hz, J=3.2 Hz, 1H); 8.155 (q, J=1.6 Hz, 1H); 12.418 (br, 1H)

mCPBA (14.0 g, 81.4 mmol) was added into a solution of 209-4 (8.0 g, 40.8 mmol) in THF (140 ml) at 0° C., and then the reaction was warmed up the room temperature for 1 h and quenched with saturated $Na_2S_2O_3$. The solution was concentrated after filtering. The crude was purified by column chromatography (0-10% methanol in ethyl acetate as the eluent) to afford 209-5 (6.3 g, 73% yield). $^1$H NMR (400 MHz, DMSO): 6.698 (s, 1H); 7.055 (t, J=6.4 Hz, 1H); 7.660 (d, J=6.0 Hz, 1H); 8.099 (d, J=6.0 Hz, 1H)

A mixture of 209-5 (3.5 g, 16.5 mmol) and acetic acid anhydride was heated at its reflux temperature for 1.5 h. The solution was then evaporated. The residue was mixed with methanol and $Et_3N$ at room temperature for 2 h. The solution was concentrated and the residue was partitioned between EtOAc and water. The organic layer was dried over anhydrous $Na_2SO_4$ and concentrated. The crude product was purified by column chromatography (10% ethyl acetate/petroleum) to afford 209-6 (1.4 g, 40% yield). $^1$H NMR (300 MHz, DMSO): 6.337 (d, J=8.1 Hz, 1H); 6.359 (s, 1H); 7.662 (d, J=8.1 Hz, 1H) MS-ESI: m/z=214.1 $[M+1]^+$ A solution of 209-6 (150 mg, 0.71 mmol) and triethylamine (470 mg, 4.2 mmol) in THF (5 mL) was stirred for 15 min before the addition of $(Boc)_2O$ (0.907 g, 4.2 mmol). The solution was stirred at room temperature overnight. Most of the solvent was removed under vacuum to get a residue, then it was partitioned between water (50 mL) and DCM (100 mL), the organic layer was separated and the aqueous layer was extracted with DCM (50 mL×2). The combined organic layer was washed with water (100 mL) and brine (100 mL), dried over $Na_2SO_4$ and concentrated to give a residue, which was purified by Prep-TLC (25% ethyl acetate in petroleum ether as the eluent) to give 209-7 (250 mg, yield 85%). $^1$H NMR (400 MHz, CDCl3): 1.558 (s, 9H); 1.684 (s, 9H); 6.673(s, 1H); 6.970 (d, J=8.4 Hz, 1H); 7.824 (d, J=8.4 Hz, 1H); MS-ESI: m/z=436.9 $[M+23]^+$ A mixture of 209-7 (550 mg, 1.33 mmol), $K_2CO_3$ (200 mg, 1.45 mmol) and methanol (8 mL) was stirred at rt for 1 h. Methanol was removed before the addition of water (50 mL), then it was extracted with DCM (50 mL×3). Combined DCM was washed with water and brine, dried over $Na_2SO_4$ and concentrated to give a residue, which was isolated by prep-TLC (50% ethyl acetate in petroleum ether as the eluent) to give 209-8 (130 mg, 31.2%) as a white solid.

$^1$H NMR (400 MHz, CDCl3): 1.699 (s, 9H); 6.404(d, J=9.2 Hz, 1H); 6.488 (s, 1H); 7.518 (d, J=9.2 Hz, 1H); MS-ESI: m/z=352.9 $[M+39]^+$

A mixture of 209-8 (50 mg, 0.16 mmol), 4-isopropoxylbenzyl boric acid (100 mg, 0.73 mmol), pyridine (0.26 mL, 3.2 mmol) and anhydrous $Cu(OAC)_2$ (10 mg, 0.05 mmol) in DCM (2 mL) was stirred over night open to air. The mixture was filtrated and evaporated to give a residue, which was isolated by Prep-TLC (20% ethyl acetate in petroleum ether as the eluent) to give 209-9 (50 mg, 78.6%) as a white solid. $^1$H NMR (400 MHz, CDCl3): 1.345 (d, J=8.0 Hz, 6H); 1.412 (s, 1H); 4.489 (m, J=8.0 Hz, 1H); 6.596 (s, 1H); 6.785 (d, J=11.2 Hz, 1H); 6.852-6.906 (m, 2H); 7.031-7.085 (m, 2H); 7.725 (d, J=11.2 Hz, 1H); MS-ESI: m/z=448.8 $[M+1]^+$ A solution of 209-9 (50 mg, 0.112 mmol) in DCM/TFA (V:V=1:1) was stirred at room temperature for 3 h. All the solvents were removed by evaporation to give a residue. It was isolated by Prep-TLC (25% ethyl acetate in petroleum ether as the eluent) to give compound 209 (30 mg, 68.5%) as a white solid. ¹H NMR (400 MHz, CDCl3): 1.350 (d, J=6.0 Hz, 6H); 4.509 (m, J=6.0 Hz, 1H); 6.440 (d, J=2.0 Hz, 1H); 6.674 (d, J=8.4 Hz, 1H); 6.899 (d, J=8.8 Hz, 2H); 7.053 (d, J=8.8 Hz, 2H); 7.774 (d, J=8.4 Hz, 1H); 8.683 (br, 1H); MS-ESI: m/z=349.2 [M+1]⁺

Synthesis of Compound 210: For compound 210, compound 247 was used as an intermediate in general procedure J amide formation to form compound 210 in 20.4% yield.

¹H NMR (300 MHz, DMSO-d6) ppm 11.65 (br. s., 1H), 9.86 (s, 1H), 7.87 (d, 1H), 7.45-7.63 (m, 4H), 7.38-7.44 (m, 1H), 7.14-7.34 (m, 3H), 6.63 (ddd, 1H), 6.24 (d, 1H), 3.73 (s, 3H)

Synthesis of Compound 211: For compound 211, compound 216 was used as an intermediate in general procedure J amide formation to form compound 211 in 52% yield. ¹H NMR (300 MHz, DMSO-d6) ppm 11.53 (br. s., 1H), 9.84 (br. s., 1H), 7.85 (d, 1H), 7.34-7.49 (m, 5H), 7.29 (s, 1H), 7.16-7.27 (m, 2H), 6.56-6.71 (m, 1H), 6.23 (d, 1H), 3.73 (s, 3H)

Synthesis of Compound 212: For compound 212, compound 216 was used as an intermediate in general procedure J amide formation to form compound 212 in 27.9% yield.

¹H NMR (300 MHz, DMSO-d6) ppm 11.18 (br. s., 1H), 7.70-7.85 (m, 1H), 7.26-7.47 (m, 4H), 6.85 (s, 1H), 6.08-6.28 (m, 1H), 3.39-3.72 (m, 4H), 1.76-1.94 (m, 4H)

Synthesis of Compound 213: For compound 213, general procedures K and J were used to obtain compound 213 in 61% yield. ¹H NMR (300 MHz, DMSO-d6) ppm 12.49 (br. s., 1H), 7.92 (d, 2H), 7.82 (d, 1H), 7.61 (d, 2H), 7.01 (s, 1H), 6.24 (d, 1H)

Synthesis of Compound 214: For compound 214, compound 216 was used as an intermediate in general procedure J amide formation to form compound 214 in 17.5% yield.

¹H NMR (300 MHz, DMSO-d6) ppm 11.17 (br. s., 1H), 8.63 (br. s., 1H), 7.80 (d, 1H), 7.19-7.46 (m, 9H), 7.04 (s, 1H), 6.18 (d, 1H), 4.42 (d, 2H)

Synthesis of Compound 215: For compound 215, general procedures K and J were used to obtain compound 215 in 93.3% yield. ¹H NMR (300 MHz, DMSO-d6) ppm 12.41 (s, 1H), 7.76 (d, 1H), 7.20 (m, 2H), 7.04 (m, 2H), 6.97 (s, 1H), 6.20 (d, 1 H), 4.68 (quin, 1H), 1.34 (d, 6H)

Synthesis of Compound 216: For compound 216, general procedures K and J were used to obtain compound 216 in 93.6% yield. ¹H NMR (300 MHz, DMSO-d6) ppm 7.77 (d, 1H), 7.24-7.50 (m, 4H), 6.89 (s, 1H), 6.19 (d, 1H)

Synthesis of Compound 217: For compound 217, compound 216 was used as an intermediate in general procedure J amide formation to form compound 217 in 31.6% yield.

¹H NMR (300 MHz, DMSO-d6) ppm 11.60 (br. s., 1H), 10.11 (br. s., 1H), 8.18 (s, 1H), 7.92 (br. s., 1H), 7.84 (d, 1H), 7.22-7.55 (m, 9H), 6.20 (d, 1H)

Synthesis of Compound 218: For compound 218, compound 216 was used as an intermediate in general procedure J amide formation to form compound 218 in 30.7% yield.

¹H NMR (300 MHz, DMSO-d6) pm 11.40 (br. s., 1H), 7.76 (d, 1H), 7.27-7.50 (m, 4 H), 6.66 (s, 1H), 6.18 (d, 1H), 3.51-3.75 (m, 4H), 2.23-2.37 (m, 4H), 2.18 (s, 3H)

Synthesis of Compound 219: For compound 219, compound 213 was used as an intermediate in general procedure J amide formation to form compound 219 in 21.9% yield.

¹H NMR (300 MHz, DMSO-d6) ppm 11.71 (s, 1H) 9.87 (s, 1H) 7.94 (d, 2H) 7.89 (d, 1H) 7.65 (d, 2H) 7.37-7.45 (m, 1H) 7.33 (s, 1H) 7.14-7.29 (m, 2H) 6.57-6.69 (m, 1H) 6.26 (d, 1H) 3.73 (s, 3H)

Synthesis of Compound 220: For compound 220, compound 213 was used as an intermediate in general procedure J amide formation to form compound 220 in 47.5% yield.

¹H NMR (300 MHz, DMSO-d6) ppm 11.53 (br. s., 1H) 7.92 (m, 2H) 7.80 (d, 1H) 7.62 (m, 2H) 6.72 (s, 1H) 6.21 (d, 1H) 3.49-3.72 (m, 8H)

Synthesis of Compound 221: For compound 221, compound 247 was used as an intermediate in general procedure J amide formation to form compound 221 in 37.9% yield.

¹H NMR (300 MHz, DMSO-d6) ppm 11.63 (s, 1H), 9.93 (s, 1H), 7.88 (d, 1H), 7.65-7.76 (m, 2H), 7.47-7.62 (m, 4H), 7.32-7.42 (m, 2H), 7.31 (d, 1H), 7.05-7.16 (m, 1H), 6.91-7.05 (m, 4H), 6.25 (d, 1H)

Synthesis of Compound 222: For compound 222, compound 216 was used as an intermediate in general procedure J amide formation to form compound 222 in 30.9% yield. ¹H NMR (300 MHz, DMSO-d6) ppm 11.51 (s, 1H) 9.91 (s, 1H) 7.86 (d, 1H) 7.65-7.76 (m, 2H) 7.32-7.50 (m, 6H) 7.29 (s, 1H) 7.06-7.15 (m, 1H) 6.92-7.05 (m, 4H) 6.24 (d, 1 H)

Synthesis of Compound 223: For compound 223, general procedure K is modified as follows.

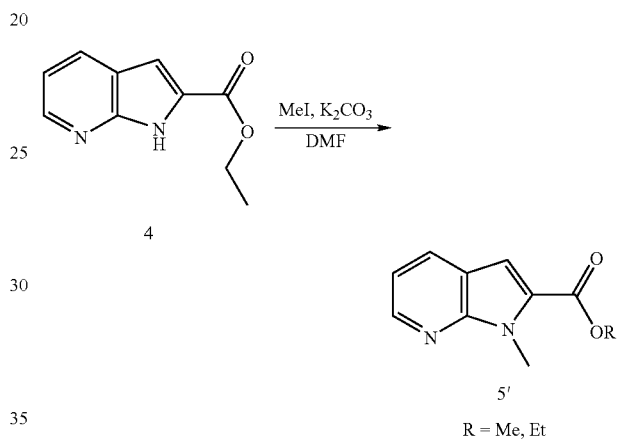

To a solution of 4 (5 g crude) in dry DMF (50 mL) anhydrous potassium carbonate (10.9 g, 79 mmol) and methyl iodide (2.5 mL, 0.039 mol) were added. The reaction was stirred at room temperature overnight. The mixture was filtered and the residue was washed with methanol. Mother liquors were concentrated and the obtained crude product was purified by column chromatography (SiO₂, hexanes:EtOAc 7:3) to obtain 1.5 g of a yellow solid (9:1 mixture of 1-Methyl-1H-pyrrolo[2,3-b]pyridine-2-carboxylic acid methyl ester and 1-Methyl-1H-pyrrolo[2,3-b]pyridine-2-carboxylic acid ethyl ester. This intermediate was then used in the subsequent reactions of general procedure K to obtain a methyl version of intermediate 8 for use in general procedure J. Following this modified procedure, compound 223 was obtained in 94% yield. ¹H NMR (300 MHz, DMSO-d6) ppm 12.98 (br. s., 1H) 8.18 (d, 1H) 7.44 (m, 2H) 7.36 (m, 2H) 7.20 (s, 1H) 6.88 (d, 1H) 3.82 (s, 3H)

Synthesis of Compound 224: For compound 224, compound 247 was used as an intermediate in general procedure J amide formation to form compound 224 in 13.4% yield.

¹H NMR (300 MHz, DMSO-d6) ppm 1.36 (br. s., 1H) 8.65 (t, 1H) 7.82 (d, 1H) 7.46-7.59 (m, 4H) 7.21 (t, 1H) 7.07 (s, 1H) 6.73-6.88 (m, 3H) 6.21 (d, 1H) 4.39 (d, 2H) 3.72 (s, 3 H)

Synthesis of Compound 225: For compound 225, general procedures K and J were used to obtain compound 225 in 83.7% yield. ¹H NMR (300 MHz, DMSO-d6) ppm 7.78 (d, 1H), 7.60 (m, 2H), 7.38 (m, 2H), 6.94 (s, 1H), 6.20 (d, 1H)

Synthesis of Compound 226: For compound 226, compound 213 was used as an intermediate in general procedure J amide formation to form compound 226 in 23.5% yield.

¹H NMR (300 MHz, DMSO-d6) ppm 11.44 (s, 1H) 7.91 (m, 2H) 7.82 (d, 1H) 7.60 (m, 2H) 6.87 (s, 1H) 6.21 (d, 1H) 3.39-3.73 (m, 4H) 1.77-1.98 (m, 4H)

Synthesis of Compound 227: For compound 227, compound 216 was used as an intermediate in general procedure J amide formation to form compound 227 in 37.2% yield.

¹H NMR (300 MHz, DMSO-d6) ppm 11.41 (br. s., 1H) 7.76 (d, 1H) 7.29-7.47 (m, 4H) 6.62-6.74 (m, 1H) 6.19 (d, 1H) 3.51-3.72 (m, 8H)

Synthesis of Compound 228: For compound 228, compound 216 was used as an intermediate in general procedure J amide formation to form compound 228 in 47.6% yield.

¹H NMR (300 MHz, DMSO-d6) ppm 11.58 (br. s., 1H) 10.01 (br. s., 1H) 7.80-7.94 (m, 2 H) 7.56-7.66 (m, 1H) 7.23-7.50 (m, 6H) 7.02-7.15 (m, 1H) 6.23 (d, 1H)

Synthesis of Compound 229: For compound 229, compound 213 was used as an intermediate in general procedure J amide formation to form compound 229 in 19% yield. ¹H NMR (300 MHz, DMSO-d6) ppm 11.55 (br. s., 1H), 7.92 (m, 2H), 7.78 (d, 1H), 7.62 (m, 2 H), 6.68 (s, 1H), 6.19 (d, 1H), 3.52-3.75 (m, 4H), 2.23-2.35 (m, 4H), 2.18 (s, 3H)

Synthesis of Compound 230: For compound 230, compound 213 was used as an intermediate in general procedure J amide formation to form compound 230 in 23% yield. ¹H NMR (300 MHz, DMSO-d6) ppm 11.43 (br. s., 1H), 7.92 (m, 2H), 7.80 (d, 1H), 7.62 (m, 2 H), 6.70 (s, 1H), 6.13-6.27 (m, 1H), 4.51-4.72 (m, 1H), 2.92 (s, 3H), 1.12 (d, 6H)

Synthesis of Compound 231: For compound 231, compound 216 was used as an intermediate in general procedure J amide formation to form compound 231 in 23% yield. ¹H NMR (300 MHz, DMSO-d6) ppm 11.23 (br. s., 1H), 7.77 (d, 1H), 7.27-7.48 (m, 4H), 6.69 (s, 1H), 6.18 (d, 1H), 4.45-4.73 (m, 1H), 2.92 (s, 3H), 1.13 (d, 6H)

Synthesis of Compound 232: For compound 232, compound 213 was used as an intermediate in general procedure J amide formation to form compound 232 in 36% yield. ¹H NMR (300 MHz, DMSO-d6) ppm 11.37 (br. s., 1H), 8.19 (br. s., 1H), 7.94 (m, 2H), 7.82 (d, 1H), 7.63 (m, 2H), 7.04 (s, 1H), 6.20 (d, 1H), 3.83-3.98 (m, 1H), 3.68-3.80 (m, 1H), 3.53-3.66 (m, 1H), 3.13-3.36 (m, 2H), 1.67-1.99 (m, 3H)

Synthesis of Compound 233: For compound 233, compound 225 was used as an intermediate in general procedure J amide formation to form compound 233 in 19% yield. ¹H NMR (300 MHz, DMSO-d6) ppm 11.34 (br. s., 1H), 7.77 (d, 1H), 7.61 (m, 2H), 7.39 (m, 2 H), 6.69 (s, 1H), 6.18 (d, 1H), 4.45-4.72 (m, 1H), 2.92 (s, 3H), 1.13 (d, 6H)

Synthesis of Compound 234: For compound 234, compound 213 was used as an intermediate in general procedure J amide formation to form compound 234 in 35% yield. ¹H NMR (300 MHz, DMSO-d6) ppm 11.80 (br. s., 1H), 10.01 (br. s., 1H), 7.81-8.01 (m, 4H), 7.56-7.70 (m, 3H), 7.26-7.42 (m, 2H), 7.03-7.16 (m, 1H), 6.25 (d, 1H)

Synthesis of Compound 235: For compound 235, compound 225 was used as an intermediate in general procedure J amide formation to form compound 235 in 19% yield. ¹H NMR (300 MHz, DMSO-d6) ppm 11.34 (br. s., 1H), 7.77 (d, 1H), 7.61 (m, 2H), 7.39 (m, 2 H), 6.69 (s, 1H), 6.18 (d, 1H), 4.45-4.72 (m, 1H), 2.92 (s, 3H), 1.13 (d, 6H)

Synthesis of Compound 236: For compound 236, compound 213 was used as an intermediate in general procedure J amide formation to form compound 236 in 45% yield. ¹H NMR (300 MHz, DMSO-d6) ppm 11.39 (br. s., 1H), 8.44 (br. s., 1H), 7.91 (m, 2H), 7.83 (d, 1H), 7.61 (m, 2H), 7.25-7.38 (m, 4H), 7.17-7.24 (m, 1H), 7.14 (s, 1 H), 6.21 (d, 1H), 4.99-5.21 (m, 1H), 1.44 (d, 3H)

Synthesis of Compound 237: For compound 237, compound 225 was used as an intermediate in general procedure J amide formation to form compound 237 in 25.1% yield. ¹H NMR (300 MHz, DMSO-d6) ppm 7.76 (d, 1H), 7.60 (m, 2H), 7.39 (m, 2H), 6.69 (s, 1 H), 6.17 (d, 1H), 3.52-3.73 (m, 8H)

Synthesis of Compound 238: For compound 238, compound 213 was used as an intermediate in general procedure J amide formation to form compound 238 in 38% yield. ¹H NMR (300 MHz, DMSO-d6) ppm 11.44 (br. s., 1H), 8.62 (br. s., 1H), 7.92 (m, 2H), 7.82 (d, 1H), 7.63 (m, 2H), 7.15-7.36 (m, 5H), 6.92-7.14 (m, 1H), 6.02-6.29 (m, 1H), 4.41 (d, 2H)

Synthesis of Compound 239: For compound 239, compound 215 was used as an intermediate in general procedure J amide formation to form compound 239 in 34% yield. ¹H NMR (300 MHz, DMSO-d6) ppm 10.91 (s, 1H), 7.75 (d, 1H), 7.22 (m, 2H), 7.06 (m, 2H), 6.67 (s, 1H), 6.17 (d, 1H), 4.64-4.75 (m, 1H), 4.53-4.64 (m, 1H), 2.91 (s, 3H), 1.33 (d, 6 H), 1.12 (d, 6H)

Synthesis of Compound 240: For compound 240, compound 215 was used as an intermediate in general procedure J amide formation to form compound 240 in 20% yield. ¹H NMR (300 MHz, DMSO-d6) ppm 10.88 (s, 1H), 8.22 (t, 1H), 7.76 (d, 1H), 7.25 (m, 2H), 7.08 (m, 2H), 6.99 (s, 1H), 6.18 (d, 1H), 4.58-4.80 (m, 1H), 3.81-3.95 (m, 1H), 3.67-3.81 (m, 1H), 3.53-3.67 (m, 1H), 3.12-3.37 (m, 2H), 1.67-1.96 (m, 3H), 1.41-1.60 (m, 1H), 1.34 (d, 6H)

Synthesis of Compound 241: For compound 241, compound 213 was used as an intermediate in general procedure J amide formation to form compound 241 in 25.3% yield.

¹H NMR (300 MHz, DMSO-d6) ppm 8.23-8.33 (m, 1H), 7.84-8.00 (m, 3H), 7.72-7.80 (m, 1H), 7.69 (d, 2H), 7.49-7.58 (m, 2H), 7.14 (br. s., 1H), 6.10 (br. s., 1 H), 3.14 (s, 3H)

Synthesis of Compound 242: For compound 242, compound 225 was used as an intermediate in general procedure J amide formation to form compound 242 in 31.8% yield.

¹H NMR (300 MHz, DMSO-d6) ppm 12.25 (br. s., 1H), 11.67 (br. s., 1H), 7.86 (d, 1H), 7.66 (m, 2H), 7.39-7.56 (m, 4H), 7.20 (d, 1H), 6.26 (d, 1H)

Synthesis of Compound 243: For compound 243, compound 225 was used as an intermediate in general procedure J amide formation to form compound 243 in 31.8% yield.

¹H NMR (300 MHz, DMSO-d6) ppm 11.50 (br. s., 1H), 7.75 (d, 1H), 7.59 (m, 2H), 7.39 (m, 2H), 6.65 (s, 1H), 6.15 (d, 1H), 3.53-3.80 (m, 4H), 2.23-2.35 (m, 4 H), 2.18 (s, 3H)

Synthesis of Compound 244: For compound 244, compound 225 was used as an intermediate in general procedure J amide formation to form compound 244 in 19.7% yield.

¹H NMR (300 MHz, DMSO-d6) ppm 11.32 (br. s., 1H), 7.79 (d, 1H), 7.60 (m, 2H), 7.38 (m, 2H), 6.86 (s, 1H), 6.20 (d, 1H), 3.56 (br. s., 4H), 1.87 (br. s., 4H)

Synthesis of Compound 245: For compound 245, compound 225 was used as an intermediate in general procedure J amide formation to form compound 245 in 26.7% yield.

¹H NMR (300 MHz, DMSO-d6) ppm 11.68 (br. s., 1H), 10.03 (s, 1H), 7.80-7.94 (m, 2H), 7.58-7.69 (m, 3H), 7.39-7.47 (m, 2H), 7.27-7.39 (m, 2H), 7.10 (ddd, 1H), 6.24 (d, 1H)

Synthesis of Compound 246: For compound 246, compound 225 was used as an intermediate in general procedure J amide formation to form compound 246 in 31.9% yield.

¹H NMR (300 MHz, DMSO-d6) ppm 11.62 (s, 1H), 9.92 (s, 1H), 7.87 (d, 1H), 7.66-7.75 (m, 2H), 7.58-7.66 (m, 2H), 7.32-7.48 (m, 4H), 7.29 (s, 1H), 7.05-7.17 (m, 1H), 6.92-7.05 (m, 4H), 6.24 (d, 1H)

Synthesis of Compound 247: For compound 247, general procedures K and J were used to obtain compound 247 in 81.5% yield. ¹H NMR (300 MHz, DMSO-d6) ppm 7.80 (d, 1H), 7.40-7.60 (m, 4H), 6.99 (s, 1H), 6.22 (d, 1H)

Synthesis of Compound 248: For compound 248, general procedures K and J were used to obtain compound 248 in 90% yield. ¹H NMR (300 MHz, DMSO-d6) ppm 12.32 (br. s., 1H), 9.69 (br. s., 1H), 7.76 (d, 1H), 7.33 (dd, 1H), 6.97 (s, 1H), 6.90 (ddd, 1H), 6.72 (ddd, 1H), 6.67 (t, 1H), 6.20 (d, 1H)

Synthesis of Compound 249: For compound 249, compound 225 was used as an intermediate in general procedure J amide formation to form compound 249 in 15.2% yield.

¹H NMR (300 MHz, DMSO-d6) ppm 8.62 (t, 1H), 7.81 (d, 1H), 7.62 (m, 2H), 7.41 (m, 2 H), 7.22 (t, 1H), 7.06 (s, 1H), 6.73-6.88 (m, 3H), 6.20 (d, 1H), 4.39 (d, 2H), 3.72 (s, 3H)

Synthesis of Compound 250: For compound 250, compound 213 was used as an intermediate in general procedure J amide formation to form compound 250 in 34.2% yield.

¹H NMR (300 MHz, DMSO-d6) ppm 11.12 (s, 1H), 8.76 (br. s., 1H), 8.32-8.58 (m, 2 H), 7.92 (m, 2H), 7.84 (d, 1H), 7.63 (m, 2H), 7.21-7.30 (m, 2H), 7.09 (s, 1 H), 6.21 (d, 1H), 4.33-4.53 (m, 2H)

Synthesis of Compound 251: For compound 251, compound 213 was used as an intermediate in general procedure J amide formation to form compound 251 in 31.1% yield.

¹H NMR (300 MHz, DMSO-d6) ppm 11.12 (s, 1H), 8.76 (br. s., 1H), 8.32-8.58 (m, 2 H), 7.92 (m, 2H), 7.84 (d, 1H), 7.63 (m, 2H), 7.21-7.30 (m, 2H), 7.09 (s, 1 H), 6.21 (d, 1H), 4.33-4.53 (m, 2H)

Synthesis of Compound 252: For compound 252, compound 215 was used as an intermediate in general procedure J amide formation to form compound 252 in 27% yield. ¹H NMR (300 MHz, DMSO-d6) ppm 10.73 (br. s., 1H), 8.44 (d, 1H), 7.77 (d, 1H), 7.13-7.40 (m, 7H), 7.00-7.13 (m, 3H), 6.18 (d, 1H), 4.99-5.20 (m, 1H), 4.58-4.76 (m, 1H), 1.44 (d, 3H), 1.33 (d, 6H)

Synthesis of Compound 253: For compound 253, compound 225 was used as an intermediate in general procedure J amide formation to form compound 253 in 23.3% yield.

¹H NMR (300 MHz, DMSO-d6) ppm 11.62 (s, 1H), 9.93 (s, 1H), 7.77-7.93 (m, 1H), 7.57-7.67 (m, 2H), 7.35-7.49 (m, 6H), 7.26-7.35 (m, 2H), 7.09-7.21 (m, 1H), 6.97-7.09 (m, 2H), 6.63-6.78 (m, 1H), 6.23 (d, 1H)

Synthesis of Compound 254: For compound 254, compound 225 was used as an intermediate in general procedure J amide formation to form compound 254 in 23.6% yield.

¹H NMR (300 MHz, DMSO-d6) ppm 11.07 (br. s., 1H), 8.47-8.78 (m, 1H), 7.81 (d, 1 H), 7.62 (m, 2H), 7.41 (m, 2H), 7.13-7.35 (m, 5H), 7.05 (s, 1H), 6.19 (d, 1 H), 4.34-4.49 (m, 2H)

Synthesis of Compound 255: For compound 255, general procedures K and J were used to obtain compound 255 in 94.7% yield. ¹H NMR (300 MHz, DMSO-d6) ppm 7.78 (d, 1H), 7.45 (dd, 1H), 7.02-7.13 (m, 1H), 6.96 (s, 1H), 6.91-6.95 (m, 1H), 6.82-6.91 (m, 1H), 6.20 (d, 1H), 3.79 (s, 3H)

Synthesis of Compound 256: For compound 256, compound 215 was used as an intermediate in general procedure J amide formation to form compound 256 in 39.1% yield.

¹H NMR (300 MHz, DMSO-d6) ppm 10.88 (s, 1H), 8.07 (q, 1H), 7.76 (d, 1H), 7.24 (m, 2 H), 7.07 (m, 2H), 6.92 (s, 1H), 6.17 (d, 1H), 4.69 (spt, 1H), 2.70 (d, 3H), 1.34 (d, 6H)

Synthesis of Compound 257: For compound 257, compound 213 was used as an intermediate in general procedure J amide formation to form compound 257 in 21.2% yield.

¹H NMR (300 MHz, DMSO-d6) ppm 12.28 (s, 1H), 11.76 (br. s., 1H), 7.97 (d, 2H), 7.89 (d, 1H), 7.69 (d, 2H), 7.50 (d, 2H), 7.20 (d, 1H), 6.28 (d, 1H)

Synthesis of Compound 258: For compound 258, compound 225 was used as an intermediate in general procedure J amide formation to form compound 258 in 41.6% yield.

¹H NMR (300 MHz, DMSO-d6) ppm 11.25 (s, 1H), 8.19 (t, 1H), 7.80 (d, 1H), 7.64 (m, 2 H), 7.42 (m, 2H), 7.02 (s, 1H), 6.19 (d, 1H), 3.81-3.97 (m, 1H), 3.68-3.81 (m, 1H), 3.50-3.68 (m, 1H), 3.10-3.38 (m, 2H), 1.67-1.96 (m, 3H), 1.39-1.63 (m, 1H)

Synthesis of Compound 259: For compound 259, compound 225 was used as an intermediate in general procedure J amide formation to form compound 259 in 28.9% yield.

¹H NMR (300 MHz, DMSO-d6) ppm 7.77 (d, 1H), 7.61 (m, 2H), 7.39 (m, 2H), 6.65 (s, 1 H), 6.18 (d, 1H), 3.52-3.63 (m, 4H), 2.66-2.77 (m, 4H)

Synthesis of Compound 260: For compound 260, compound 225 was used as an intermediate in general procedure J amide formation to form compound 260 in 51.9% yield.

¹H NMR (300 MHz, DMSO-d6) ppm 11.27 (br. s., 1H), 7.95 (br. s., 1H), 7.77 (d, 1H), 7.61 (m, 2H), 7.40 (m, 2H), 6.90 (s, 1H), 6.14 (d, 1H), 2.70 (d, 3H)

Synthesis of Compound 261: For compound 261, compound 225 was used as an intermediate in general procedure J amide formation to form compound 261 in 25% yield. ¹H NMR (300 MHz, DMSO-d6) ppm 8.30 (t, 1H), 7.76-7.86 (m, 1H), 7.62 (m, 2H), 7.39 (m, 2H), 7.02 (s, 1H), 6.20 (d, 1H), 3.37-3.49 (m, 2H), 2.91 (br. s., 6H), 1.80 (br. s., 4H)

Synthesis of Compound 262: For compound 262, compound 225 was used as an intermediate in general procedure J amide formation to form compound 262 in 25.4% yield.

¹H NMR (300 MHz, DMSO-d6) ppm 12.20 (br. s., 1H), 11.15 (br. s., 1H), 8.77 (t, 1H), 7.83 (d, 1H), 7.63 (m, 2H), 7.47-7.59 (m, 1H), 7.36-7.47 (m, 3H), 7.10-7.18 (m, 2H), 7.09 (s, 1H), 6.21 (d, 1H), 4.59-4.69 (m, 2H)

Synthesis of Compound 263: For compound 263, compound 215 was used as an intermediate in general procedure J amide formation to form compound 263 in 10% yield. ¹H NMR (300 MHz, DMSO-d6) ppm 8.74 (br. s., 1H), 7.63 (d, 1H), 7.27 (m, 2H), 7.05 (m, 2 H), 6.82 (s, 1H), 6.43 (d, 1H), 5.90 (br. s., 2H), 4.54-4.67 (m, 1H), 1.40 (d, 6H)

Synthesis of Compound 264: For compound 264, compound 215 was used as an intermediate in general procedure J amide formation to form compound 264 in 55% yield. ¹H NMR (300 MHz, DMSO-d6) ppm 10.94 (br. s., 1H), 7.74 (d, 1H), 7.22 (m, 2H), 7.05 (m, 2 H), 6.73 (s, 1H), 6.17 (d, 1H), 4.57-4.80 (m, 1H), 3.06 (br. s., 6H), 1.33 (d, 6H)

Synthesis of Compound 265: For compound 265, compound 213 was used as an intermediate in general procedure J amide formation to form compound 265 in 19.3% yield.

¹H NMR (300 MHz, DMSO-d6) ppm 11.75 (br. s., 1H), 9.91 (br. s., 1H), 7.78-7.99 (m, 3 H), 7.59-7.70 (m, 2H), 7.23-7.51 (m, 6H), 7.10-7.20 (m, 1H), 6.99-7.08 (m, 2H), 6.71 (dd, 1H), 6.23 (d, 1H)

Synthesis of Compound 266: For compound 266, compound 213 was used as an intermediate in general procedure J amide formation to form compound 266 in 33.5% yield.

¹H NMR (300 MHz, DMSO-d6) ppm 12.19 (br. s., 1H), 11.36 (br. s., 1H), 8.74 (br. s., 1 H), 7.93 (m, 2H), 7.84 (d, 1H), 7.63 (m, 2H), 7.31-7.59 (m, 2H), 7.02-7.19 (m, 3H), 6.20 (d, 1H), 4.53-4.70 (m, 2H)

Synthesis of Compound 267: For compound 267, compound 216 was used as an intermediate in general procedure J amide formation to form compound 267 in 25% yield. ¹H NMR (300 MHz, DMSO-d6) ppm 11.55 (br. s., 1H), 9.91 (br. s., 1H), 7.83 (d, 1H), 7.21-7.52 (m, 10H), 7.10-7.21 (m, 1H), 7.04 (d, 2H), 6.63-6.80 (m, 1H), 6.10-6.33 (m, 1H)

Synthesis of Compound 268: For compound 268, compound 247 was used as an intermediate in general procedure J amide formation to form compound 268 in 46% yield. ¹H NMR (300 MHz, DMSO-d6) ppm 11.29 (br. s., 1H), 8.45 (d, 1H), 7.82 (d, 1H), 7.43-7.59 (m, 4H), 7.24-7.38 (m, 4H), 7.16-7.24 (m, 1H), 7.13 (s, 1H), 6.20 (d, 1 H), 5.09 (quin, 1 H), 1.44 (d, 3H)

Synthesis of Compound 269: For compound 269, compound 216 was used as an intermediate in general procedure J amide formation to form compound 269 in 42% yield. $^1$H NMR (300 MHz, DMSO-d6) ppm 11.15 (br. s., 1H) 8.05 (br. s., 1H) 7.79 (d, 1H) 7.30-7.52 (m, 4H) 6.94 (s, 1H) 6.18 (d, 1H) 2.71 (d, 3H)

Synthesis of Compound 270: For compound 270, compound 247 was used as an intermediate in general procedure J amide formation to form compound 270 in 34% yield. $^1$H NMR (300 MHz, DMSO-d6) ppm 11.30 (s, 1H), 7.98-8.15 (m, 1H), 7.81 (d, 1H), 7.39-7.61 (m, 4H), 6.95 (s, 1H), 6.20 (d, 1H), 2.71 (d, 3H)

Synthesis of Compound 271: For compound 271, compound 247 was used as an intermediate in general procedure J amide formation to form compound 271 in 44.9% yield.

$^1$H NMR (300 MHz, DMSO-d6) ppm 12.19 (br. s., 1H), 11.36 (s, 1H), 8.80 (t, 1H), 7.84 (d, 1H), 7.31-7.61 (m, 6H), 7.11-7.19 (m, 2H), 7.10 (s, 1H), 6.22 (d, 1H), 4.62 (d, 2H)

Synthesis of Compound 272: For compound 272, compound 216 was used as an intermediate in general procedure J amide formation to form compound 272 in 36% yield. $^1$H NMR (300 MHz, DMSO-d6) ppm 10.67 (s, 1H), 8.61 (dd, 1H), 7.80 (d, 1H), 7.32-7.49 (m, 4H), 7.22 (dd, 1H), 7.05 (s, 1H), 6.74-6.89 (m, 3H), 6.19 (d, 1H), 4.33-4.43 (m, 2 H), 3.71 (s, 3H)

Synthesis of Compound 273: For compound 273, compound 247 was used as an intermediate in general procedure J amide formation to form compound 273 in 43% yield. $^1$H NMR (300 MHz, DMSO-d6) ppm 11.73 (br. s., 1H), 10.28 (s, 1H), 8.26-8.33 (m, 1H), 8.02-8.16 (m, 1H), 7.90 (d, 1H), 7.47-7.68 (m, 6H), 7.38 (s, 1H), 6.26 (d, 1H), 3.19 (s, 3 H)

Synthesis of Compound 274: For compound 274, compound 255 was used as an intermediate in general procedure J amide formation to form compound 274 in 31.9% yield.

$^1$H NMR (300 MHz, DMSO-d6) ppm 10.93 (br. s., 1H) 9.76 (s, 1H) 8.54-8.77 (m, 1H) 7.78 (d, 1H) 7.19-7.40 (m, 6H) 7.03 (s, 1H) 6.92 (dd, 1H) 6.76 (d, 1H) 6.70 (t, 1H) 6.18 (d, 1H) 4.42 (d, 2H)

Synthesis of Compound 275: For compound 275, compound 213 was used as an intermediate in general procedure J amide formation to form compound 275 in 26% yield. $^1$H NMR (300 MHz, DMSO-d6) ppm 11.75 (br. s., 1H), 9.90 (br. s., 1H), 7.78-8.03 (m, 3H), 7.57-7.77 (m, 4H), 7.32-7.44 (m, 2H), 7.28 (br. s., 1H), 7.05-7.17 (m, 1 H), 6.90-7.05 (m, 4H), 6.12-6.34 (m, 1H)

Synthesis of Compound 276: For compound 276, compound 215 was used as an intermediate in general procedure J amide formation to form compound 276 in 28% yield. $^1$H NMR (300 MHz, DMSO-d6) ppm 11.07 (br. s., 1H), 9.42 (br. s., 1H), 8.38 (t, 1H), 7.80 (d, 1H), 7.22 (m, 2H), 7.08 (m, 2H), 7.01 (d, 1H), 6.20 (d, 1H), 4.69 (quin, 1H), 3.42-3.71 (m, 4H), 3.16-3.35 (m, 2H), 2.91-3.16 (m, 2H), 1.77-2.07 (m, 4H), 1.34 (d, 6H)

Synthesis of Compound 277: For compound 277, compound 216 was used as an intermediate in general procedure J amide formation to form compound 277 in 31% yield. $^1$H NMR (300 MHz, DMSO-d6) ppm 11.62 (br. s., 1H), 10.26 (s, 1H), 8.22-8.32 (m, 1H), 8.00-8.14 (m, 1H), 7.88 (d, 1H), 7.53-7.68 (m, 2H), 7.26-7.52 (m, 5H), 6.25 (d, 1H), 3.19 (s, 3H)

Synthesis of Compound 278: For compound 278, compound 215 was used as an intermediate in general procedure J amide formation to form compound 278 in 30% yield. $^1$H NMR (300 MHz, DMSO-d6) ppm 11.40 (br. s., 1H), 10.24 (s, 1H), 8.14-8.24 (m, 1H), 7.91-8.06 (m, 1H), 7.85 (d, 1H), 7.59 (dd, 1H), 7.36-7.45 (m, 1H), 7.32 (s, 1H), 7.25 (m, 2H), 7.07 (m, 2H), 6.24 (d, 1H), 4.70 (quin, 1H), 2.62 (s, 6H), 1.35 (d, 6H)

Synthesis of Compound 279: For compound 279, compound 215 was used as an intermediate in general procedure J amide formation to form compound 279 in 26% yield. $^1$H NMR (300 MHz, DMSO-d6) ppm 11.33 (br. s., 1H), 10.03 (br. s., 1H), 7.79-7.90 (m, 2H), 7.54-7.66 (m, 1H), 7.35 (dd, 1H), 7.20-7.31 (m, 3H), 7.01-7.17 (m, 3H), 6.23 (d, 1H), 4.70 (quin, 1H), 1.35 (d, 6H)

Synthesis of Compound 280: For compound 280, compound 255 was used as an intermediate in general procedure J amide formation to form compound 280 in 34.9% yield.

$^1$H NMR (300 MHz, DMSO-d6) ppm 10.69 (s, 1H), 9.75 (br. s., 1H), 7.77 (d, 1H), 7.35 (dd, 1H), 6.91 (dd, 1H), 6.85 (d, 1H), 6.71-6.79 (m, 1H), 6.69 (t, 1H), 6.19 (d, 1H), 3.66 (br. s., 2H), 3.47 (br. s., 2H), 1.88 (br. s., 2H)

Synthesis of Compound 281: For compound 281, compound 215 was used as an intermediate in general procedure J amide formation to form compound 281 in 22.5% yield.

$^1$H NMR (300 MHz, DMSO-d6) ppm 7.73 (d, 1H), 7.22 (m, 2H), 7.05 (m, 2H), 6.63 (s, 1 H), 6.17 (d, 1H), 4.56-4.79 (m, 1H), 3.54-3.64 (m, 4H), 2.66-2.79 (m, 4), 1.33 (d, 6 H)

Synthesis of Compound 282: For compound 282, compound 225 was used as an intermediate in general procedure J amide formation to form compound 282 in 49% yield. $^1$H NMR (300 MHz, DMSO-d6) ppm 10.68 (br. s., 1H), 8.73 (br. s., 1H), 8.48 (dd, 2H), 7.81 (d, 1H), 7.61 (m, 2H), 7.41 (m, 2H), 7.25 (d, 2H), 7.06 (s, 1H), 6.19 (d, 1H), 4.43 (d, 2H)

Synthesis of Compound 283: For compound 283, compound 247 was used as an intermediate in general procedure J amide formation to form compound 283 in 52% yield. $^1$H NMR (300 MHz, DMSO-d6) ppm 12.28 (s, 1H), 11.69 (s, 1H), 7.86 (d, 1H), 7.58 (s, 4H), 7.49 (d, 1H), 7.47 (br. s., 1H), 7.19 (d, 1H), 6.26 (d, 1H)

Synthesis of Compound 284: For compound 284, a similar modified general procedure K and J as for compound 223 was followed. Compound 284 was obtained in 27% yield. $^1$H NMR (300 MHz, DMSO-d6) ppm 12.54 (br. s., 1H), 8.24 (d, 1H), 7.66 (s, 1H), 7.56 (d, 1H), 7.45 (m, 2H), 7.38 (m, 2H), 7.28 (d, 1H), 6.91 (d, 1H), 3.88 (s, 3H)

Synthesis of Compound 285: For compound 285, compound 216 was used as an intermediate in general procedure J amide formation to form compound 285 in 33% yield. $^1$H NMR (300 MHz, DMSO-d6) ppm 11.14 (br. s., 1H), 8.19 (t, 1H), 7.79 (d, 1H), 7.34-7.51 (m, 4H), 7.02 (s, 1H), 6.19 (d, 1H), 3.81-3.97 (m, 1H), 3.68-3.81 (m, 1 H), 3.52-3.67 (m, 1H), 3.11-3.38 (m, 2H), 1.68-1.97 (m, 3H), 1.40-1.62 (m, 1H)

Synthesis of Compound 286: For compound 286, compound 213 was used as an intermediate in general procedure J amide formation to form compound 286 in 46% yield. $^1$H NMR (300 MHz, DMSO-d6) ppm 8.10 (t, 1H), 7.93 (m, 2H), 7.83 (d, 1H), 7.62 (m, 2 H), 7.00 (s, 1H), 6.20 (d, 1H), 3.22-3.38 (m, 2H), 2.40-2.60 (m, 6H), 1.55-1.76 (m, 4H)

Synthesis of Compound 287: For compound 287, compound 216 was used as an intermediate in general procedure J amide formation to form compound 287 in 38% yield. $^1$H NMR (300 MHz, DMSO-d6) ppm 12.20 (br. s., 1H), 11.22 (br. s., 1H), 8.75-8.82 (m, 1H), 7.83 (d, 1H), 7.29-7.60 (m, 6H), 7.04-7.19 (m, 3H), 6.21 (d, 1H), 4.55-4.68 (m, 2H)

Synthesis of Compound 288: For compound 288, compound 215 was used as an intermediate in general procedure J amide formation to form compound 288 in 41.7% yield.

$^1$H NMR (300 MHz, DMSO-d6) ppm 11.36 (s, 1H), 10.25 (s, 1H), 8.23-8.30 (m, 1H), 8.02-8.12 (m, 1H), 7.85 (d, 1H), 7.56-7.65 (m, 2H), 7.32 (s, 1H), 7.27 (m, 2H), 7.08 (m, 2 H), 6.24 (d, 1H), 4.70 (spt, 1H), 3.19 (s, 3H), 1.35 (d, 6H)

Synthesis of Compound 289: For compound 289, compound 247 was used as an intermediate in general procedure J amide formation to form compound 289 in 13% yield. $^1$H NMR (300 MHz, DMSO-d6) ppm 11.36 (s, 1H), 8.66 (t, 1H), 7.82 (d, 1H), 7.45-7.60 (m, 4H), 7.14-7.36 (m, 5H), 7.06 (s, 1H), 6.20 (d, 1H), 4.42 (d, 2H)

Synthesis of Compound 290: For compound 290, compound 225 was used as an intermediate in general procedure J amide formation to form compound 290 in 18% yield. $^1$H NMR (300 MHz, DMSO-d6) ppm 11.70 (br. s., 1H), 10.26 (s, 1H), 8.24-8.30 (m, 1H), 8.01-8.14 (m, 1H), 7.88 (d, 1H), 7.53-7.69 (m, 4H), 7.43 (m, 2H), 7.34-7.38 (m, 1H), 6.25 (d, 1H), 3.19 (s, 3H)

Synthesis of Compound 291: For compound 291, compound 255 was used as an intermediate in general procedure J amide formation to form compound 291 in 56% yield. $^1$H NMR (300 MHz, DMSO-d6) ppm 11.31 (br. s., 1H), 10.04 (br. s., 1H), 9.75 (s, 1H), 7.86-7.88 (m, 1H), 7.84 (d, 1H), 7.59 (d, 1H), 7.37 (dd, 1H), 7.35 (dd, 1H), 7.28 (s, 1H), 7.05-7.15 (m, 1H), 6.88-6.99 (m, 1H), 6.77 (d, 1H), 6.70-6.74 (m, 1H), 6.23 (d, 1H)

Synthesis of Compound 292: For compound 292, compound 215 was used as an intermediate in general procedure J amide formation to form compound 292 in 35.3% yield.

$^1$H NMR (300 MHz, DMSO-d6) ppm 12.20 (br. s., 1H), 10.68 (br. s., 1H), 8.80 (t, 1H), 7.79 (d, 1H), 7.32-7.62 (m, 2H), 7.25 (m, 2H), 6.99-7.17 (m, 5H), 6.19 (d, 1H), 4.64-4.74 (m, 1H), 4.56-4.64 (m, 2H), 1.32 (d, 6H)

Synthesis of Compound 293: For compound 293, compound 213 was used as an intermediate in general procedure J amide formation to form compound 293 in 32.6% yield.

$^1$H NMR (300 MHz, DMSO-d6) ppm 11.39 (br. s., 1H), 7.99-8.15 (m, 1H), 7.94 (m, 2 H), 7.83 (d, 1H), 7.62 (m, 2H), 6.96 (s, 1H), 6.21 (d, 1H), 2.71 (d, 3H)

Synthesis of Compound 294: For compound 294, compound 216 was used as an intermediate in general procedure J amide formation to form compound 294 in 30.7% yield.

$^1$H NMR (300 MHz, DMSO-d6) ppm 12.25 (br. s., 1H), 11.59 (br. s., 1H), 7.85 (d, 1H), 7.36-7.57 (m, 6H), 7.19 (d, 1H), 6.26 (d, 1H)

Synthesis of Compound 295: For compound 295, compound 225 was used as an intermediate in general procedure J amide formation to form compound 295 in 18% yield. $^1$H NMR (300 MHz, DMSO-d6) ppm 11.67 (br. s., 1H), 10.16 (br. s., 1H), 8.19 (s, 1H), 7.95 (br. s., 1H), 7.87 (d, 1H), 7.63 (m, 2H), 7.47-7.55 (m, 2H), 7.44 (m, 3H), 7.20-7.39 (m, 2H), 6.23 (d, 1H)

Synthesis of Compound 296: For compound 296, compound 216 was used as an intermediate in general procedure J amide formation to form compound 296 in 31.9% yield.

$^1$H NMR (300 MHz, DMSO-d6) ppm 11.20 (s, 1H), 8.43 (d, 1H), 7.81 (d, 1H), 7.25-7.47 (m, 8H), 7.15-7.25 (m, 1H), 7.12 (s, 1H), 6.19 (d, 1H), 5.10 (quin, 1H), 1.44 (d, 3H)

Synthesis of Compound 297: For compound 297, compound 215 was used as an intermediate in general procedure J amide formation to form compound 297 in 35.8% yield.

$^1$H NMR (300 MHz, DMSO-d6) ppm 11.25 (s, 1H), 9.90 (s, 1H), 7.83 (d, 1H), 7.60-7.70 (m, 1H), 7.30-7.41 (m, 1H), 7.19-7.30 (m, 3H), 7.01-7.19 (m, 3H), 6.22 (d, 1H), 4.70 (quin, 1H), 3.81 (s, 3H), 1.35 (d, 6H)

Synthesis of Compound 298: Compound 298 was prepared by mixing a methoxy intermediate in anhydrous DCM and 2 eq of BBr$_3$ at 0° C. After the reaction was complete (about 1-2 hours), it was washed with saturated NaHCO$_3$ several times until neutral. Organic solution was dried (sodium sulfate) and evaporated. Compound 298 was isolated by pre-TLC to give pure product (82% yield) as a white solid. MS-ESI: m/z=202.1 [M+1]$^+$ Synthesis of Compound 299: Similar to the synthesis of compound 298, compound 299 was prepared in 87% yield as a white solid. MS-ESI: m/z=202.3 [M+1]$^+$ Synthesis of Compound 300: Following general procedure A, compound 300 was prepared in 42% yield as a white solid. MS-ESI: m/z=204.3 [M+1]$^+$ Synthesis of Compound 301: Following general procedure A, compound 301 was prepared in 9% yield as a solid. MS-ESI: m/z=204.3 [M+1]$^+$ Synthesis of Compound 302: Following general procedure A, compound 302 was prepared in 27.3% yield as a white solid. MS-ESI: m/z=220.3 [M+1]$^+$; 222.2 [M+3]$^+$ Synthesis of Compound 303: Following general procedure A, compound 303 was prepared in 20% yield as a white solid. MS-ESI: m/z=216.3 [M+1]$^+$ Synthesis of Compound 304: Following general procedure A, compound 304 was prepared in 66% yield as a white solid. MS-ESI: m/z=216.3 [M+1]$^+$ Synthesis of Compound 305: Following general procedure A, compound 305 was prepared in 50% yield as a yellowish solid. MS-ESI: m/z=216.3 [M+1]$^+$ Synthesis of Compound 306: Following general procedure A, compound 306 was prepared in 43% yield as an oil. MS-ESI: m/z=244.0 [M+1]$^+$ Synthesis of Compound 307: Following general procedure A, compound 307 was prepared in 81% yield as an oil. MS-ESI: m/z=244.1 [M+1]$^+$ Synthesis of Compound 308: Following general procedure A, compound 308 was prepared in 87% yield as a reddish brown solid. MS-ESI: m/z=244.2 [M+1]$^+$ Synthesis of Compound 309: Following general procedure A, compound 309 was prepared in 80% yield as a yellowish solid. MS-ESI: m/z=234.3 [M+1]$^+$ Synthesis of Compound 310: Following general procedure A, compound 310 was prepared in 85% yield as a light yellow solid. MS-ESI: m/z=248.2 [M+1]$^+$ Synthesis of Compound 311: Following general procedure A, compound 311 was prepared in 76% yield as a white solid. MS-ESI: m/z=250.2 [M+1]$^+$ Synthesis of Compound 312: Following general procedure A, compound 312 was prepared in 22% yield as a white solid. MS-ESI: m/z=266.2 [M+1]$^+$ Synthesis of Compound 313: Following general procedure A, compound 313 was prepared in 25% yield as a light yellow solid. MS-ESI: m/z=230.2 [M+1]$^+$ Synthesis of Compound 314: Following general procedure A, compound 314 was prepared in 27% yield as a colorless oil. MS-ESI: m/z=242.2 [M+1]$^+$ Synthesis of Compound 315: Following general procedure A, compound 315 was prepared in 32% yield as a white solid. MS-ESI: m/z=240.1 [M+1]$^+$ Synthesis of Compound 316: Following general procedure A, compound 316 was prepared in 92% yield as a light yellow solid. MS-ESI: m/z=202.2 [M+1]$^+$ Synthesis of Compound 317: Following general procedure A, compound 317 was prepared in 28% yield as a white solid. MS-ESI: m/z=186.2 [M+1]$^+$ Synthesis of Compound 318: Compound 318 was prepared as follows.

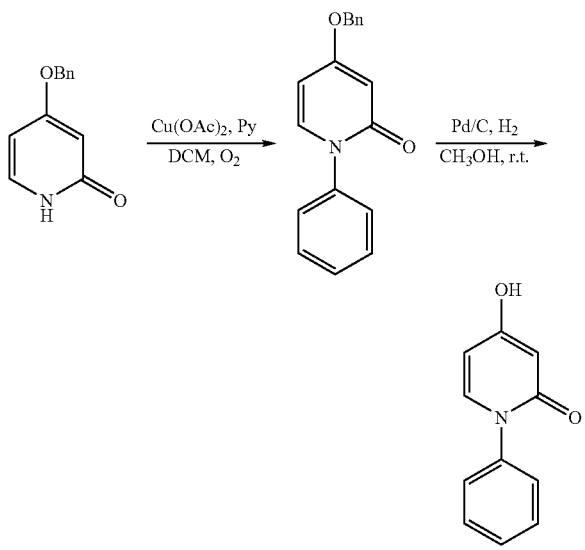

Following general procedure A, the intermediate compound was prepared in 78% yield as a white solid. MS-ESI: m/z=278.1 [M+1]+ To a solution of the intermediate (3.5 g, 10.8 mmol) in methanol (200 ml) was added Pd/C (300 mg) catalyst under N2 atmosphere, and then stirred for 2 h under H2 atmosphere (1 atm, 25° C.). The catalyst was filtered off through the celite pad, and the filtrate was concentrated in vacuo to give compound 318 (2.2 g, 93% yields) as a white solid. MS-ESI: m/z=188.2 [M+1]+

Synthesis of Compound 319: Following general procedure A, compound 319 was prepared in 85% yield as a white solid. MS-ESI: m/z=206.3 [M+1]+

Synthesis of Compound 320: Following general procedure A, compound 320 was prepared in 84% yield as a white solid. MS-ESI: m/z=240.3 [M+1]+

Synthesis of Compound 321: Following general procedure A, compound 321 was prepared in 79% yield as a solid. MS-ESI: m/z=206.2 [M+1]+; 208.2 [M+3]+

Synthesis of Compound 322: Compound 322 was synthesized as follows.

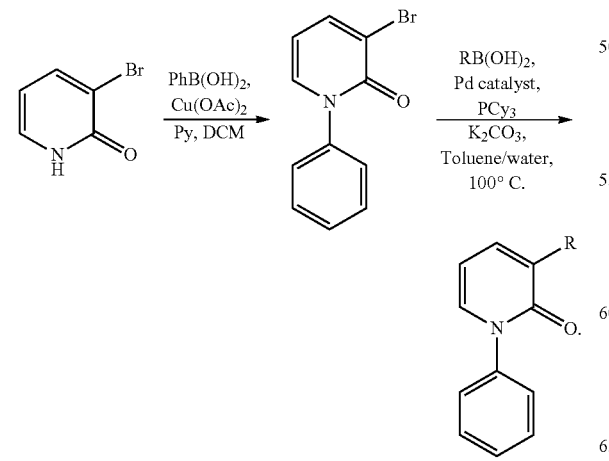

To a solution Br-substitution-1-Phenyl-1H-pyridin-2-one (1 eq), the appropriate boromic acid (1.2 eq), potassium phosphate (3.5 eq) and tricyclohexylphosphine (0.1 eq) in toluene/water (2:/1, V:V) under a nitrogen atmosphere was added palladium acetate (0.05 eq). The mixture was heated to 100° C. for 2-3 h, and then cooled to room temperature, water was added and the mixture was extracted with EtOAc, the combined organics were washed with brine and water, dried over anhydrous Na2SO4, and concentrated in vacuo. The residue was purified by pre-TLC to afford the desired compound 322 in 70% yield as a pink solid. MS-ESI: m/z=212.2 [M+1]+

Synthesis of Compound 323: Similar to compound 322, compound 323 was prepared in 60% yield as a yellow solid. MS-ESI: m/z=274.3 [M+1]+

Synthesis of Compound 324: Compound 324 was synthesized as follows. To compound 318 (2.2 g, 11.8 mmol) in DCM (120 ml) was added triethylanine (1.7 g, 16.8 mmol) at −78° C., followed by the addition of trifluoromethanesulfonic anhydride (4.76 g, 16.9 mmol). The resulting mixture was stirred at −78° C. for 15 min and quenched with ammonium chloride solution (10 ml). After warming to room temperature, water (30 ml) and DCM (50 ml) were added and separated. The intermediate triflate was obtained by washing the crude with methanol and gave 2.12 g pure compound in 90% yield. A solution of the intermediate triflate (trifluoro-methanesulfonic acid 2-oxo-1-phenyl-1,2-dihydro-pyridin-4-yl ester) (0.79 mmol) and tetrakis(triphenylphosphine)palladium (0.011 g, 0.0095 mmol) in dimethoxyethane (1 ml) was stirred at room temperature for 15 min followed by the addition of the solution arylboronic acid (0.21 mmol) in dimethoxyethane (1 ml) and 2M sodium carbonate (1 ml). The resulting mixture was refluxed for 14 hr and cooled down to room temperature. Water and ethyl acetate were added. After separation, the aqueous layer was extracted with ethyl acetate. The combined ethyl acetate solution was dried (Na2SO4) and filtered, and the filtrate was concentrated in vacuo to dryness. Compound 324 was obtained in 51.6% yield as a solid. MS-ESI: m/z=248.3 [M+1]+

Synthesis of Compound 325: Similar to compound 324, compound 325 was prepared in 60.2% yield as a solid. MS-ESI: m/z=212.2 [M+1]+

Synthesis of Compound 326: Following general procedure A, compound 326 was prepared in 15% yield. MS-ESI: m/z=212.3 [M+1]+

Synthesis of Compound 327: Compound 327 was prepared as follows.

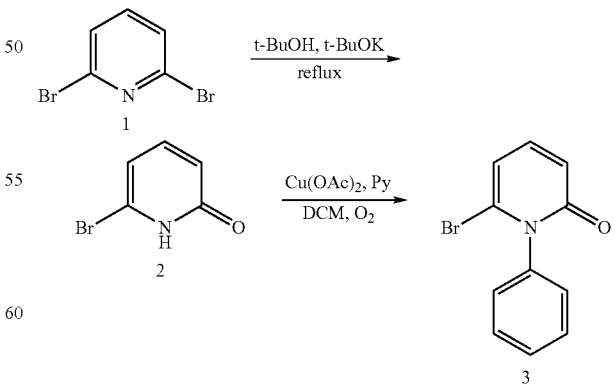

A mixture of 2,6-dibromopyridine (4 g, 17 mmol), potassium t-butoxide (20 g, 0.27 mol), and redistilled t-butyl alcohol (100 ml) was refluxed overnight. After cooling, the solvent was removed in vacuo, ice/water was carefully added, and the aqueous layer was extracted with chloroform (100 ml×2), which removed the unreacted staring material. The aqueous layer was acidified with 3 N HCl, extracted with chloroform (100 ml×2), washed with brine, dried over anhydrous Na$_2$SO$_4$ and concentrated affording pure 6-bromo-2-pyridone (2.5 g, 85% yield) as a white solid. Intermediate 3 was prepared following general procedure A in 73% yield. Intermediate 3 was then reacted with the appropriate boronic acid, Pd (OAc)$_2$, PCy$_3$, K$_3$PO$_4$ at 100° C. to afford compound 327 in 40% yield as an oil. MS-ESI: m/z=248.3 [M+1]$^+$ Synthesis of Compound 328: Similar to compound 327, compound 328 was prepared in 9.48% yield as an oil. MS-ESI: m/z=212.2 [M+1]$^+$ Synthesis of Compound 329: Following general procedure A, compound 329 was prepared in 90% yield as a white solid. MS-ESI: m/z=298.3 [M+1]$^+$ Synthesis of Compound 330: Following general procedure A, compound 330 was prepared in 75% yield as a yellowish solid. MS-ESI: m/z=230.4 [M+1]$^+$ Synthesis of Compound 331: Following general procedure A, compound 331 was prepared in 81% yield as an oil. MS-ESI: m/z=262.1 [M+1]$^+$ Synthesis of Compound 332: Following general procedure A, compound 332 was prepared in 80% yield as a solid. MS-ESI: m/z=276.2 [M+1]$^+$ Synthesis of Compound 333: Following general procedure F, compound 333 was prepared in 65% yield to give a yellowish solid. MS-ESI: m/z=280.1 [M+1]$^+$ Synthesis of Compound 334: Following general procedure F, compound 334 was prepared in 59% yield. MS-ESI: m/z=256.2 [M+1]$^+$, 258.2. [M+3]$^+$ Synthesis of Compound 335: Compound 335 was prepared as follows.

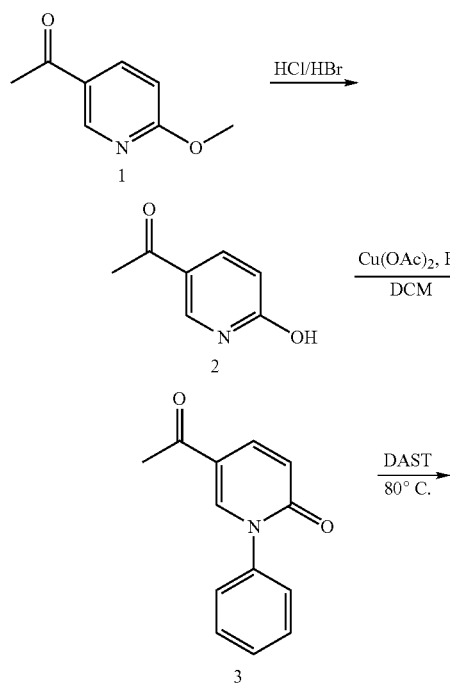

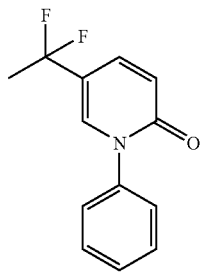

A mixture of compound 1 (200 mg, 1.3 mmol) in AcOH (4 ml) was added HBr (aq. 40%, 1 ml), then heated to reflux for 2 h. The compound 2 was obtained by evaporated in vacuo (160 mg, 90%). To a mixture of compound 2 (160 mg, 1.2 mmol), phenylboronic acid (293 mg, 2.4 mmol) and Cu(OAc)$_2$ (36 mg, 0.2 mmol) in DCM, pyridine (190 mg, 2.4 mmol) was added slowly. After the suspension was stirred overnight at room temperature, it was checked by TLC and the starting material was completely vanished, and then washed with saturated NaHCO$_3$. The DCM layer was dried over sodium sulfate, and evaporated to obtain the crude product. The crude product was purified by preparative TLC to afford the compound 3 (110 mg, 43%). A mixture of compound 3 (110 mg, 0.5 mmol) in DAST (2.5 ml) was heated to 80° C. for 4 h. The reaction mixture was extracted by DCM and saturated NaHCO$_3$, and the crude product was purified by preparative TLC to give compound 335 (40 mg, 34% yield) as yellow solid. MS-ESI: m/z=236.3 [M+1]$^+$ Synthesis of Compound 336: Similar to the synthesis of compound 91, compound 336 was prepared in 63% yield as a white solid. MS-ESI: m/z=262.1 [M+1]$^+$ Synthesis of Compound 337: Similar to the synthesis of compound 91, compound 337 was prepared in 70% yield to give a white solid. MS-ESI: m/z=238.2 [M+1]$^+$, 240.3 [M+3]$^+$ Synthesis of Compound 338: Compound 338 was synthesized as follows.

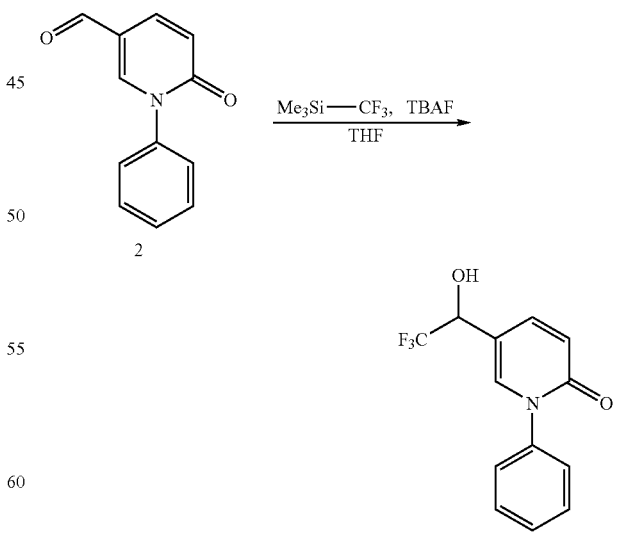

A mixture of compound 2 (1 g, 5 mmol) and trimethyl-trifluoromethyl-silane (3.5 ml, 2M in THF, 7 mmol) in THF (20 ml) cooled to 0° C. in an ice bath was treated with tetrabutylammonium fluoride (0.25 ml, 1 m in THF, 0.25 mmol) under nitrogen atmosphere at 0° C. for 30 min. The mixture was raised to room temperature and stirred 24 h. Then 1 M HCl (50 ml) was added and the mixture was stirred overnight. The aqueous layer was extracted with EtOAc (50 ml×2) and the organics was concentrated. The desired product was separated by columnar chromatography to give compound 338 (0.94 g, 70% yields) as yellow solid. MS-ESI: m/z=270.2 [M+1]$^+$ Synthesis of Compound 339: Compound 339 was prepared from compound 338 as follows. Compound 338 (50 mg, 0.19 mmol) and manganese dioxide (165 mg, 1.9 mmol) were stirred overnight at room temperature in DCM (5 ml). The reaction was detected by TLC. Upon completion, the crude mixture was filtered through a pad of celite and the filtrate was concentrated. The desired compound was isolated by washing the crude with PE to give pure intermediate product (36 mg, 70% yields) as a white solid. A mixture of this intermediate (100 mg, 0.37 mmol) and trimethyl-trifluoromethyl-silane (0.27 ml, 2 M in THF, 0.54 mmol) in THF (2 ml) cooled to 0° C. in an ice bath is treated with tetrabutylammonium fluoride (0.02 ml, 1 M in THF, 0.02 mmol) under nitrogen atmosphere at 0° C. for 30 min. The mixture was raised to room temperature and stirred 24 h. Then 1 M HCl (20 ml) was added and the mixture was stirred overnight. The aqueous layer was extracted with EtOAc (30 ml×3) and the organics was concentrated. The desired product was separated out by washing the crude with EtOAc to give compound 339 (54 mg, 43% yield) as a white solid. MS-ESI: m/z=338.2 [M+1]$^+$ Synthesis of Compound 340: Compound 340 was prepared from compound 338 as follows. Compound 338 (50 mg, 0.19 mmol) in dry DCM (1 ml) was added at the temperature of −78° C. under $N_2$ atmosphere to a solution of DAST (34 mg, 0.21 mmol) in DCM (1 ml). The mixture was stirred at −78° C. for 2 h, and then warmed to room temperature overnight. The reaction mixture was diluted with DCM (20 ml), and poured into saturated $NaHCO_3$ (30 ml). Organic phase was separated and dried over $Na_2SO_4$ and concentrated in vacuo. Desired compound was isolated by thin-layer chromatography to give pure compound 340 (16 mg, 30% yields) as a yellowish solid. MS-ESI: m/z=272.2 [M+1]$^+$ Synthesis of Compound 341: Compound 341 was prepared from compound 338 as follows. Compound 338 (50 mg, 0.19 mmol) and manganese dioxide (165 mg, 1.9 mmol) were stirred overnight at room temperature in DCM (5 ml). The reaction was detected by TLC. Upon completion, the crude mixture was filtered through a pad of celite and the filtrate was concentrated. The desired compound was isolated by washing the crude with PE to give pure intermediate product (36 mg, 70% yield) as a white solid.
To a suspension of methyltriphosphonium bromide (336 mg, 0.96 mmol) in tetrahydrofuran (16 ml) maintained at 0° C. was added n-butyllithium (0.4 ml, 2.5 M solution in THF). The resulting solution was stirred for fifteen minutes prior to the addition of a solution of this intermediate (200 mg, 0.76 mmol.) in tetrahydrofuran (10 ml). The reaction mixture was stirred for about 1 h before quenching by dilution with water. The second intermediate product was extracted into EA and the combined organic layers were evaporated under reduced pressure, the second intermediate product was isolated by TLC (150 mg, 76% yield). 1-phenyl-5-(3,3,3-trifluoroprop-1-en-2-yl)pyridine-2(1H)-one (the second intermediate product) (100 mg, 0.38 mmol) in $C_2H_5OH$ (8 ml) was added Pd/C (10 mg) under $N_2$. The reaction mixture was stirred for 2 h under $H_2$, then filtered, extracted by DCM, washed by brine, dried by $Na_2SO_4$. Compound 341 was isolated by TLC (79 mg, 79% yield) as oil. MS-ESI: m/z=268.3 [M+1]$^+$ Synthesis of Compound 342: Compound 342 was prepared from compound 338 as follows. Compound 338 (50 mg, 0.19 mmol) and manganese dioxide (165 mg, 1.9 mmol) were stirred overnight at room temperature in DCM (5 ml). The reaction was detected by TLC. Upon completion, the crude mixture was filtered through a pad of celite and the filtrate was concentrated. The desired compound was isolated by washing the crude with PE to give pure intermediate product (36 mg, 70% yield) as a white solid. Then, following general procedure D, compound 342 was prepared in 64% yield as a white solid. MS-ESI: m/z=290.3 [M+1]$^+$ Synthesis of Compound 343: Compound 343 was prepared as follows.

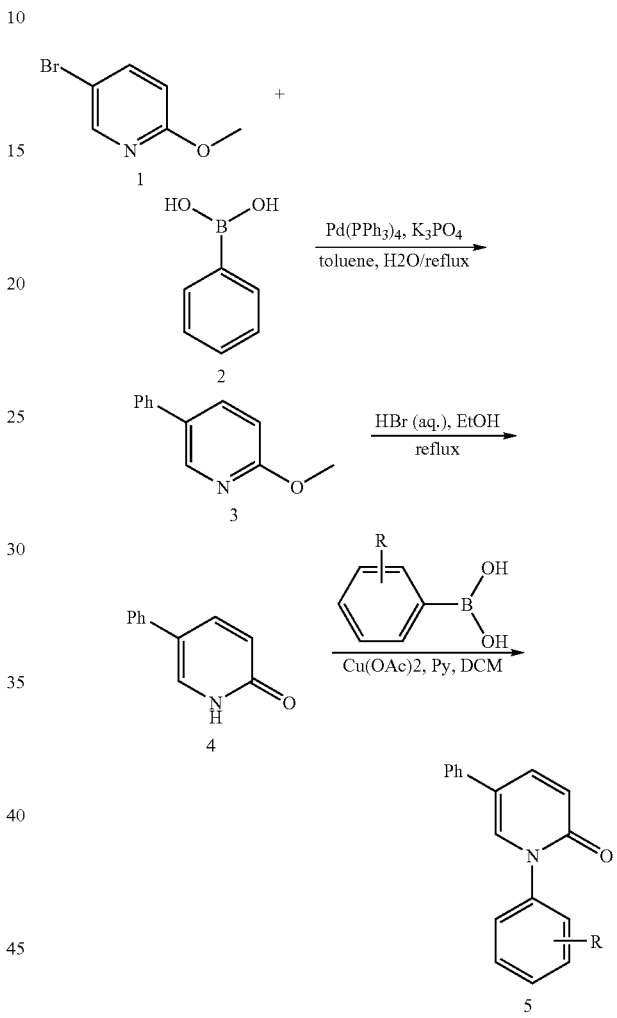

Intermediate 3 was prepared thus. To a solution of compound 1 (3.0 g, 16 mmol), compound 2 (2.5 g, 21 mmol), $K_3PO_4$ (12.5 g, 57 mmol) in toluene/water (60 ml/3 ml) under a nitro atmosphere was added Pd(PPh$_3$)$_4$ (2.0 g, 1.6 mmol). The mixture was heated to reflux for 3 h and then cooled to room temperature. Water was added and the mixture extracted with EtOAc, the combined organics were washed with brine, dried over $Na_2SO_4$ and concentrated in vacuo. The product was isolated by column chromatography afforded the compound 3. (2.1 g, 69%). Intermediate 3 (2.0 g, 11 mmol) in HBr (aq. 40%)/EtOH (20 ml/4 ml) was heated to reflux for 2 h, the reaction was monitored by TLC, when completed, the mixture was cooled to r.t. The reaction mixture was neutralized by $NaHCO_3$, then extracted with EtOAc several times. The combined organics was washed with brine, dried over $Na_2SO_4$ and concentrated in vacuo to afford the compound 4 (1.7 g, 91%) Following general procedure A, compound 343 was prepared from intermediate 4 in 50% as an oil. MS-ESI: m/z=306.0 [M+1]$^+$ Synthesis of Compound 344: Similar to compound 343, compound 344 was prepared in 15% yield as a white solid. MS-ESI: m/z=277.9 [M+1]$^+$ Synthesis of Compound 345: Similar to compound 343, compound 345 was prepared in 60% yield as a white solid. MS-ESI: m/z=281.9 [M+1]$^+$ Synthesis of Compound 346: Similar to compound 343, compound 346 was prepared in 90% yield as a yellowish solid. MS-ESI: m/z=305.9 [M+1]$^+$ Synthesis of Compound 347: Similar to compound 343, compound 347 was prepared in 85% yield as a solid. MS-ESI: m/z=278.0 [M+1]$^+$ Synthesis of Compound 348: Similar to compound 343, compound 348 was prepared in 50% yield as a white solid. MS-ESI: m/z=331.8 [M+1]$^+$ Synthesis of Compound 351: Following general procedure A, compound 351 was prepared in 55% yield as a white solid. MS-ESI: m/z=269.9 [M+1]$^+$ Synthesis of Compound 352: Following general procedure A, compound 352 was prepared in 70% yield as a reddish liquid. MS-ESI: m/z=298 [M+1]$^+$ Synthesis of Compound 353: Following general procedure A, compound 353 was prepared in 85% yield as a white solid. MS-ESI: m/z=270.0 [M+1]$^+$ Synthesis of Compound 354: Following general procedure A, compound 354 was prepared in 78% yield as a solid. MS-ESI: m/z=273.9 [M+1]$^+$ Synthesis of Compound 355: Following general procedure A, compound 355 was prepared in 68% yield as a white solid. MS-ESI: m/z=244.1 [M+1]$^+$ Synthesis of Compound 356: Following general procedure A, compound 356 was prepared in 65% yield as a white solid. MS-ESI: m/z=270.0 [M+1]$^+$ Synthesis of Compound 357: Following general procedure F, compound 357 was prepared in 68% yield. MS-ESI: m/z=305.9 [M+1]$^+$ Synthesis of Compound 358: Similar to the synthesis of compound 100, compound 358 was prepared in 80% yield as a white solid. MS-ESI: m/z=300.2 [M+1]$^+$ Synthesis of Compound 359: Compound 359 was prepared as follows.

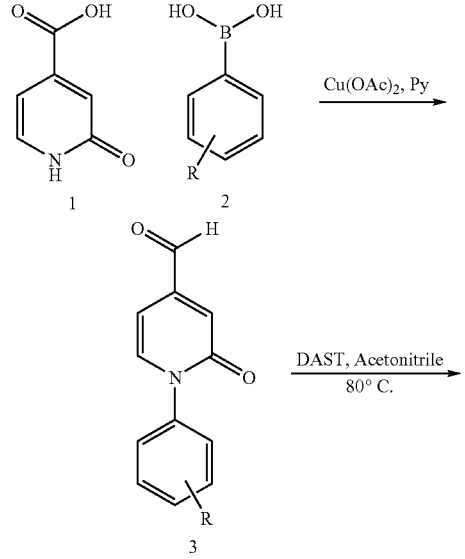

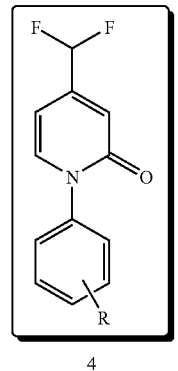

A mixture of reagent 1 (0.5-1 mmol, 1 eq.), boronic acids 2 (2 eq.), copper(II) acetate (0.4-0.6 eq.), pyridine (2 eq.) and molecular sieves 4 A in dichloromethane (5 ml/1 mmol reagent 1) was stirred for overnight at the room temperature opened to the air. The reactions were monitored by TLC, and when found to be completed washed with saturated sodium bicarbonate with EDTA and dried over sodium sulfate. Compounds 3 were isolated by pre-TLC (using EA/PE as solvent). Reagent 3 (0.3-0.5 mmol, 1 eq.) was dissolved in acetonitrile (3 mL/1 mmol reagent 3), DAST (2 eq.) was added slowly at room temperature. The resulting solution was stirred at 80° C. in a capped plastic tube overnight. After cooling to room temperature, it was diluted with DCM, washed with aqueous solution of saturated sodium bicarbonate, water and brine, dried over Na$_2$SO$_4$, concentrated to give a residue, which was purified by pre-TLC (using EA/PE as solvent) to give target compound. Following this procedure, compound 359 was prepared in 13.9% yield as a white solid. $^1$H NMR (400 MHz, CDCl3): 2.98 (s, 6H); 3.323~6.341 (t, J=5.6 Hz, 1H); 6.460~6.599 (d, J=55.6 Hz, 1H); 6.639~6.657 (d, J=7.2 Hz, 2H); 6.765~6.790 (d, J=10.0 Hz, 2H); 7.314~7.353 (t, J=8.0 Hz, 1H); 7.446~7.464 (d, J=7.2 Hz, 1H) MS-ESI: m/z=265.1 [M+1]$^+$ Synthesis of Compound 360: Similar to preparation of compound 359, compound 360 was prepared in 19.7% yield as a white solid. $^1$H NMR (400 MHz, CDCl3): 6.278~6.647 (m, 2H); 6.679 (s, 1H); 7.314~7.343 (t, J=11.6 Hz, 2H); 7.395~7.419 (d, J=9.6 Hz, 1H); 7.459~7.498 (q, J=15.6 Hz, 2H) MS-ESI: m/z=256.3 [M+1]$^+$ Synthesis of Compound 361: Similar to preparation of compound 359, compound 361 was prepared in 19.8% yield as a white solid. $^1$H NMR (400 MHz, CDCl3): 1.350~1.371 (d, J=8.4 Hz, 6H), 4.554~4.594 (t, J=16 Hz, 1H), 6.274~6.643 (m, 2H); 6.777 (s, 1H); 6.673 (s, 1H); 6.950~6.980 (q, J=12 Hz, 2H); 7.242~7.272 (q, J=12 Hz, 2H), 7.422~7.446 (d, J=9.6 Hz, 1H) MS-ESI: m/z=280.2 [M+1]$^+$ Synthesis of Compound 362: Similar to preparation of compound 359, compound 362 was prepared in 20.1% yield as a white solid. $^1$H NMR (400 MHz, CDCl3): 6.289~6.697 (m, 2H); 6.679 (s, 1H); 7.410~7.435 (d, J=10 Hz, 1H); 7.531~7.569 (d, J=15.2 Hz, 2H); 7.770~7.812 (d, J=16.8 Hz, 2H) MS-ESI: m/z=290.3 [M+1]$^+$ Synthesis of Compound 363: Similar to preparation of compound 359, compound 363 was prepared in 20.1% yield as a white solid. $^1$H NMR (400 MHz, CDCl3): 3.847 (s, 1H), 6.320~6.596 (m, 2H); 6.758 (s, 1H); 6.979~7.018 (m, 2H); 7.273~7.303 (m, 2H); 7.420~7.438 (d, J=7.2 Hz, 1H) MS-ESI: m/z=252.3 [M+1]$^+$ Synthesis of Compound 364: Similar to preparation of compound 359, compound 364 was prepared in 27.8% yield as a white solid. ¹H NMR (400 MHz, CDCl3): 6.335~6.612 (m, 2H); 6.784~6.786 (d, J=0.8 Hz 1H); 7.349~7.372 (t, J=9.2 Hz, 2H); 7.419~7.449 (m, 3H) MS-ESI: m/z=306.3 [M+1]⁺

Synthesis of Compound 367: Similar to preparation of compound 359, compound 367 was prepared in 7.8% yield as a white solid. ¹H NMR (400 MHz, CDC13): 1.907~1.998 (t, J=36.4 Hz, 3H), 6.338~6.614 (m, 2H); 6.780 (s, 1H); 7.436~7.601 (m, 5H) MS-ESI: m/z=286.3 [M+1]⁺

Synthesis of Compound 368: Similar to preparation of compound 359, compound 368 was prepared in 10.2% yield as a white solid. ¹H NMR (400 MHz, CDCl3): 1.905~1.996 (t, J=36.4 Hz, 3H), 6.338~6.614 (m, 2H); 6.788 (s, 1H); 7.423~7.466 (t, J=17.2 Hz, 3H), 7.646~7.668 (d, J=8.8 Hz, 2H) MS-ESI: m/z=286.3 [M+1]⁺

Synthesis of Compound 371: Similar to the synthesis of compound 95, compound 371 was prepared in 82% yield as a white solid. MS-ESI: m/z=246.2 [M+1]⁺, 248.2 [M+3]⁺

Synthesis of Compound 372: Similar to the synthesis of compound 95, compound 372 was prepared in 86% yield as a white solid. MS-ESI: m/z=270.0[M+1]⁺

Synthesis of Compound 373: Similar to the synthesis of compound 95, compound 373 was prepared in 88% yield as a white solid. MS-ESI: m/z=242.3 [M+1]⁺

Synthesis of Compound 374: Similar to the synthesis of compound 95, compound 374 was prepared in 60% yield as a white solid. MS-ESI: m/z=296.3 [M+1]⁺

Synthesis of Compound 376: Compound 376 was prepared as follows.

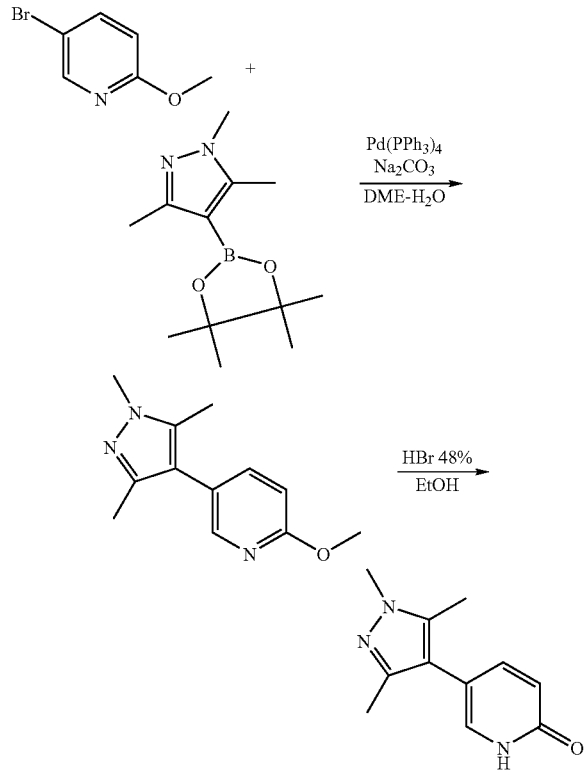

5-bromo-2-methoxypyridine (0.66 g, 3.49 mmol) and 1,3,5-trimethyl-1 h-pyrazole-4-boronic acid pinacol ester (0.99 g, 4.19 mmol) were dissolved in a degassed DME/H₂O mixture (14 mL, 10:1 ratio). Solid Na₂CO₃ (1.1 g, 10.47 mmol) was added, followed by Pd(PPh₃)₄ (0.2 g, 0.17 mmol). The reaction mixture was heated at 80° C. for 18 h. Water was added until complete dissolution of the residual carbonate and the solution was stirred for additional 6 h at the same temperature. The organic layer was separated and evaporated under reduced pressure and the resulting crude mixture was purified by flash chromatography (SiO₂; DCM/MeOH 20:1). 440 mg (66% yield) of pure product were obtained as a pale yellow solid. MS-ESI: m/z=218.3 [M+1]⁺5-(1,3,5-trimethyl-1H-pyrazol-4-yl)pyridin-2(1H)-one (0.44 g, 2.3 mmol) was dissolved in EtOH (3 mL). An excess of 48% HBr aqueous solution (10 mL) was added and the reaction was heated at 90° C. for 24 h. The solvent was removed under reduced pressure and the crude was purified by flash chromatography (SiO₂; AcOEt to AcOEt/MeOH 3.5:1). 400 mg (92% yield) of pure intermediate product were obtained as an off-white foam.

Following general procedure H1A, compound 376 was prepared from this intermediate in 58% yield. ¹H NMR (300 MHz, DMSO-d6) ppm 7.39-7.57 (m, 7H), 6.54 (d, 1H), 3.66 (s, 3H), 2.20 (s, 3H), 2.11 (s, 3H)

Synthesis of Compound 377: Similar to the procedure for compound 376, compound 377 was prepared in 30% yield. ¹H NMR (300 MHz, DMSO-d6) ppm 10.11 (s, 1H), 7.73 (dd, 1H), 7.51-7.63 (m, 1H), 7.47 (dd, 1H), 7.42 (dd, 1H), 7.39 (d, 1H), 7.03-7.15 (m, 1H), 6.53 (d, 1H), 3.66 (s, 3H), 2.19 (s, 3H), 2.10 (s, 3H), 2.05 (s, 3H)

Synthesis of Compound 378: Compound 378 was prepared as follows.

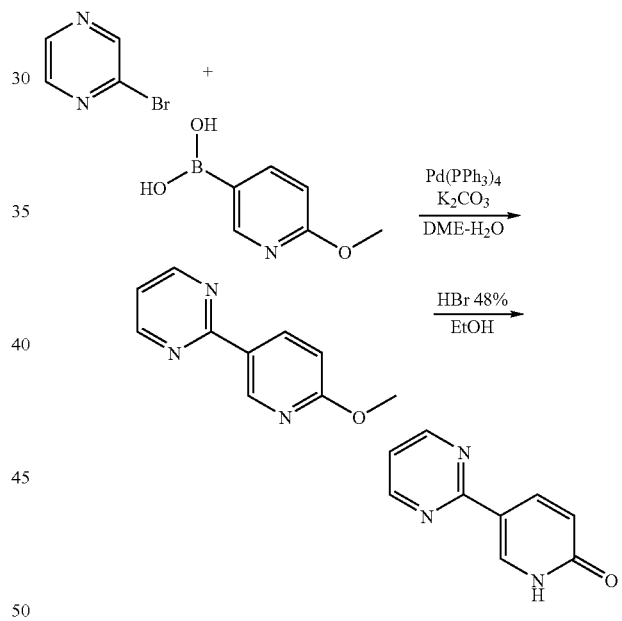

2-bromo pyrimidine (0.55 g, 3.49 mmol) and 2-methoxy-5-pyridineboronic acid (0.53 g, 3.49 mmol) were dissolved in a degassed mixture of DME/H₂O (11 mL, 10:1 ratio). Solid K₂CO₃ (1.4 g, 10.47 mmol) was added, followed by Pd(PPh₃)₄ (0.2 g, 0.17 mmol). The reaction mixture was heated at 90° C. for 18 h. The organic layer was separated and evaporated under vacuum. The resulting crude was purified by flash chromatography (SiO₂; Pet. Ether/AcOEt 1:1). 420 mg (65% yield) of pure product were obtained as a pale yellow solid. MS-ESI: m/z=188 [M+1]⁺ 2-(6-methoxypyridin-3-yl)pyrimidine (0.78 g, 4 mmol) was dissolved in EtOH (5 mL). An excess of 48% HBr aqueous solution (10 mL) was added and the reaction was heated at 90° C. for 24 h. The solvent was removed under reduced pressure and the residual hydrobromic acid was stripped at reduced pressure, at 40° C. The resulting off white solid was used in the next step without further purification. MS-ESI: m/z=174 [M+1]⁺

Following general procedure H1A, compound 378 was prepared from this intermediate in 30% yield. $^1$H NMR (300 MHz, DMSO-d6) ppm 8.82 (d, 2H) 8.56 (dd, 1 H) 8.41 (dd, 1H) 7.70 (m, 2H) 7.51-7.60 (m, 2H) 7.38 (t, 1H) 6.66 (dd, 1 H)

Synthesis of Compound 379: Compound 379 was prepared as follows.

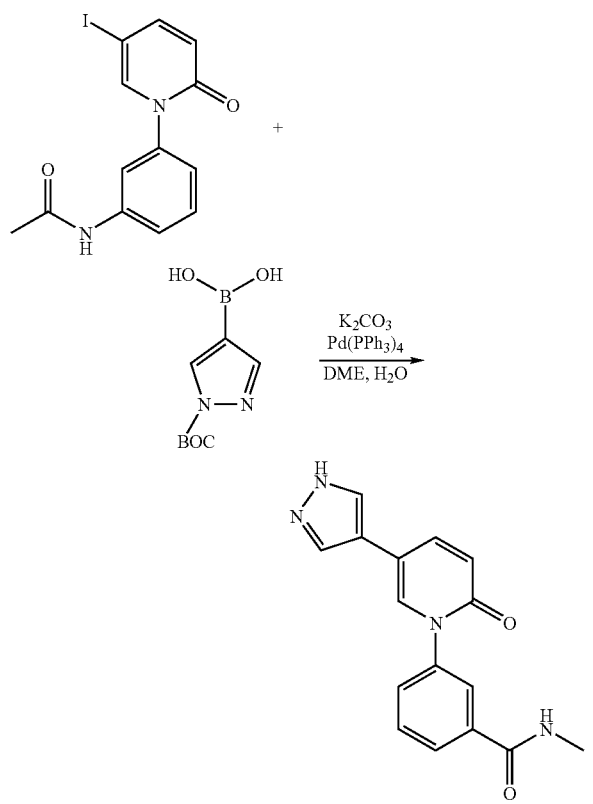

The 5-iodo-1-arylpyridin-2(1H)-one (1 eq), the boronic acid (1.2 eq) and K$_2$CO$_3$ (3 eq) were dissolved in a 10:1 mixture of DME/H$_2$O (4 ml/mmol). The solution was degassed by bubbling N$_2$ for 15 min and then Pd(PPh$_3$)$_4$ (0.05 eq) was added. The reaction mixture was heated at 90° C. for 18 h, after which time, BOC protecting group was completely cleaved. Mixture was cooled at room temperature, diluted with AcOEt and filtered on a celite plug. The filtrate was washed with brine. The separated organic phase was dried over Na$_2$SO$_4$ and concentrated under reduced pressure. The obtained residue was purified by column chromatography (EtOAc:Hexanes 3:7 to 1:1) to afford compound 379 as a pale yellow solid (11% yield). $^1$H NMR (300 MHz, DMSO-d6) ppm 10.12 (s, 1H), 7.98 (s, 2H), 7.80-7.87 (m, 1H), 7.69 (t, 1H), 7.56-7.64 (m, 1H), 7.10 (ddd, 1H), 6.54 (dd, 1H), 2.06 (s, 3H)

Synthesis of Compound 380: Compound 380 was prepared as follows.

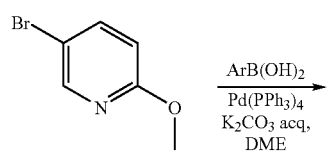

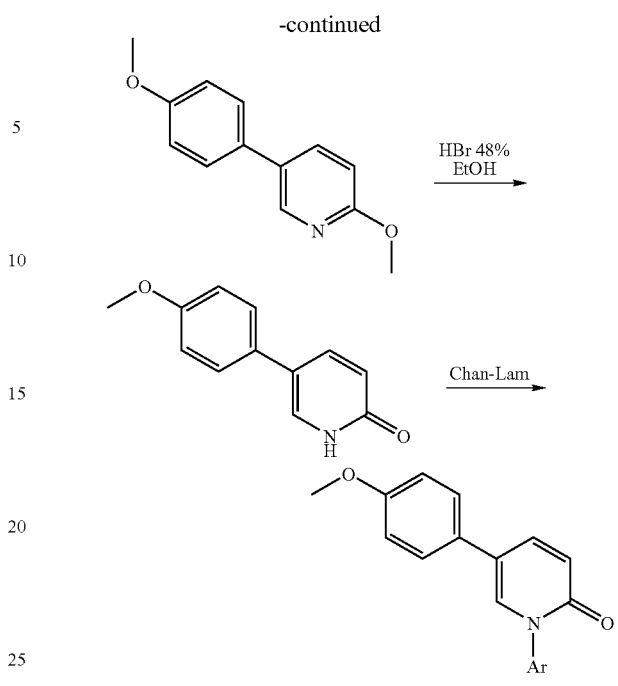

Following the standard procedure for Suzuki coupling the intermediate was obtained by reaction of 3 g (16 mmol) of 5-bromo-2-methoxy-pyridine. After purification (SiO$_2$; Hexanes:EtOAc 9:1) 1.4 g (31% yield) of pure product were obtained as white solid. 2-methoxy-5-(4-methoxyphenyl)pyridine (1.4 g, 4.96 mmol) was dissolved in HBr 48% (12 ml) and EtOH (6 ml) and the solution was heated at reflux for 24 h. After evaporation of volatiles the desired pyridone was obtained as white solid (0.99 g, quantitative yield).

Following general procedure H1A, compound 380 was prepared in 40% yield. $^1$H NMR (300 MHz, DMSO-d6) ppm 7.85-7.98 (m, 2H), 7.66 (m, 2H), 7.47-7.61 (m, 4H), 6.97 (m, 2H), 6.51-6.65 (m, 1H), 3.77 (s, 3H)

Synthesis of Compound 381: Compound 381 was prepared as follows.

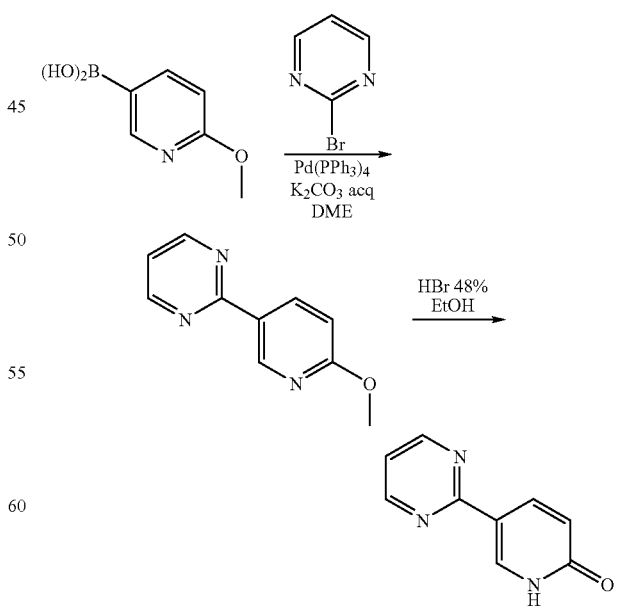

The product was obtained by reaction of 963 mg (6.3 mmol) of 2-methoxy-pyridine-5-boronic acid. After purification (SiO$_2$; Hexanes:EtOAc 1:1) 747 mg (65% yield) of pure product were obtained as white solid. 2-(6-methoxypyridin-3-yl)pyrimidine (747 mg) was dissolved in HBr 48% (10 ml) and EtOH (5 ml) and the solution was heated at reflux overnight. After evaporation of volatiles the desired pyridone was obtained as white solid (1.016 g, quantitative yield).

Following general procedure H1A, compound 381 was prepared from this intermediate in 14% yield. $^1$H NMR (300 MHz, DMSO-d6) ppm 8.81 (d, 2H), 8.53 (dd, 1H), 8.40 (dd, 1H), 7.42-7.65 (m, 5H), 7.37 (dd, 1H), 6.65 (d, 1H)

Synthesis of Compound 382: Similar to compound 381, compound 382 was prepared in 33% yield. $^1$H NMR (300 MHz, DMSO-d6) ppm 10.16 (s, 1H), 8.81 (d, 2H), 8.53 (dd, 1H), 8.39 (dd, 1H), 7.76-7.84 (m, 1H), 7.55-7.66 (m, 1H), 7.47 (dd, 1H), 7.37 (dd, 1H), 7.18 (ddd, 1H), 6.64 (dd, 1H), 2.07 (s, 3H)

Synthesis of Compound 383: Compound 383 was prepared as follows.

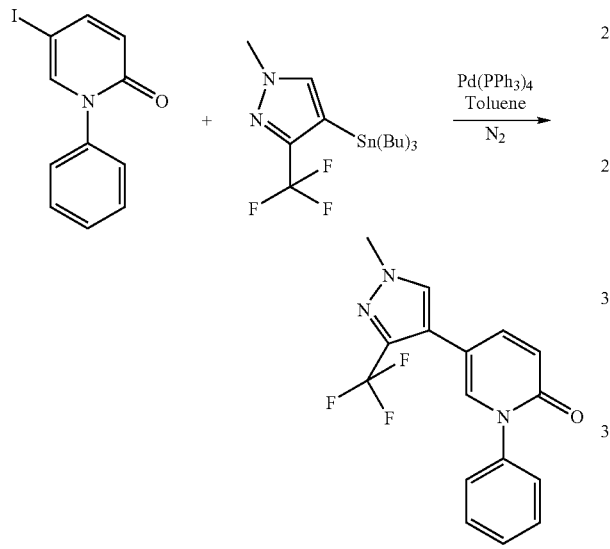

5-iodo-1-phenyl-1H-pyridin-2-one (0.34 g, 1.13 mmol) was dissolved in dry and degassed toluene 5 mL). The catalyst was then added (0.065 g, 0.057 mmol) and the mixture was stirred for 10 minutes. 1-methyl-4-(tributylstannyl)-3-(trifluoromethyl)-1H-pyrazole (0.49 g, 1.13 mmol) was added and the reaction was heated at 90° C. for 18 h under nitrogen atmosphere. Conc. NH$_4$OH was added. The solvent was removed at reduced pressure and the crude was purified by elution through basic alumina (Hexanes:EtOAc 1:1). 37 mg (10% yield) of compound 383 were obtained as a pale yellow solid. $^1$H NMR (300 MHz, DMSO-d6) d ppm 7.99 (d, 1H), 7.75 (dd, 1H), 7.38-7.62 (m, 5H), 6.91 (s, 1H), 6.62 (dd, 1H), 3.94 (s, 3H)

Synthesis of Compound 384: Compound 384 was prepared as follows.

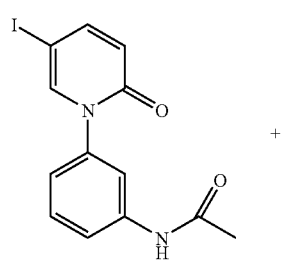

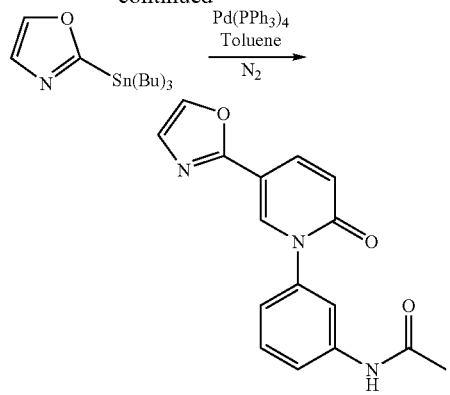

N-(3-(5-iodo-2-oxopyridin-1(2H)-yl)phenyl)acetamide (0.050 g, 0.14 mmol) was dissolved in dry and degassed toluene (3 mL). The catalyst was then added (0.008 g, 0.007 mmol) and the mixture was stirred for 10 minutes. 2-(tributylstannyl)oxazole (0.050 g, 0.14 mmol) was added and the reaction was heated at 90° C. for 18 h under nitrogen atmosphere. Conc. NH$_4$OH was added. The solvent was removed at reduced pressure and the crude was purified by preparative HPLC. 16 mg (38.7% yield) of compound 384 were obtained as a pale yellow solid. 1H NMR (300 MHz, DMSO-d6) ppm 10.15 (br. s., 1H), 8.16-8.21 (m, 1H), 8.14 (d, 1H), 8.02 (dd, 1H), 7.76 (t, 1H), 7.61 (ddd, 1H), 7.46 (dd, 1H), 7.32 (d, 1H), 7.16 (ddd, 1H), 6.65 (dd, 1H), 2.07 (s, 3H)

Synthesis of Compound 385: Compound 385 was prepared as follows.

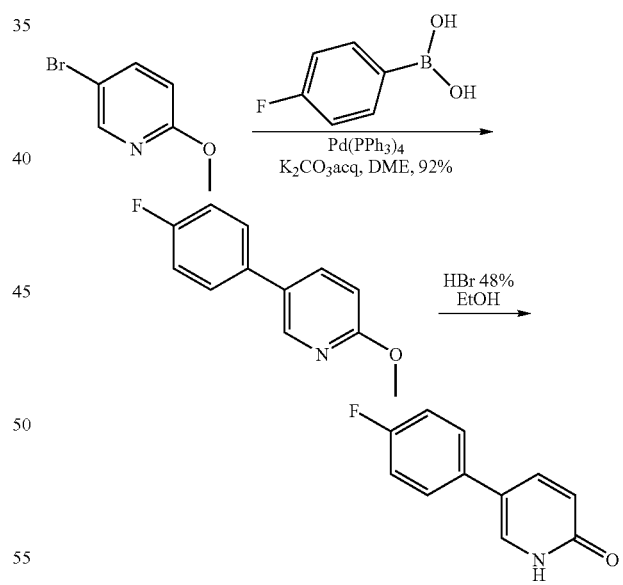

Following standard Suzuki coupling, the product was obtained by reaction of 2.82 g (15 mmol) of 5-bromo-2-methoxy-pyridine. After purification (SiO$_2$; Hexanes:EtOAc 9:1) 2.8 g (92% yield) of pure product were obtained as white solid. The intermediate (900 mg) was dissolved in HBr 48% (10 ml) and EtOH (3 ml) and the solution was heated at reflux for 3 h. After evaporation of volatiles the desired pyridone was obtained as white solid (780 mg, 93% yield).

Following general procedure H1A, compound 385 was prepared in 35% yield. $^1$H NMR (300 MHz, DMSO-d6) ppm 7.86-7.99 (m, 1H), 7.82 (d, 1H), 7.58-7.73 (m, 2H), 7.12-7.30 (m, 3H), 6.94 (d, 1H), 6.87 (dd, 1H), 6.58 (d, 1H), 4.08 (q, 2H), 2.04 (s, 3H), 1.35 (t, 3H)

Synthesis of Compound 386: Compound 386 was prepared as follows.

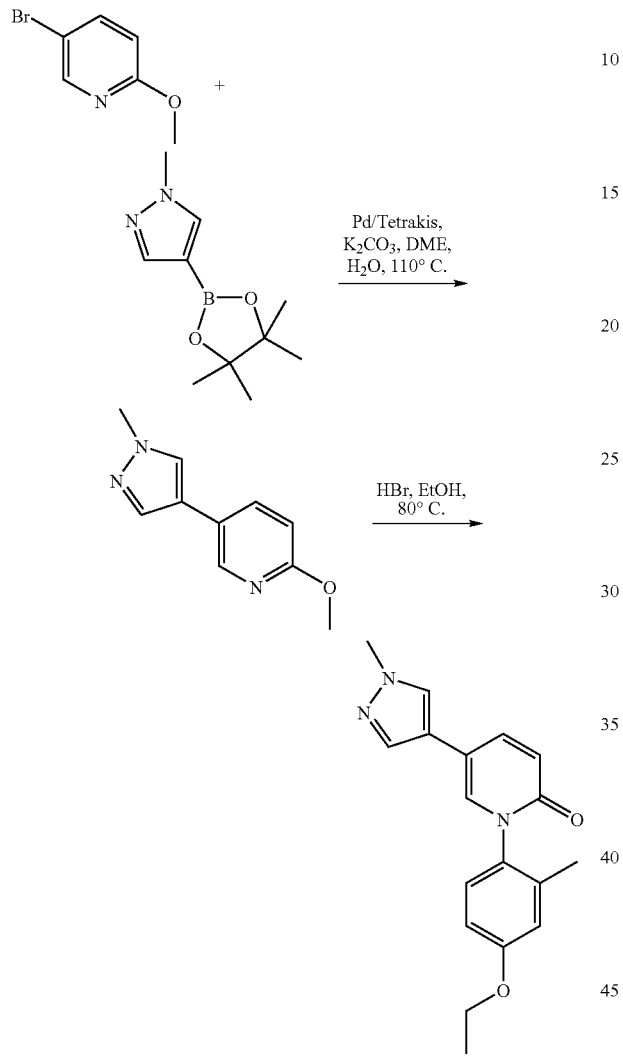

Synthesis of Compound 387: Compound 387 was prepared as follows.

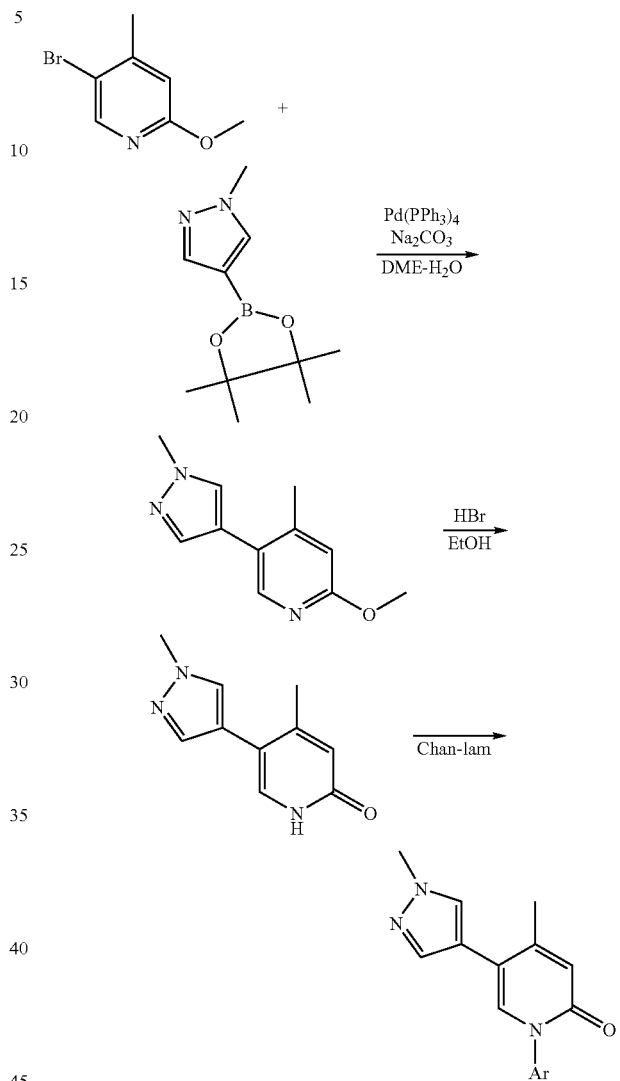

Following standard procedure for Suzuki coupling, the intermediate was obtained by reaction of 3 g (16 mmol) of 5-bromo-2-methoxy-pyridine. After purification (SiO$_2$; Hexanes:EtOAc 20:1 to 100% EtOAc) 2.2 g (51% yield) of pure product were obtained as white solid. To a magnetically stirred solution of 2-Methoxy-5-(1-methyl-1H-pyrazol-4-yl)-pyridine (1.2 g, 6.3 mmol), in 3 mL of EtOH, 15 mL of HBr were added. The mixture was heated at 80° C. for 20 h. The reaction was cooled at room temperature. The solvent was evaporated under vacuum. Purification by flash column chromatography (SiO$_2$; 100% AcOEt) afforded 1.1 g of the intermediate compound (quantitative yield).

Following general provedure H1A, compound 386 was prepared from this intermediate in 22% yield. $^1$H NMR (300 MHz, DMSO-d6) ppm 8.01 (s, 1H), 7.71-7.81 (m, 3H), 7.16 (d, 1H), 6.94 (d, 1H), 6.86 (dd, 1H), 6.52 (dd, 1H), 4.08 (q, 2H), 3.81 (s, 3 H), 2.02 (s, 3H), 1.35 (t, 3H)

Following the standard procedure for Suzuki coupling, the intermediate was obtained by reaction of 3.2 g (16 mmol) of 5-bromo-2-methoxy-4-methylpyridine. After purification (SiO$_2$; Hexanes:EtOAc 20:1 to 100% EtOAc) 2 g (62% yield) of pure product was obtained as white solid. A solution of 2-methoxy-4-methyl-5-(1-methyl-1H-pyrazol-4-yl)pyridine (2 g, 9.9 mmol) in EtOH (6 ml) and HBr 48% (12 ml) was stirred at 90° C. for 24 h. The solvent was evaporated and the crude compound (as hydrobromide salt) was utilized in the next step without any purification. Quantitative yield.

Following general procedure H1A, compound 387 was prepared from this intermediate in 33% yield. $^1$H NMR (300 MHz, DMSO-d6) ppm 7.88 (s, 1H), 7.59 (d, 1 H), 7.34-7.55 (m, 6H), 6.43 (s, 1H), 3.84 (s, 3H), 2.23 (d, 3H)

Synthesis of Compound 388: Similar to compound 387, compound 388 was prepared in 41% yield. $^1$H NMR (300 MHz, DMSO-d6) ppm 10.10 (s, 1H), 7.87 (s, 1H), 7.69 (t, 1H), 7.51-7.61 (m, 2H), 7.48 (s, 1H), 7.41 (dd, 1H), 7.08 (ddd, 1H), 6.42 (s, 1H), 3.84 (s, 3H), 2.23 (d, 3H), 2.05 (s, 3H)

Synthesis of Compound 389: Compound 389 was prepared as follows.

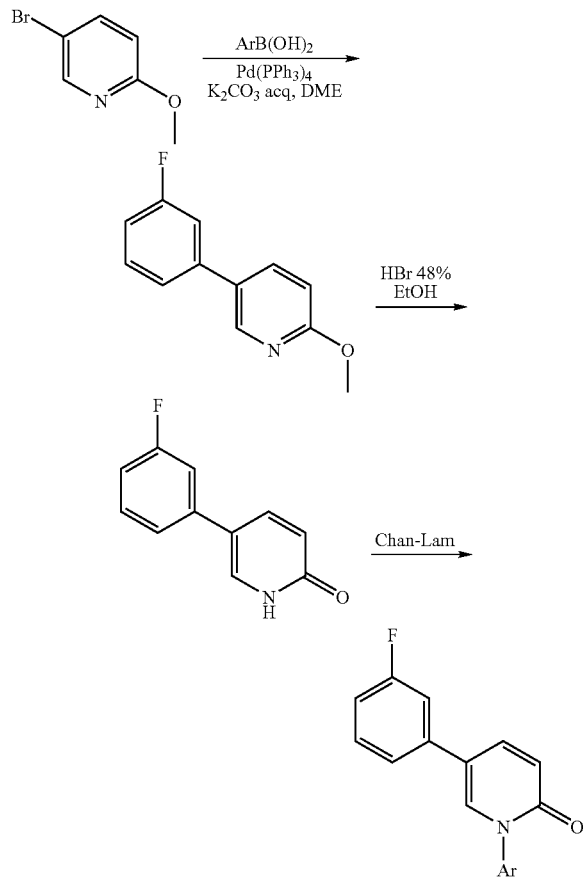

Following standard procedure for Suzuki coupling, the intermediate was obtained by reaction of 420 mg (3 mmol) of 5-bromo-2-methoxy-pyridine. After purification (SiO$_2$; Hexanes:EtOAc 95:5) 390 mg (65% yield) of pure product was obtained as white solid. The intermediate (390 mg) was dissolved in HBr 48% (5 ml) and EtOH (5 ml) and the solution was heated at reflux for 24 h. After evaporation of volatiles the desired pyridone was obtained as white solid (359 mg, quantitative yield).

Following general procedure H1A, compound 389 was prepared from this intermediate in 51% yield. $^1$H NMR (300 MHz, DMSO-d6) ppm 8.06 (d, 1H), 7.97 (dd, 1 H), 7.34-7.61 (m, 8H), 7.00-7.20 (m, 1H), 6.60 (d, 1H)

Synthesis of Compound 390: Similar to compound 389, compound 390 was prepared in 38% yield. $^1$H NMR (300 MHz, DMSO-d6) ppm 10.13 (s, 1H), 8.05 (d, 1H), 7.97 (dd, 1H), 7.70-7.77 (m, 1H), 7.58-7.65 (m, 1H), 7.49-7.58 (m, 1 H), 7.36-7.49 (m, 3H), 7.02-7.20 (m, 2H), 6.60 (d, 1H), 2.06 (s, 3H)

Synthesis of Compound 391: Similar to compound 387, compound 391 was prepared in 26% yield. $^1$H NMR (300 MHz, DMSO-d6) ppm 7.86 (s, 1H), 7.57 (d, 1H), 7.35 (s, 1H), 7.12 (d, 1H), 6.91 (d, 1H), 6.84 (dd, 1H), 6.40 (s, 1H), 4.06 (q, 2H), 3.83 (s, 3H), 2.24 (d, 3H), 2.02 (s, 3H), 1.34 (t, 3H)

Synthesis of Compound 392: Compound 392 was prepared from the intermediate aryl group as follows.

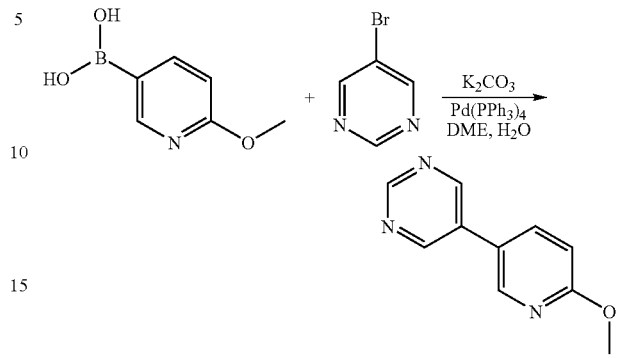

Following the standard procedure for Suzuki coupling, the product was obtained by reaction of 2.7 g (14.4 mmol) of 5-bromo-2-methoxy-pyridine. After purification (SiO$_2$; Hexanes:EtOAc 1:1 to 100% EtOAc) 1.29 g mg (48% yield) of pure product was obtained as white solid. A solution of 5-(6-Methoxy-pyridin-3-yl)-pyrimidine (1.29 g, 6.9 mmol) in EtOH (4 ml) and HBr 48% (10 ml) was stirred at 90° C. for 7 h. The solvent was evaporated and the crude compound (as hydrobromide salt) was utilized in the next step without any purification.

Following general procedure H1A, compound 392 was prepared from this intermediate in 21% yield. $^1$H NMR (300 MHz, DMSO-d6) ppm 9.07-9.12 (m, 3H), 8.14 (dd, 1H), 8.06 (dd, 1H), 7.21 (d, 1H), 6.96 (d, 1H), 6.88 (dd, 1H), 6.64 (dd, 1H), 4.08 (q, 2H), 2.06 (s, 3H), 1.35 (t, 3H)

Synthesis of Compound 393: Similar to synthesis of compound 380, compound 393 was prepared in 41% yield. $^1$H NMR (300 MHz, DMSO-d6) ppm 8.66-8.83 (m, 2H), 7.85-7.97 (m, 2H), 7.61-7.68 (m, 2H), 7.58 (m, 2H), 6.98 (m, 2H), 6.54-6.66 (m, 1H), 3.78 (s, 3H)

Synthesis of Compound 394: Similar to synthesis of compound 380, compound 394 was prepared in 33% yield. 1H NMR (300 MHz, DMSO-d6) ppm 7.82-7.92 (m, 2H), 7.43-7.61 (m, 7H), 6.97 (m, 2H), 6.58 (dd, 1H), 3.77 (s, 3H)

Synthesis of Compound 395: Similar to synthesis of compound 380, compound 395 was prepared in 42% yield. $^1$H NMR (300 MHz, DMSO-d6) ppm 10.12 (s, 1H), 7.88 (dd, 1H), 7.83 (d, 1H), 7.70-7.76 (m, 1H), 7.58-7.64 (m, 1H), 7.54 (m, 2 H), 7.44 (dd, 1 H), 7.14 (ddd, 1H), 6.97 (m, 2H), 6.57 (d, 1H), 3.77 (s, 3H), 2.06 (s, 3H)

Synthesis of Compound 396: Similar to compound 387, compound 396 was prepared in 23% yield. $^1$H NMR (300 MHz, DMSO-d6) ppm 7.88 (s, 1H), 7.43-7.69 (m, 6H), 6.45 (s, 1H), 3.84 (s, 3H), 2.24 (d, 3H)

Synthesis of Compound 397: Compound 397 was prepared from an intermediate heteroaryl prepared as follows.

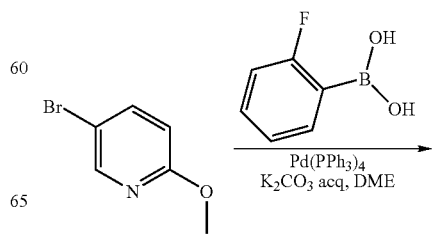

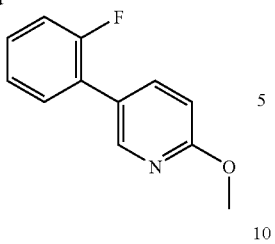

Following the standard procedure for Suzuki coupling, the intermediate was obtained by reaction of 3 g (16 mmol) of 5-bromo-2-methoxy-pyridine. After purification (SiO$_2$; Hexanes:EtOAc 1:1 to 100% EtOAc) 750 mg (31% yield) of pure product was obtained as white solid. 5-(2-fluorophenyl)-2-methoxypyridine (750 mg) was dissolved in HBr 48% (10 ml) and EtOH (3 ml) and the solution was heated at reflux for 3 h. After evaporation of volatiles the desired pyridone was obtained as white solid (700 mg, quantitative yield).

Following general procedure H1A, compound 397 was prepared from this intermediate in 34% yield. $^1$H NMR (300 MHz, DMSO-d6) ppm 7.74-7.83 (m, 1H), 7.67-7.73 (m, 1H), 7.51-7.61 (m, 1H), 7.17-7.42 (m, 4H), 6.94 (d, 1H), 6.87 (dd, 1H), 6.59 (dd, 1H), 4.08 (q, 2H), 2.05 (s, 3H), 1.35 (t, 3H)

Synthesis of Compound 398: Similar to compound 389, compound 398 was prepared in 30% yield. $^1$H NMR (300 MHz, DMSO-d6) ppm 8.13 (d, 1H), 7.99 (dd, 1H), 7.62-7.76 (m, 2H), 7.34-7.62 (m, 5H), 7.02-7.20 (m, 1H), 6.62 (d, 1H)

Synthesis of Compound 399: Following general procedure A, compound 399 was prepared in 44% yield. $^1$H NMR (300 MHz, DMSO-d6) ppm 12.24 (br. s., 1H), 10.11 (s, 1 H), 7.73 (m, 1H), 7.57 (m, 1H), 7.51 (dd, 1H), 7.35-7.47 (m, 2H), 7.10 (ddd, 1H), 6.54 (d, 1H), 2.17 (br. s., 6H), 2.06 (s, 3H)

Synthesis of Compound 400: Similar to synthesis of compound 380, compound 400 was prepared in 36% yield. $^1$H NMR (300 MHz, DMSO-d6) ppm 7.89 (dd, 1H), 7.72 (d, 1H), 7.53 (m, 2H), 7.19 (d, 1H), 6.91-7.04 (m, 3H), 6.86 (dd, 1H), 6.56 (d, 1H), 4.08 (q, 2H), 3.77 (s, 3H), 2.04 (s, 3H), 1.35 (t, 3H)

Synthesis of Compound 401: Compound 401 was synthesized as follows.

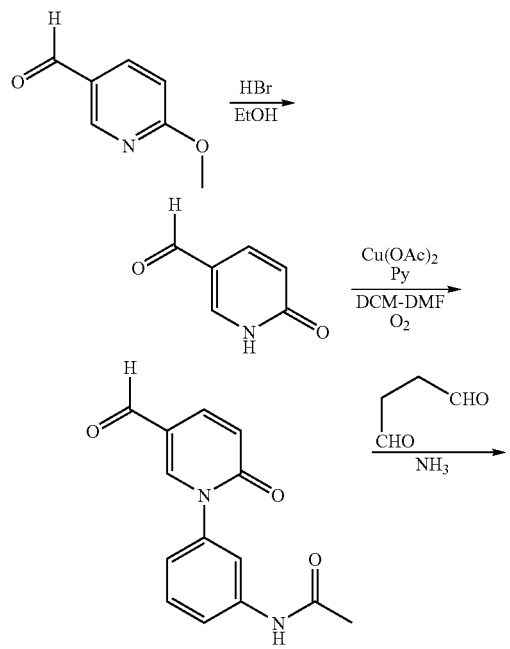

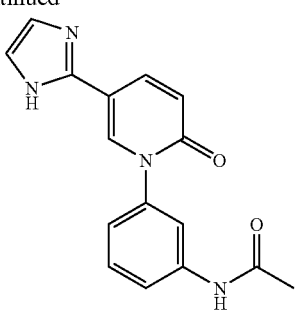

6-methoxynicotinaldehyde (1.0 g, 7.2 mmol) was dissolved in HBr 48% (10 mL) and EtOH (3 mL) and the solution was heated at reflux for 2 h. After evaporation of volatiles 1.6 g of the desired pyridone was obtained. The product was used in the next step without further purification. To a solution of 6-oxo-1,6-dihydropyridine-3-carbaldehyde (300 mg, 2.4 mmol) in DMF (10 mL), Cu(OAc)2 (0.88 g, 4.8 mmol), 3-acetamidophenyl boronic acid (0.5 g, 2.8 mmol), pyridine (0.42 mL, 2.8 mmol) and finely grounded, activated 4 A molecular sieves (1 g) were added. The mixture was stirred at room temperature for 24 h. A concentrated solution of NH$_4$OH was added. The solvents were evaporated under vacuum, and the resulting crude was purified by chromatographic column (SiO$_2$; Hexanes:EtOAc 9:1 to 100% EtOAc). 370 mg (38.5% yield) of pure product were obtained as a white solid. To a solution of N-(3-(5-formyl-2-oxopyridin-1 (2H)-yl)phenyl)acetamide (370 mg, 0.94 mmol) in MeOH (20 mL), glioxal (0.4 mL, 3.4 mmol) was added at 0° C. Gaseous NH$_3$ was bubbled into the mixture at 0° C. for 1 h. The reaction was warmed at room temperature and stirred for 24 h. The solvent was evaporated under vacuum and the resulting crude was purified by flash chromatography (SiO$_2$, Hexanes:EtOAc 9:1 to 100% EtOAc). 100 mg (24.6% yield) of compound 401 were obtained. $^1$H NMR (300 MHz, DMSO-d6) ppm 10.20 (s, 1H), 8.49 (d, 1H), 8.03 (dd, 1H), 7.83-7.91 (m, 1H), 7.67 (s, 2H), 7.54-7.62 (m, 1H), 7.50 (dd, 1H), 7.15 (ddd, 1H), 6.75 (d, 1H), 2.07 (s, 3H)

Synthesis of Compound 402: Following general procedure H1A, compound 402 was prepared in 17% yield. $^1$H NMR (300 MHz, DMSO-d6) ppm 10.16 (s, 1H), 8.24-8.34 (m, 1H), 8.19 (d, 1H), 7.69-7.79 (m, 1H), 7.56-7.65 (m, 1H), 7.38-7.51 (m, 1H), 7.16 (ddd, 1H), 2.06 (s, 3H)

Synthesis of Compound 403: Similar to compound 387, compound 403 was prepared in 34% yield. $^1$H NMR (300 MHz, DMSO-d6) ppm 8.71 (dd, 2H), 7.90 (s, 1H), 7.54-7.64 (m, 4H), 6.47 (s, 1H), 3.85 (s, 3H), 2.24 (d, 3H)

Synthesis of Compound 405: Compound 405 was prepared from an intermediate heteroaryl synthesized as follows.

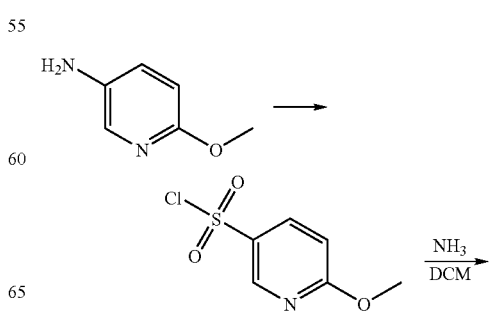

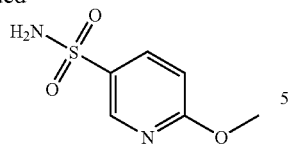

A mixture of 2-methoxy-5-aminopyridine (10 g, 0.08 mol) in AcOH (125 mL), and concentrated HCl (150 mL) was cooled at 0° C. in an ice/water bath. A solution of NaNO₂ (4.0 g, 0.058 mol) in water (15 mL) was added dropwise at 0° C. The resulting mixture was stirred for 45 minutes at 0° C. In the meantime, in a separate round bottom flask, 150 mL of concentrated HCl was added dropwise to a sodium bisulphite solution. The gaseous SO₂ thus formed was purged for 2-3 h into a third round bottom flask containing AcOH cooled at −20° C. CuCl₂ (18 g) was added, and the reaction was stirred for 20 minutes at −20° C. The mixture was added dropwise to the 2-methoxy-5-aminopyridine/AcOH/concentrated HCl mixture maintained at 0° C. The reaction was allowed to warm up to room temperature and stirred overnight. The mixture was quenched with water and the solid thus formed was filtered, re-dissolved in DCM and filtered through celite. The clear solution was dried over Na₂SO₄ and concentrated under vacuum to afford 10.2 g (61% yield) of pure 6-methoxy-pyridine-3-sulfonyl chloride. 6-Methoxy-pyridine-3-sulfonyl chloride (5.0 g, 0.025 mol) was dissolved in DCM and cooled at 0° C. Gasseous NH₃ was bubbled in the solution for 10 min. The resulting pale brown suspension was filtered and the solid was triturated with water. The resulting white solid was filtered and dried under vacuum to afford 3.2 g (70.6% yield) of pure 6-Methoxy-pyridine-3-sulfonamide. 6-Methoxy-pyridine-3-sulfonamide (0.752 g, 4.0 mmol) was dissolved in EtOH (6 mL). An excess of 48% HBr aqueous solution (12 mL) was added and the reaction was heated at 90° C. for 20 h. The solvent was removed under reduced pressure and the residual hydrobromic acid was further dried under reduced pressure, at 40° C. Quantitative yield.

Following general procedure H1A, compound 405 was prepared from this intermediate in 28% yield. ¹H NMR (300 MHz, DMSO-d6) ppm 7.86 (d, 1H), 7.79 (dd, 1 H), 7.35 (s, 2H), 7.19 (d, 1H), 6.96 (d, 1H), 6.88 (dd, 1H), 6.64 (d, 1H), 4.08 (q, 2H), 2.02 (s, 3H), 1.35 (t, 3H)

Synthesis of Compound 406: Following general procedure H1A, compound 406 was prepared in 38% yield. ¹H NMR (300 MHz, DMSO-d6) ppm 8.29 (dd, 1H), 8.20 (d, 1 H), 7.42-7.65 (m, 5H)

Synthesis of Compound 407: Compound 407 was prepared as follows:

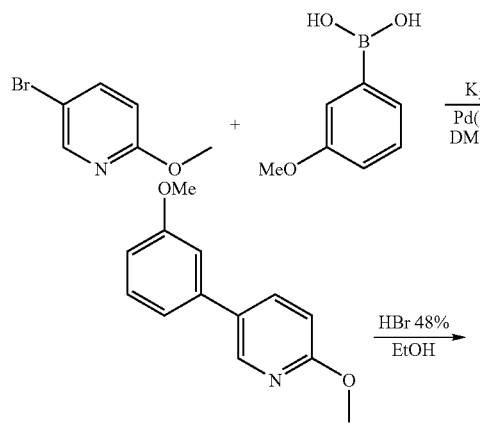

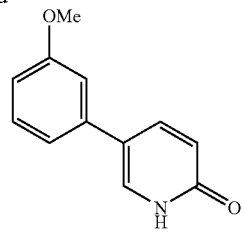

Following the standard procedure for Suzuki coupling, the product was obtained by reaction of 1.02 g (5.4 mmol) of 5-bromo-2-methoxy-pyridine. After purification (SiO₂; Hexanes:EtOAc 20:1 to 100% EtOAc) 1.12 g (96% yield) of pure product were obtained as white solid. A solution of 2-Methoxy-5-(4-methoxy-phenyl)-pyridine (1.12 g, 5.2 mmol) in EtOH (5 ml) and HBr 48% (10 ml) was stirred at 80° C. for 48 h. The solvent was evaporated and the crude compound (as hydrobromide salt) was utilized in the next step without any purification (quantitative yield).

Compound 407 was prepared from this intermediate using general procedure H1A in 35% yield. ¹H NMR (300 MHz, DMSO-d6) ppm 7.98 (dd, 1H), 7.93 (dd, 1H), 7.39-7.62 (m, 5H), 7.32 (dd, 1H), 7.13-7.23 (m, 2H), 6.81-6.92 (m, 1H), 6.59 (dd, 1H), 3.80 (s, 3H)

Synthesis of Compound 408: Similar to compound 407, compound 408 was prepared in 38% yield. ¹H NMR (300 MHz, DMSO-d6) ppm 8.05 (d, 1H), 7.95 (dd, 1H), 7.67 (m, 2H), 7.54 (m, 2H), 7.32 (dd, 1H), 7.15-7.24 (m, 2H), 6.83-6.93 (m, 1H), 6.61 (d, 1H), 3.80 (s, 3H)

Synthesis of Compound 409: Compound 409 was prepared as follows.

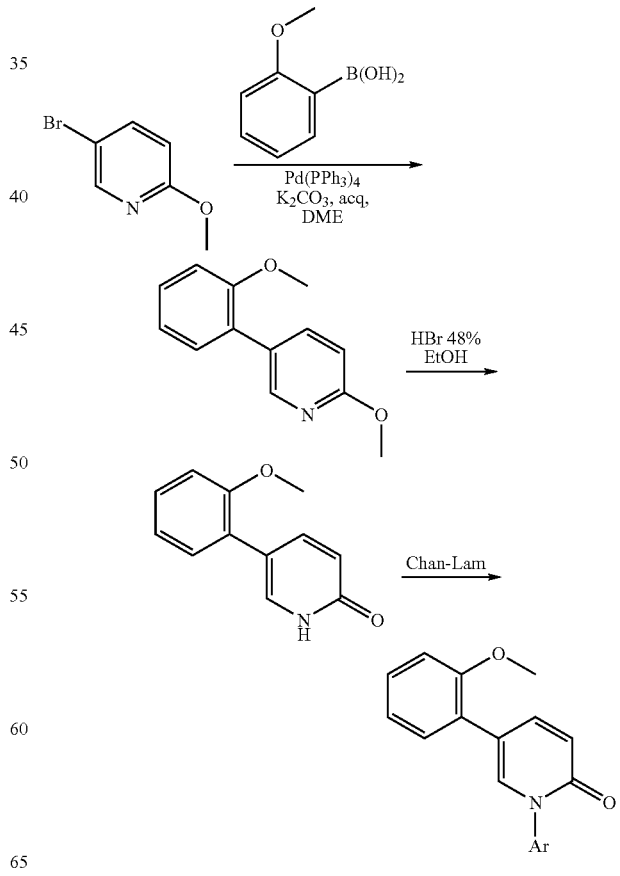

Following standard procedure for Suzuki coupling the intermediate was obtained by reaction of 3 g (16 mmol) of 5-bromo-2-methoxy-pyridine. After purification (SiO$_2$; Hexanes:EtOAc 9:1) 3.1 g (70% yield) of pure product were obtained as white solid. The intermediate (3.1 g) was dissolved in HBr 48% (10 ml) and EtOH (5 ml) and the solution was heated at reflux for 24 h. After evaporation of volatiles the desired pyridone was obtained as white solid (2.9 g, quantitative yield).

Compound 409 was prepared following general procedure H1A in 36% yield. $^1$H NMR (300 MHz, DMSO-d6) ppm 7.73 (dd, 1H), 7.69 (dd, 1H), 7.41-7.57 (m, 5H), 7.37 (dd, 1H), 7.32 (ddd, 1H), 7.09 (dd, 1H), 6.99 (ddd, 1H), 6.53 (dd, 1H), 3.80 (s, 3H)

Synthesis of Compound 410: Similar to the preparation of compound 409, compound 410 was prepared in 13% yield. $^1$H NMR (300 MHz, DMSO-d6) ppm 7.70-7.79 (m, 2H), 7.66 (m, 2H), 7.52 (m, 2H), 7.38 (dd, 1H), 7.33 (ddd, 1H), 7.10 (dd, 1H), 6.99 (td, 1H), 6.55 (d, 1H), 3.80 (s, 3H)

Synthesis of Compound 411: Following general procedure A, compound 411 was prepared in 51% yield. $^1$H NMR (300 MHz, DMSO-d6) ppm 12.24 (br. s., 1H), 7.37-7.59 (m, 7H), 6.54 (dd, 1H), 2.17 (br. s., 6H)

Synthesis of Compound 412: Similar to the preparation of compound 409, compound 412 was prepared in 26% yield. $^1$H NMR (300 MHz, DMSO-d6) ppm 7.74 (dd, 1H), 7.55 (d, 1H), 7.25-7.38 (m, 2H), 7.18 (d, 1H), 7.08 (dd, 1H), 6.98 (ddd, 1H), 6.94 (d, 1H), 6.85 (dd, 1H), 6.52 (d, 1H), 4.07 (q, 2H), 3.79 (s, 3H), 2.06 (s, 3H), 1.35 (t, 3H)

Synthesis of Compound 413: Compound 413 was prepared as follows.

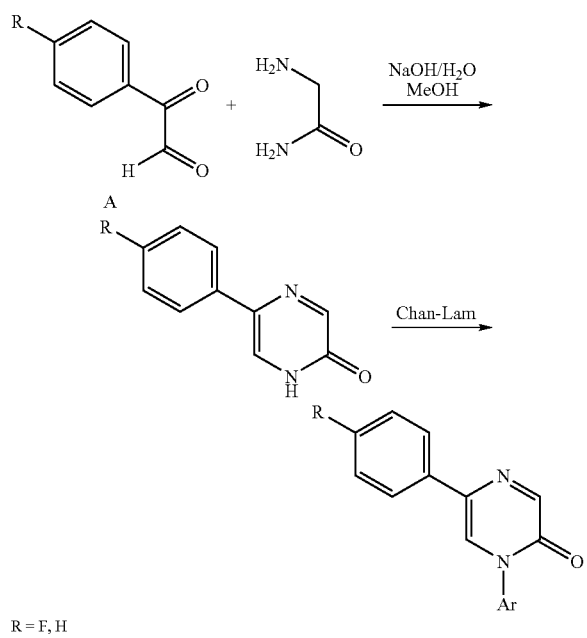

R = F, H

To a suspension of A (2.9 mmol) in a MeOH:Water (10 mL:1 mL) mixture, a solution of NaOH in water (2.9 mmol in 2 mL of Water) was added at −30° C. To the stirred reaction, a solution of 2-aminoacetamide (2.9 mmol) in MeOH (2 mL) was added. The mixture was stirred at the same temperature for 1 h, then warmed at room temperature and stirred for additional 3 h. AcOH was added until pH 5 and the volatile portion was evaporated under vacuum. The remaining mixture was portioned between Water (10 mL) and Ethyl Acetate (10 mL). The organic layer was dried over Na$_2$SO$_4$, filtered and evaporated under vacuum.

Following general procedure H1A, compound 413 was prepared from this intermediate in 51% yield. $^1$H NMR (300 MHz, DMSO-d6) ppm 8.26 (d, 1H), 8.21 (d, 1 H), 7.87-8.00 (m, 2H), 7.48-7.62 (m, 5H), 7.38-7.47 (m, 2H), 7.28-7.36 (m, 1H)

Synthesis of Compound 415: Similar to compound 407, compound 415 was prepared in 23% yield. $^1$H NMR (300 MHz, DMSO-d6) ppm 10.12 (s, 1H), 7.86-8.01 (m, 2H), 7.73 (t, 1H), 7.53-7.68 (m, 1H), 7.44 (dd, 1H), 7.32 (dd, 1H), 7.10-7.23 (m, 3H), 6.80-6.93 (m, 1H), 6.59 (dd, 1H), 3.79 (s, 3H), 2.06 (s, 3H)

Synthesis of Compound 416: Compound 416 was prepared as follows.

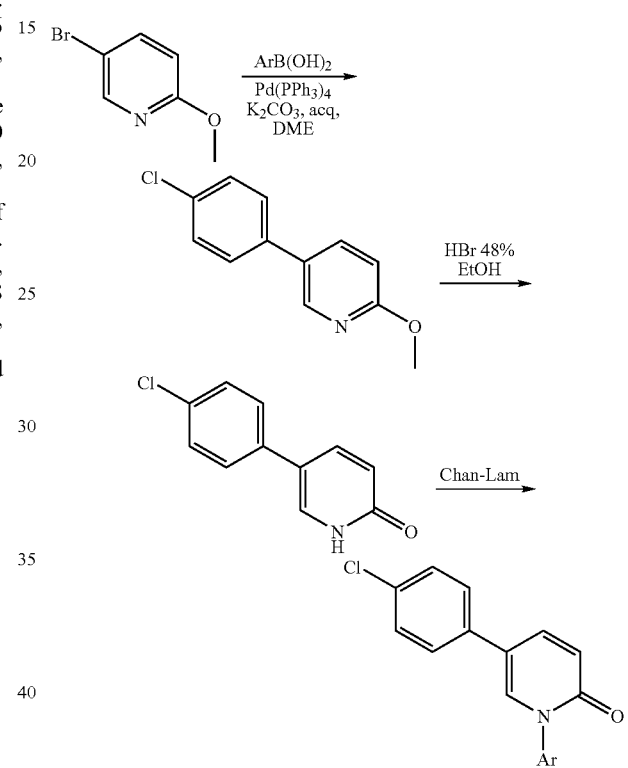

Following the standard procedure for Suzuki coupling, the product was obtained by reaction of 1.02 g (5.4 mmol) of 5-bromo-2-methoxy-pyridine. After purification (SiO$_2$; Hexanes:EtOAc 20:1 to 100% EtOAc)) 1.06 g (89% yield) of pure product were obtained as white solid. A solution of 2-Methoxy-5-(4-methoxy-phenyl)-pyridine (1.12 g, 5.2 mmol) in EtOH (5 ml) and HBr 48% (10 ml) was stirred at 80° C. overnight. The solvent was evaporated and the crude compound (as hydrobromide salt) was utilized in the next step without any purification (quantitative yield).

Compound 416 was prepared from this intermediate following general procedure H1A in 41% yield. $^1$H NMR (300 MHz, DMSO-d6) ppm 8.00 (d, 1H), 7.93 (dd, 1H), 7.68 (m, 2H), 7.36-7.59 (m, 7H), 6.60 (d, 1H)

Synthesis of Compound 417: Similar to compound 416, compound 417 was prepared in 44% yield. $^1$H NMR (300 MHz, DMSO-d6) ppm 10.13 (s, 1H), 7.99 (d, 1H), 7.93 (dd, 1H), 7.71-7.78 (m, 1H), 7.67 (m, 2H), 7.54-7.63 (m, 1H), 7.39-7.49 (m, 3H), 7.07-7.19 (m, 1H), 6.60 (d, 1H), 2.06 (s, 3H)

Synthesis of Compound 418: Similar to compound 407, compound 418 was prepared in 16% yield. $^1$H NMR (300 MHz, DMSO-d6) ppm 7.95 (dd, 1H), 7.86 (d, 1H), 7.30 (dd, 1H), 7.11-7.24 (m, 3H), 6.95 (d, 1H), 6.80-6.91 (m, 2H), 6.57 (d, 1H), 4.08 (q, 2H), 3.79 (s, 3H), 2.04 (s, 3H), 1.35 (t, 3H)

Synthesis of Compound 419: Following general procedure H1A, compound 419 was prepared in 28% yield. $^1$H NMR (300 MHz, DMSO-d6) ppm 8.33-8.44 (m, 1H), 8.21 (d, 1H), 7.68 (m, 2H), 7.56 (m, 2H)

Synthesis of Compound 420: Similar to compound 416, compound 420 was prepared in 33.8% yield. $^1$H NMR (300 MHz, DMSO-d6) ppm 7.94 (dd, 1H), 7.89 (d, 1 H), 7.65 (m, 2H), 7.44 (m, 2H), 7.20 (d, 1H), 6.94 (d, 1H), 6.87 (dd, 1H), 6.59 (d, 1H), 4.08 (q, 2H), 2.04 (s, 3H), 1.35 (t, 3H)

Synthesis of Compound 421: Similar to compound 416, compound 421 was prepared in 31.5% yield. $^1$H NMR (300 MHz, DMSO-d6) ppm 8.07 (d, 1H), 7.95 (dd, 1 H), 7.63-7.73 (m, 4H), 7.53 (m, 2H), 7.46 (m, 2H), 6.62 (d, 1H)

Synthesis of Compound 422: Similar to compound 413, compound 422 was prepared in 35% yield. $^1$H NMR (300 MHz, DMSO-d6) ppm 8.25 (d, 1H), 8.23 (d, 1H), 7.91-8.03 (m, 2H), 7.44-7.65 (m, 5H), 7.17-7.33 (m, 2H)

Synthesis of Compound 423: Similar to compound 407, compound 423 was prepared in 34% yield. $^1$H NMR (300 MHz, DMSO-d6) ppm 8.63-8.87 (m, 2H), 8.04 (d, 1H), 7.97 (dd, 1H), 7.58-7.69 (m, 2H), 7.33 (t, 1H), 7.15-7.27 (m, 2H), 6.81-6.94 (m, 1 H), 6.63 (d, 1H), 3.80 (s, 3H)

Synthesis of Compound 424: Compound 424 was prepared as follows.

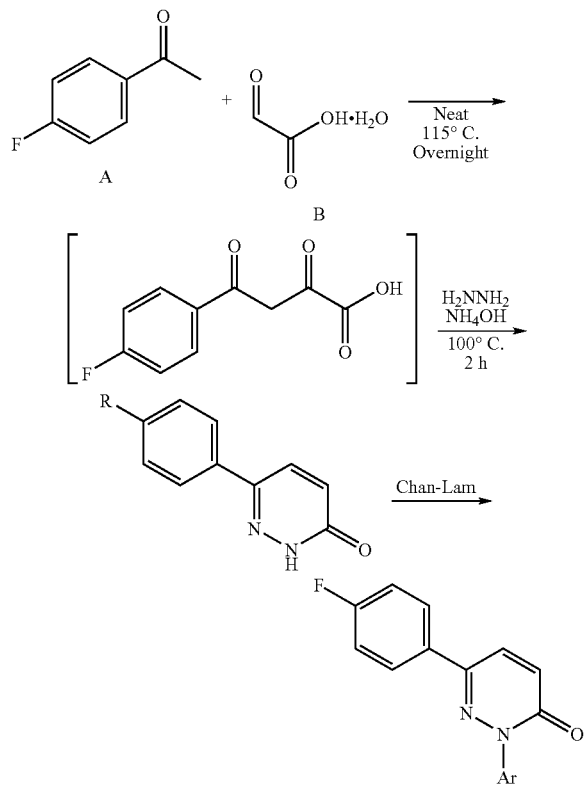

In a round bottom flask, glyoxylic acid acid B (22 mmol) and 4-F acetophenone A (8 mmol) were mixed together and the reaction was heated at 115° C. overnight, then allowed to cool down at room temperature. Water (5 mL) and concentrated NH$_4$OH (1 mL), were poured into the reaction vessel and the mixture was extracted with DCM (3×5 mL). To the aqueous basic solution hydrazine (8 mmol) was added and the reaction was stirred at 100° C. for 2 h. The precipitate thus formed was collected by filtration and washed with plenty of water. The desired compound was recovered as a light yellow solid (45% yield). $^1$H NMR (300 MHz, DMSO-d6) ppm 13.15 (br. s., 1H) 8.01 (d, 1H) 7.91 (m, 2H) 7.31 (m, 2H) 6.97 (d, 1H)

Following general procedure H1A, compound 424 was prepared from this intermediate in 74% yield. $^1$H NMR (300 MHz, DMSO-d6) ppm 10.12 (s, 1H), 8.14 (d, 1 H), 7.94-8.01 (m, 2H), 7.90-7.94 (m, 1H), 7.57-7.66 (m, 1H), 7.43 (t, 1 H), 7.28-7.39 (m, 3H), 7.18 (d, 1H), 2.06 (s, 3H)

Synthesis of Compound 425: Compound 425 was prepared as follows.

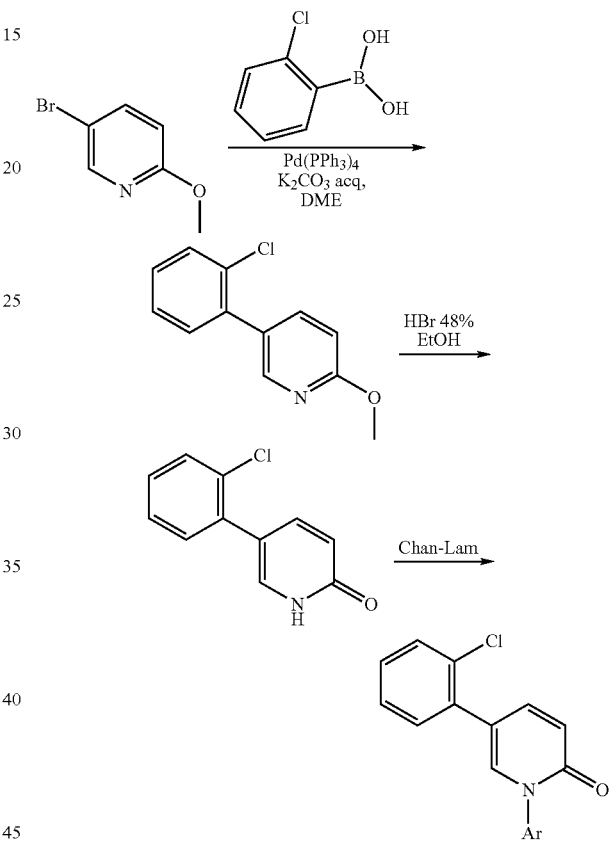

Following standard procedure for Suzuki coupling, the intermediate was obtained by reaction of 3 g (16 mmol) of 5-bromo-2-methoxy-pyridine. After purification (SiO$_2$; Hexanes:EtOAc 1:1 to 100% EtOAc) 3.99 g (95% yield) of pure product was obtained as white solid. The intermediate (3.99 g) was dissolved in HBr 48% (12 ml) and EtOH (6 ml) and the solution was heated at reflux for 24 h. After evaporation of volatiles the desired pyridone was obtained as white solid (3.72 g, quantitative yield).

Compound 425 was prepared following general procedure H1A with this intermediate in 42% yield. $^1$H NMR (300 MHz, DMSO-d6) ppm 7.74 (d, 1H), 7.67 (dd, 1 H), 7.32-7.60 (m, 9H), 6.57 (d, 1H)

Synthesis of Compound 426: Following general procedure H1A, compound 426 was prepared in 8% yield. $^1$H NMR (300 MHz, DMSO-d6) ppm 9.30 (s, 1H), 9.04 (s, 2H), 8.47-8.64 (m, 1H), 8.28 (d, 1H)

Synthesis of Compound 427: Similar to the preparation of compound 409, compound 427 was prepared in 45% yield. $^1$H NMR (300 MHz, DMSO-d6) ppm 8.67-8.79 (m, 2H), 7.68-7.82 (m, 2H), 7.59-7.68 (m, 2H), 7.39 (dd, 1H), 7.34 (ddd, 1H), 7.10 (dd, 1H), 7.00 (td, 1H), 6.54-6.61 (m, 1H), 3.80 (s, 3H)

Synthesis of Compound 428: Similar to compound 424, compound 428 was prepared in 94% yield. $^1$H NMR (300 MHz, DMSO-d6) ppm 8.14 (d, 1H), 7.90-8.04 (m, 2 H), 7.61-7.71 (m, 2H), 7.49-7.59 (m, 2H), 7.40-7.49 (m, 1H), 7.26-7.40 (m, 2H), 7.19 (d, 1H)

Synthesis of Compound 429: Following general procedure A, compound 429 was prepared in 26% yield. $^1$H NMR (300 MHz, DMSO-d6) ppm 10.14 (s, 1H), 8.19 (t, 1H), 8.17 (d, 1H), 7.94-8.08 (m, 2H), 7.69-7.81 (m, 2H), 7.52-7.66 (m, 2H), 7.45 (dd, 1H), 7.10-7.21 (m, 1H), 6.62 (d, 1H), 2.07 (s, 3H)

Synthesis of Compound 430: Following general procedure A, compound 430 was prepared in 44% yield. $^1$H NMR (300 MHz, DMSO-d6) ppm 10.13 (s, 1H), 8.17 (d, 1H), 7.98-8.06 (m, 1H), 7.81-7.91 (m, 4H), 7.71-7.78 (m, 1H), 7.56-7.66 (m, 1H), 7.45 (t, 1 H), 7.15 (ddd, 1H), 6.63 (d, 1H), 2.06 (s, 3H)

Synthesis of Compound 431: Similar to compound 416, compound 431 was prepared in 20.3% yield. $^1$H NMR (300 MHz, DMSO-d6) ppm 9.25 (s, 1H), 9.07 (s, 2H), 8.22 (d, 1H), 8.00 (dd, 1H), 7.69 (m, 2H), 7.48 (m, 2H), 6.66 (d, 1H)

Synthesis of Compound 432: Similar to preparation of compound 433, compound 432 was prepared in 6.7% yield. $^1$H NMR (300 MHz, DMSO-d6) ppm 9.26 (s, 1H), 9.08 (s, 2H), 8.29 (d, 1H), 8.04 (dd, 1H), 7.79 (t, 1H), 7.60-7.69 (m, 1H), 7.46 (dd, 1H), 7.33-7.42 (m, 1H), 6.67 (d, 1H)

Synthesis of Compound 433: Compound 433 was prepared as follows.

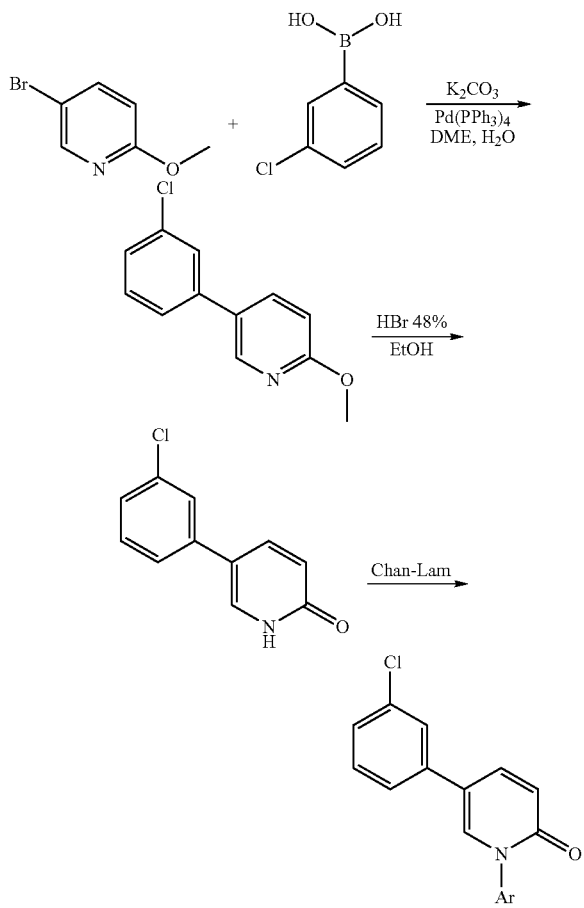

Following standard procedure for Suzuki coupling, the product was obtained by reaction of 1.02 g (5.4 mmol) of 5-bromo-2-methoxy-pyridine. After purification (SiO$_2$; Hexanes:EtOAc 20:1 to 100% EtOAc) 1.06 g (80% yield) of pure product were obtained as white solid. A solution of 2-Methoxy-5-(4-methoxy-phenyl)-pyridine (949 mg, 4.3 mmol) in EtOH (10 ml) and HBr 48% (10 ml) was stirred at 80° C. overnight. The solvent was evaporated and the crude compound (as hydrobromide salt) was utilized in the next step without any purification (quantitative yield).

Compound 433 was prepared following general procedure H1A from this intermediate in 13% yield. $^1$H NMR (300 MHz, DMSO-d6) ppm 8.14 (d, 1H), 7.98 (dd, 1 H), 7.78 (t, 1H), 7.67 (m, 2H), 7.62 (ddd, 1H), 7.54 (m, 2H), 7.43 (dd, 1H), 7.35 (ddd, 1 H), 6.62 (d, 1H)

Synthesis of Compound 434: Similar to the preparation of compound 425, compound 434 was prepared in 30% yield. $^1$H NMR (300 MHz, DMSO-d6) ppm 10.12 (br. s., 1H), 7.74-7.78 (m, 1H), 7.70-7.74 (m, 1H), 7.67 (dd, 1H), 7.47-7.62 (m, 3H), 7.35-7.47 (m, 3H), 7.14 (ddd, 1H), 6.57 (dd, 1H), 2.06 (s, 3H)

Synthesis of Compound 435: Similar to the preparation of compound 409, compound 435 was prepared in 20% yield. $^1$H NMR (300 MHz, DMSO-d6) ppm 10.12 (s, 1 H), 7.77 (t, 1H), 7.72 (dd, 1H), 7.69 (dd, 1H), 7.52-7.61 (m, 1H), 7.43 (dd, 1H), 7.28-7.39 (m, 2H), 7.14 (ddd, 1H), 7.09 (dd, 1H), 6.99 (ddd, 1H), 6.53 (dd, 1H), 3.80 (s, 3H), 2.06 (s, 3H)

Synthesis of Compound 436: Similar to the preparation of compound 409, compound 436 was prepared in 23% yield. $^1$H NMR (300 MHz, DMSO-d6) ppm 9.24 (s, 1 H), 9.06 (s, 2H), 7.89 (dd, 1H), 7.79 (dd, 1H), 7.40 (dd, 1H), 7.35 (ddd, 1H), 7.11 (dd, 1 H), 7.01 (td, 1H), 6.59 (dd, 1H), 3.81 (s, 3H)

Synthesis of Compound 437: Similar to the preparation of compound 425, compound 437 was prepared in 20% yield. $^1$H NMR (300 MHz, DMSO-d6) ppm 8.65-8.82 (m, 2H), 7.83 (d, 1H), 7.71 (dd, 1H), 7.61-7.66 (m, 2H), 7.50-7.61 (m, 2H), 7.36-7.45 (m, 2H), 6.62 (d, 1H)

Synthesis of Compound 438: Compound 438 was prepared as follows.

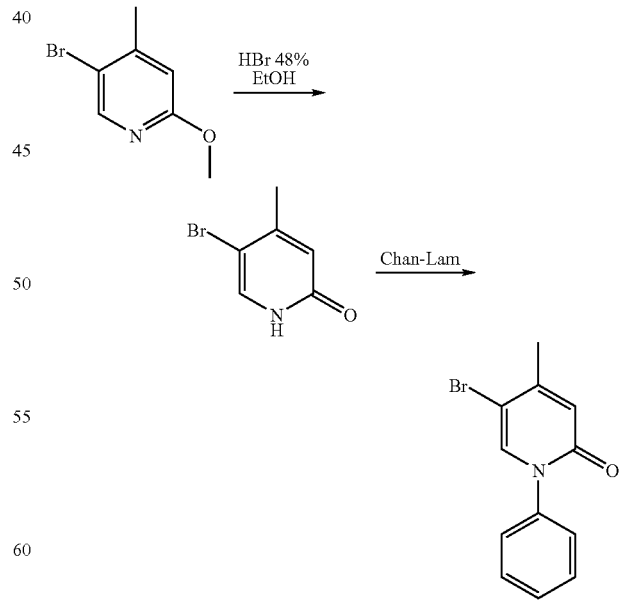

5-bromo-2-methoxy-4-methylpyridine (1.0 g, 4.95 mmol) was dissolved in HBr 48% (10 mL) and EtOH (10 mL) and the solution was heated at 90° C. for 24 h. After evaporation of volatiles, 930 mg (quantitative yield) of the desired pyridone were obtained as a white solid. 5-bromo-4-methyl-1-phenylpyridin-2(1H)-one was obtained by reaction of 450 mg (2.39 mmol) of 5-bromo-4-methylpyridin-2(1H)-one with phenylboronic acid. After purification (SiO$_2$; Hexanes: EtOAc 9:1 to 1:1) 250 mg (39.7% yield) of compound 438 were obtained as a white solid. $^1$H NMR (300 MHz, DMSO-d6) ppm 7.93 (s, 1H), 7.32-7.58 (m, 5H), 6.47-6.57 (m, 1H), 2.24 (d, 3H)

Synthesis of Compound 439: Similar to compound 385, compound 439 was prepared in 51% yield. $^1$H NMR (300 MHz, DMSO-d6) ppm 7.84-7.98 (m, 2H), 7.58-7.74 (m, 2H), 7.43 (t, 1H), 7.16-7.30 (m, 2H), 6.97-7.13 (m, 3H), 6.59 (dd, 1H), 3.81 (s, 3H)

Synthesis of Compound 440: Similar to compound 385, compound 440 was prepared in 47% yield. $^1$H NMR (300 MHz, DMSO-d6) ppm 7.98 (dd, 1H), 7.92 (dd, 1H), 7.64-7.74 (m, 2H), 7.57 (ddd, 1H), 7.29-7.41 (m, 2H), 7.15-7.29 (m, 2H), 6.61 (dd, 1 H)

Synthesis of Compound 441: Similar to compound 385, compound 441 was prepared in 55% yield. $^1$H NMR (300 MHz, DMSO-d6) ppm 7.95 (dd, 1H), 7.91 (dd, 1H), 7.62-7.72 (m, 2H), 7.50-7.62 (m, 2H), 7.29-7.42 (m, 2H), 7.16-7.29 (m, 2H), 6.59 (dd, 1H)

Synthesis of Compound 442: Following general procedure A, compound 442 was prepared in 68% yield. $^1$H NMR (300 MHz, DMSO-d6) ppm 10.13 (s, 1H), 8.02 (d, 1H), 7.94-8.01 (m, 1H), 7.78 (dd, 1H), 7.71 (t, 1H), 7.56-7.65 (m, 2H), 7.52 (dd, 1H), 7.45 (t, 1H), 7.12 (ddd, 1H), 6.57 (d, 1H), 2.06 (s, 3H)

Synthesis of Compound 443: Following general procedure A, compound 443 was prepared in 55% yield. $^1$H NMR (300 MHz, DMSO-d6) ppm 10.14 (s, 1H), 8.16 (d, 1H), 8.03 (dd, 1H), 7.93 (s, 4H), 7.76 (s, 1H), 7.61 (dt, 1H), 7.46 (t, 1H), 7.16 (ddd, 1H), 6.64 (d, 1H), 3.23 (s, 3H), 2.07 (s, 3H)

Synthesis of Compound 444: Following general procedure A, compound 444 was prepared in 70% yield. $^1$H NMR (300 MHz, DMSO-d6) ppm 10.14 (s, 1H), 8.18 (d, 1H), 8.14 (t, 1H), 8.03 (dd, 1H), 7.94-8.01 (m, 1H), 7.79-7.88 (m, 1H), 7.75 (s, 1H), 7.68 (t, 1H), 7.60-7.65 (m, 1H), 7.46 (t, 1H), 7.09-7.23 (m, 1H), 6.64 (d, 1H), 3.25 (s, 3H), 2.07 (s, 3H)

Synthesis of Compound 445: Similar to compound 385, compound 445 was prepared in 54% yield. $^1$H NMR (300 MHz, DMSO-d6) ppm 11.29 (s, 1H), 10.06 (s, 1H), 8.44 (s, 1H), 8.03-8.11 (m, 1H), 7.85 (d, 1H), 7.65-7.76 (m, 1H), 7.62 (s, 1H), 7.36-7.48 (m, 2H), 7.22-7.35 (m, 3H), 7.02-7.14 (m, 2H), 6.23 (d, 1H), 4.71 (spt, 1H), 1.35 (d, 6H)

Synthesis of Compound 446: Following general procedure A, compound 446 was prepared in 78% yield. $^1$H NMR (300 MHz, DMSO-d6) ppm 8.19-8.21 (m, 1H), 8.17 (d, 1 H), 7.93-8.07 (m, 2H), 7.74 (ddd, 1H), 7.60 (dd, 1H), 7.43-7.58 (m, 5H), 6.62 (d, 1H)

Synthesis of Compound 447: Similar to compound 385, compound 447 was prepared in 25% yield. $^1$H NMR (300 MHz, DMSO-d6) ppm 7.82-7.94 (m, 2H), 7.57-7.74 (m, 2H), 7.41 (m, 2H), 7.16-7.30 (m, 2H), 7.06 (m, 2H), 6.48-6.65 (m, 1H), 3.82 (s, 3H)

Synthesis of Compound 448: Similar to compound 385, compound 448 was prepared in 33% yield. $^1$H NMR (300 MHz, DMSO-d6) ppm 7.89 (dd, 1H), 7.83 (d, 1H), 7.57-7.69 (m, 2H), 7.39-7.51 (m, 1H), 7.35 (dd, 1H), 7.14-7.28 (m, 3H), 7.08 (td, 1H), 6.56 (d, 1H), 3.77 (s, 3H)

Synthesis of Compound 449: Similar to compound 385, compound 449 was prepared in 38% yield. $^1$H NMR (300 MHz, DMSO-d6) ppm 7.99 (d, 1H), 7.92 (dd, 1H), 7.63-7.74 (m, 3H), 7.44-7.61 (m, 3H), 7.16-7.30 (m, 2H), 6.60 (dd, 1H)

Synthesis of Compound 450: Following general procedure A, compound 450 was prepared in 82% yield. $^1$H NMR (300 MHz, DMSO-d6) ppm 8.17-8.21 (m, 1H), 8.15 (t, 1 H), 7.97-8.07 (m, 2H), 7.83 (ddd, 1H), 7.68 (dd, 1H), 7.41-7.62 (m, 5H), 6.64 (d, 1H), 3.25 (s, 3H)

Synthesis of Compound 451: Following general procedure A, compound 451 was prepared in 70% yield. $^1$H NMR (300 MHz, DMSO-d6) ppm 8.04 (d, 1H), 7.97 (dd, 1H), 7.78 (dd, 1H), 7.40-7.63 (m, 7H), 6.57 (dd, 1H)

Synthesis of Compound 452: Following general procedure A, compound 452 was prepared in 65% yield. $^1$H NMR (300 MHz, DMSO-d6) ppm 9.40 (s, 1H), 7.43-7.64 (m, 8H), 7.40 (dd, 1H), 7.32 (td, 1H), 7.24 (td, 1H), 6.57 (dd, 1H), 1.97 (s, 3H)

Synthesis of Compound 453: Similar to preparation of compound 433, compound 453 was prepared in 52% yield. $^1$H NMR (300 MHz, DMSO-d6) ppm 10.13 (s, 1H), 8.07 (d, 1H), 7.96 (dd, 1H), 7.69-7.78 (m, 2H), 7.56-7.67 (m, 2H), 7.45 (dd, 1H), 7.43 (dd, 1 H), 7.35 (ddd, 1H), 7.15 (ddd, 1H), 6.59 (d, 1H), 2.06 (s, 3H)

Synthesis of Compound 454: Following general procedure A, compound 454 was prepared in 60% yield. $^1$H NMR (300 MHz, DMSO-d6) ppm 9.95 (s, 1H), 7.84-7.95 (m, 2 H), 7.39-7.66 (m, 9H), 6.53-6.64 (m, 1H), 2.04 (s, 3H)

Synthesis of Compound 455: Following general procedure A, compound 455 was prepared in 74% yield. $^1$H NMR (300 MHz, DMSO-d6) ppm 8.43 (dd, 1H), 7.98 (dd, 1H), 7.96 (d, 1H), 7.87-7.94 (m, 1H), 7.36-7.59 (m, 5H), 6.85 (dd, 1H), 6.60 (dd, 1H), 3.87 (s, 3H)

Synthesis of Compound 456: Following general procedure A, compound 456 was prepared in 82% yield. $^1$H NMR (300 MHz, DMSO-d6) ppm 7.83 (d, 1H), 7.73 (dt, 1H), 7.64 (td, 1H), 7.42-7.58 (m, 5H), 7.34 (ddd, 1H), 7.15 (dddd, 1H), 6.60 (d, 1H)

Synthesis of Compound 457: Following general procedure A, compound 457 was prepared in 82% yield. $^1$H NMR (300 MHz, DMSO-d6) ppm 10.11 (s, 1H), 7.81-7.92 (m, 2H), 7.73 (t, 1H), 7.60 (ddd, 1H), 7.44 (dd, 1H), 7.24 (d, 1H), 7.14 (ddd, 1H), 7.08 (dd, 1 H), 6.94 (d, 1H), 6.51-6.60 (m, 1H), 6.03 (s, 2H), 2.06 (s, 3H)

Synthesis of Compound 458: Following general procedure A, compound 458 was prepared in 89% yield. $^1$H NMR (300 MHz, DMSO-d6) ppm 10.13 (s, 1H), 9.93 (s, 1H), 7.81-7.87 (m, 1H), 7.78-7.81 (m, 1H), 7.75 (br. s., 2H), 7.57-7.65 (m, 1 H), 7.49-7.55 (m, 1H), 7.45 (dd, 1H), 7.33 (dd, 1H), 7.28 (dt, 1H), 7.14 (ddd, 1H), 6.62 (dd, 1H), 2.06 (s, 3H), 2.04 (s, 3H)

Synthesis of Compound 459: Following general procedure A, compound 459 was prepared in 56% yield. $^1$H NMR (300 MHz, DMSO-d6) ppm 9.68 (s, 1H), 7.74-7.85 (m, 2H), 7.40-7.58 (m, 5H), 7.33 (dd, 1H), 7.07-7.18 (m, 1H), 6.92 (dt, 1H), 6.85 (tt, 1H), 6.54 (dd, 1H)

Synthesis of Compound 460: Following general procedure A, compound 460 was prepared in 63% yield. $^1$H NMR (300 MHz, DMSO-d6) ppm 10.13 (br. s., 1H), 9.42 (br. s., 1H), 7.79-7.85 (m, 1H), 7.46-7.58 (m, 4H), 7.44 (dd, 1H), 7.38 (dd, 1H), 7.32 (td, 1H), 7.23 (td, 1H), 7.10 (ddd, 1H), 6.56 (d, 1H), 2.06 (s, 3H), 1.97 (s, 3H)

Synthesis of Compound 461: Similar to compound 385, compound 461 was prepared in 52% yield. $^1$H NMR (300 MHz, DMSO-d6) ppm 10.10 (s, 1H), 7.82-7.96 (m, 2H), 7.58-7.75 (m, 4H), 7.35-7.46 (m, 2H), 7.16-7.30 (m, 2H), 6.58 (dd, 1H), 2.08 (s, 3H)

Synthesis of Compound 462: Following general procedure A, compound 462 was prepared in 45% yield. $^1$H NMR (300 MHz, DMSO-d6) ppm 10.13 (s, 1H), 8.06-8.14 (m, 1H), 7.92 (d, 1H), 7.84 (dd, 1H), 7.65-7.73 (m, 2H), 7.57-7.65 (m, 1 H), 7.44 (dd, 1H), 7.10 (ddd, 1H), 6.94 (dd, 1H), 6.56 (dd, 1H), 2.06 (s, 3H)

Synthesis of Compound 463: Following general procedure A, compound 463 was prepared in 28% yield. $^1$H NMR (300 MHz, DMSO-d6) ppm 8.17 (d, 1H), 8.02 (dd, 1H), 7.93 (s, 4H), 7.41-7.61 (m, 5H), 6.64 (d, 1H), 3.23 (s, 3H)

Synthesis of Compound 464: Following general procedure A, compound 464 was prepared in 82% yield. $^1$H NMR (300 MHz, DMSO-d6) ppm 7.84 (dd, 1H), 7.70 (dd, 1H), 7.44-7.57 (m, 5H), 7.43 (d, 1H), 6.60 (dd, 1H), 6.40 (d, 1H), 3.85 (s, 3 H)

Synthesis of Compound 465: Following general procedure A, compound 465 was prepared in 81% yield. $^1$H NMR (300 MHz, DMSO-d6) ppm 10.12 (s, 1H), 7.84 (d, 1H), 7.79 (dd, 1H), 7.71 (dd, 1H), 7.56-7.63 (m, 1H), 7.44 (dd, 1H), 7.21 (d, 1H), 7.11 (ddd, 1 H), 6.97-7.06 (m, 1H), 6.56 (d, 1H), 2.19 (s, 3H), 2.06 (s, 3H)

Synthesis of Compound 466: Following general procedure A, compound 466 was prepared in 74% yield. $^1$H NMR (300 MHz, DMSO-d6) ppm 10.12 (s, 1H), 9.44 (s, 1H), 7.78-7.92 (m, 2H), 7.74 (t, 1H), 7.60 (d, 1H), 7.44 (dd, 1H), 7.20 (dd, 1H), 7.14 (ddd, 1 H), 7.01 (d, 1H), 6.95 (dd, 1H), 6.66-6.77 (m, 1H), 6.53-6.63 (m, 1H), 2.06 (s, 3H)

Synthesis of Compound 467: Following general procedure A, compound 467 was prepared in 76% yield. $^1$H NMR (300 MHz, DMSO-d6) ppm 10.12 (s, 1H), 8.42 (d, 1H), 7.85-8.04 (m, 3H), 7.74 (t, 1H), 7.56-7.66 (m, 1H), 7.44 (dd, 1H), 7.14 (ddd, 1H), 6.85 (dd, 1H), 6.60 (dd, 1H), 3.87 (s, 3H), 2.06 (s, 3H)

Synthesis of Compound 468: Following general procedure A, compound 468 was prepared in 57% yield. $^1$H NMR (300 MHz, DMSO-d6) ppm 10.15 (s, 1H), 8.04-8.11 (m, 2H), 7.92-8.04 (m, 2H), 7.69-7.85 (m, 3H), 7.56-7.67 (m, 1H), 7.42-7.55 (d, 2H), 7.37 (br. s., 1H), 7.11-7.20 (m, 1H), 6.63 (d, 1H), 2.07 (s, 3H)

Synthesis of Compound 469: Following general procedure A, compound 469 was prepared in 68% yield. $^1$H NMR (300 MHz, DMSO-d6) ppm 10.13 (s, 1H), 8.06 (d, 1H), 7.98-8.03 (m, 1H), 7.94-7.98 (m, 1H), 7.86-7.94 (m, 2H), 7.66-7.78 (m, 3H), 7.57-7.65 (m, 1H), 7.45 (dd, 1H), 7.31 (br. s., 1H), 7.11-7.20 (m, 1H), 6.62 (d, 1H), 2.07 (s, 3 H)

Synthesis of Compound 470: Following general procedure A, compound 470 was prepared in 74% yield. $^1$H NMR (300 MHz, DMSO-d6) ppm 10.12 (s, 1H), 7.96 (dd, 1H), 7.83 (d, 1H), 7.71-7.80 (m, 2H), 7.56-7.66 (m, 1H), 7.35-7.50 (m, 3H), 7.33 (d, 1H), 7.17 (ddd, 1H), 6.59 (dd, 1H), 6.42 (dd, 1H), 3.80 (s, 3H), 2.07 (s, 3H)

Synthesis of Compound 471: Following general procedure A, compound 471 was prepared in 85% yield. $^1$H NMR (300 MHz, DMSO-d6) ppm 7.95 (dd, 1H), 7.84 (d, 1H), 7.78 (d, 1H), 7.43-7.59 (m, 6H), 7.40 (dd, 1H), 7.33 (d, 1H), 6.60 (d, 1 H), 6.42 (dd, 1H), 3.80 (s, 3H)

Synthesis of Compound 473: Following general procedure A, compound 473 was prepared in 66% yield. $^1$H NMR (300 MHz, DMSO-d6) ppm 10.13 (s, 1H), 7.69-7.78 (m, 1H), 7.55-7.68 (m, 3H), 7.42 (d, 1H), 7.43 (dd, 1H), 7.13 (ddd, 1H), 6.97 (d, 1H), 6.58 (d, 1H), 2.24 (s, 3H), 2.06 (s, 3H)

Synthesis of Compound 474: Similar to compound 385, compound 474 was prepared in 9% yield. $^1$H NMR (300 MHz, DMSO-d6) ppm 9.36 (br. s., 1H), 7.90 (dd, 1 H), 7.72 (d, 1H), 7.54-7.70 (m, 3H), 7.29-7.50 (m, 3H), 7.13-7.29 (m, 2 H), 6.57 (d, 1 H), 1.89 (s, 3H)

Synthesis of Compound 475: Following general procedure A, compound 475 was prepared in 94% yield. $^1$H NMR (300 MHz, DMSO-d6) ppm 10.12 (s, 1H), 7.88 (dd, 1H), 7.82 (d, 1H), 7.71-7.75 (m, 1H), 7.60 (d, 1H), 7.53 (m, 2H), 7.44 (dd, 1 H), 7.09-7.18 (m, 1H), 6.95 (m, 2H), 6.57 (d, 1H), 4.04 (q, 2H), 2.06 (s, 3H), 1.33 (t, 3H)

Synthesis of Compound 476: Following general procedure A, compound 476 was prepared in 51% yield. $^1$H NMR (300 MHz, DMSO-d6) ppm 9.93 (s, 1H), 7.80-7.88 (m, 2H), 7.75 (t, 1H), 7.43-7.59 (m, 6H), 7.23-7.39 (m, 2H), 6.58-6.66 (m, 1H), 2.04 (s, 3 H)

Synthesis of Compound 477: Following general procedure A, compound 477 was prepared in 41% yield. $^1$H NMR (300 MHz, DMSO-d6) ppm 9.44 (br. s., 1H), 7.85 (dd, 1 H), 7.83 (s, 1H), 7.36-7.64 (m, 5H), 7.20 (t, 1H), 7.03 (ddd, 1H), 6.96 (dd, 1H), 6.72 (ddd, 1H), 6.51-6.64 (m, 1H)

Synthesis of Compound 478: Following general procedure A, compound 478 was prepared in 54% yield. $^1$H NMR (300 MHz, DMSO-d6) ppm 7.59-7.69 (m, 2H), 7.43-7.57 (m, 5H), 7.42 (d, 1H), 6.97 (d, 1H), 6.58 (dd, 1H), 2.25 (s, 3H)

Synthesis of Compound 479: Following general procedure A, compound 479 was prepared in 64% yield. $^1$H NMR (300 MHz, DMSO-d6) ppm 7.86 (d, 1H), 7.79 (dd, 1H), 7.36-7.60 (m, 5H), 7.22 (d, 1H), 7.03 (t, 1H), 6.57 (d, 1H), 2.19 (d, 3 H)

Synthesis of Compound 480: Following general procedure A, compound 480 was prepared in 25% yield. $^1$H NMR (300 MHz, DMSO-d6) ppm 9.45 (br. s., 1H), 7.84 (dd, 1 H), 7.77 (dd, 1H), 7.44-7.57 (m, 5H), 7.42 (m, 2H), 6.79 (m, 2H), 6.56 (dd, 1H)

Synthesis of Compound 481: Following general procedure A, compound 481 was prepared in 64% yield. $^1$H NMR (300 MHz, DMSO-d6) ppm 7.78-7.94 (m, 2H), 7.37-7.61 (m, 5H), 7.26 (d, 1H), 7.09 (dd, 1H), 6.94 (d, 1H), 6.56 (d, 1H), 6.03 (s, 2H)

Synthesis of Compound 482: Compound 482 was prepared as follows.

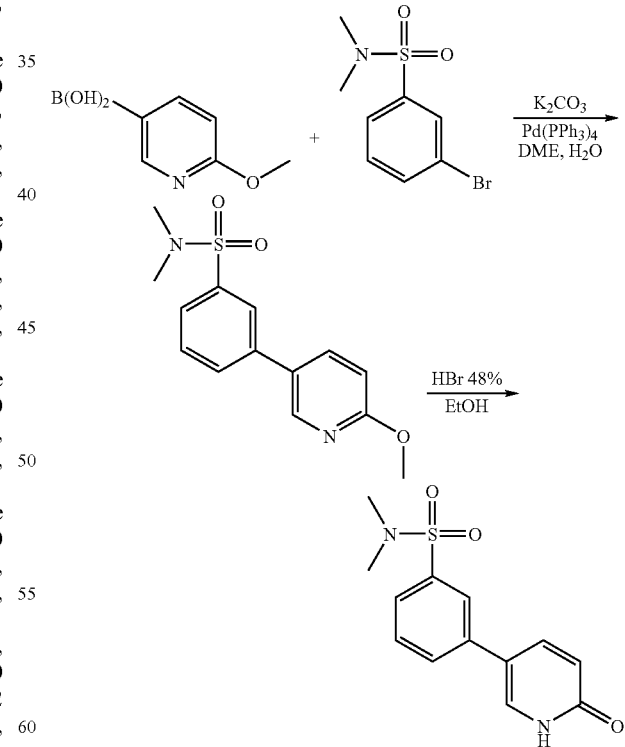

Following standard procedure for Suzuki coupling, the product was obtained by reaction of 264 mg (1.0 mmol) of 3-bromo-N,N-dimethylbenzenesulfonamide. After purification (SiO$_2$; Hexanes:EtOAc 1:1) 293 mg (quantitative yield) of pure product were obtained as white solid. A solution of 3-(6-methoxypyridin-3-yl)-N,N-dimethylbenzenesulfonamide (292 mg, 1.0 mmol) in EtOH (4 ml) and HBr 48% (4 ml) was stirred at 80° C. overnight. The solvent was evaporated and the crude compound (as hydrobromide salt) was purified by flash chromatography (DCM:MeOH 9:1). 278 mg were obtained as a pale yellow solid (quantitative yield).

Following general procedure H1A, compound 482 was prepared from this intermediate in 69% yield. $^1$H NMR (300 MHz, DMSO-d6) ppm 8.13 (d, 1H), 7.94-8.04 (m, 2H), 7.92 (s, 1H), 7.63-7.74 (m, 2H), 7.37-7.61 (m, 5H), 6.63 (d, 1 H), 2.64 (s, 6H)

Synthesis of Compound 483: Compound 483 was prepared as follows.

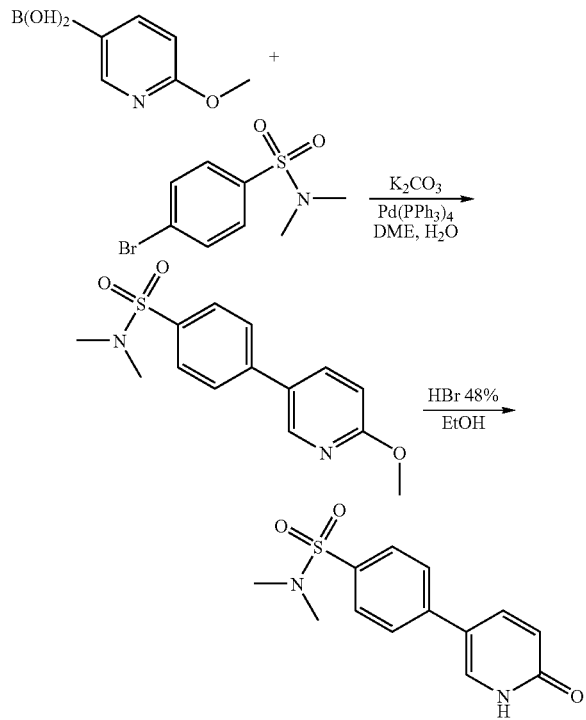

Following the standard procedure for Suzuki coupling, the product was obtained by reaction of 264 mg (1.0 mmol) of 4-bromo-N,N-dimethylbenzenesulfonamide. After purification (SiO$_2$; Hexanes:EtOAc 1:1) 292 mg (quantitative yield) of pure product were obtained as white solid. A solution of 4-(6-methoxypyridin-3-yl)-N,N-dimethylbenzenesulfonamide (292 mg, 1.0 mmol) in EtOH (4 ml) and HBr 48% (4 ml) was stirred at 80° C. overnight. The solvent was evaporated and the crude compound (as hydrobromide salt) was purified by flash chromatography (DCM:MeOH 9:1). 278 mg were obtained as a pale yellow solid (quantitative yield).

Following general procedure H1A, compound 483 was prepared from this intermediate in 79% yield. $^1$H NMR (300 MHz, DMSO-d6) ppm 8.15 (d, 1H), 8.02 (dd, 1 H), 7.92 (m, 2H), 7.74 (m, 2H), 7.40-7.60 (m, 5H), 6.64 (d, 1H), 2.62 (s, 6H)

Synthesis of Compound 484: Following general procedure H1A and similar to compound 482, compound 484 was prepared in 56% yield. $^1$H NMR (300 MHz, DMSO-d6) ppm 10.14 (s, 1H), 8.12 (d, 1H), 7.93-8.04 (m, 2H), 7.91 (s, 1H), 7.73-7.79 (m, 1H), 7.54-7.73 (m, 3H), 7.46 (dd, 1H), 7.09-7.21 (m, 1H), 6.63 (d, 1H), 2.64 (s, 6H), 2.07 (s, 3H)

Synthesis of Compound 485: Following general procedure H1A and similar to compound 483, compound 485 was prepared in 53% yield. $^1$H NMR (300 MHz, DMSO-d6) ppm 10.14 (s, 1H), 8.14 (d, 1H), 7.98-8.08 (m, 1H), 7.86-7.98 (m, 2H), 7.69-7.79 (m, 3 H), 7.56-7.64 (m, 1H), 7.45 (dd, 1H), 7.15 (ddd, 1H), 6.63 (d, 1H), 2.62 (s, 3H)

Synthesis of Compound 486: Following general procedure A, compound 486 was prepared in 58% yield. $^1$H NMR (300 MHz, DMSO-d6) ppm 10.12 (s, 1H), 9.69 (s, 1H), 7.70-7.85 (m, 3H), 7.52-7.63 (m, 1H), 7.43 (t, 1H), 7.31 (dd, 1H), 7.07-7.19 (m, 2H), 6.92 (dd, 1H), 6.84 (td, 1H), 6.53 (dd, 1H), 2.06 (s, 3H)

Synthesis of Compound 487: Following general procedure A, compound 487 was prepared in 56% yield. $^1$H NMR (300 MHz, DMSO-d6) ppm 10.12 (s, 1H), 7.86-8.00 (m, 2H), 7.69-7.75 (m, 1H), 7.56-7.64 (m, 1H), 7.44 (t, 1H), 7.30 (t, 1H), 7.08-7.21 (m, 3 H), 6.77-6.90 (m, 1H), 6.57 (dd, 1H), 4.07 (q, 2H), 2.06 (s, 3H), 1.32 (t, 3H)

Assessment of Biological Activity

Example 1

Compounds were screened for their ability to inhibit the activity of p38 MAP kinase in vitro using the Transcreener KinasePlus assay (Madison, Wis.). This assay determines p38 activity by measuring ATP consumption in the presence of a relevant peptide substrate. This assay is commonly used in the characterization of kinases (Lowrey and Kleman-Leyer, *Expert Opin Ther Targets* 10(1):179-90 (2006)). The Transcreener KinasePlus assay measures the p38 catalyzed conversion of ATP to ADP using a florescence polarization-based approach. The p38 reaction is performed as usual and stopped by addition of Stop-Detect reagents. These reagents halt further conversion of ATP to ADP and facilitate quantification of product ADP. Detection of ADP is made possible by an ADP-specific antibody and corresponding fluorescently lableled tracer in the Stop-Detect mix. In the absence of ADP, the fluorescently labeled tracer is bound by the ADP-specific antibody resulting in a complex with high fluorescence polarization (FP). Product ADP competes with the fluorescently labeled tracer for binding to the ADP-specific antibody and results in lower fluorescence polarization.

p38 gamma was obtained from Millipore, Inc (Billerica, Ma.). p38 MAP Kinases are recombinant human full-length proteins with an amino-terminal GST fusion, expressed in and purified from *E. coli*. Proteins were aliquoted and stored at −80° C. Assays for p38 activity were performed in the presence of an EGF receptor peptide (sequence KRELVE-PLTPSGEAPNQALLR—SEQ ID NO: 1) that was obtained from Midwest Biotech (Fishers, Ind.). EGFR peptide was aliquotted and stored at −20° C.

p38 MAP kinase assays were performed using p38 assay buffer containing 20 mM HEPES, pH 7.5, 10 mM MgCl$_2$, 2 mM DTT, 0.01% Triton X-100, 10% glycerol, and 0.0002% bovine serum albumin (BSA). This buffer was supplemented with 10 µM ATP, 25 µM EGFR peptide and 1 nM p38-γ. Compounds were weighed and dissolved to a known final concentration in DMSO.

The assay and compound dilutions were conducted on a Janus liquid handling platform (Perkin Elmer, Waltham, Mass.) at room temperature (about 25° C.). Compounds in DMSO were placed in column 1 of a Costar V-bottom 96 well plate and diluted serially across the plate (3.3× dilutions). Columns 11 and 12 contain DMSO only (no inhibitor). Each compound dilution was 30-fold higher than the desired final concentration. A daughter plate was created by placing 180

μL of p38 assay buffer in each well of a second Costar V-bottom 96 well plate and 20 μL of the diluted compound stocks in DMSO were transferred and mixed. The assay was conducted in a black Proxipate F-Plus 384 well plate (Perkin Elmer, Waltham, Mass.). All subsequent transfers were conducted using a 96 well head such that the final assay was quad mapped with 4 replicates of each reaction. 5 μL of the compound mixture was transferred from the daughter plate to the assay plate. 5 μL of a mixture containing enzyme and EGFR peptide at 3-fold the desired final concentration in p38 assay buffer was then added to the appropriate wells. The reactions in the final two columns of the 384 well plate received a mixture of EGFR peptide in p38 assay buffer in the absence of enzyme. These wells served as a control for complete inhibition of enzyme. After the compound and EGFR/enzyme (or EGFR only) mixtures were added these component are pre-incubated for 5 minutes. The assay was initiated by addition of 5 μL ATP in p38 assay buffer with mixing. The final reaction volume was 15 μL and the reaction was allowed to run for 1 hour at room temperature. The reaction was stopped by addition of 5 μL of Transcreener Stop-Detect solution containing 8 nM ADP Far Red Tracer and 41.6 μg/mL ADP-Anti-body in 100 mM HEPES, pH 7.5, 0.8 M sodium chloride, 0.04% BRIJ-35, and 40 mM EDTA. Following addition of the Stop-Detect solution, the contents of the plate were mixed and incubated for 1 hour at room temperature.

The plates were read for fluorescence polarization (FP) on a PerkinElmer EnVision using 3 filters (Cy5 Ex 620/40; Cy5 Em FP P-pol 688 nm; Cy5 Em FP S-pol 688 nm), and a mirror (Cy5 FP D658/fp688). Each read was integrated for 100 flashes. The formula $$1000*(S-G*P)/(S+G*P)$$

was used to convert the 2 emission readouts into mP; S=S-pol filter signal, P=P-pol filter signal, and G=gain.

The mP output from the EnVision (a 384 matrix) was transferred to a plot of mP versus compound concentration. XLfit (IDBS, Guildford, England) was used to apply a 4-parameter logistic fit to the data and determine the median inhibitory concentration ($IC_{50}$). Preferred compounds exhibit $IC_{50}$ values of between about 0.05 μM and about 10 μM, preferably about 0.1 μM to about 5 μM.

Example 2

Compounds were screened for the ability to inhibit TNFα release from THP-1 cells stimulated with lipopolysaccharide (LPS) in vitro. The ability of compounds to inhibit TNFα release in this in vitro assay was correlated with the inhibition of p38 activity and TNFα expression in vivo, and was therefore an indicator of potential in vivo therapeutic activity (Lee et al. *Ann. N.Y. Acad. Sci.* 696:149-170 (1993); and Nature 372:739-746 (1994)).

THP-1 cells from ATCC (TIB202) were maintained at 37° C., 5% $CO_2$ in RPMI 1640 media (MediaTech, Herndon, Va.) containing 4.5 g/L glucose, supplemented with 10% fetal bovine serum, 1% penicillin/streptomycin and 50 μM β-mercaptoethanol.

Test compounds were initially dissolved in DMSO. Compounds were then diluted in DMSO for all subsequent dilutions. The compounds were diluted in RPMI Media immediately prior the addition to the THP-1 cells to a final concentration of 1.25% DMSO (v/v) upon addition to the cells. Compounds were tested at a final concentration on cells of 750 to 1000 μM. Where data indicates it was appropriate compounds were tested at a 5-10 fold lower concentration. The assay was performed under sterile conditions. THP-1 cells at a culture density of 6-8×$10^5$ cells/mL were collected and resuspended in the RPMI media at 1×$10^6$ cells/mL. 100 μl of resuspended cells were added to each well, which contained 100 μl of RPMI medium with test compound. Test compounds were prepared at 2.5 times the final concentration. Final DMSO concentration was no more than 0.5% (v/v). Cells were preincubated with compound for 60 minutes at 37° C., 5% $CO_2$ prior to stimulation with lipopolysaccharide (LPS) (Sigma L-2880, 1 mg/ml stock in PBS). The final LPS concentration in each well was 200 ng/ml for TNFα release. Unstimulated control cell suspensions received DMSO/RPMI Media vehicle only. Cell mixtures were incubated for 4 hours for TNFα release. 80 μl of supernatants were taken and transferred to a fresh plate and stored at −70° C. until further analysis. TNFα levels were measured using ELISA kits (R&D systems PDTA00C). A SpectraMAX M5 was used as the plate reader. The calculated amount of TNFα released was expressed as a percentage of the vehicle+LPS control.

Some compounds were tested for a TNFα dose response. Test compounds were initially dissolved in DMSO. Compounds were then serially diluted in DMSO over an appropriate range of concentrations between 2 mM and 4 μM. The compounds were diluted in RPMI Media immediately prior the addition to the THP-1 cells to a final concentration of 0.5% DMSO (v/v) upon addition to the cells. The assay was performed under sterile conditions. THP-1 cells at a culture density of 6-8×$10^5$ cells/mL were collected and resuspended in the RPMI media at 1×$10^6$ cells/mL. 100 μl of resuspended cells were added to each well, which contained 100 μl of RPMI media with test compound. Test compounds were prepared at 2.5 times the final concentration. Final DMSO concentration was no more than 0.5% (v/v). Cells were preincubated with compound for 60 minutes at 37° C., 5% $CO_2$ prior to stimulation with lipopolysaccharide (LPS) (Sigma L-2880, 1 mg/ml stock in PBS). The final LPS concentration in each well was 200 ng/ml for TNFα release. Unstimulated control cell suspensions received DMSO/RPMI Media vehicle only. Cell mixtures were incubated for 4 hours for TNFα release. 80 μl of supernatants were taken and transferred to a fresh plate and stored at −70° C. until further analysis. TNFα levels were measured using ELISA kits (R&D systems PDTA00C). A SpectraMAX M5 was used as the plate reader. Analysis was performed by non-linear regression to generate a dose response curve. The calculated $IC_{50}$ value was the concentration of the test compound that caused a 50% decrease in TNFα levels.

Compounds inhibit the release of TNFα in this in vitro assay. Preferred compounds exhibit $IC_{50}$ values for TNFα between about 1 μM and about 1000 μM, preferably about 1 μM to about 800 μM.

Example 3

Compounds were tested for cytotoxicity using an ATPlite assay (Perkin Elmer 6016731). THP-1 cells were treated with compounds as described for TNFα tests. 4 hours after LPS addition, 80 μl of media is removed for ELISA. 48 hrs after LPS addition of media and cells were mixed with 100 μl of ATPlite reagent. The mixture was shaken for 2 minutes then read for luminescence. A SpectraMAX M5 is used as the plate reader.

The calculated cytotoxicity is expressed as a percentage of the LPS/DMSO control compound. Compounds which had a low score in ATPlite compared to the LPS/DMSO control were classified as cytotoxic rather than TNFα inhibitors. Where appropriate compounds were tested at 5-10 fold lower concentrations to determine whether the compound had activity at lower, non cytotoxic concentrations.

For serial dilutions of compound, analysis is performed by non-linear regression to generate a dose response curve. The calculated $CC_{50}$ value is the concentration of the test compound that causes a 50% decrease in ATP levels.

Compounds may exhibit cytotoxicity which can also lower TNFα release in this in vitro assay. Preferred compounds show an ATPlite value which is 100% of the LPS/DMSO control. Preferred compounds exhibit $CC_{50}$ values of greater than 1 mM, preferably of undetectable toxicity.

Example 4

Compounds are screened for the ability to inhibit TNFα release from primary human peripheral blood mononuclear cells (PBMC) stimulated with lipopolysaccharide (LPS) in vitro. The ability of compounds to inhibit TNFα release in this in vitro assay is correlated with the inhibition of p38 activity and is therefore an indicator of potential in vivo therapeutic activity (*Osteoarthritis & Cartilage* 10:961-967 (2002); and Laufer, et al., *J. Med. Chem.* 45: 2733-2740 (2002)).

Human peripheral blood mononuclear cells (PBMC) are isolated by differential centrifugation through a Ficoll-Hy-Paque density gradient from pooled serum of 3-8 individual blood donors. Isolated PBMC contain approximately 10% CD-14 positive monocytes, 90% lymphocytes and <1% granulocytes and platelets. PBMC (106/ml) are cultured in polystyrene plates and stimulated with lipopolysaccharide (LPS; 50 ng/ml; Sigma, St. Louis, Mo.) in the presence and absence of the test compound in serial dilutions, in duplicate, for 24 hr at 37° C. in GIBCO™ RPM1 medium (Invitrogen, Carlsbad, Calif.) without serum. The TNFα level in cell supernatants is determined by ELISA using a commercially available kit (MDS Panlabs #309700).

Preferred compounds inhibit the release of TNFα in this assay with an $IC_{50}$ value of between about 100 µM and about 1000 µM, preferably about 200 µM to about 800 µM.

Example 5

Compounds are screened for the ability to inhibit the release of TNFα in an in vivo animal model (See, e.g., Griswold et al. *Drugs Exp. Clin. Res.* 19:243-248 (1993); Badger, et al. *J. Pharmacol. Exp. Ther.* 279:1453-1461 (1996); Dong, et al. *Annu. Rev. Immunol.* 20:55-72 (2002) (and references cited therein); Ono, et al., *Cellular Signalling* 12:1-13 (2000) (and references cited therein); and Griffiths, et al. *Curr. Rheumatol. Rep.* 1:139-148 (1999)).

Without being bound by any particular theory, it is believed that inhibition of TNFα in this model is due to inhibition of p38 MAP kinase by the compound.

Male Sprague-Dawley rats (0.2-0.35 kg) are randomly divided into groups of six or more and are dosed intravenously by infusion or bolus injection, or are dosed orally with test compounds in a suitable formulation in each case. At ten minutes to 24 hr following treatment lipopolysaccharide *E. coli*/0127:B8 (0.8 mg/kg) is administered IV in the presence of D-galactosamine. Blood levels are samples are collected 1.5 hours post-treatment with LPS. Serum TNFα and/or IL-6 determined using an appropriate ELISA kit and compared to that from vehicle-treated control.

Preferred compounds inhibit the release of TNFα in this in vivo assay. Preferred compounds exhibit an $ED_{50}$ value of less than 500 mg/kg, preferably less than 400 mg/kg, preferably less than 200 mg/kg, preferably less than 100 mg/kg, more preferably, less than 50 mg/kg, more preferably, less than 40 mg/kg, more preferably, less than 30 mg/kg, more preferably, less than 20 mg/kg, more preferably, less than 10 mg/kg.

The methods of determining the $IC_{50}$ of the inhibition of p38 by a compound include any methods known in the art that allow the quantitative detection of any of the downstream substrates of p38 MAPK as described above. Therefore, these methods additionally include but limited to detection of expression of genes known to be regulated by p38 either individually, or by gene arrays.

Results of Biological Tests

The data sets for each compound assayed as described in Examples 2 (TNFα inhibition) and 3 (ATPlite assay), above were binned based on percentage of control (POC) data. For a subset of compounds with data from dose response curves, calculated POC values at the 750 µM screening concentration were derived from the existing $EC_{50}$, $CC_{50}$ and Hill Slope values using the standard four-paramater curve fit equation assuming an upper asymptote of 100% and a lower asymptope of 0%. The relevant equations are: $POC_{TNF\alpha}=(100-0)/(1+(750/EC_{50})^{Hill\ Slope})$ and $POC_{ATPlite}=(100-0)/(1+(750/CC_{50})^{Hill\ Slope})$. These values were averaged with existing POC determinations create a data set that could be appropriately binned.

Data were binned using the following criteria: Bin A (greatest inhibition) POC<33; Bin B POC 33 and <66; Bin C 66-100, with either ATPlite POC>90 or an ATPlite POC at least two-fold above the TNFα POC. When ATPlite POC for a given compound was not either 1) greater than 90, or 2) at least two-fold above the TNFα POC the compound was placed in bin C regardless of the TNFα POC. Adjustments were made to the binning of compounds 10, 21, 47, 160, 179, 189, 193, based on full dose response curves with $CC_{50}$:$EC_{50}$ ratios that were either >2 or <2, respectively. In the former case, the compounds were left in the appropriate bin based on TNFα POC and in the latter case they were placed in bin C.

TABLE 2

| Example | Bin |
|---------|-----|
| 1 | A |
| 2 | C |
| 3 | C |
| 4 | C |
| 5 | C |
| 6 | A |
| 7 | C |
| 8 | B |
| 9 | C |
| 10 | C |
| 11 | C |
| 12 | C |
| 13 | C |
| 14 | C |
| 15 | C |
| 16 | C |
| 17 | C |
| 18 | B |
| 19 | A |
| 20 | C |
| 21 | C |
| 22 | A |
| 23 | C |
| 24 | C |
| 25 | C |
| 26 | C |
| 27 | C |
| 28 | C |

TABLE 2-continued

| Example | Bin |
|---|---|
| 29 | A |
| 30 | C |
| 31 | C |
| 32 | C |
| 33 | C |
| 34 | C |
| 35 | C |
| 36 | C |
| 37 | C |
| 38 | C |
| 39 | C |
| 40 | C |
| 41 | A |
| 42 | C |
| 43 | C |
| 44 | C |
| 45 | C |
| 46 | C |
| 47 | A |
| 48 | C |
| 49 | C |
| 50 | B |
| 51 | C |
| 52 | C |
| 53 | C |
| 54 | C |
| 56 | C |
| 58 | C |
| 59 | C |
| 60 | A |
| 61 | C |
| 62 | C |
| 63 | C |
| 64 | C |
| 65 | C |
| 66 | C |
| 67 | C |
| 68 | C |
| 69 | C |
| 70 | C |
| 72 | A |
| 73 | A |
| 74 | A |
| 75 | C |
| 77 | C |
| 78 | C |
| 79 | C |
| 80 | A |
| 81 | C |
| 82 | A |
| 83 | C |
| 84 | A |
| 85 | C |
| 86 | C |
| 87 | C |
| 88 | C |
| 89 | A |
| 90 | B |
| 91 | C |
| 92 | C |
| 93 | A |
| 94 | A |
| 96 | A |
| 97 | A |
| 98 | C |
| 99 | C |
| 100 | C |
| 101 | C |
| 102 | A |
| 103 | C |
| 104 | C |
| 105 | A |
| 106 | A |
| 107 | C |
| 108 | C |
| 109 | A |
| 110 | C |
| 111 | C |

TABLE 2-continued

| Example | Bin |
|---|---|
| 112 | C |
| 113 | C |
| 114 | B |
| 115 | C |
| 116 | C |
| 117 | A |
| 118 | A |
| 119 | C |
| 120 | B |
| 121 | A |
| 122 | C |
| 123 | C |
| 124 | C |
| 125 | C |
| 126 | C |
| 127 | B |
| 128 | A |
| 129 | B |
| 130 | A |
| 131 | C |
| 132 | A |
| 133 | C |
| 134 | C |
| 135 | A |
| 136 | A |
| 137 | A |
| 138 | A |
| 139 | A |
| 140 | B |
| 141 | A |
| 142 | C |
| 143 | C |
| 144 | C |
| 145 | A |
| 147 | A |
| 148 | C |
| 149 | C |
| 150 | C |
| 151 | C |
| 152 | A |
| 153 | A |
| 154 | C |
| 155 | A |
| 156 | C |
| 158 | C |
| 159 | A |
| 160 | C |
| 161 | C |
| 162 | C |
| 163 | B |
| 164 | C |
| 166 | C |
| 167 | B |
| 168 | B |
| 169 | A |
| 171 | C |
| 172 | A |
| 173 | C |
| 174 | C |
| 177 | A |
| 178 | A |
| 179 | C |
| 182 | C |
| 183 | A |
| 184 | C |
| 185 | C |
| 186 | C |
| 187 | C |
| 188 | C |
| 189 | B |
| 190 | C |
| 192 | C |
| 193 | B |
| 195 | C |
| 197 | C |
| 200 | A |
| 201 | C |
| 202 | C |

TABLE 2-continued

| Example | Bin |
|---|---|
| 203 | A |
| 209 | C |
| 210 | C |
| 211 | A |
| 212 | C |
| 213 | C |
| 214 | A |
| 215 | C |
| 216 | B |
| 217 | A |
| 218 | C |
| 219 | C |
| 220 | C |
| 221 | C |
| 222 | C |
| 223 | C |
| 224 | C |
| 225 | B |
| 226 | C |
| 227 | C |
| 228 | A |
| 229 | C |
| 230 | C |
| 231 | C |
| 232 | B |
| 233 | C |
| 234 | C |
| 235 | A |
| 236 | A |
| 237 | C |
| 238 | B |
| 239 | C |
| 240 | B |
| 241 | A |
| 242 | A |
| 243 | C |
| 244 | C |
| 245 | A |
| 246 | C |
| 247 | C |
| 248 | C |
| 249 | A |
| 250 | B |
| 251 | C |
| 252 | A |
| 253 | C |
| 254 | A |
| 255 | C |
| 256 | C |
| 257 | A |
| 258 | A |
| 259 | C |
| 260 | B |
| 261 | C |
| 262 | B |
| 263 | C |
| 264 | C |
| 265 | C |
| 266 | C |
| 267 | A |
| 268 | A |
| 269 | C |
| 270 | C |
| 271 | C |
| 272 | A |
| 273 | A |
| 274 | A |
| 275 | C |
| 276 | C |
| 277 | A |
| 278 | A |
| 279 | A |
| 280 | C |
| 281 | C |
| 282 | B |
| 283 | A |
| 284 | C |
| 285 | A |
| 286 | C |
| 287 | B |
| 288 | A |
| 289 | C |
| 290 | A |
| 291 | A |
| 292 | C |
| 293 | C |
| 294 | A |
| 295 | A |
| 296 | C |
| 297 | C |

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are incorporated herein by reference.

What is claimed is:

1. A compound of formula II

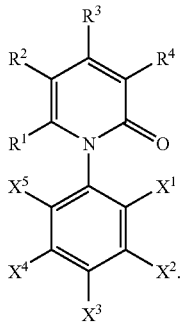

(II)

wherein $R^1$ is selected from the group consisting of hydrogen, alkyl, cycloalkyl, alkenyl, cyano, sulfonamido, halo, alkenylenearyl, and heteroaryl;

$R^2$ is selected from the group consisting of aryl; unsubstituted heteroaryl; heteroaryl substituted with one or more substituents selected from halo, unsubstituted alkyl, alkenyl, $OCF_3$, $NO_2$, CN, NC, OH, alkoxy, haloalkoxy, amino, $CO_2H$, and $CO_2$alkyl; haloalkylcarbonyl; cycloalkyl; hydroxylalkyl; sulfonamide; unsubstituted cycloheteroalkyl and cycloheteroarlkyl substituted with one to three substituents independently selected from alkyleneOH, $C(O)NH_2$, $NH_2$, aryl, haloalkyl, halo, and OH; or $R^2$ and $R^1$ together form an optionally substituted 5-membered nitrogen-containing heterocyclic ring;

$R^3$ is selected from the group consisting of hydrogen, aryl, alkenylenearyl, heteroaryl, alkyl, alkenyl, haloalkyl, amino, and hydroxy;

$R^4$ is selected from the group consisting of hydrogen, haloalkyl, alkoxy, alkenyl, and alkenylenearyl;

$X^1$, $X^2$, $X^3$, and $X^4$ are independently selected from the group consisting of hydrogen, alkyl, alkenyl, halo, hydroxy, amino, aryl, cycloalkyl, thioalkyl, alkoxy, haloalkyl, haloalkoxy, alkoxyalkyl, cyano, aldehydro, alkylcarbonyl, amido, haloalkylcarbonyl, sulfonyl, and sulfonamide, or $X^2$ and $X^3$ together form a 5- or 6-membered ring comprising —$O(CH_2)_nO$—, wherein n is 1 or 2, wherein at least one of $X^1$, $X^2$, $X^3$, and $X^4$ is not hydrogen; and $X^5$ is hydrogen, with the proviso that (a) at least one of $X^1$, $X^2$, $X^3$, and $X^4$ is not selected from the group consisting of hydrogen, halo, alkoxy, and hydroxy or (b) at least one of $R^1$, $R^2$, $R^3$, or $R^4$ is not selected from the group consisting of hydrogen, alkyl, alkenyl, haloalkyl, hydroxyalkyl, alkoxy, phenyl, substituted phenyl, halo, hydroxy, and alkoxyalkyl, or a pharmaceutically acceptable salt, or ester thereof.

2. The compound of claim 1, wherein one of $X^1$, $X^2$, and $X^3$ is not hydrogen.

3. A compound having a structure of formula (III) or formula (IV)

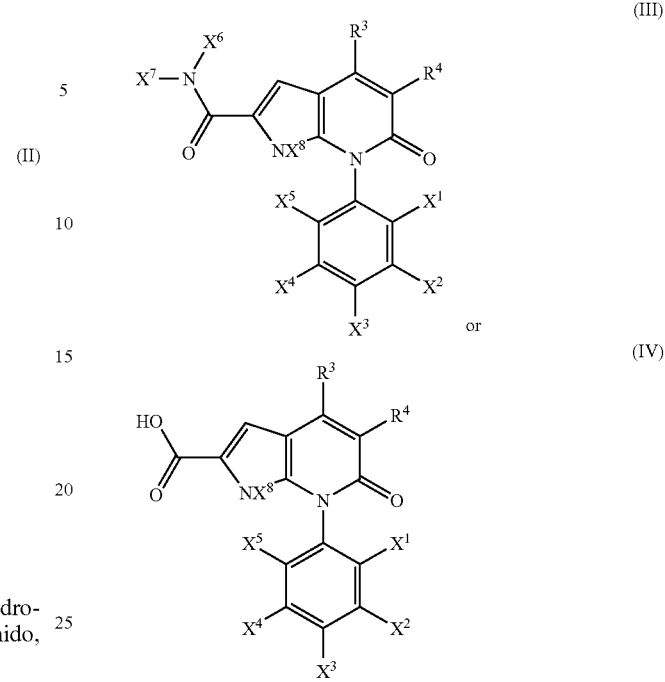

wherein $R^3$ is selected from the group consisting of hydrogen, aryl, alkenylenearyl, heteroaryl, alkyl, alkenyl, haloalkyl, amino, and hydroxy;

$R^4$ is selected from the group consisting of hydrogen, haloalkyl, alkoxy, alkenyl, and alkenylenearyl;

$X^1$, $X^2$, $X^3$, and $X^4$ are independently selected from the group consisting of hydrogen, alkyl, alkenyl, halo, hydroxy, amino, aryl, cycloalkyl, thioalkyl, alkoxy, haloalkyl, haloalkoxy, alkoxyalkyl, cyano, aldehydro, alkylcarbonyl, amido, haloalkylcarbonyl, sulfonyl, and sulfonamide, or $X^2$ and $X^3$ together form a 5- or 6-membered ring comprising —$O(CH_2)_nO$—, wherein n is 1 or 2, wherein at least one of $X^1$, $X^2$, $X^3$, and $X^4$ is not hydrogen;

$X^5$ is hydrogen; and $X^8$ is hydrogen or alkyl; and $X^6$ and $X^7$ are independently selected from the group consisting of hydrogen, aryl, heteroaryl, cycloalkyl, heterocycloalkyl, alkylenylaryl, alkylenylheteroaryl, alkylenylheterocycloalkyl, alkylenylcycloalkyl, or $X^6$ and $X^7$ together form an optionally substituted 5 or 6 membered heterocyclic ring, or a pharmaceutically acceptable salt, or ester thereof.

4. The compound of claim 3, wherein $X^7$ is hydrogen.

5. The compound of claim 1, wherein $R^1$ is selected from the group consisting of hydrogen, 4-pyridyl, cyclopropanyl, 2-furanyl, cyano, $H_2NSO_2$, $(CH_3)_2NSO_2$, fluoro, 4-(3,5-dimethyl)-isoxazolyl, 4-pyrazolyl, 4-(1-methyl)-pyrazolyl, 5-pyrimidinyl, 2-imidazolyl, and thiazolyl.

6. The compound of claim 1, wherein at least one of $X^1$, $X^2$, or $X^3$ is alkyl or cycloalkyl.

7. The compound of claim 1, wherein at least one of $X^1$, $X^2$, or $X^3$ is haloalkyl.

8. The compound of claim 1, wherein at least one of $X^1$, $X^2$, or $X^3$ is alkenyl.

9. The compound of claim 1, wherein at least one of $X^1$, $X^2$, or $X^3$ is amino.

10. The compound of claim 1 having a structure selected from the group consisting of:
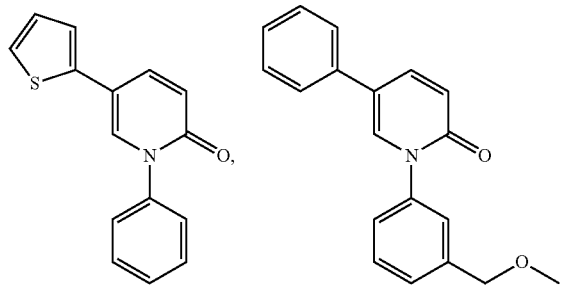
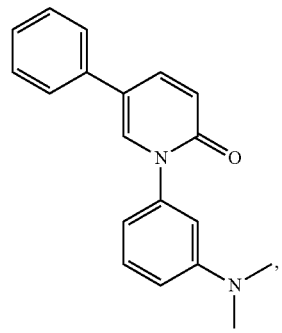
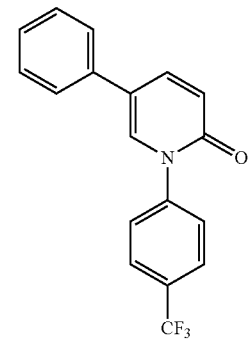
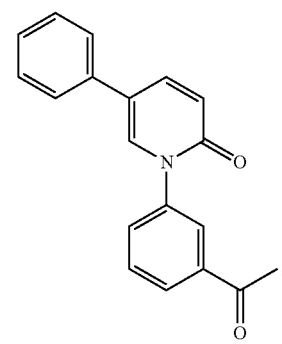
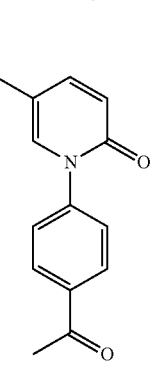
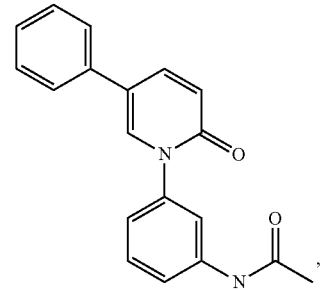
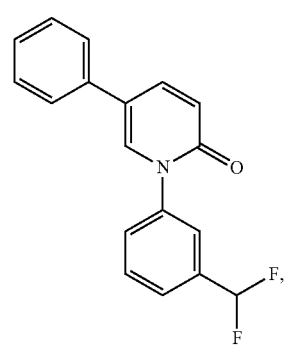
-continued
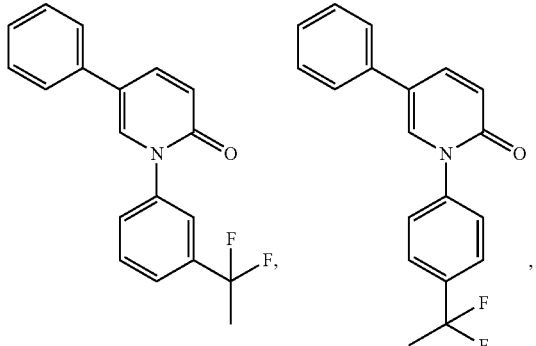
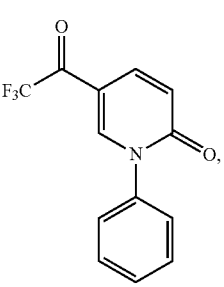
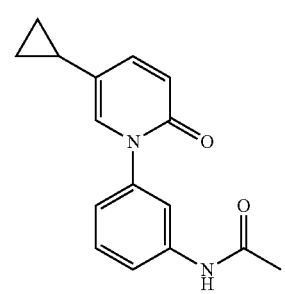
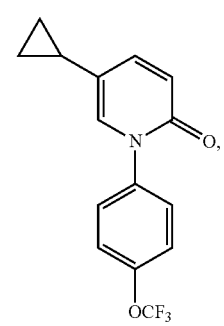
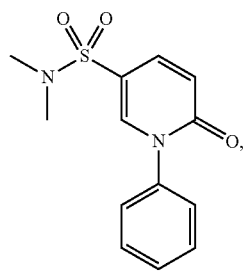
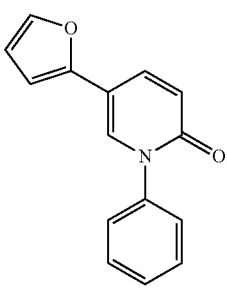
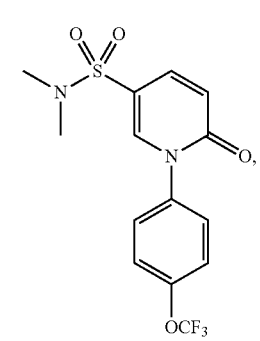
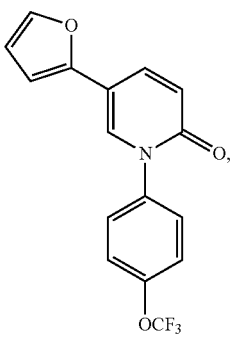

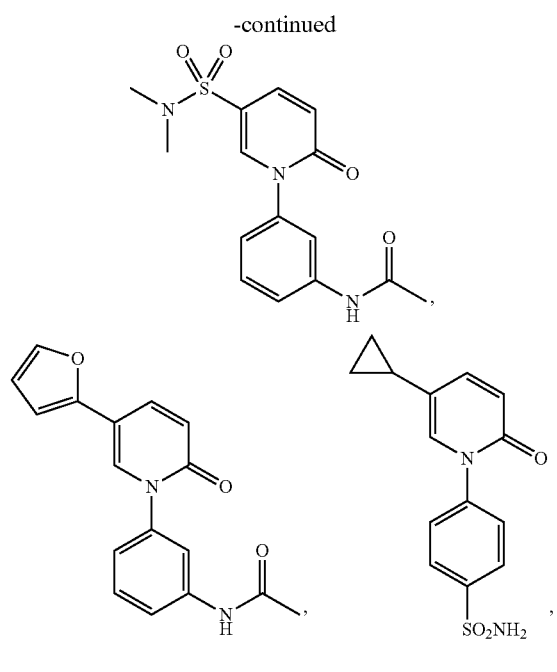
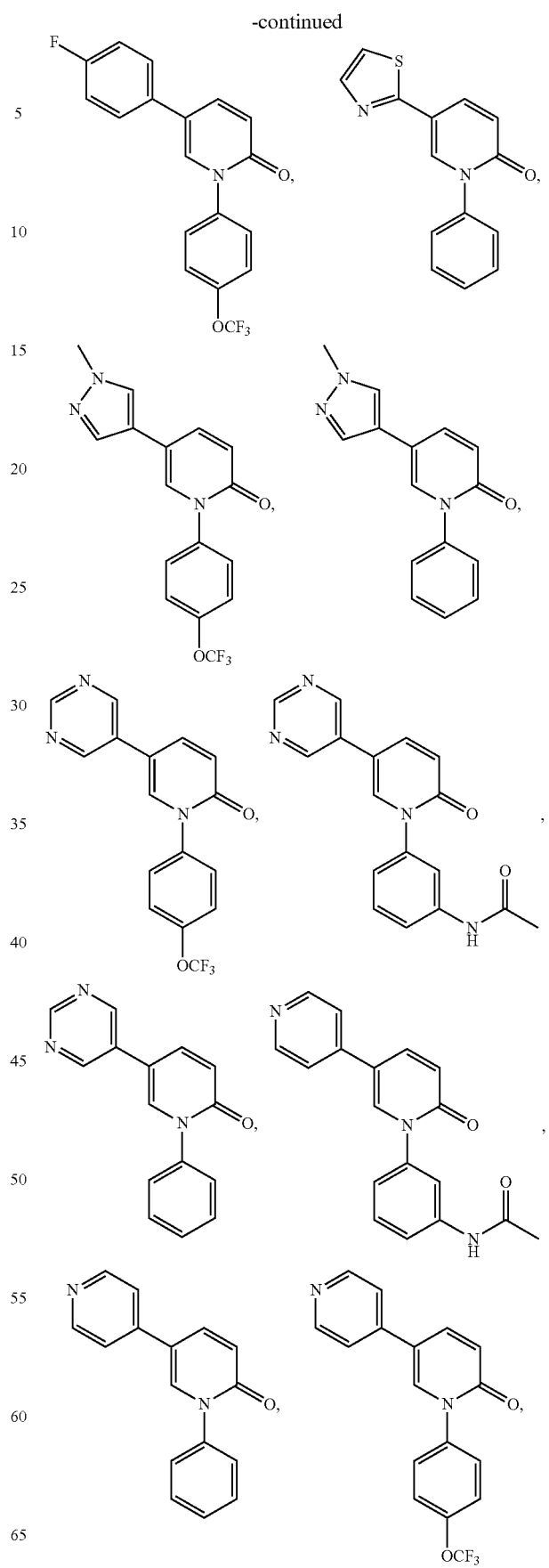

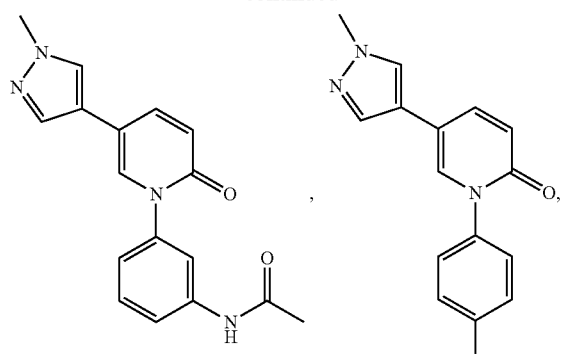
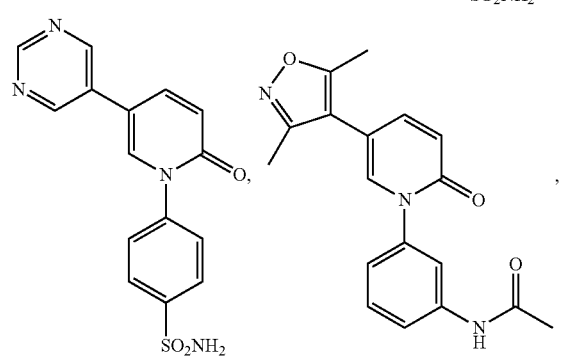
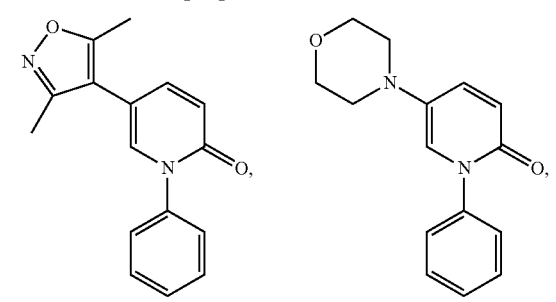
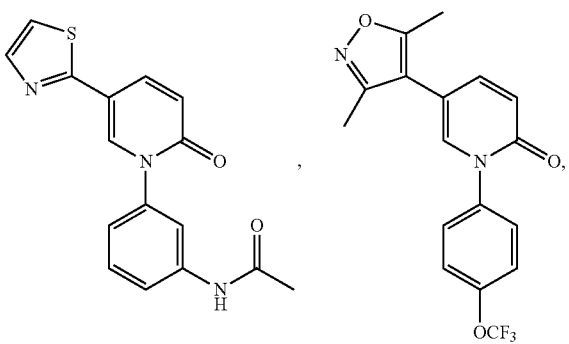
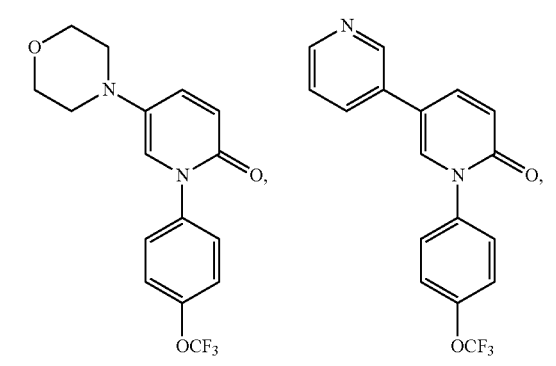
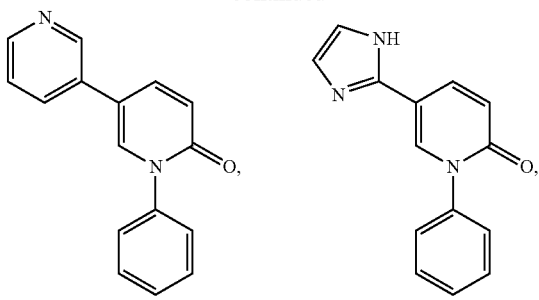
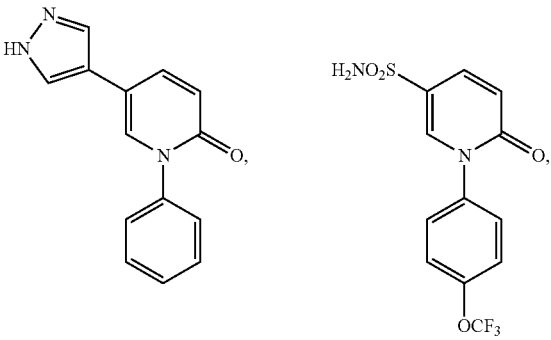
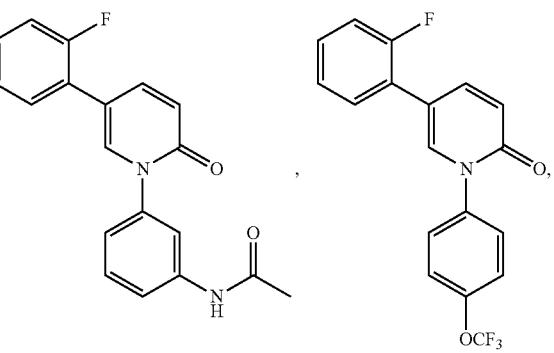
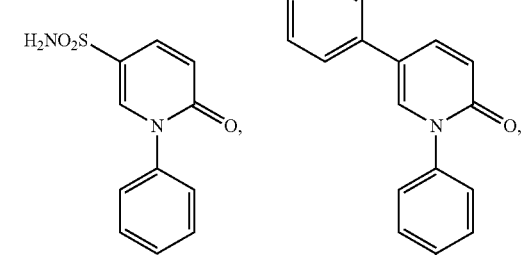
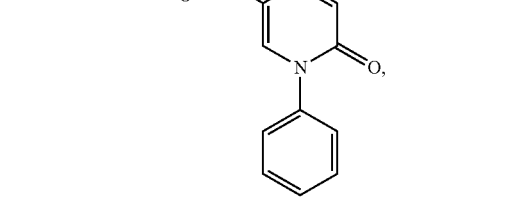

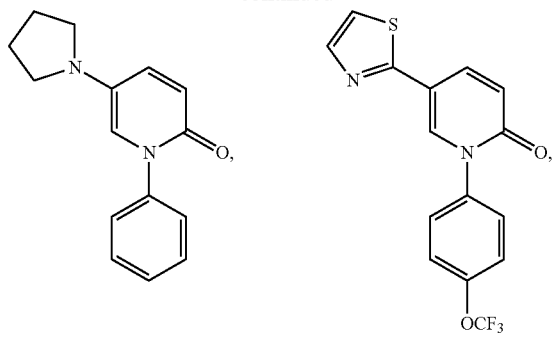
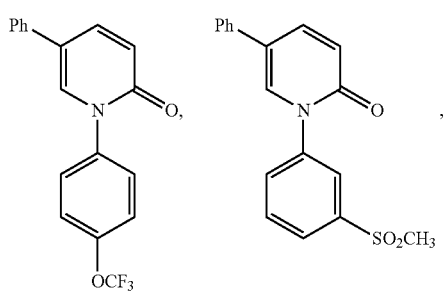
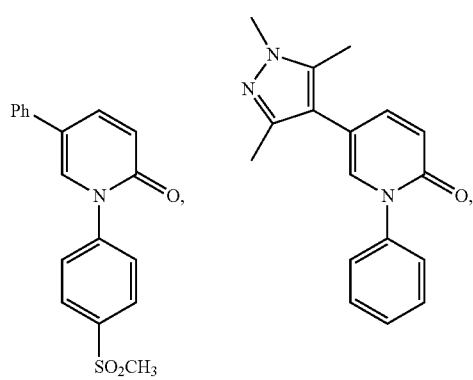
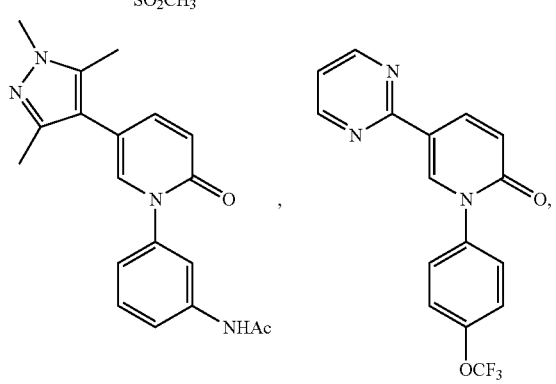
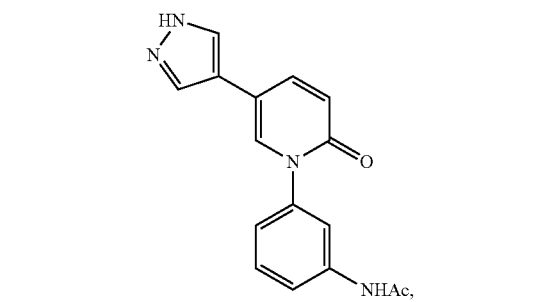
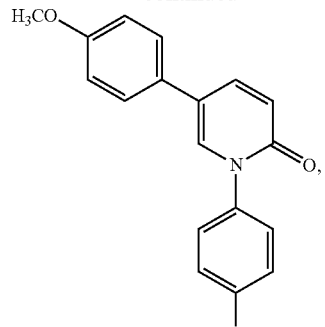
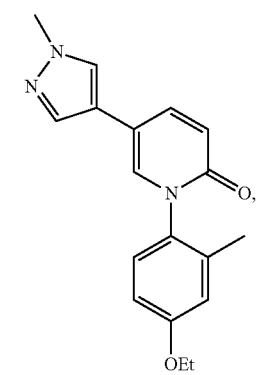
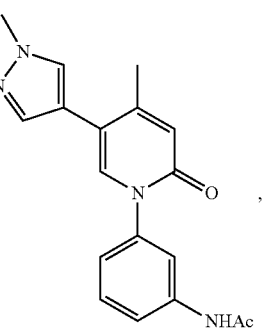
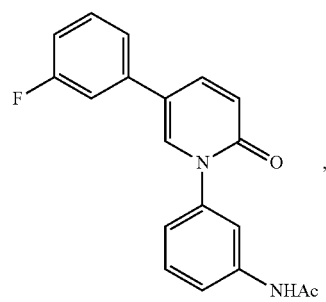

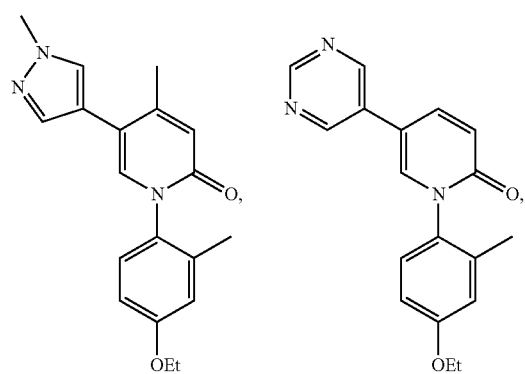
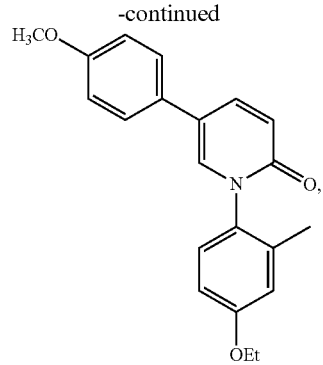

249
-continued
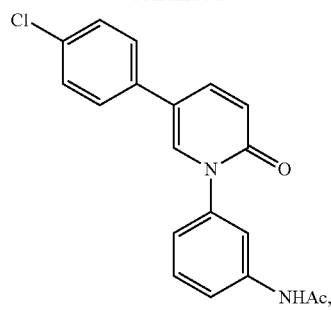
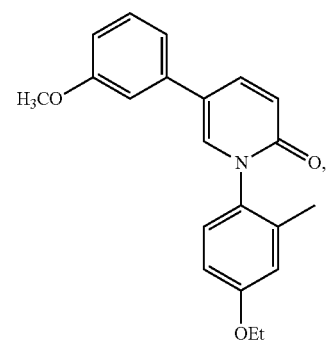
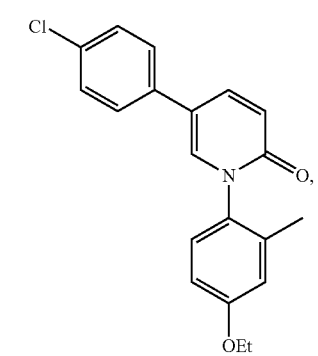
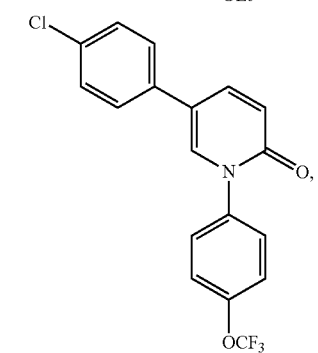
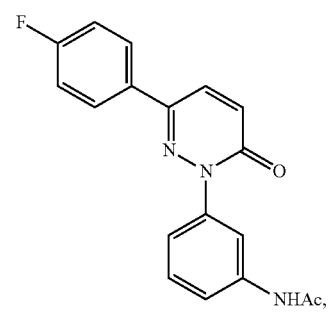
250
-continued
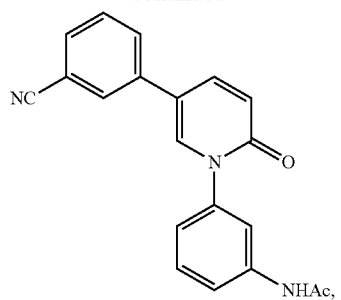
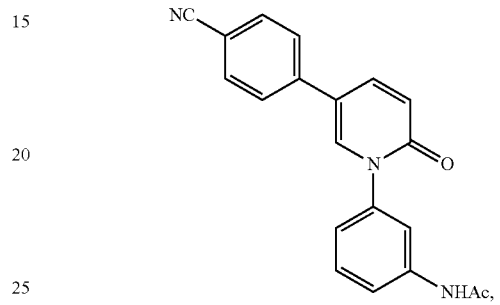
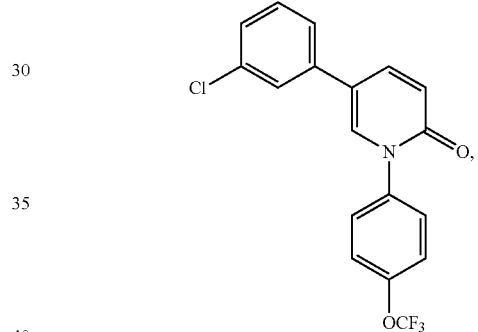
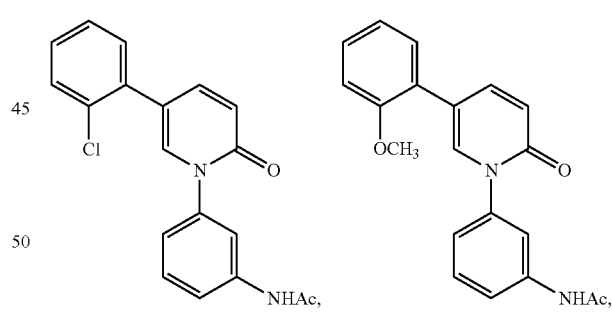
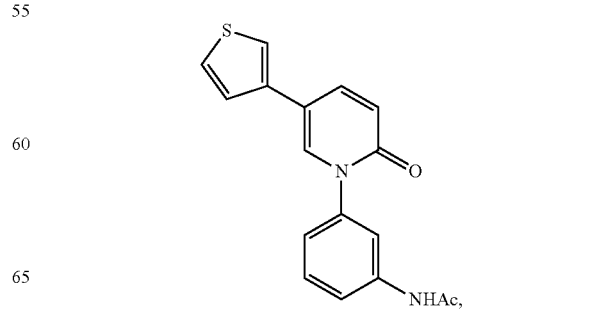

251
-continued
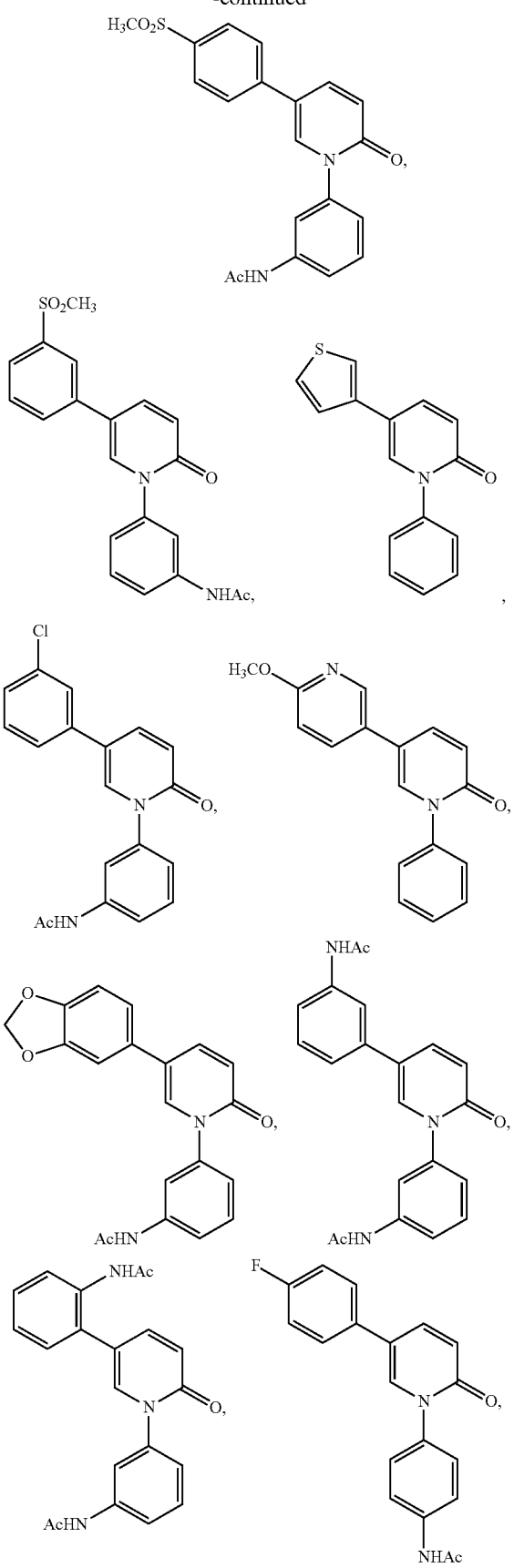
252
-continued
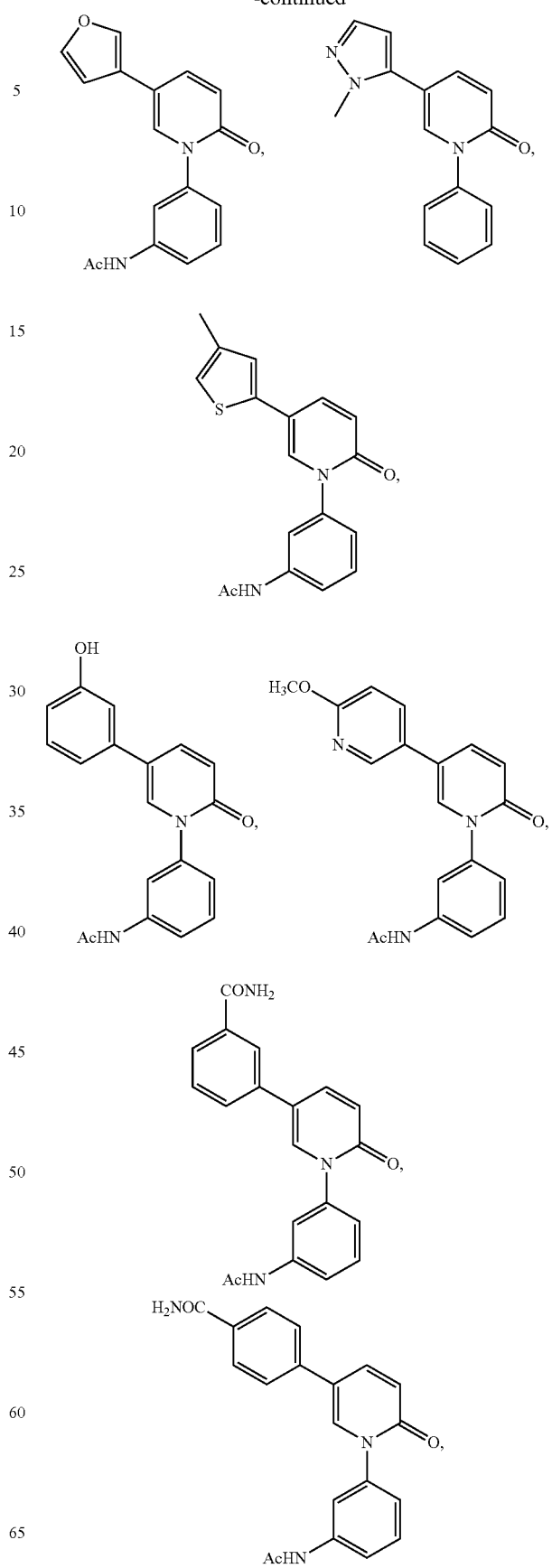

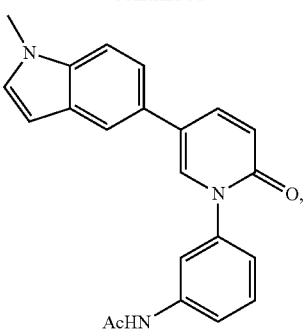
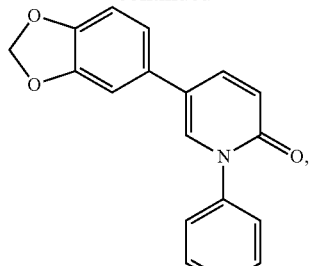
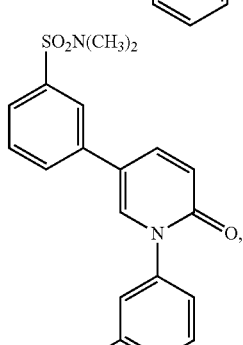
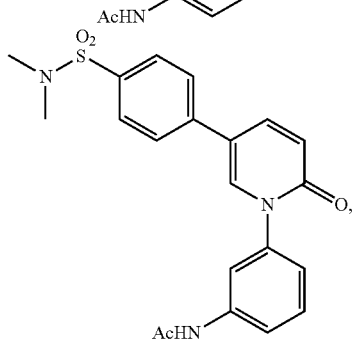
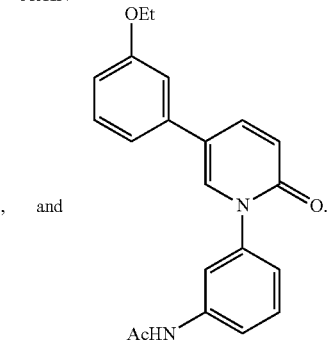

or a pharmaceutically acceptable salt thereof.

11. The compound of claim 1, wherein the compound exhibits an $IC_{50}$ in a range of about 100 μM to about 1000 μM for inhibition of p38 MAPK.

12. The compound of claim 11, wherein the compound exhibits an $IC_{50}$ is in the range of about 200 μM to about 800 μM.

13. The compound of claim 1, wherein the compound exhibits an $EC_{50}$ in the range of about 0.1 μM to about 1000 μM for inhibition of TNFα secretion in a bodily fluid in vivo.

14. A composition comprising a compound of claim 1 and a pharmaceutically acceptable excipient.

15. The compound of claim 2, wherein $R^2$ is selected from the group consisting of aryl; unsubstituted heteroaryl; heteroaryl substituted with one or more substituents selected from halo, unsubstituted alkyl, alkenyl, $OCF_3$, $NO_2$, CN, NC, OH, alkoxy, haloalkoxy, amino, CO$_2$H, and CO$_2$alkyl; haloalkylcarbonyl; cycloalkyl; hydroxylalkyl; sulfonamido; and unsubstituted cycloheteroalkyl; or R$^2$ and R$^1$ together form an optionally substituted 5-membered nitrogen-containing heterocyclic ring.

16. The compound of claim 15, selected from the group consisting of:

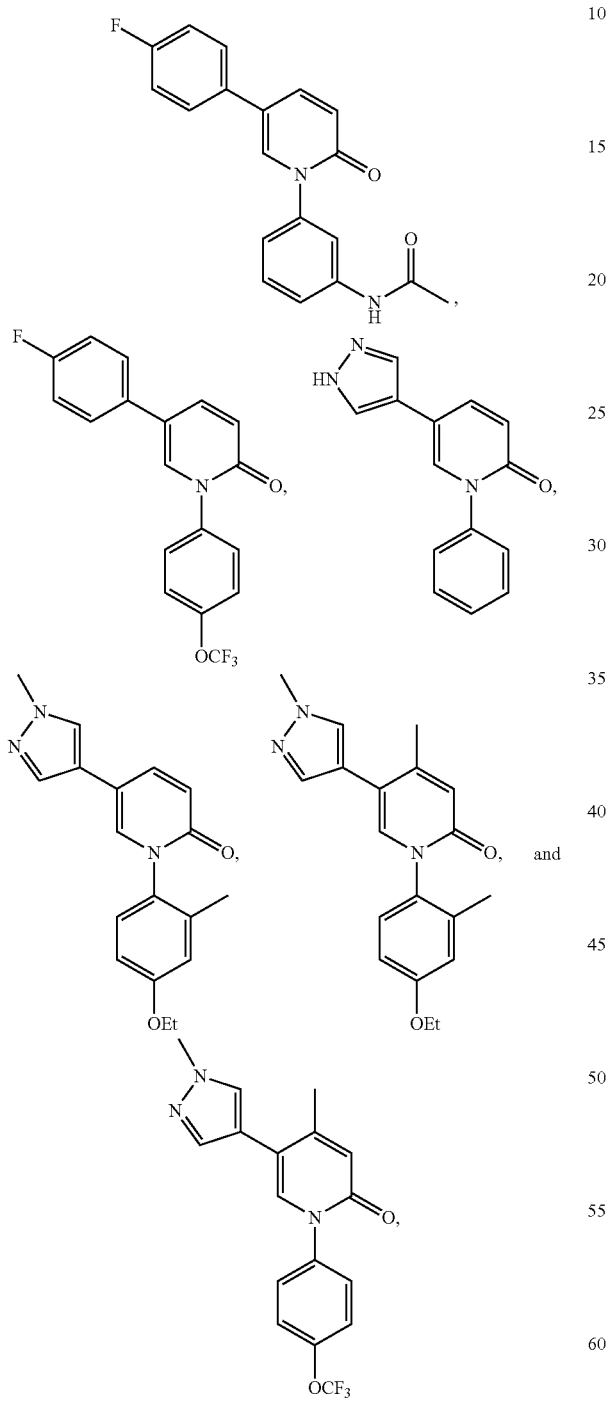

or a pharmaceutically acceptable salt thereof.

17. A compound selected from the group consisting of:

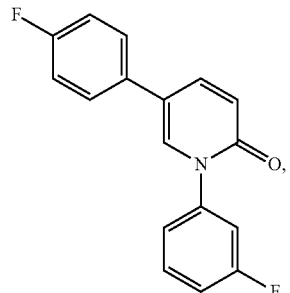

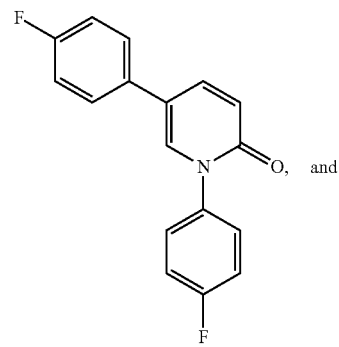

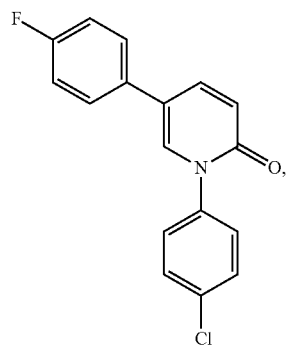

or a pharmaceutically acceptable salt thereof.

18. The compound of claim 3 having a structure selected from the group consisting of:

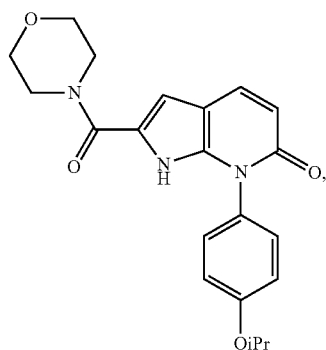

257
-continued

258
-continued

259
-continued
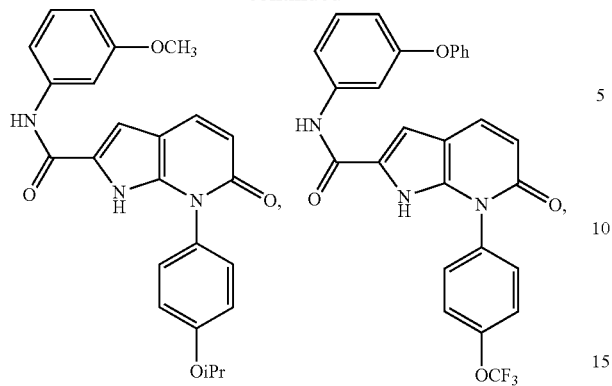
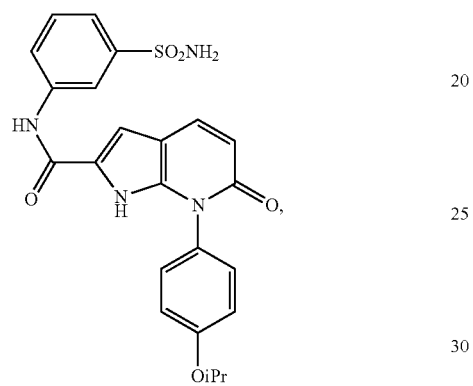
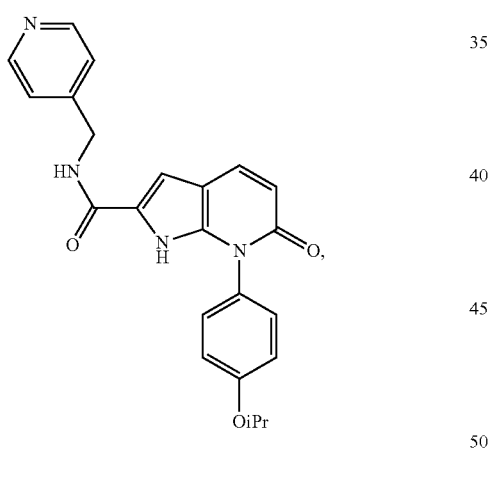
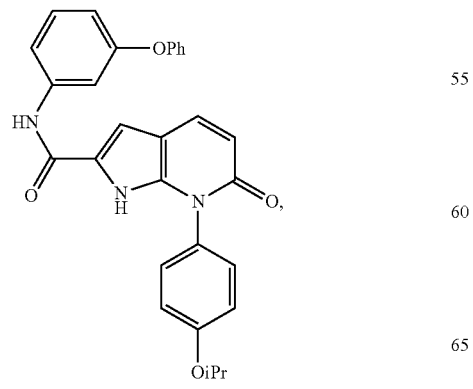
260
-continued
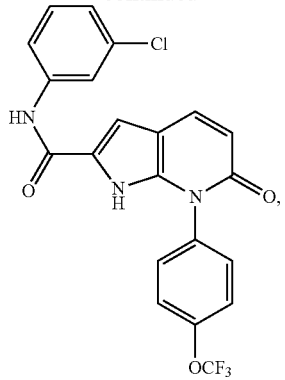
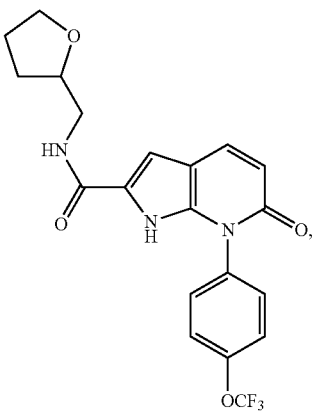
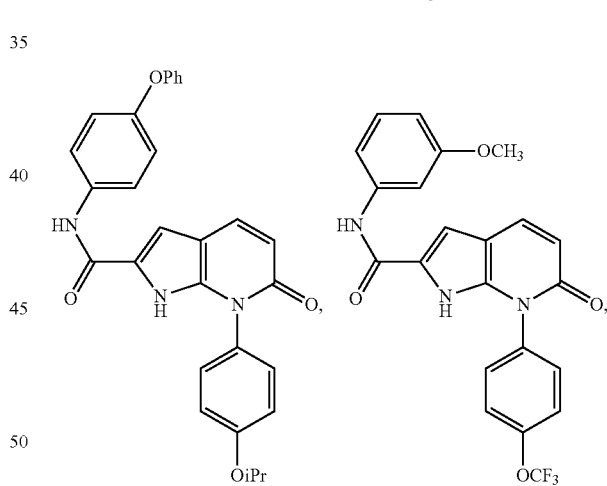
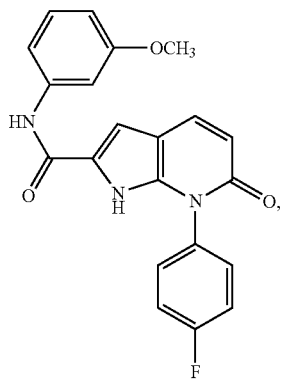

261
-continued
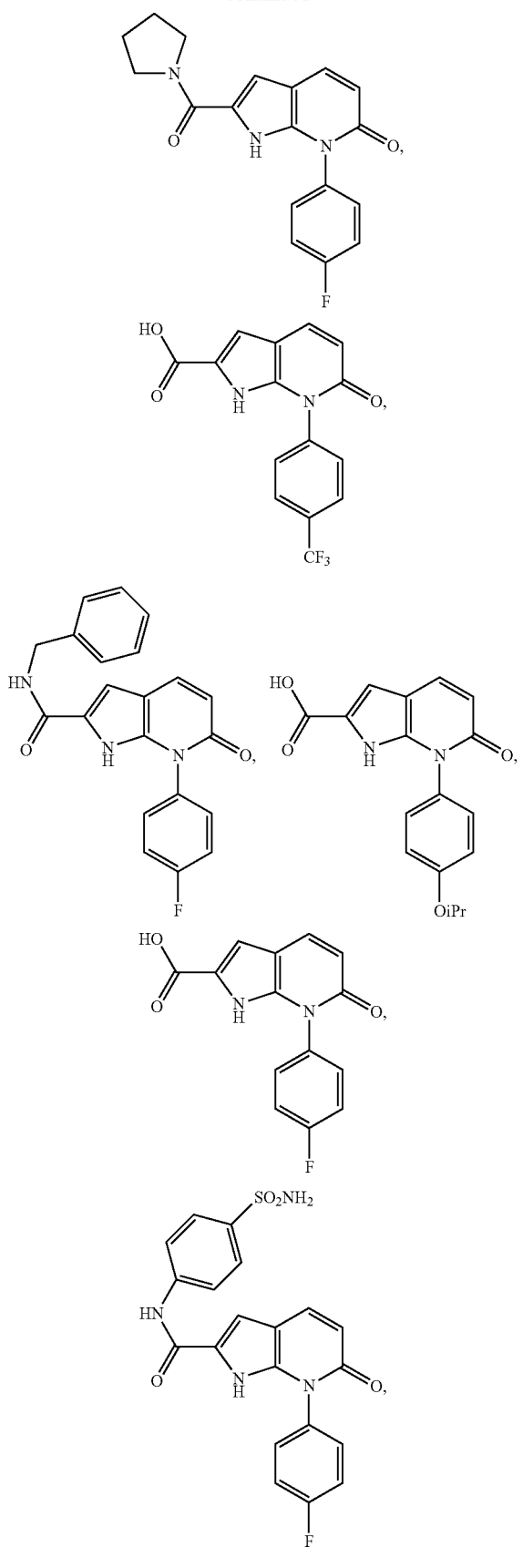
262
-continued
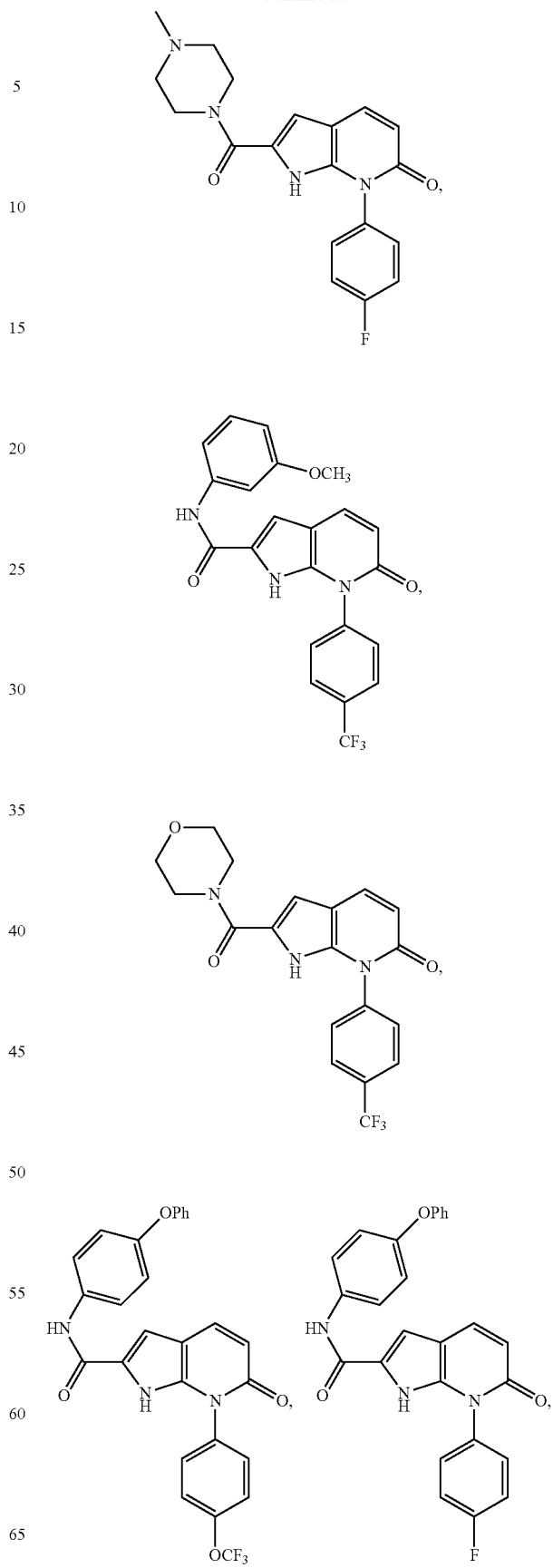

263
-continued
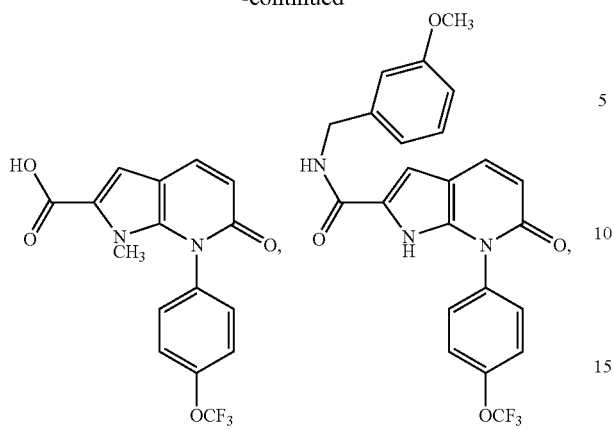
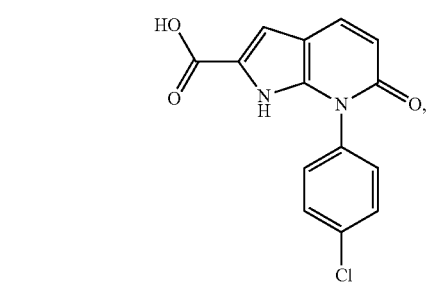
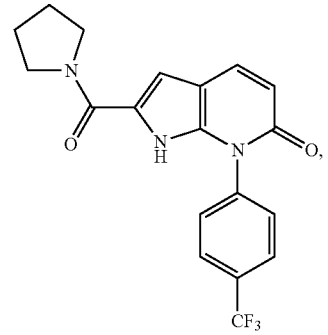
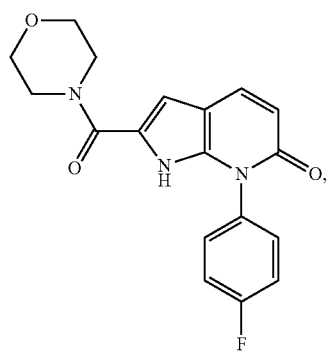
264
-continued
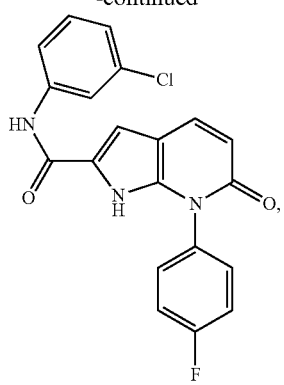
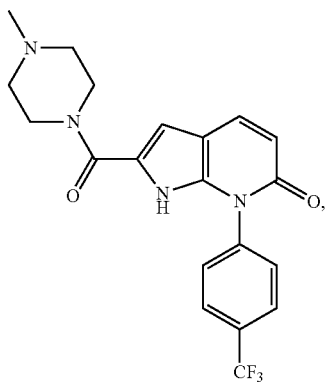
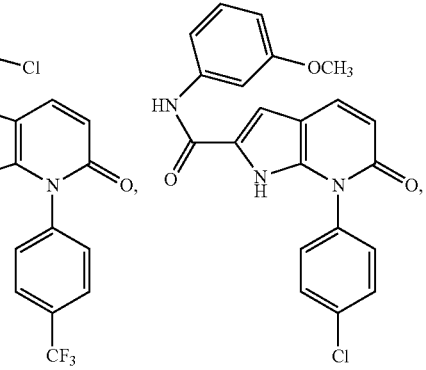

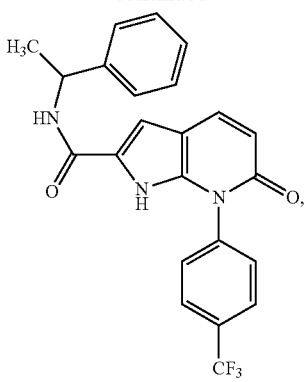
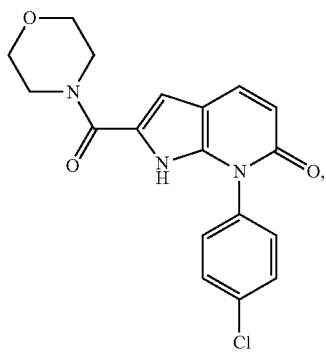
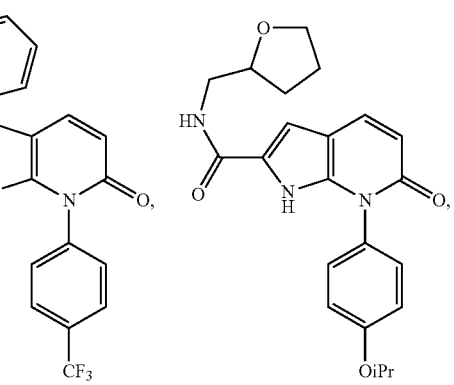
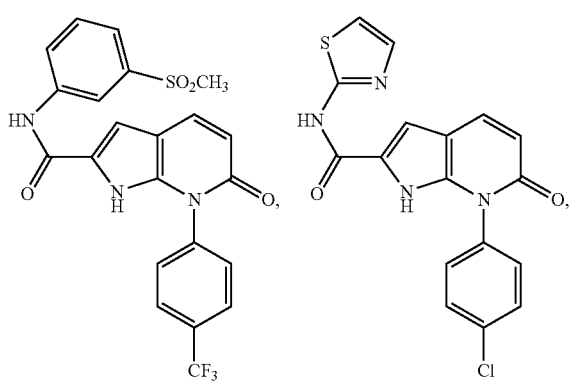
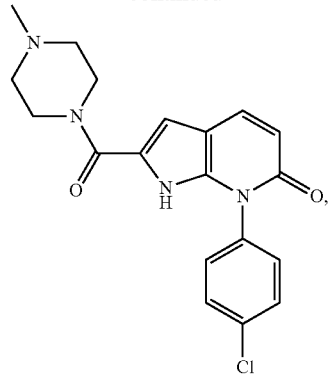
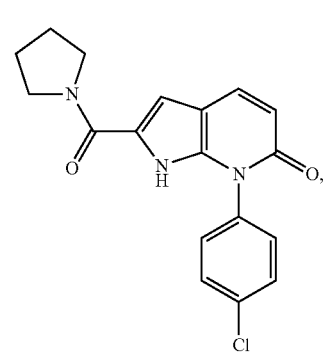
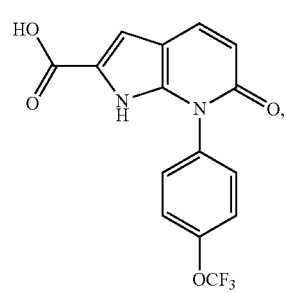

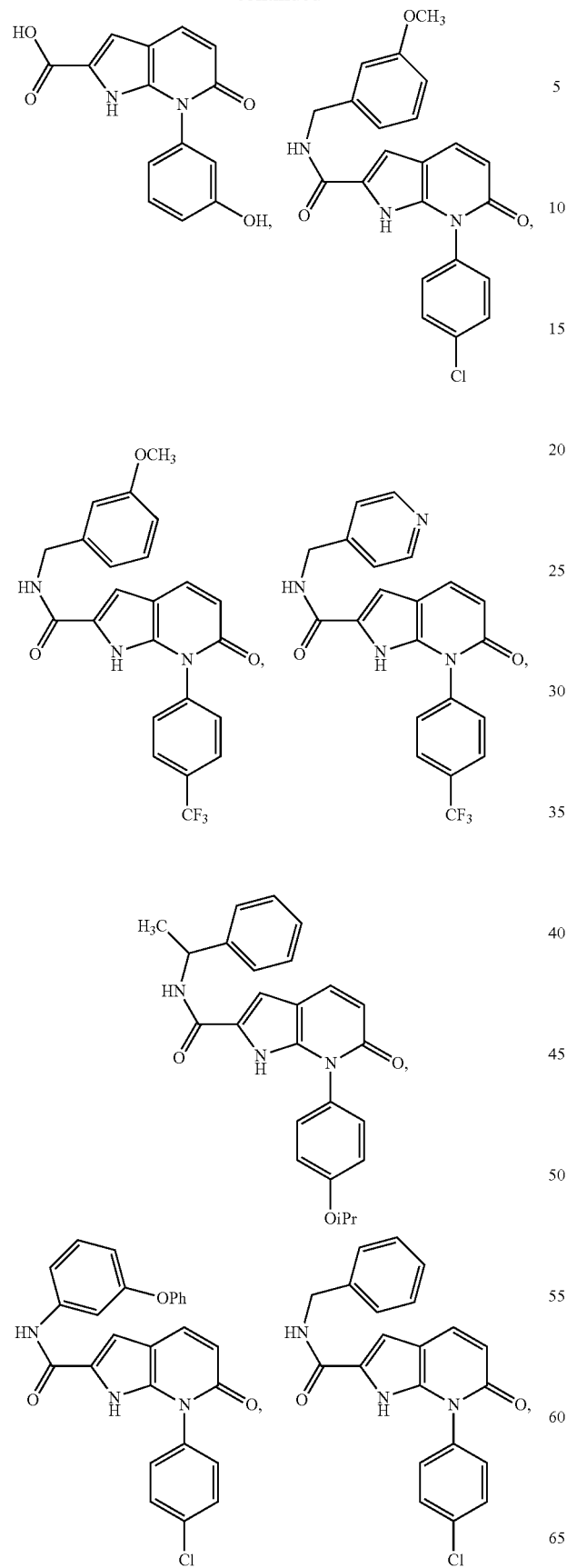
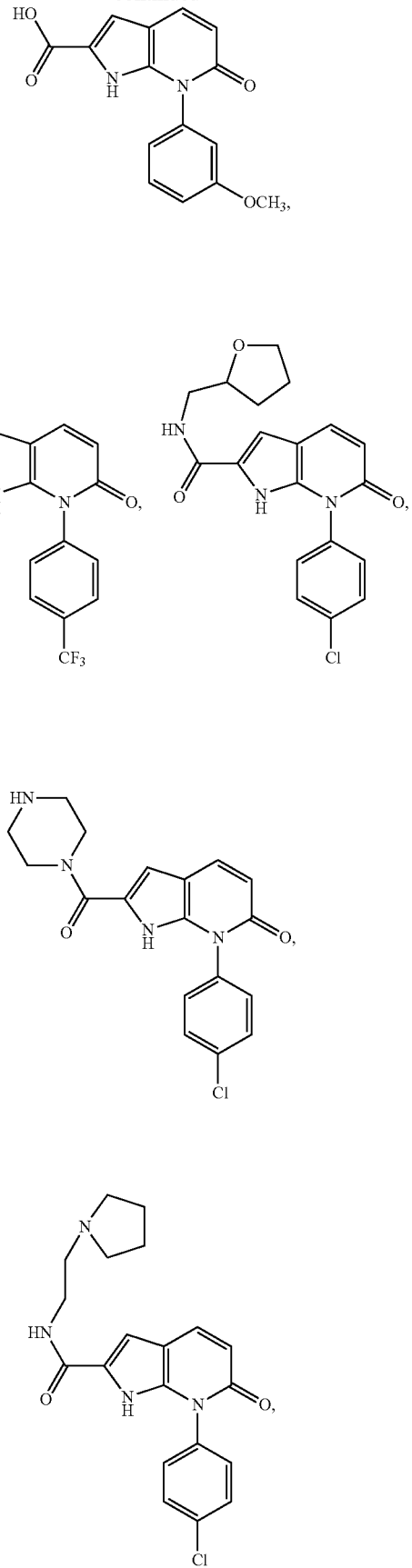

269
-continued
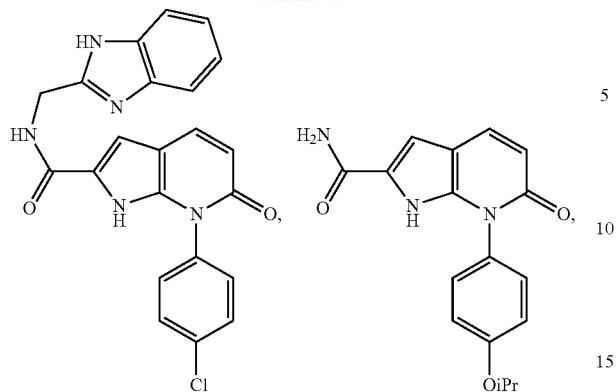
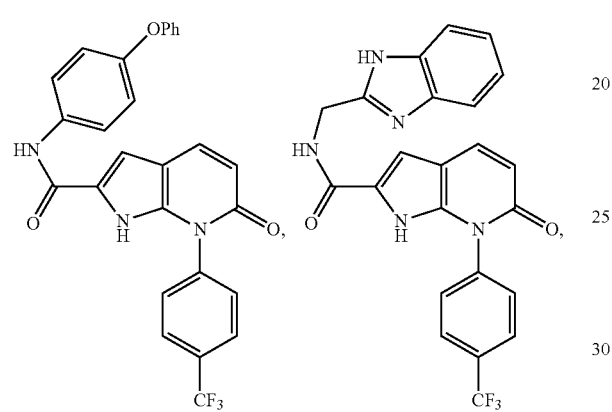
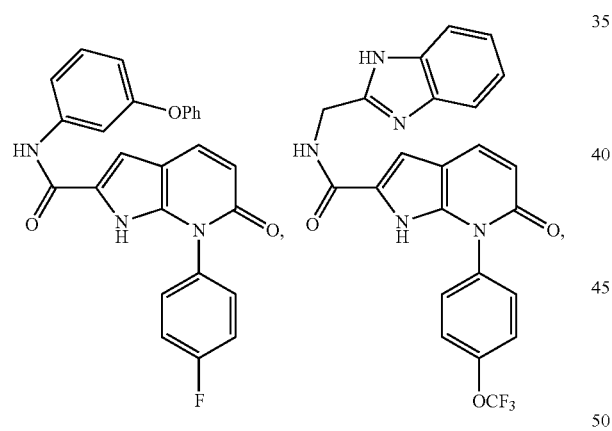
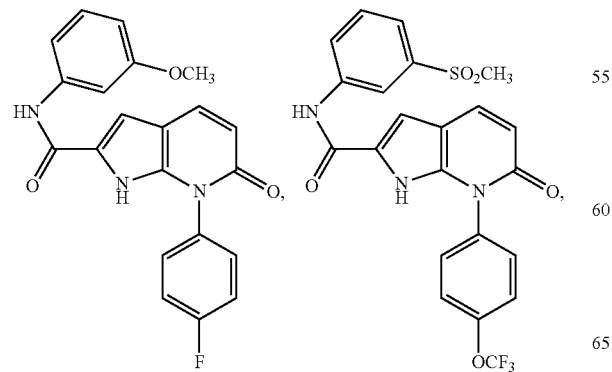
270
-continued
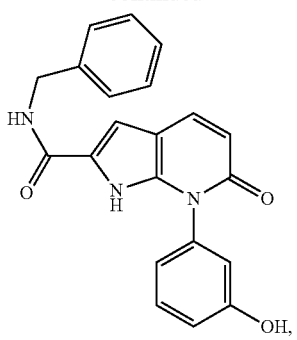
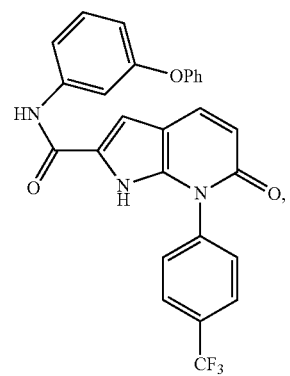
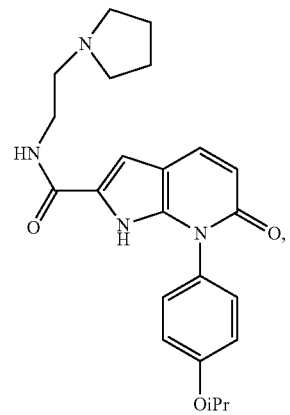
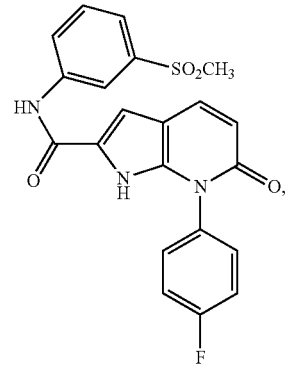

271
-continued
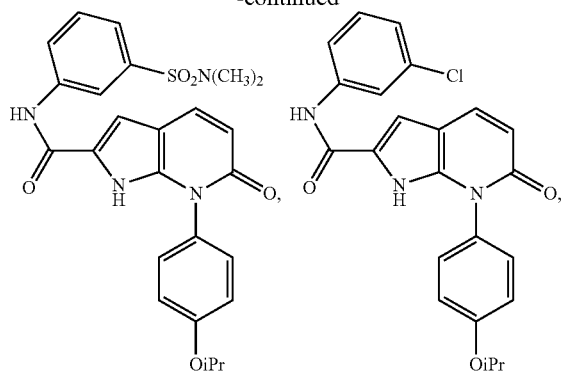
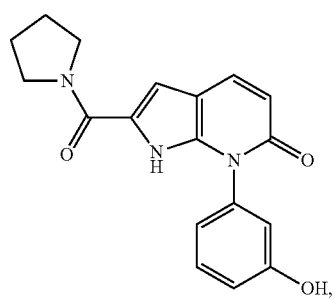
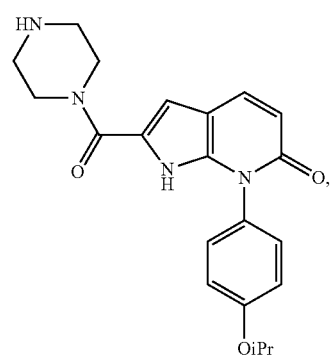
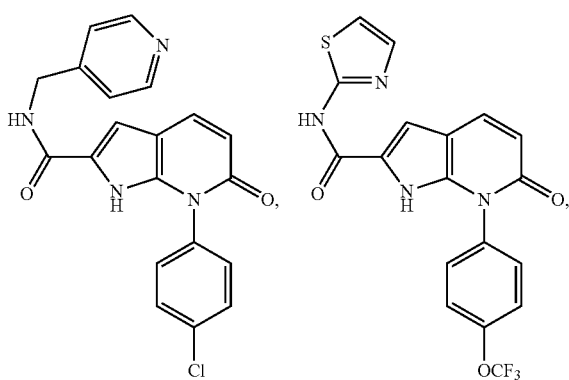
272
-continued
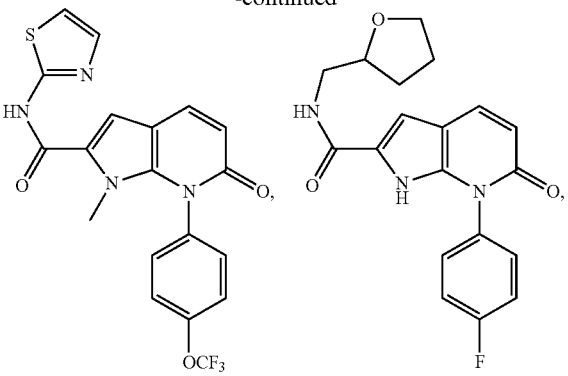
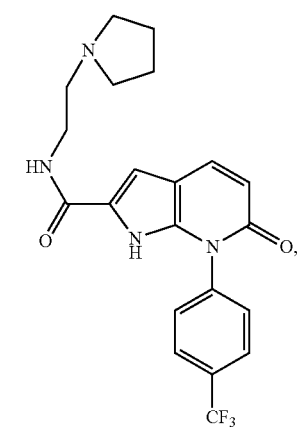
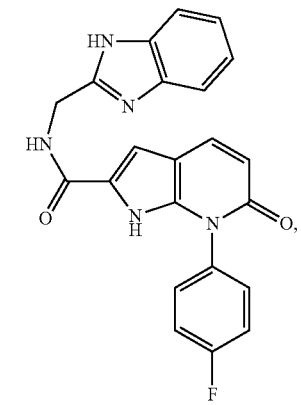
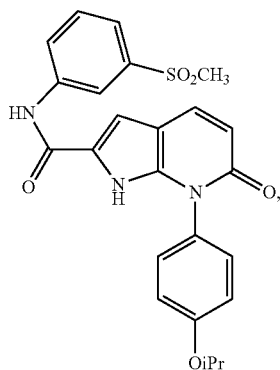

273
-continued
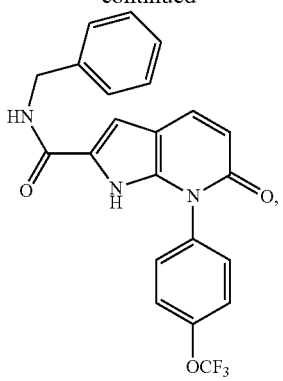
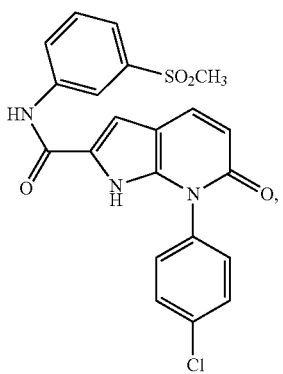
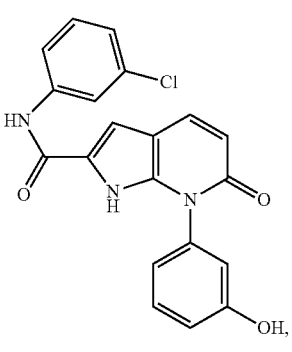
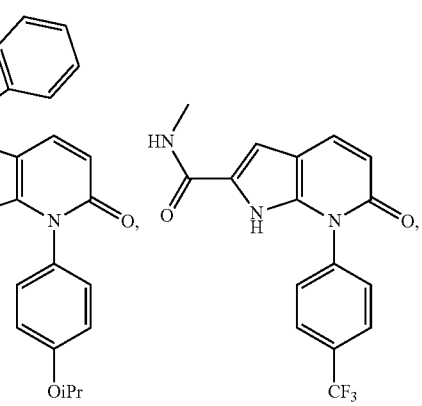
274
-continued
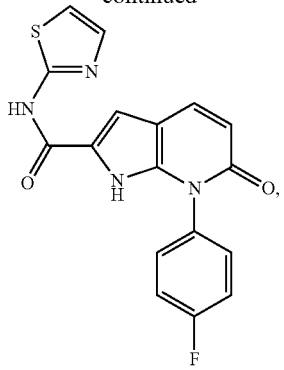
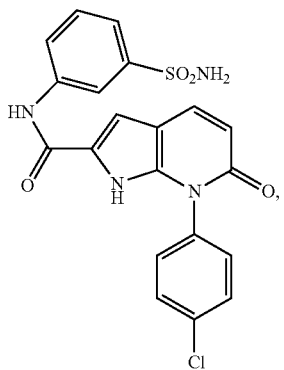
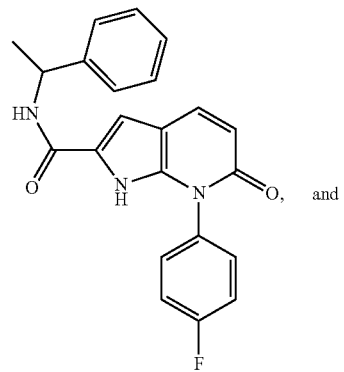
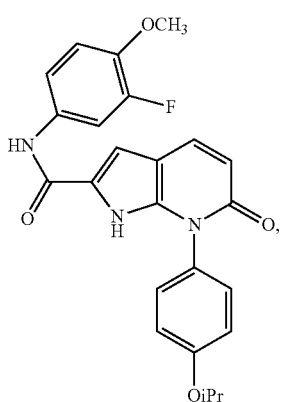
or a pharmaceutically acceptable salt thereof.

19. A compound selected from the group consisting of:
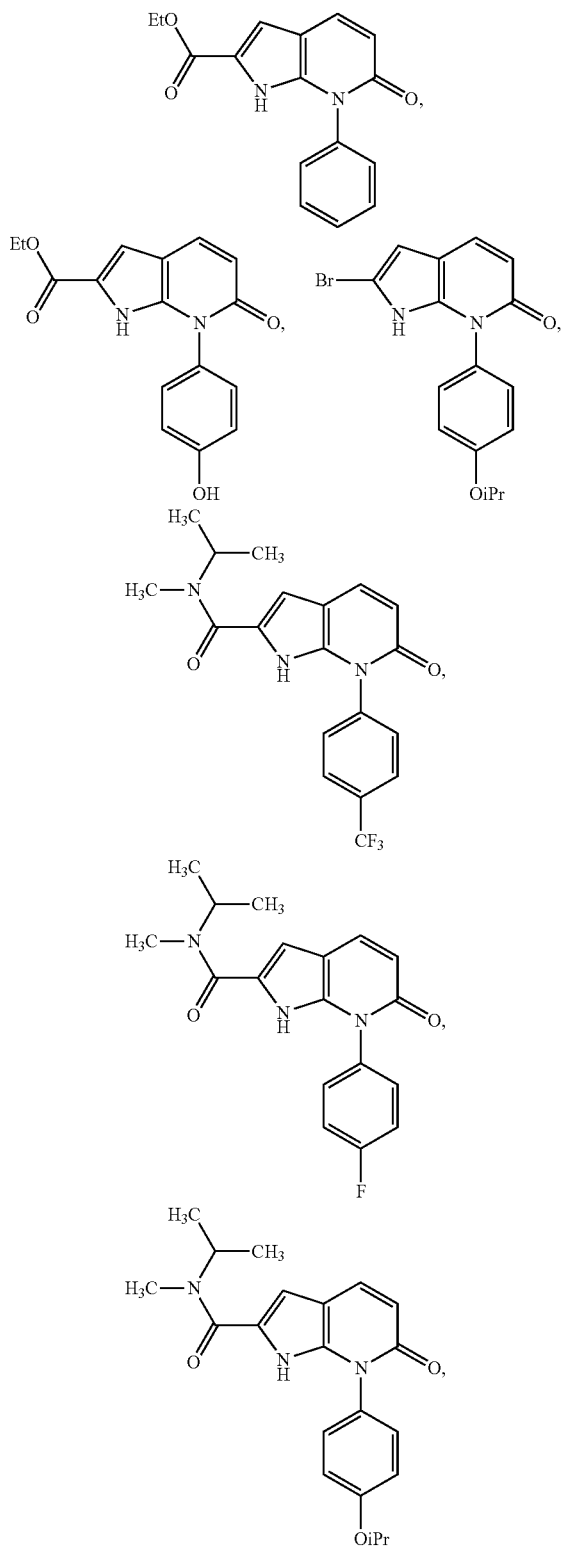
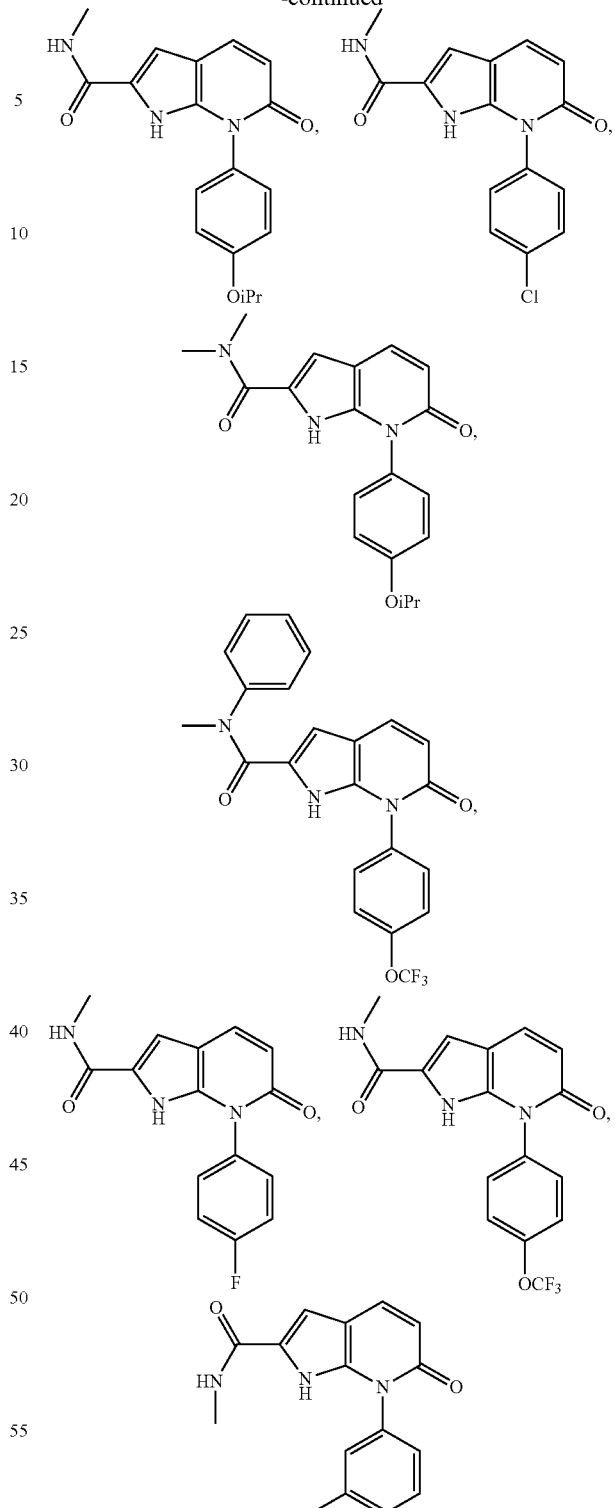
and, or a pharmaceutically acceptable salt thereof.
* * * * *